US010005820B2

(12) United States Patent
Giacalone et al.

(10) Patent No.: US 10,005,820 B2
(45) Date of Patent: Jun. 26, 2018

(54) THERAPEUTIC COMPOSITIONS AND METHODS FOR ANTIBODY AND FC-CONTAINING TARGETING MOLECULE-BASED TARGETED DELIVERY OF BIOACTIVE MOLECULES BY BACTERIAL MINICELLS

(75) Inventors: Matthew J. Giacalone, San Diego, CA (US); Michael J. Newman, San Diego, CA (US)

(73) Assignee: VAXIION THERAPEUTICS, LLC, San Diego, CA (US)

(*) Notice: Subject to any disclaimer, the term of this patent is extended or adjusted under 35 U.S.C. 154(b) by 0 days. days.

(21) Appl. No.: 13/397,313

(22) Filed: Feb. 15, 2012

(65) Prior Publication Data

US 2012/0207754 A1 Aug. 16, 2012

Related U.S. Application Data

(60) Provisional application No. 61/442,999, filed on Feb. 15, 2011, provisional application No. 61/526,219, filed on Aug. 22, 2011.

(51) Int. Cl.

| | |
|---|---|
| ***C07K 14/195*** | (2006.01) |
| ***C12N 1/02*** | (2006.01) |
| ***C12N 1/20*** | (2006.01) |
| ***C12N 15/00*** | (2006.01) |
| ***C12N 15/10*** | (2006.01) |
| ***C07K 16/00*** | (2006.01) |
| ***C12N 15/70*** | (2006.01) |
| *C12N 15/74* | (2006.01) |

(52) U.S. Cl.

CPC ............ *C07K 14/195* (2013.01); *C07K 16/00* (2013.01); *C12N 1/02* (2013.01); *C12N 1/20* (2013.01); *C12N 15/00* (2013.01); *C12N 15/1037* (2013.01); *C12N 15/70* (2013.01); *C07K 2319/00* (2013.01); *C07K 2319/705* (2013.01); *C12N 15/74* (2013.01)

(58) Field of Classification Search

None

See application file for complete search history.

(56) References Cited

U.S. PATENT DOCUMENTS

| | | | |
|---|---|---|---|
| 4,190,495 | A | 2/1980 | Curtiss |
| 4,311,797 | A | 1/1982 | Khachatourians |
| 4,431,740 | A | 2/1984 | Bell et al. |
| 4,732,852 | A | 3/1988 | Cohen et al. |
| 4,782,022 | A | 11/1988 | Puhler et al. |
| 4,895,724 | A | 1/1990 | Cardinal et al. |
| 4,968,619 | A | 11/1990 | Curtiss |
| 5,066,596 | A | 11/1991 | Manning et al. |
| 5,314,695 | A | 5/1994 | Brown |
| 5,338,842 | A | 8/1994 | Isberg et al. |
| 5,348,867 | A | 9/1994 | Georgiou et al. |
| 5,519,134 | A | 5/1996 | Acevedo et al. |
| 5,525,735 | A | 6/1996 | Gallop et al. |
| 5,549,974 | A | 8/1996 | Holmes |
| 5,744,336 | A | 4/1998 | Hodges et al. |
| 5,808,032 | A | 9/1998 | Kurihara et al. |
| 5,830,710 | A | 11/1998 | Progulske-Fox et al. |
| 5,834,591 | A | 11/1998 | Normark et al. |
| 5,877,159 | A | 3/1999 | Powell et al. |
| 5,888,799 | A | 3/1999 | Curtiss |
| 5,922,583 | A | 7/1999 | Morsey |
| 5,981,182 | A | 11/1999 | Jacobs et al. |
| 6,004,815 | A | 12/1999 | Portney |
| 6,030,805 | A | 2/2000 | Normark et al. |
| 6,080,849 | A | 6/2000 | Bermudes et al. |
| 6,100,066 | A | 8/2000 | Potter et al. |
| 6,143,566 | A | 11/2000 | Heintz et al. |
| 6,150,170 | A | 11/2000 | Powell et al. |
| 6,168,945 | B1 | 1/2001 | Sokatch et al. |
| 6,172,189 | B1 | 1/2001 | Devare et al. |
| 6,248,543 | B1 | 6/2001 | de Boer et al. |
| 6,258,359 | B1 | 7/2001 | Labigne et al. |
| 6,270,776 | B1 | 8/2001 | Bloom et al. |
| 6,291,649 | B1 | 9/2001 | Lindberg et al. |
| 6,329,503 | B1 | 12/2001 | Afar et al. |
| 7,183,105 | B2 * | 2/2007 | Sabbadini et al. ......... 435/320.1 |
| 8,067,377 | B2 | 11/2011 | Arap et al. |
| 8,101,396 | B2 | 1/2012 | Sabbadini et al. |
| 8,187,571 | B1 | 5/2012 | Sung et al. |

(Continued)

FOREIGN PATENT DOCUMENTS

| | | |
|---|---|---|
| EP | 2272946 | 1/2011 |
| JP | 2008-510794 | 4/2008 |

(Continued)

OTHER PUBLICATIONS

Moks et al. European Journal of Biochemistry. vol. 156, issue 3, p. 637-643, 1986.*

Patyar et al. Journal of Biomedical Science 2010, 17: 21.*

Stone et al. The Journal of Immunology. vol. 143, 565-570, No. 2, Jul. 15, 1989.*

Tai et al. Human Gene Therapy 14:789-802 (May 20, 2003).*

Jansson et al. FEMS Immunology and Medical Microbiology 20 (1998) 69-78.*

Henderson et al. Microbiology and Molecular Biology Reviews, Dec. 2004, p. 692-744.*

Nilsson et al (Protein Engineering vol. 1 No. 2 pp. 107-113, 1987).*

Han et al., "Ligand-directed retroviral targeting of human breast cancer cells" Proc. Natl. Acad. Sci. USA, 92:9747-9751, 1995 (1995).

(Continued)

*Primary Examiner* — Oluwatosin A Ogunbiyi

(74) *Attorney, Agent, or Firm* — Knobbe Martens Olson & Bear LLP

(57) ABSTRACT

The present application relates to the use of bacterial minicells as targeted delivery agents in vivo and in vitro. Described herein are genetically engineered eubacterial minicells designed to preferentially target and deliver therapeutically relevant agents using a minicell surface coupling molecule capable of binding and displaying antibodies or other Fc-containing targeting moiety fusions and conjugates.

24 Claims, 7 Drawing Sheets

(56) References Cited

U.S. PATENT DOCUMENTS

| | | | | |
|---|---|---|---|---|
| 2003/0105310 | A1 | 6/2003 | Ashkar | |
| 2003/0166099 | A1 | 9/2003 | Sabbadini et al. | |
| 2003/0166279 | A1 | 9/2003 | Sabbadini et al. | |
| 2003/0190601 | A1 | 10/2003 | Sabbadini et al. | |
| 2003/0190683 | A1 | 10/2003 | Sabbadini et al. | |
| 2003/0190749 | A1 | 10/2003 | Surber et al. | |
| 2003/0194714 | A1 | 10/2003 | Sabbadini et al. | |
| 2003/0194798 | A1 | 10/2003 | Surber et al. | |
| 2003/0198995 | A1 | 10/2003 | Sabbadini et al. | |
| 2003/0198996 | A1 | 10/2003 | Surber et al. | |
| 2003/0199088 | A1 | 10/2003 | Sabbadini et al. | |
| 2003/0199089 | A1 | 10/2003 | Surber et al. | |
| 2003/0202937 | A1 | 10/2003 | Sabbadini et al. | |
| 2003/0203411 | A1 | 10/2003 | Sabbadini et al. | |
| 2003/0203481 | A1 | 10/2003 | Surber et al. | |
| 2003/0207833 | A1 | 11/2003 | Berkley et al. | |
| 2003/0211086 | A1 | 11/2003 | Berkley et al. | |
| 2003/0211599 | A1 | 11/2003 | Sabbadini et al. | |
| 2003/0219408 | A1 | 11/2003 | Sabbadini et al. | |
| 2003/0219888 | A1 | 11/2003 | Segall et al. | |
| 2003/0224369 | A1 | 12/2003 | Surber et al. | |
| 2003/0224444 | A1 | 12/2003 | Sabbadini et al. | |
| 2003/0232335 | A1 | 12/2003 | Surber et al. | |
| 2004/0005700 | A1 | 1/2004 | Surber et al. | |
| 2005/0147590 | A1 | 7/2005 | Sabbadini et al. | |
| 2006/0002956 | A1 | 1/2006 | Surber et al. | |
| 2007/0237744 | A1 | 10/2007 | Brahmbhatt et al. | |
| 2007/0298056 | A1 | 12/2007 | Brahmbhatt et al. | |
| 2008/0051469 | A1 * | 2/2008 | Brahmbhatt et al. | 514/773 |
| 2010/0112670 | A1 | 5/2010 | Giacalone et al. | |
| 2012/0142079 | A1 | 6/2012 | Sabbadini et al. | |

FOREIGN PATENT DOCUMENTS

| | | | |
|---|---|---|---|
| WO | WO 93/10214 | | 5/1993 |
| WO | WO 1997/014810 | | 4/1997 |
| WO | WO 98/52547 | | 11/1998 |
| WO | WO 1999/013053 | | 3/1999 |
| WO | WO 1999/052563 | | 10/1999 |
| WO | WO 99/59643 | * | 11/1999 |
| WO | WO 2000/009733 | | 2/2000 |
| WO | WO 02/070645 | * | 9/2002 |
| WO | WO 2002/072759 | | 9/2002 |
| WO | WO 2003/033519 | | 4/2003 |
| WO | WO 2003/072014 | | 9/2003 |
| WO | WO 2005/056749 | | 6/2005 |
| WO | WO 2005/079854 | | 9/2005 |
| WO | WO 2006/021894 | | 3/2006 |
| WO | WO 2006/055024 | * | 5/2006 |
| WO | WO 2009/158364 | * | 12/2009 |

OTHER PUBLICATIONS

Iijima et al., "Nanocapsules incorporating IgG Fc-binding domain derived from *Staphylococcus aureus* protein A for displaying IgGs on immunosensor chips," *Biomaterials*, 32: 1453-1464, (2011).

Klier et al., Combining bacterial-immunotherapy with therapeutic antibodies: a novel therapeutic concept, Vaccine, 30:2786-2794 (2012), published ahead of print Feb. 13, 2012 (online).

MacDiarmid et al., "Bacterially Derived 400 nm Particles for Encapsulation and Cancer Cell Targeting of Chemotherapeutics," *Cancer Cell*, 11: 431-445, (May 2007).

Extended European Search Report dated Apr. 22, 2014 in European Application No. 12747781.8.

International Search Report and Written Opinion dated Mar. 23, 2012 of International Patent Application PCT/US2012/025272, filed Feb. 15, 2012.

Ackley, et al., Defensive applications of gene transfer technology in the face of bioterrorism: DNA-based vaccines and immune targeting, Expert Opin. Biol. Ther. 3(8):1279-1289 (2003).

Acres et al., Vaccination of Cows with Purified K99 Antigen, K99+ Anucleated Live *E. coli*, and Whole Cell Bacterins Containing Enterotoxigenic *E. coli* for Prevention of Enterotoxigenic Colibacillosis of Calves, Proceedings of Second International Symposium on Neonatal Diarrhea pp. 443-456 (1979).

Adler et al., Genetic Control of Cell Division in Bacteria, National Academy of Sciences, abstracts of paper presented at the auumn meeting, p. 417 (Oct. 17-19, 1966).

Adler et al., Miniature *Escherichia coli* Cells Deficient in DNA, Microbiology 57:321-326 (1966).

Barker et al., Isolation by Differential and Zonal Centrifugation of Minicells Segregated by *Escherichia coli*, Jo. General Microbiology 111:387-397 (1979).

Bollon, et al. DNA Transformation Efficiency of Various Bacterial and Yeast Host-Vector Systems Journal of Clinical Hematology and Oncology 10:39-48 (1980).

Bonner & Curtiss, Use of Minicells in Vaccination Against Salmonella Infection, Abstract (1976).

Botstein, et al. Making Mutations In Vitro and Putting Them Back Into Yeast, Miami Winter Symposia 19:265-275 (1982).

Bouvier et al., A Gene for a New Lipoprotein in the dapA-purC Interval of the *Escherichia coli* Chromosome, J. of Bacteriology 173(17):5523-5531 (1991).

Broach, James R. The Yeast: Plasmid 2u Circle, The Molecular Biology of the Yeast *Saccharomyces* : Life Cycle and Inheritance 445-470 (1981).

Broach James R. The Yeast: Plasmid 2u Circle Cell 28:203-204 (1982).

Brunel et al., Cloning and Expression of Trypanosome brucei kinetoplast DNA in *Escherichia coli*, Gene 12:223-234 (1980).

Clark-Curtiss et al., Analysis of Recombinant DNA Using *Escherichia coli* Minicells, Methods in Enzymology 101:347-362 (1983).

Courvalin et al., Gene Transfer from Bacteria to Mammalian Cells, C.R. Acad. Sci. 318:1207-12 (1995).

Coyne & Mendelson, Use of Bacillus subtilis Minicells to Demonstrate an Antegenic Relationship Between the Poles and Lateral Cylindrical Regions of Rod-Shaped Cells, Infection and Immunity 12:1189-1194 (1975).

Curtiss III, Roy, Genetic Manipulation of Microorganisms: Potential Benefits and Biohazards Ann. Rev. Microbial. 30:507-533 (1976).

Curtiss III, Roy, Research on bacterial conjugation with minicells and minicell-producing *E. coli* strains, Microbial Drug Resistance p. 169. Baltimore University Park Press (1976).

de Boer et al., A Division Inhibitor and a Topological Specificity Factor Coded for by the Minicell Locus Determine Proper Placement of the Division Septum in *E. coli* Cell 56:641-649 (1989).

Eck et al., Cloning and characterization of a gene coding for the caterchol 1,2-dioxygenase of *Arthrobacter* sp. mA3 Gene 123:87-92 (1993).

Eck et al., Gene-Based Therapy, Goodman & Gilmans The Pharmacological Basis of Therapeutics, McGraw-Hill, New York, NY., 9.sup.th Ed., pp. 77-101 (1996).

Edge, et al., Chemical Synthesis of a human interferon-.alpha..sub.2 gene and its expression in *Escherichia coli*, Nucleic Acids Research 11(18):6419-6435 (1983).

Eick et al., From initiation to elongation: comparison of transcription by prokaryotic and eukaryotic RNA polymerases, TIG 10(8):292-296 (1994).

Fox, et al., Fate of the DNA in Plasmid-Containing *Escherichia coli* Minicells Ingested by Human Neutrohils, Blood 69(5): 1394-1400 (1987).

Francisco, et al. "Production and Fluorescence-Activated Cell Sorting of *Escherichia coli* Expressing a Functional Antibody Fragment on the External Surface", Proceedings of the National Academy of Sciences, USA, 90(22): 1044-48.

Frazer et al., Production, Properties and Utility of Bacterial Minicells, 69 Curr. Top. Microbiol. Immunol. 1:3-84 (1975).

Gabel et al., The KdpF Subunit s Part of the K.sup.+-translocating Kdp Complex of *Escherichia coli* and is Responsible for Stabilization of the Complex in Vitro, J. Biol. Chem. 274(53):37901-37907 (1999).

Giacalone et al., Immune responses elicited by bacterial minicells capable of simultaneous DNA and protein antigen delivery, Vaccine 24 6009-6017 (2006).

(56) References Cited

OTHER PUBLICATIONS

Gemski & Griffin, Isolation and Characterization of Minicell-Producing Mutants of Shigella spp, Infection & Immunity 30:297-302 (1980).
Griillot-Courvalin et al., Bacteria as gene delivery vectors for mammalian cells, Current Opinion in Biotechnology 10:477-481 (1999).
Gyongyossy-Issa et al., Tumour Minicells: Single, Large Vesicles Released From Cultured Mastocytoma Cells, Tissue & Cell 17(6):801-809 (1985).
Gyuris, et al., High-Efficiency Transformation of *Saccharomyces cerevisiae* Cells by Bacterial Minicell Protoplast Fusion, Mol. Cell. Biol. 6(9) 3295-97 (1986).
Hanson et al., Molecular cloning, partial purification, and characterization of a haemin-binding lipoprotein from Haemophilus influenzae type b, Molecular Microbiology 5(2):267-278 (1991).
Harlow et al., Cloning and Characterization of the gsk Gene Encoding Guanosine Kinase of *Escherichia coli*, J. of Bacteriology 177(8):2236-2240 (1995).
Hollenberg et al., Mapping of Regions on Cloned *Saccharomyces cerevisiae* 2-um DNA Coding for Polypeptides Synthesized in *Escherichia coli* Minicells, Molec. Gen. Genet. 162:23-34 (1978).
Horig et al., Strategies for cancer therapy using carcinoembryonic antigen vaccines, Expert Reviews in Molecular Medicine, 1-24 (Apr. 19, 2000).
Isaacson et al., In Vitro Adhesion of *Escherichia coli* to Porcine Small Intestinal Epithelial Cells: Pili as Adhesive Factors, Infection and Immunity 21:392-397 (1978).
Jacobs, et al., Expression of *Mycobacterium leprae* genes from a *Streptococcus mutans* promoter in *Escherichia coli* K-12, Proc. Natl. Acad. Sci. USA 83:1926-1930 (1986).
Jannatipour et al., Translocation of Vibrio harveyi N. N'-Diacetylchitobiase to the Outer Membrane of *Escherichia coli*, J. of Bacteriology 169(8):3785-3791 (1987).
Kawahara et al., Identification and mappin gof mba regions of the *Salmonella choleraesuis* virulence plasmid of pKDSC50 responsible for mouse bacteremia, Microbial Pathogenesis 8:13-21 (1990).
Khachatourians & Berezowsky, Expression of Recombinant DNA Functional Products in *Escherichia coli* Anucleate Minicells, Biotech. Adv. 4:75-93 (1986).
Khachatourians et al, A New Method for the Preparation of Minicells for Physiological Studies, Preparative Biochemistry 3:291-298 (1973).
Khachatourians et al., Fate of Conjugally Transferred DNA in Minicells of *Escherichia coli* K-12, Molec. gen. Genet. 128:23-42 (1974).
Khachatourians G., The Potential Use of Minicell Cultures in *E. coli* Vaccines, Proceedings of Minisymposium on Neonatal Diarrhea in Calves and Pigs, 82-91 (1976).
Khachatourians et al., Use of Anucleated Minicells in Vaccination Against Enteropathogenic *E. coli*, Abstract 443-455 (1979).
Khachatourians, G., The Use of Anucleated Minicells in Biotechnology: An Overview, Biotechnology pp. 309-319 (1985).
Khachatourians, G., Minicells as Specialized Vaccines and Vaccine Carriers, Isaacson, R.E. (Ed.). Recombinant DNA Vaccines: Rationale and Strategy, pp. 323-333, (1992).
Kool et al., Proteins Synthesized by a Non-Induced Bacteriocinogenic Factor in Minicells of *Escherichia coli*, Mole. Gen. Genetics 115:314-323 (1972).
Kopylova-Sviridova et al., Synthesis of Proteins Coded by Plasmid Vectors of pCV Series (Ap.sup.r, Tc.sup.r) and their Recombinant Derivatives (pDm) in *E. coli* Minicells, Gene 7:121-139 (1979).
Kozak, Marilyn, Initiation of Translation in Prokaryotes and Eukaryotes Gene 234:187-208 (1999).
Lee & McCubrey, The Raf/MEK/ERK signal transduction cascade as a target for chemotherapeutic intervention in leukemia, 16:486-507 (2002).
Leung, et al., The yopM Gene of Yersinia pestis Encodes a Released Protein Having Homology with the Human Platelet Surface Protein GPlb alpha, J. of Bacteriology 171(9):4623-4632 (1989).
Lienard et al., Cloning, sequencing and expression of the genes encoding the sodium translocating N5-methyltetrahydromethanopterin: coenzyme M methyltransferase of the methylotrophic archaeon Methanosarcina mazei Gö1, FEBS Letters 425:204-208 (1998).
MacConnell et al., Expression of FBJ-MSV Oncogene (fos) Product in Bacteria, Virology 131:367-374 (1983).
Maniatis, Tom Recombinant DNA Procedures in the Study of Eukaryotic Genes Cell Biology 3:563-608 (1980).
Martinez-Salas, et al. Functional Interactions in Internal Translation Initiation Directed by Viral and Cellular IRES Elements, Journal of General Virology 82:973-984 (2001).
Mathias et al. Signal transduction of stress via ceramide, Biochem. J. 335:465-480 (1998).
Matsumura et al., Synthesis of mot and the gene products of *Escherichia coli* programmed by hybrid ColE1 plasmids in minicells, J. Bacteriol. 132(3):996-1002 (Dec. 1977).
Meagher et al., Protein Expression in *E. coli* Minicells by Recombinant Plasmids, Cell 10:521-536 (1977).
Miller et al., Translation in *Escherichia Coli* minicells containing Hamster mitochondrial DNA-ColE1 $Amp^r$ Recombinant Plasmids, Biochemica et Biophysica Acta 477:323-333 (1977).
Noegel et al., Plasmid Cistrons Controlling Synthesis and Excretion of the Exotoxin alpha-Haemolysin of *Escherichia coli*, Molec. gen. Genet. 175:343-350 (1979).
Ono & Han, The p38 single transduction pathway activation and function, Cellular Signaling, 12:1-13 (2000).
Parkhill, et al. Genome Sequence of *Yersina pestis*, the Causative Agent of Plaque Nature Publishing Group 413:523-527 (2001).
Perry, et al. *Yersinia pestis*-Etiologic Agent of Plaque Clinical Microbiology Reviews 10:35-66 (1997).
Pickett et al., Cloning, Sequencing, and Expression of the *Escherichia coli* Cytolethal Distending Toxin Genes, Infection and Immunity 62(3):1046-1051 (1994).
Purcell et al., Molecular Cloning and Characterization of the 15-Kilodalton Major Immunogen of *Treponema pallidum*, Infection and Immunity 57(12):3708-3714 (1989).
Reeve et al., Minicells of Bacillus subtilis a Unique System for Transport Studies, Biochimica et Biophysica Acta 352:298-306 (1974).
Roozen et al., Synthesis of Ribonucleic Acid and Protein in Plasmid-Containing Minicells of *Escherichia coli* K-12, J. of Bacteriology 107(1):21-33 (1971).
Rosner et al., Expression of a cloned bovine growth hormone gene in *Escherichia coli* minicells, Can. J. Biochem. 60:521-524 (1982).
Schaumberg et al., Genetic Mapping of the minB Locus in *Escherichia coli* K-12, J. of Bacteriology 153(2):1063-1065 (1983).
Schlosser et al., Subcloning, Nucleotide Sequence, and Expression of trkG, a Gene That Encodes an Integral Membrane Protein Involved in Potassium Uptake via the Trk system of *Escherichia coli*, J. of Bacteriology 173(10):3170-3176 (1991).
Sizemore, et al., Attenuated Shigella as a DNA Delivery Vehicle for DNA-Mediated Immunization, Science 270:299-302 (1995).
Sizemore, et al., Attenuated bacteria as a DNA delivery vehicle for DNA-mediated immunization, Vaccine 15(8):804-807 (1997).
Stieglitz, et al., Cloning, Sequencing, and Expression in Ficoll-Generated Minicells of an *Escherichia coli* Heat-Stable Enterotoxin Gene, Plasmid 20:42-53 (1988).
Suzuki, et al., Production in *Escherichia coli* of biologically active secretin, a gastrointestinal hormone, Proc. Natl. Acad. Sci. USA, vol. 79, pp. 2475-2479 (1982).
Tankersley et al., Induction and Isolation of a Minicell-Producing Strain of *Salmonella typhimurium*, Proceedings of the Society for Experimental Biology and Medicine 145:802-805 (1974).
Tibbles & Woodgett, The stress-activated protein kinase pathways, CMLS, Cell. Mol. Life Sci. 55:1230-1254 (1999).
Zink, Gilbert L. Immunizing Agents and Diagnostic Antigens Remington's Pharmaceutical Sciences (73)1324-1340 (1980).
Zubay, Geoffrey, The Isolation and Properties of CAP, the Catabolite Gene Activator, Methods in Enzymology 65:856-877 (1980).
Supplementary European Search Report dated Oct. 31, 2006, issued in Application No. 02747872.6.

(56) References Cited

OTHER PUBLICATIONS

Office Action issued in U.S. Appl. No. 10/832,000, dated Apr. 9, 2007.
Office Action issued in U.S. Appl. No. 11/096,646, dated Oct. 30, 2007.
Hale et al. Characterization of virulent plasmid and plasmid-associated outer membrane protein in *Shigella flexneri, Shigella sonnei*, and *Escherichia coli*, Infection and Immunity, 40(1):340-350 (1983).
Jaffe et al. Minicell-forming mutants of *Escherichia coli*: Production of minicells and anucleate rods, J. Bacteriol., 170(7):3094-3101 (1988).
Barrett-Bee, K. et al., The accumulation of novobiocin by *Escherichia coli* and *Staphylococcal aureus*, Journal of Antimicrobial Chemotherapy, 33; 1165-1171 (1994).
Clark, The fermentation pathways of *Escherichia coli*, FEMS Microbiology Reviews, 63:223-234 (1989).
Desai et al., The mechanism of uptake of biodegradable microparticles in Caco-2 cells is size dependent, Pharm. Res., 14(11): 1568-1573 (1997).
Dmitriev et al., Ectodomain of coxsackievirus and adenovirus receptor genetically fused to epidermal growth factor mediates adenovirus targeting to epidermal growth factor receptor-positive cells, J. Virol., 74(15): 6875-6884 (2000).
Eliasson et al., Direct visualization of plasmid DNA in bacterial cells, Molecular Microbiology, 6(2):165-170 (1992).
Fantappie et al., The MDR phenotype is associated with the expression of COX-2 and iNOS in a human hepatocellular carcinoma cell line, Hepatology, 35(4): 843-852 (2002).
Giacalone et al., The use of bacterial minicells to transfer plasmid DNA to eukaryotic cells, Cell. Microbiol. 8(10):1624-1633 (2006).
Giacalone et al., Immunization with non-replicating *E. coli* minicells delivering both protein antigen and DNA protects mice from lethal challenge with Lymphocytic choriomeningitis virus, Vaccine, 25(12):2279-2287 (2007).
Giannakakou et al., Paclitaxel-resistant human ovarian cancer cells have mutant beta-tubulins that exhibit impaired paclitaxel-driven polymerization, Journal of Biological Chemistry, 272(27):11718-11725 (1997).
Gomez-Eichelmann et al., Effect of nalidixic acid and novobiocin on pBR322 genetic expression in *Escherichia coli* minicells, Journal of Bacteriology, 148(3):745-752, (Dec. 1981).
Guindulain et al., Involvement of RNA and DNA in the staining of *Escherichia coli* by SYTO 13, Letters Applied Microbiology, 34(3): 182-188 (2002).
Huda et al., "Molecular Cloning and Characterization of an ABC Multidrug Efflux Pump, VcaM, in Non-O1 *Vibrio cholerae*", Antimicrobial Agents and Chemotherapy, 47(8):2413-2417 (2003).
Iida, et al., "Cell wall alterations of gram-negative bacteria by aminoglycoside antibiotics," Antimicrobial Agents and Chemotherapy, 5(1): 95-97 (1974).
Ishii et al., "A methylated oligonucleotide induced methylation of GSTP1 promoter and suppressed its expression in A549 lung adenocarcinoma cells," Cancer Letters, 212(2): 211-223 (2004).
Izquierdo, et al., "Broad distribution of the multidrug resistance-related vault lung resistance protein in normal human tissues and tumors," American Journal of Pathology, 148(3): 877-887 (1996).
Katsui et al., "Heat-induced blebbing and vesiculation of the outer membrane of *Escherichia coli*," J. Bacteriol., 151(3):1523-1531 (1982).
Kaneko, et al., "Energetics of tetracycline efflux system encoded by Tn10 in *Escherichia coli*." FEBS, 193(2):194-198 (1985).
Knox et al., "Relation between excreted lipopolysaccharide complexes and surface structures of a lysine-limited culture of *Escherichia coli*," J. Bacteriol., 92(4):1206-1217 (1966).
Kuypers, et al., "Cloning of the replication gene O of *E. coli* bacteriophage lambda and its expression under the control of the lac promoter," Gene, 10(3):195-203 (1980).
Levenson et al., "Pleiotropic resistance to DNA-interactive drugs is associated with increased expression of genes involved in DNA replication, repair, and stress response," Cancer Research, 60(18): 5027-5030 (2000).
Ling, "Multidrug resistance: molecular mechanisms and clinical relevance," Cancer Chemotherapy & Pharmacology, 40 Suppl:S3-8 (1997).
Ma et al., "Molecular cloning and Characterization of acrA and acrE Genes in *Escherichia coli*", Journal of Bacteriology, 175(19):6299-6313 (1993).
Ma et al., "Genes acrA and acrB encode a stress-induced efflux system of *Escherichia coli*", Molecular Microbiology 16(1):45-55 (1995).
Mamot et al., "Epidermal growth factor receptor (EGFR)-targeted immunoliposomes mediate specific and efficient drug delivery to EDFR- and EGFRvIII-overexpressing tumor cells," Cancer Res.; 63: 3154-3161 (2003).
Mobley et al, "Energetics of plasmid-mediated arsenate resistance in *Escherichia coli*", Proceedings of the national Academy of Sciences (USA), 79:6119-6122 (1982).
Monfort et al., "Cell cycle characteristics and changes in membrane potential during the growth of *Escherichia coli* as determined by a cyanine fluorescent dye and flow cytometry", Journal of Microbiological Methods, 25:79-86 (1996).
Murakami et al., "Extramembrane Central Pore of Multidrug Exporter AcrB in *Escherichia coli* Plays an Important Role in Drug Transport", The Journal of Biological Chemistry, 279(5):3743-3748 (2004).
Naito et al., "Mechanisms of drug resistance in chemotherapy for urogenital carcinoma," Int. J. Urol., 6(9):427-439 (1999).
Nieva-Gomez and Gennis, "Affinity of intact *Escherichia coli* for hydrophobic membrane probes is a function of the physiological state of the cells", PNAS USA, 74(5):1811-1815 (1977).
Nikaido, "Antibiotic Resistance Caused by Gram-Negative Multidrug Efflux Pumps", Clinical Infectious Disease, 27 (Suppl 1):S32-41 (1998).
Nishino et al., "Overexpression of the Response Regulator evgA of the Two-Component Signal Transduction System Modulates Multidrug Resistance Conferred by Multidrug Resistance Transporters", Journal of Bacteriology, 183(4):1455-1458 (2001).
Pal, et al., "Plasmid-associated adherence of Shigella flexneri in a HeLa cell model," Infection Immun., Aug. 57(8): 2580-2582 (1989).
Paulsen et al., "Proton-Dependent Multidrug Efflux Systems", Microbiological Reviews, 60(4):575-608 (1996).
Perreten et al., "Mdt(A), a New Efflux Protein Conferring Multiple Antibiotic Resistance in Lactobacillus lactis and *Escherichia coli*.", Antimicrobial Agents and Chemotherapy, 45(4):1109-1114 (2001).
Peterkofsky et al., "Glucose and the Metabolism of Adenosine 3':5'-Cyclic Monophosphate in *Escherichia coli*", PNAS, USA, 68(11):2794-2798 (1971).
Plesiat, et al., "Outer membranes of Gram-negative bacteria are permeable to steroid probes", Molecular Microbiology, 6(10):1323-1333 (1992).
Scherer, et al., "The viral range in vitro of a malignant human epithelial cell (strain HeLa, Gey). III. Studies with pseudolymphocytic choriomeningitis virus; general discussion." Am. J. Pathol., 31(1):31-39 (1955).
Scherer, et al., "Studies on the propagation in vitro of poliomyelitis viruses. IV. Viral multiplication in a stable strain of human malignant epithelial cells (strain HeLa) derived from an epidermoid carcinoma of the cervix," J. Exp. Med., 97(5):695-710 (1953).
Schindler et al., "Action of polymyxin B on bacterial membranes: morphological changes in the cytoplasm and in the outer membrane of *Salmonella typhimurium* and *Escherichia coli* B," Antimicrobial Agents and Chemotherapy, 8(1):95-104 (1975).
Sheehy et al., "Molecular Studies on Entry Exclusion in *Escherichia coli* Minicells", Journal of Bacteriology, 112(2):861-869 (1972).
Someya et al., "Morphological changes of *Escherichia coli* induced by bicyclomycin," Antimicrobial Agents and Chemotherapy, Jul. vol. 16 (1): 84-88 (1979).
Verfaillie, et al., "Gene therapy for chronic myelogenous leukemia," Molecular Medicine Today, 5(8):359-366 (1999).

(56) References Cited

OTHER PUBLICATIONS

Wacheck et al., "Small interfering RNA targeting bcl-2 sensitizes malignant melanoma," Oligonucleotides, 13(5): 393-400 (2003).
Walmsley-Borges et al., "Structure and function of efflux pumps that confer resistance to drugs", Biochemical Journal, 376: 313-388 (2003).
Watarai et al., "Interaction of Ipa proteins of Shigella flexneri with alpha5betal integrin promotes entry of the bacteria into mammalian cells," J. Exp. Med., 183: 991-999 (1996).
Williams, et al., "Accumulation of Rifampicin by *Escherichia coli* and *Staphylococcus aureus*", Journal of Antimicrobial Chemotherapy, 42:597-603 (1998).
Yang et al., "Synthesis of an R plasmid protein associated with tetracycline resistance is negatively regulated", PNAS USA, 73(5):1509-1512 (1976).
Youn et al., "Oncogenic H-Ras up-regulates expression of ERCC1 to protect cells from platinum-based anticancer agents," Cancer Research, 64(14): 4849-4857 (2004).
Zusman et al., "Cell Division in *Escherichia coil*: analysis of double mutants for filamentation and abnormal septation of deoxyribonucleic acid-less cells," J. Bacteriol., 120(3):1427-1433 (1974).
Cheng et al., "Type III machines of Gram-negative bacteria: delivering the goods," Trends Microbiol., 8(5):214-220 (2000).
Winstanley et al., "Type III secretion systems and pathogenicity islands," J. Med. Microbiol., 50:116-126 (2001).
Galan et al., "Type III secretion machines: bacterial devices for protein delivery into host cells," Science 284:1322-1328 (1999).
European Extended Search Report dated Jun. 27, 2011, issued in European Application No. 10008869.9.
European Extended Search Report dated Nov. 2, 2011, issued in European Application No. 11000796.0.
Office Action dated Feb. 7, 2012, issued in Canadian Application No. 2,517,027.
Elkins et al. Cloning and constitutive expression of structural genes encoding gonococcal porin protein in *Escherichia coli* and attenuated *Salmonella typhimurium* vaccine strains, Gene, 138:43-50 (1994).
Isberg et al. Identification of invasion: a protein that allows enteric bacteria to penetrate cultured mammalian cells, Cell, 50:769-776 (1987).
Lee & Isaacson, Expression of the gene cluster associated with the *Escherichia coli* pilus adhsin K99, Infection and Immunity, 63(10):4143-4149 (1995).
Nikaido, Porins and specific diffusion channels in bacterial outer membrane, The Journal of Biological Chemistry, 269(6):3905-3908 (1994).
Rosenshine et al. Tyrosine protein kinas inhibitors block invain-promoted bacteria uptake by epithelial cells, Infection and Immunity, 60(6): 2211-2217 (1992).
Scholdel et al. Hybrid Hepatitis B virus Core-Pre-S proteins synthesized in avirulent *Salmonella typhimurium* and *Salmonella typhi* for oral vaccination, Infection and Immunity, 62(5):1669-1676 (1994).
Simon & Rest, *Escherichia coli* expressing a Neisseria gonorrhoeae opacity-associated outer membrane protein invade human cervical and endometrial epithelial cell lines, PNAS, USA, 89:5512-5515 (1992).
Su et al. Construction of stable LamB-Shiga toxin B subunit hybrids: analysis of expression in *Salmonella typhimurium* aroA strains and stimulation of B subunit-specific mucosal and serum antibody responses, Infection and Immunity, 60(8):3345-3359 (1992).
Weickert et al., Optimization of heterologous protein production in *Escherichia coli*, Current Opinion in Biotechnology, 7:494-499 (1996).
Statement of Grounds and Particulars of Opposition dated Mar. 15, 2012 filed in Australian Application No. 2008201082.
Statutory Declaration by Renato Morona (Expert Witness) along with Exhibits RM-1 to RM-6 dated Sep. 13, 2012 and submitted as evidence in support of the Opposition filed in Australian Application No. 2008201082.
Ng, "Inhibition of Phosphatidylinositide 3-Kinase Enhances Gemcitabine-induced Apoptosis in Human Pancreatic Cancer Cells", Cancer Research, 60:5451-5455 (Oct. 1, 2000).
Lee et al. Antimetastatic efficacy of Adjuvant Gemcitabine in a pancreatic cancer Orthotopic Model, Clinical and Experimental Metastasis, 18:379-384 (2001).
http://www.pharmacology2000.com/Anticancer/classes1.htm, posted on internet in 2001 ("Cancer Chemotherapy: Drug Classification and Mechanism of Action", No author given, no journal, no volume, no issue, no pages (total of 6 pages).
Office Action dated Jun. 15, 2012 for U.S. Appl. No. 13/294,911, filed Aug. 1, 2013.
Final Office Action dated Feb. 28, 2013 for U.S. Appl. No. 13/294,911, filed Aug. 1, 2013.
Examination Report dated May 22, 2014 for European Patent Application No. 11000796.0 filed on May 28, 2002.
Office Action dated Jul. 15, 2014 for U.S. Appl. No. 13/957,372.
Office Action dated Jul. 10, 2014 for European Patent Application No. 02747872.6.
Kuroda et al. "Hepatitis B Virus Envelope L Protein Particles." The Journal of Biological Chemistry, vol. 267, No. 3, pp. 1953-1961, 1992.
Tsutsui et al., "Development of bionanocapsules targeting brain tumors" Journal of Control Release, vol. 122, Issue 2, Sep. 26, 2007, pp. 159-164.
Office Action dated Dec. 22, 2015, issued in Japanese Patent Application No. 2013-554578.
Office Action dated Jan. 19, 2016, issued in European Patent Application No. 12247781.8.
Final Decision of Rejection dated Nov. 22, 2016 in Japanese Patent Application No. 2013-554578 filed Aug. 15, 2013.
Office Action dated Dec. 5, 2016 in European Patent Application No. 12474781.8 filed Sep. 12, 2013.
Office Action dated May 2, 2016, issued in Australian Patent Application No. 2012217728.
Office Action dated Dec. 27, 2017 and issued in Canadian Patent Application No. 2,827,443.

* cited by examiner

H460 cells $EGFR^{wt}$

A.

MOI=2,500:1
αEGFR

B.

MOI=2,500:1
αKLH

C.

MOI=2,500:1
αCD123

D.

MOI=2,500:1
NoAb

SEQUENCE LISTING

<160> NUMBER OF SEQ ID NOS: 42

<210> SEQ ID NO 1
<211> LENGTH: 5748
<212> TYPE: DNA
<213> ORGANISM: Artificial Sequence
<220> FEATURE:
<223> OTHER INFORMATION: pVX-119

<400> SEQUENCE: 1
tcgacatgaa agctaccaaa ctggttctgg gtgctgtcat cctgggctca acgctgctgg 60
cgggctgttc ttccaatgcg aaaatcgatc aaggcattaa cccgtatgtc ggctttgaaa 120
tgggttacga ttggctgggt cgtatgccgt ataaaggcag cgttgaaaat ggtgcataca 180
aagctcaggg cgtccaactg accgctaaac tgggttatcc gattaccgat gacctggata 240
tctacacgcg tctgggcggt atggtctggc gtgcagatac caaatcaaac gtgtatggca 300
aaaatcatga cacgggtgtg tcgccggttt ttgcaggcgg tgttgaatat gctattaccc 360
cggaaatcgc gacgcgtctg gaataccagt ggacgaacaa tattggcgat gcgcatacca 420
tcggtacgcg tccggacaac ggtattccgg gtgcagccaa tgcagctcag cacgatgaag 480
cgcagcaaaa cgccttttat caggtgctga atatgccgaa cctgaatgcc gatcagcgca 540
acggcttcat ccaaagcctg aaagatgacc cgagccagtc tgccaacgtt ctgggtgaag 600
cacagaaact gaatgatagc caagcgccga aagcggacgc ccagcagaac aacttcaaca 660
aagatcagca atctgctttc tatgaaattc tgaacatgcc gaacctgaat gaagcgcagc 720
gtaatggctt tatccaaagt ctgaaagatg acccgagtca gtccaccaac gtgctgggtg 780
aagccaaaaa actgaatgaa tcccaggcgc cgaaagccga taacaacttc aacaaagaac 840
agcaaaacgc attctacgaa atcctgaata tgccgaatct gaatgaagaa cagcgcaatg 900
gcttcatcca atcactgaaa gatgacccgt cacagtcggc taacctgctg agcgaggcga 960
aaaaattaaa cgaatcccag gcaccgaaag ctgataacaa atttaataaa gaacagcaaa 1020
acgccttcta tgaaattctg catctgccga atctgaacga agaacagcgt aatggtttta 1080
tccaatcgct gaaagacgat ccgagccagt ctgcgaacct gctggcagaa gctaaaaaac 1140
tgaatgatgc gcaggccccg aaagccgaca acaaatttaa caaagaacaa cagaatgcat 1200
tctacgaaat tctgcacctg ccgaacctga ccgaagaaca acgtaatggc ttcatccaat 1260
ccctgaaaga tgacccgagt gtctccaaag aaatcctggc tgaagcgaaa aaactgaacg 1320
atgctcaagc tccgaaataa taatctagag gatccccgcg ccctcatccg aaagggcgta 1380
tgggtaccga gctcgaattc gtaatcatgg tcatagctgt ttcctgtgtg aaattgttat 1440
ccgctcacaa ttccacacaa catacgagcc ggaagcataa agtgtaaagc ctggggtgcc 1500
taatgagtga gctaactcac attaattgcg ttgcgctcac tgcccgcttt ccagtcggga 1560
aacctgtcgt gccagctgca ttaatgaatc ggccaacgcg cggggagagg cggtttgcgt 1620
attgggcgct cttccgcttc ctcgctcact gactcgctgc gctcggtcgt tcggctgcgg 1680
cgagcggtat cagctcactc aaaggcggta atacggttat ccacagaatc aggggataac 1740
gcaggaaaga acatgtgagc aaaaggccag caaaagccca ggaaccgtaa aaaggccgcg 1800
ttgctggcgt ttttccatag gctccgcccc cctgacgagc atcacaaaaa tcgacgctca 1860
agtcagaggt ggcgaaaccc gacaggacta taaagatacc aggcgtttcc ccctggaagc 1920
tccctcgtgc gctctcctgt tccgaccctg ccgcttaccg gatacctgtc cgcctttctc 1980
ccttcgggaa gcgtggcgct ttctcatagc tcacgctgta ggtatctcag ttcggtgtag 2040

```
gtcgttcgct ccaagctggg ctgtgtgcac gaaccccccg ttcagcccga ccgctgcgcc   2100
ttatccggta actatcgtct tgagtccaac ccggtaagac acgacttatc gccactggca   2160
gcagccactg gtaacaggat tagcagagcg aggtatgtag gcggtgctac agagttcttg   2220
aagtggtggc ctaactacgg ctacactaga aggacagtat ttggtatctg cgctctgctg   2280
aagccagtta ccttcggaaa aagagttggt agctcttgat ccggcaaaca aaccaccgct   2340
ggtagcggtg gtttttttgt ttgcaagcag cagattacgc gcagaaaaaa aggatctcaa   2400
gaagatcctt tgatcttttc tacggggtct gacgctcagt ggaacgaaaa ctcacgttaa   2460
gggattttgg tcatgagatt atcaaaaagg atcttcacct agatcctttt aaattaaaaa   2520
tgaagtttta gcacgtgcta ttattgaagc atttatcagg gttattgtct catgagcgga   2580
tacatatttg aatgtattta gaaaaataaa caaatagggg ttccgcgcac atttccccga   2640
aaagtgccac ctgtatgcgg tgtgaaatac cgcacagatg cgtaaggaga aaataccgca   2700
tcaggaaatt gtaagcgtta ataattcaga agaactcgtc aagaaggcga tagaaggcga   2760
tgcgctgcga atcgggagcg gcgataccgt aaagcacgag gaagcggtca gcccattcgc   2820
cgccaagctc ttcagcaata tcacgggtag ccaacgctat gtcctgatag cggtccgcca   2880
cacccagccg gccacagtcg atgaatccag aaaagcggcc attttccacc atgatattcg   2940
gcaagcaggc atcgccatgg gtcacgacga gatcctcgcc gtcgggcatg ctcgccttga   3000
gcctggcgaa cagttcggct ggcgcgagcc cctgatgctc ttcgtccaga tcatcctgat   3060
cgacaagacc ggcttccatc cgagtacgtg ctcgctcgat gcgatgtttc gcttggtggt   3120
cgaatgggca ggtagccgga tcaagcgtat gcagccgccg cattgcatca gccatgatgg   3180
atactttctc ggcaggagca aggtgagatg acaggagatc ctgccccggc acttcgccca   3240
atagcagcca gtcccttccc gcttcagtga caacgtcgag cacagctgcg caaggaacgc   3300
ccgtcgtggc cagccacgat agccgcgctg cctcgtcttg cagttcattc agggcaccgg   3360
acaggtcggt cttgacaaaa agaaccgggc gcccctgcgc tgacagccgg aacacggcgg   3420
catcagagca gccgattgtc tgttgtgccc agtcatagcc gaatagcctc tccacccaag   3480
cggccggaga acctgcgtgc aatccatctt gttcaatcat gcgaaacgat cctcatcctg   3540
tctcttgatc agagcttgat cccctgcgcc atcagatcct tggcggcgag aaagccatcc   3600
agtttacttt gcagggcttc ccaaccttac cagagggcgc cccagctggc aattccggtt   3660
cgcttgctgt ccataaaacc gcccagtaga agcatatgaa gcttaattaa tctttctgcg   3720
aattgagatg acgccactgg ctgggcgtca tcccggtttc ccgggtaaac accaccgaaa   3780
aatagttact atcttcaaag ccacattcgg tcgaaatatc actgattaac aggcggctat   3840
gctggagaag atattgcgca tgacacactc tgacctgtcg cagatattga ttgatggtca   3900
ttccagtctg ctggcgaaat tgctgacgca aaacgcgctc actgcacgat gcctcatcac   3960
aaaatttatc cagcgcaaag ggacttttca ggctagccgc cagccgggta atcagcttat   4020
ccagcaacgt ttcgctggat gttggcggca acgaatcact ggtgtaacga tggcgattca   4080
gcaacatcac caactgcccg aacagcaact cagccatttc gttagcaaac ggcacatgct   4140
gactactttc atgctcaagc tgaccgataa cctgccgcgc ctgcgccatc cccatgctac   4200
ctaagcgcca gtgtggttgc cctgcgctgg cgttaaatcc cggaatcgcc ccctgccagt   4260
caagattcag cttcagacgc tccgggcaat aaataatatt ctgcaaaacc agatcgttaa   4320
cggaagcgta ggagtgttta tcgtcagcat gaatgtaaaa gagatcgcca cgggtaatgc   4380
```

gataagggcg atcgttgagt acatgcaggc cattaccgcg ccagacaatc accagctcac 4440
aaaaatcatg tgtatgttca gcaaagacat cttgcggata acggtcagcc acagcgactg 4500
cctgctggtc gctggcaaaa aaatcatctt tgagaagttt taactgatgc gccaccgtgg 4560
ctacctcggc cagagaacga agttgattat tcgcaatatg gcgtacaaat acgttgagaa 4620
gattcgcgtt attgcagaaa gccatcccgt ccctggcgaa tatcacgcgg tgaccagtta 4680
aactctcggc gaaaaagcgt cgaaaagtgg ttactgtcgc tgaatccaca gcgataggcg 4740
atgtcagtaa cgctggcctc gctgtggcgt agcagatgtc gggctttcat cagtcgcagg 4800
cggttcaggt atcgctgagg cgtcagtccc gtttgctgct taagctgccg atgtagcgta 4860
cgcagtgaaa gagaaaattg atccgccacg gcatcccaat tcacctcatc ggcaaaatgg 4920
tcctccagcc aggccagaag caagttgaga cgtgatgcgc tgttttccag gttctcctgc 4980
aaactgcttt tacgcagcaa gagcagtaat tgcataaaca agatctcgcg actggcggtc 5040
gagggtaaat cattttcccc ttcctgctgt tccatctgtg caaccagctg tcgcacctgc 5100
tgcaatacgc tgtggttaac gcgccagtga gacggatact gcccatccag ctcttgtggc 5160
agcaactgat tcagcccggc gagaaactga aatcgatccg gcgagcgata cagcacattg 5220
gtcagacaca gattatcggt atgttcatac agatgccgat catgatcgcg tacgaaacag 5280
accgtgccac cggtgatggt atagggctgc ccattaaaca catgaatacc cgtgccatgt 5340
tcgacaatca caatttcatg aaaatcatga tgatgttcag gaaaatccgc ctgcgggagc 5400
cggggttcta tcgccacgga cgcgttacca gacggaaaaa aatccacact atgtaatacg 5460
gtcatactgg cctcctgatg tcgtcaacac ggcgaaatag taatcacgag gtcaggttct 5520
taccttaaat tttcgacgga aaaccacgta aaaaacgtcg atttttcaag atacagcgtg 5580
aattttcagg aaatgcggtg agcatcacat caccacaatt cagcaaattg tgaacatcat 5640
cacgttcatc tttccctggt tgccaatggc ccattttcct gtcagtaacg agaaggtcgc 5700
gaattcaggc gctttttaga ctggtcgtaa tgaaattcag gaggatgg 5748

<210> SEQ ID NO 2
<211> LENGTH: 5484
<212> TYPE: DNA
<213> ORGANISM: Artificial Sequence
<220> FEATURE:
<223> OTHER INFORMATION: pVX-120

<400> SEQUENCE: 2
aagcttaatt aatctttctg cgaattgaga tgacgccact ggctgggcgt catcccggtt 60
tcccgggtaa acaccaccga aaaatagtta ctatcttcaa agccacattc ggtcgaaata 120
tcactgatta acaggcggct atgctggaga agatattgcg catgacacac tctgacctgt 180
cgcagatatt gattgatggt cattccagtc tgctggcgaa attgctgacg caaaacgcgc 240
tcactgcacg atgcctcatc acaaaattta tccagcgcaa agggactttt caggctagcc 300
gccagccggg taatcagctt atccagcaac gtttcgctgg atgttggcgg caacgaatca 360
ctggtgtaac gatggcgatt cagcaacatc accaactgcc cgaacagcaa ctcagccatt 420
tcgttagcaa acggcacatg ctgactactt tcatgctcaa gctgaccgat aacctgccgc 480
gcctgcgcca tccccatgct acctaagcgc cagtgtggtt gccctgcgct ggcgttaaat 540
cccggaatcg ccccctgcca gtcaagattc agcttcagac gctccgggca ataaataata 600
ttctgcaaaa ccagatcgtt aacggaagcg taggagtgtt tatcgtcagc atgaatgtaa 660
aagagatcgc cacgggtaat gcgataaggg cgatcgttga gtacatgcag gccattaccg 720

```
cgccagacaa tcaccagctc acaaaaatca tgtgtatgtt cagcaaagac atcttgcgga    780
taacggtcag ccacagcgac tgcctgctgg tcgctggcaa aaaaatcatc tttgagaagt    840
tttaactgat gcgccaccgt ggctacctcg gccagagaac gaagttgatt attcgcaata    900
tggcgtacaa atacgttgag aagattcgcg ttattgcaga aagccatccc gtccctggcg    960
aatatcacgc ggtgaccagt taaactctcg gcgaaaaagc gtcgaaaagt ggttactgtc   1020
gctgaatcca cagcgatagg cgatgtcagt aacgctggcc tcgctgtggc gtagcagatg   1080
tcgggctttc atcagtcgca ggcggttcag gtatcgctga ggcgtcagtc ccgtttgctg   1140
cttaagctgc cgatgtagcg tacgcagtga aagagaaaat tgatccgcca cggcatccca   1200
attcacctca tcggcaaaat ggtcctccag ccaggccaga agcaagttga gacgtgatgc   1260
gctgttttcc aggttctcct gcaaactgct tttacgcagc aagagcagta attgcataaa   1320
caagatctcg cgactggcgg tcgagggtaa atcattttcc ccttcctgct gttccatctg   1380
tgcaaccagc tgtcgcacct gctgcaatac gctgtggtta acgcgccagt gagacggata   1440
ctgcccatcc agctcttgtg gcagcaactg attcagcccg gcgagaaact gaaatcgatc   1500
cggcgagcga tacagcacat tggtcagaca cagattatcg gtatgttcat acagatgccg   1560
atcatgatcg cgtacgaaac agaccgtgcc accggtgatg gtatagggct gcccattaaa   1620
cacatgaata cccgtgccat gttcgacaat cacaatttca tgaaaatcat gatgatgttc   1680
aggaaaatcc gcctgcggga gccggggttc tatcgccacg gacgcgttac cagacggaaa   1740
aaaatccaca ctatgtaata cggtcatact ggcctcctga tgtcgtcaac acggcgaaat   1800
agtaatcacg aggtcaggtt cttaccttaa attttcgacg gaaaaccacg taaaaaacgt   1860
cgatttttca agatacagcg tgaattttca ggaaatgcgg tgagcatcac atcaccacaa   1920
ttcagcaaat tgtgaacatc atcacgttca tctttccctg gttgccaatg gcccattttc   1980
ctgtcagtaa cgagaaggtc gcgaattcag gcgcttttta gactggtcgt aatgaaattc   2040
aggaggatgg tcgacatgaa agccacgaaa ctggttctgg gtgctgttat cctgggttcc   2100
acgctgctgg cgggttgttc ctctaatgcg aaaatcgatc aaggcatcaa cccgtatgtg   2160
ggctttgaaa tgggttacga ttggctgggt cgtatgccgt ataaaggcag cgttgaaaat   2220
ggtgcataca aagctcaggg cgtccaactg accgcgaaac tgggttatcc gatcacggat   2280
gacctggata tttacacccg tctgggcggt atggtctggc gtgcagatac gaaaagcaac   2340
gtgtatggca aaaatcatga caccggtgtg tctccggttt tcgcgggcgg tgttgaatat   2400
gccatcacgc cggaaattgc aacccgtctg gaataccagt ggaccaacaa tatcggcgat   2460
gcacacacga ttggtacccg cccggataac ggcattccgg gtatcgacga aattctggcg   2520
gccctgccga aaacggatac ctataaactg attctgaatg gcaaaacgct gaaaggtgaa   2580
accacgaccg aagctgttga cgcagctacc gcggaaaaag tcttcaaaca atacgctaac   2640
gataatggcg tggacggtga atggacctac gatgacgcga cgaaaacctt cacggtcacc   2700
gaaaaaccgg aagtgatcga tgccagtgaa ctgacgccgg cagttacgac ctataaactg   2760
gtcattaacg gcaaaaccct gaaaggtgaa acgaccacgg aagctgtgga tgcagcaacc   2820
gcagaaaaag ttttcaaaca gtacgccaat gacaacggtg tggacggcga atggacgtac   2880
gatgacgcaa cgaaaacctt cacggtgacc gaaaaaccgg aagttatcga tgcctccgaa   2940
ctgaccccgg cagtcaccac gtataaactg gtgatcaatg gtaaaacgct gaaaggcgaa   3000
accacgacca aagcggttga tgccgaaacc gcagaaaaag cttttaaaca atacgcgaat   3060
```

-continued gacaatggcg tggatggcgt gtggacctac gatgatgcga ccaaaacctt taccgttacc 3120
gaataataat ctagaggatc cccgcgccct catccgaaag ggcgtatggg taccgagctc 3180
gaattcgtaa tcatggtcat agctgtttcc tgtgtgaaat tgttatccgc tcacaattcc 3240
acacaacata cgagccggaa gcataaagtg taaagcctgg ggtgcctaat gagtgagcta 3300
actcacatta attgcgttgc gctcactgcc cgctttccag tcgggaaacc tgtcgtgcca 3360
gctgcattaa tgaatcggcc aacgcgcggg gagaggcggt ttgcgtattg ggcgctcttc 3420
cgcttcctcg ctcactgact cgctgcgctc ggtcgttcgg ctgcggcgag cggtatcagc 3480
tcactcaaag gcggtaatac ggttatccac agaatcaggg gataacgcag gaaagaacat 3540
gtgagcaaaa ggccagcaaa agcccaggaa ccgtaaaaag gccgcgttgc tggcgttttt 3600
ccataggctc cgcccccctg acgagcatca caaaaatcga cgctcaagtc agaggtggcg 3660
aaacccgaca ggactataaa gataccaggc gtttccccct ggaagctccc tcgtgcgctc 3720
tcctgttccg accctgccgc ttaccggata cctgtccgcc tttctccctt cgggaagcgt 3780
ggcgctttct catagctcac gctgtaggta tctcagttcg gtgtaggtcg ttcgctccaa 3840
gctgggctgt gtgcacgaac cccccgttca gcccgaccgc tgcgccttat ccggtaacta 3900
tcgtcttgag tccaacccgg taagacacga cttatcgcca ctggcagcag ccactggtaa 3960
caggattagc agagcgaggt atgtaggcgg tgctacagag ttcttgaagt ggtggcctaa 4020
ctacggctac actagaagga cagtatttgg tatctgcgct ctgctgaagc cagttacctt 4080
cggaaaaaga gttggtagct cttgatccgg caaacaaacc accgctggta gcggtggttt 4140
ttttgtttgc aagcagcaga ttacgcgcag aaaaaaagga tctcaagaag atcctttgat 4200
cttttctacg gggtctgacg ctcagtggaa cgaaaactca cgttaaggga ttttggtcat 4260
gagattatca aaaaggatct tcacctagat ccttttaaat taaaaatgaa gttttagcac 4320
gtgctattat tgaagcattt atcagggtta ttgtctcatg agcggataca tatttgaatg 4380
tatttagaaa aataaacaaa taggggttcc gcgcacattt ccccgaaaag tgccacctgt 4440
atgcggtgtg aaataccgca cagatgcgta aggagaaaat accgcatcag gaaattgtaa 4500
gcgttaataa ttcagaagaa ctcgtcaaga aggcgataga aggcgatgcg ctgcgaatcg 4560
ggagcggcga taccgtaaag cacgaggaag cggtcagccc attcgccgcc aagctcttca 4620
gcaatatcac gggtagccaa cgctatgtcc tgatagcggt ccgccacacc cagccggcca 4680
cagtcgatga atccagaaaa gcggccattt tccaccatga tattcggcaa gcaggcatcg 4740
ccatgggtca cgacgagatc ctcgccgtcg ggcatgctcg ccttgagcct ggcgaacagt 4800
tcggctggcg cgagcccctg atgctcttcg tccagatcat cctgatcgac aagaccggct 4860
tccatccgag tacgtgctcg ctcgatgcga tgtttcgctt ggtggtcgaa tgggcaggta 4920
gccggatcaa gcgtatgcag ccgccgcatt gcatcagcca tgatggatac tttctcggca 4980
ggagcaaggt gagatgacag gagatcctgc cccggcactt cgcccaatag cagccagtcc 5040
cttcccgctt cagtgacaac gtcgagcaca gctgcgcaag gaacgcccgt cgtggccagc 5100
cacgatagcc gcgctgcctc gtcttgcagt tcattcaggg caccggacag gtcggtcttg 5160
acaaaaagaa ccgggcgccc ctgcgctgac agccggaaca cggcggcatc agagcagccg 5220
attgtctgtt gtgcccagtc atagccgaat agcctctcca cccaagcggc cggagaacct 5280
gcgtgcaatc catcttgttc aatcatgcga aacgatcctc atcctgtctc ttgatcagag 5340
cttgatcccc tgcgccatca gatccttggc ggcgagaaag ccatccagtt tactttgcag 5400
ggcttcccaa ccttaccaga gggcgcccca gctggcaatt ccggttcgct tgctgtccat 5460
aaaaccgccc agtagaagca tatg 5484

<210> SEQ ID NO 3
<211> LENGTH: 7051
<212> TYPE: DNA
<213> ORGANISM: Artificial Sequence
<220> FEATURE:
<223> OTHER INFORMATION: pVX-127

<400> SEQUENCE: 3
aagcttaatt aatctttctg cgaattgaga tgacgccact ggctgggcgt catcccggtt 60
tcccgggtaa acaccaccga aaaatagtta ctatcttcaa agccacattc ggtcgaaata 120
tcactgatta acaggcggct atgctggaga agatattgcg catgacacac tctgacctgt 180
cgcagatatt gattgatggt cattccagtc tgctggcgaa attgctgacg caaaacgcgc 240
tcactgcacg atgcctcatc acaaaattta tccagcgcaa agggactttt caggctagcc 300
gccagccggg taatcagctt atccagcaac gtttcgctgg atgttggcgg caacgaatca 360
ctggtgtaac gatggcgatt cagcaacatc accaactgcc cgaacagcaa ctcagccatt 420
tcgttagcaa acggcacatg ctgactactt tcatgctcaa gctgaccgat aacctgccgc 480
gcctgcgcca tccccatgct acctaagcgc cagtgtggtt gccctgcgct ggcgttaaat 540
cccggaatcg ccccctgcca gtcaagattc agcttcagac gctccgggca ataaataata 600
ttctgcaaaa ccagatcgtt aacggaagcg taggagtgtt tatcgtcagc atgaatgtaa 660
aagagatcgc cacgggtaat gcgataaggg cgatcgttga gtacatgcag gccattaccg 720
cgccagacaa tcaccagctc acaaaaatca tgtgtatgtt cagcaaagac atcttgcgga 780
taacggtcag ccacagcgac tgcctgctgg tcgctggcaa aaaaatcatc tttgagaagt 840
tttaactgat gcgccaccgt ggctacctcg gccagagaac gaagttgatt attcgcaata 900
tggcgtacaa atacgttgag aagattcgcg ttattgcaga aagccatccc gtccctggcg 960
aatatcacgc ggtgaccagt taaactctcg gcgaaaaagc gtcgaaaagt ggttactgtc 1020
gctgaatcca cagcgatagg cgatgtcagt aacgctggcc tcgctgtggc gtagcagatg 1080
tcgggctttc atcagtcgca ggcggttcag gtatcgctga ggcgtcagtc ccgtttgctg 1140
cttaagctgc cgatgtagcg tacgcagtga aagagaaaat tgatccgcca cggcatccca 1200
attcacctca tcggcaaaat ggtcctccag ccaggccaga agcaagttga gacgtgatgc 1260
gctgttttcc aggttctcct gcaaactgct tttacgcagc aagagcagta attgcataaa 1320
caagatctcg cgactggcgg tcgagggtaa atcattttcc ccttcctgct gttccatctg 1380
tgcaaccagc tgtcgcacct gctgcaatac gctgtggtta acgcgccagt gagacggata 1440
ctgcccatcc agctcttgtg gcagcaactg attcagcccg gcgagaaact gaaatcgatc 1500
cggcgagcga tacagcacat tggtcagaca cagattatcg gtatgttcat acagatgccg 1560
atcatgatcg cgtacgaaac agaccgtgcc accggtgatg gtatagggct gcccattaaa 1620
cacatgaata cccgtgccat gttcgacaat cacaatttca tgaaaatcat gatgatgttc 1680
aggaaaatcc gcctgcggga gccggggttc tatcgccacg gacgcgttac cagacggaaa 1740
aaaatccaca ctatgtaata cggtcatact ggcctcctga tgtcgtcaac acggcgaaat 1800
agtaatcacg aggtcaggtt cttaccttaa attttcgacg gaaaaccacg taaaaaacgt 1860
cgatttttca agatacagcg tgaattttca ggaaatgcgg tgagcatcac atcaccacaa 1920
ttcagcaaat tgtgaacatc atcacgttca tctttccctg gttgccaatg gcccattttc 1980

-continued

```
ctgtcagtaa cgagaaggtc gcgaattcag gcgcttttta gactggtcgt aatgaaattc   2040
aggaggatgg tcgacatgaa agccacgaaa ctggttctgg gtgctgttat cctgggttcc   2100
acgctgctgg cgggttgttc ctctaatgcg aaaatcgatc aaggcatcaa cccgtatgtg   2160
ggctttgaaa tgggttacga ttggctgggt cgtatgccgt ataaaggcag cgttgaaaat   2220
ggtgcataca aagctcaggg cgtccaactg accgcgaaac tgggttatcc gatcacggat   2280
gacctggata tttacacccg tctgggcggt atggtctggc gtgcagatac gaaaagcaac   2340
gtgtatggca aaaatcatga caccggtgtg tctccggttt tcgcgggcgg tgttgaatat   2400
gccatcacgc cggaaattgc aacccgtctg gaataccagt ggaccaacaa tatcggcgat   2460
gcacacacga ttggtacccg cccggataac ggcattccgg gtatcgacga aattctggcg   2520
gccctgccga aaacggatac ctataaactg attctgaatg gcaaaacgct gaaaggtgaa   2580
accacgaccg aagctgttga cgcagctacc gcggaaaaag tcttcaaaca atacgctaac   2640
gataatggcg tggacggtga atggacctac gatgacgcga cgaaaacctt cacggtcacc   2700
gaaaaaccgg aagtgatcga tgccagtgaa ctgacgccgg cagttacgac ctataaactg   2760
gtcattaacg gcaaaaccct gaaaggtgaa acgaccacgg aagctgtgga tgcagcaacc   2820
gcagaaaaag ttttcaaaca gtacgccaat gacaacggtg tggacggcga atggacgtac   2880
gatgacgcaa cgaaaacctt cacggtgacc gaaaaaccgg aagttatcga tgcctccgaa   2940
ctgaccccgg cagtcaccac gtataaactg gtgatcaatg gtaaaacgct gaaaggcgaa   3000
accacgacca aagcggttga tgccgaaacc gcagaaaaag cttttaaaca atacgcgaat   3060
gacaatggcg tggatggcgt gtggacctac gatgatgcga ccaaaacctt taccgttacc   3120
gaataataat ctagagctga ggagggattg agcgatgtct gcattcaata aagaaaattc   3180
aatttcatcc atggcaccac cagcatctcc gcctgcaagt cctaagacgc caatcgaaaa   3240
gaaacacgcg gatgaaatcg ataagtatat acaaggattg gattacaata aaaacaatgt   3300
attagtatac cacggagatg cagtgacaaa tgtgccgcca agaaaaggtt acaaagatgg   3360
aaatgaatat attgttgtgg agaaaaagaa gaaatccatc aatcaaaata atgcagacat   3420
tcaagttgtg aatgcaattt cgagcctaac ctatccaggt gctctcgtaa aagcgaattc   3480
ggaattagta gaaaatcaac cagatgttct ccctgtaaaa cgtgattcat taacactcag   3540
cattgatttg ccaggtatga ctaatcaaga caataaaata gttgtaaaaa atgccactaa   3600
atcaaacgtt aacaacgcag taaatacatt agtggaaaga tggaatgaaa aatatgctca   3660
agcttatcca aatgtaagtg caaaaattga ttatgatgac gaaatggctt acagtgaatc   3720
acaattaatt gcgaaatttg gtacagcatt taaagctgta aataatagct tgaatgtaaa   3780
cttcggcgca atcagtgaag ggaaaatgca agaagaagtc attagtttta aacaaattta   3840
ctataacgtg aatgttaatg aacctacaag accttccaga tttttcggca aagctgttac   3900
taaagagcag ttgcaagcgc ttggagtgaa tgcagaaaat cctcctgcat atatctcaag   3960
tgtggcgtat ggccgtcaag tttatttgaa attatcaact aattcccata gtactaaagt   4020
aaaagctgct tttgatgctg ccgtaagcgg aaaatctgtc tcaggtgatg tagaactaac   4080
aaatatcatc aaaaattctt ccttcaaagc cgtaatttac ggaggttccg caaaagatga   4140
agttcaaatc atcgacggca acctcggaga cttacgcgat attttgaaaa aaggcgctac   4200
ttttaatcga gaaacaccag gagttcccat tgcttataca acaaacttcc taaaagacaa   4260
tgaattagct gttattaaaa acaactcaga atatattgaa acaacttcaa aagcttatac   4320
agatggaaaa attaacatcg atcactctgg aggatacgtt gctcaattca acatttcttg   4380
```

```
ggatgaagta aattatgatc ctgaaggtaa cgaaattgtt caacataaaa actggagcga   4440
aaacaataaa agcaagctag ctcatttcac atcgtccatc tatttgcctg gtaacgcgag   4500
aaatattaat gtttacgcta aagaatgcac tggtttagct tgggaatggt ggagaacggt   4560
aattgatgac cggaacttac cacttgtgaa aaatagaaat atctccatct ggggcaccac   4620
gctttatccg aaatatagta ataaagtaga taatccaatc gaatatgatt ataaagatga   4680
cgatgacaaa taataatcta gaggatcccc gcgccctcat ccgaaagggc gtatgggtac   4740
cgagctcgaa ttcgtaatca tggtcatagc tgtttcctgt gtgaaattgt tatccgctca   4800
caattccaca caacatacga gccggaagca taaagtgtaa agcctggggt gcctaatgag   4860
tgagctaact cacattaatt gcgttgcgct cactgcccgc tttccagtcg ggaaacctgt   4920
cgtgccagct gcattaatga atcggccaac gcgcggggag aggcggtttg cgtattgggc   4980
gctcttccgc ttcctcgctc actgactcgc tgcgctcggt cgttcggctg cggcgagcgg   5040
tatcagctca ctcaaaggcg gtaatacggt tatccacaga atcaggggat aacgcaggaa   5100
agaacatgtg agcaaaaggc cagcaaaagc ccaggaaccg taaaaaggcc gcgttgctgg   5160
cgtttttcca taggctccgc ccccctgacg agcatcacaa aaatcgacgc tcaagtcaga   5220
ggtggcgaaa cccgacagga ctataaagat accaggcgtt tccccctgga agctccctcg   5280
tgcgctctcc tgttccgacc ctgccgctta ccggatacct gtccgccttt ctcccttcgg   5340
gaagcgtggc gctttctcat agctcacgct gtaggtatct cagttcggtg taggtcgttc   5400
gctccaagct gggctgtgtg cacgaacccc ccgttcagcc cgaccgctgc gccttatccg   5460
gtaactatcg tcttgagtcc aacccggtaa gacacgactt atcgccactg gcagcagcca   5520
ctggtaacag gattagcaga gcgaggtatg taggcggtgc tacagagttc ttgaagtggt   5580
ggcctaacta cggctacact agaaggacag tatttggtat ctgcgctctg ctgaagccag   5640
ttaccttcgg aaaaagagtt ggtagctctt gatccggcaa acaaaccacc gctggtagcg   5700
gtggtttttt tgtttgcaag cagcagatta cgcgcagaaa aaaaggatct caagaagatc   5760
ctttgatctt ttctacgggg tctgacgctc agtggaacga aaactcacgt taagggattt   5820
tggtcatgag attatcaaaa aggatcttca cctagatcct tttaaattaa aaatgaagtt   5880
ttagcacgtg ctattattga agcatttatc agggttattg tctcatgagc ggatacatat   5940
ttgaatgtat ttagaaaaat aaacaaatag gggttccgcg cacatttccc cgaaaagtgc   6000
cacctgtatg cggtgtgaaa taccgcacag atgcgtaagg agaaaatacc gcatcaggaa   6060
attgtaagcg ttaataattc agaagaactc gtcaagaagg cgatagaagg cgatgcgctg   6120
cgaatcggga gcggcgatac cgtaaagcac gaggaagcgg tcagcccatt cgccgccaag   6180
ctcttcagca atatcacggg tagccaacgc tatgtcctga tagcggtccg ccacacccag   6240
ccggccacag tcgatgaatc cagaaaagcg gccattttcc accatgatat tcggcaagca   6300
ggcatcgcca tgggtcacga cgagatcctc gccgtcgggc atgctcgcct tgagcctggc   6360
gaacagttcg gctggcgcga gcccctgatg ctcttcgtcc agatcatcct gatcgacaag   6420
accggcttcc atccgagtac gtgctcgctc gatgcgatgt ttcgcttggt ggtcgaatgg   6480
gcaggtagcc ggatcaagcg tatgcagccg ccgcattgca tcagccatga tggatacttt   6540
ctcggcagga gcaaggtgag atgacaggag atcctgcccc ggcacttcgc ccaatagcag   6600
ccagtccctt cccgcttcag tgacaacgtc gagcacagct gcgcaaggaa cgcccgtcgt   6660
ggccagccac gatagccgcg ctgcctcgtc ttgcagttca ttcagggcac cggacaggtc   6720
```

ggtcttgaca aaaagaaccg ggcgcccctg cgctgacagc cggaacacgg cggcatcaga 6780
gcagccgatt gtctgttgtg cccagtcata gccgaatagc ctctccaccc aagcggccgg 6840
agaacctgcg tgcaatccat cttgttcaat catgcgaaac gatcctcatc ctgtctcttg 6900
atcagagctt gatcccctgc gccatcagat ccttggcggc gagaaagcca tccagtttac 6960
tttgcagggc ttcccaacct taccagaggg cgccccagct ggcaattccg gttcgcttgc 7020
tgtccataaa accgcccagt agaagcatat g 7051

<210> SEQ ID NO 4
<211> LENGTH: 7340
<212> TYPE: DNA
<213> ORGANISM: Artificial Sequence
<220> FEATURE:
<223> OTHER INFORMATION: pVX-175

<400> SEQUENCE: 4
aagcttaatt aatctttctg cgaattgaga tgacgccact ggctgggcgt catcccggtt 60
tcccgggtaa acaccaccga aaaatagtta ctatcttcaa agccacattc ggtcgaaata 120
tcactgatta acaggcggct atgctggaga agatattgcg catgacacac tctgacctgt 180
cgcagatatt gattgatggt cattccagtc tgctggcgaa attgctgacg caaaacgcgc 240
tcactgcacg atgcctcatc acaaaattta tccagcgcaa agggactttt caggctagcc 300
gccagccggg taatcagctt atccagcaac gtttcgctgg atgttggcgg caacgaatca 360
ctggtgtaac gatggcgatt cagcaacatc accaactgcc cgaacagcaa ctcagccatt 420
tcgttagcaa acggcacatg ctgactactt tcatgctcaa gctgaccgat aacctgccgc 480
gcctgcgcca tccccatgct acctaagcgc cagtgtggtt gccctgcgct ggcgttaaat 540
cccggaatcg ccccctgcca gtcaagattc agcttcagac gctccgggca ataaataata 600
ttctgcaaaa ccagatcgtt aacggaagcg taggagtgtt tatcgtcagc atgaatgtaa 660
aagagatcgc cacgggtaat gcgataaggg cgatcgttga gtacatgcag gccattaccg 720
cgccagacaa tcaccagctc acaaaaatca tgtgtatgtt cagcaaagac atcttgcgga 780
taacggtcag ccacagcgac tgcctgctgg tcgctggcaa aaaaatcatc tttgagaagt 840
tttaactgat gcgccaccgt ggctacctcg gccagagaac gaagttgatt attcgcaata 900
tggcgtacaa atacgttgag aagattcgcg ttattgcaga aagccatccc gtccctggcg 960
aatatcacgc ggtgaccagt taaactctcg gcgaaaaagc gtcgaaaagt ggttactgtc 1020
gctgaatcca cagcgatagg cgatgtcagt aacgctggcc tcgctgtggc gtagcagatg 1080
tcgggctttc atcagtcgca ggcggttcag gtatcgctga ggcgtcagtc ccgtttgctg 1140
cttaagctgc cgatgtagcg tacgcagtga aagagaaaat tgatccgcca cggcatccca 1200
attcacctca tcggcaaaat ggtcctccag ccaggccaga agcaagttga gacgtgatgc 1260
gctgttttcc aggttctcct gcaaactgct tttacgcagc aagagcagta attgcataaa 1320
caagatctcg cgactggcgg tcgagggtaa atcattttcc ccttcctgct gttccatctg 1380
tgcaaccagc tgtcgcacct gctgcaatac gctgtggtta acgcgccagt gagacggata 1440
ctgcccatcc agctcttgtg gcagcaactg attcagcccg gcgagaaact gaaatcgatc 1500
cggcgagcga tacagcacat tggtcagaca cagattatcg gtatgttcat acagatgccg 1560
atcatgatcg cgtacgaaac agaccgtgcc accggtgatg gtatagggct gcccattaaa 1620
cacatgaata cccgtgccat gttcgacaat cacaatttca tgaaaatcat gatgatgttc 1680
aggaaaatcc gcctgcggga gccggggttc tatcgccacg gacgcgttac cagacggaaa 1740

```
aaaatccaca ctatgtaata cggtcatact ggcctcctga tgtcgtcaac acggcgaaat   1800
agtaatcacg aggtcaggtt cttaccttaa attttcgacg gaaaaccacg taaaaaacgt   1860
cgatttttca agatacagcg tgaattttca ggaaatgcgg tgagcatcac atcaccacaa   1920
ttcagcaaat tgtgaacatc atcacgttca tctttccctg gttgccaatg gcccattttc   1980
ctgtcagtaa cgagaaggtc gcgaattcag gcgcttttta gactggtcgt aatgaaattc   2040
aggaggatgg tcgacatgaa agccacgaaa ctggttctgg gtgctgttat cctgggttcc   2100
acgctgctgg cgggttgttc ctctaatgcg aaaatcgatc aaggcatcaa cccgtatgtg   2160
ggctttgaaa tgggttacga ttggctgggt cgtatgccgt ataaaggcag cgttgaaaat   2220
ggtgcataca aagctcaggg cgtccaactg accgcgaaac tgggttatcc gatcacggat   2280
gacctggata tttacacccg tctgggcggt atggtctggc gtgcagatac gaaaagcaac   2340
gtgtatggca aaaatcatga caccggtgtg tctccggttt tcgcgggcgg tgttgaatat   2400
gccatcacgc cggaaattgc aacccgtctg gaataccagt ggaccaacaa tatcggcgat   2460
gcacacacga ttggtacccg cccggataac ggcattccgg gtatcgacga aattctggcg   2520
gccctgccga aaacggatac ctataaactg attctgaatg gcaaaacgct gaaaggtgaa   2580
accacgaccg aagctgttga cgcagctacc gcggaaaaag tcttcaaaca atacgctaac   2640
gataatggcg tggacggtga atggacctac gatgacgcga cgaaaacctt cacggtcacc   2700
gaaaaaccgg aagtgatcga tgccagtgaa ctgacgccgg cagttacgac ctataaactg   2760
gtcattaacg gcaaaaccct gaaaggtgaa acgaccacgg aagctgtgga tgcagcaacc   2820
gcagaaaaag ttttcaaaca gtacgccaat gacaacggtg tggacggcga atggacgtac   2880
gatgacgcaa cgaaaacctt cacggtgacc gaaaaaccgg aagttatcga tgcctccgaa   2940
ctgaccccgg cagtcaccac gtataaactg gtgatcaatg gtaaaacgct gaaaggcgaa   3000
accacgacca aagcggttga tgccgaaacc gcagaaaaag cttttaaaca atacgcgaat   3060
gacaatggcg tggatggcgt gtggacctac gatgatgcga ccaaaacctt taccgttacc   3120
gaataataat ctagaaggag gaacaatatg aaaaagatta tgctggtctt tattaccctg   3180
attctggtct ctctgccgat tgctcaacaa acggaagctg gcgacgcaag cgcattcaac   3240
aaagaaaaca gcatcagctc tatggcaccg ccggcttcac cgccggcatc gccgaaaacc   3300
ccgatcgaga aaaaacatgc tgatgaaatc gacaaataca tccagggcct ggactacaat   3360
aaaaacaatg tgctggttta tcacggtgat gccgttacga atgtcccgcc gcgtaaaggc   3420
tataaagacg gtaacgaata catcgtggtt gaaaagaaaa agaaaagcat caaccagaac   3480
aatgctgata ttcaagtcgt gaacgcgatc agttccctga cctatccggg cgcactggtc   3540
aaagctaata gcgaactggt ggaaaaccag ccggatgtgc tgccggttaa acgtgacagc   3600
ctgaccctgt ctattgatct gccgggtatg acgaaccaag ataacaaaat cgttgtcaaa   3660
aacgcaacca aaagtaacgt caacaatgct gtgaatacgc tggttgaacg ctggaacgaa   3720
aaatatgcgc aggcctaccc gaatgtgtcc gccaaaattg attatgatga cgaaatggcg   3780
tactcagaat cgcaactgat cgccaaattt ggcaccgcgt tcaaagccgt taacaatagc   3840
ctgaacgtca attttggcgc gatttctgaa ggtaaaatgc aggaaatggt gatctcattc   3900
aaacaaatct actacaacgt caacgtgaac gaaccgaccc gtccgtcgcg ctttttcggc   3960
aaagccgtca cgaaagaaca gctgcaagcg ctgggtgtga atgccgaaaa cccgccggca   4020
tatatttcat cggtggcgta tggtcgccag gtttacctga aactgagcac caacagccat   4080
```

-continued tctacgaaag ttaaagcggc ctttaaagca gctgtctctg gcaaaagtgt ctccggtgat 4140
gtggaactga ccaacatcat caaaaacagc tctttcaaag ccgttattta tggcggttct 4200
gcaaaagatg aagtccagat tatcgacggc aatctgggtg atctgcgtga cattctgaaa 4260
aaaggcgcga cctttaaccg cgaaacgccg ggtgtgccga tcgcctacac cacgaatttc 4320
ctgaaagata acgaactggc agttatcaaa aacaactcag aatacatcga aaccacgtcg 4380
aaagcttaca ccgatggcaa aattaatatc gaccacagtg gcggttatgt tgcacagttt 4440
aacatttcct gggatgaagt gaattacgac ccggagggta acgaaatcgt tcaacataaa 4500
aactggagtg aaaacaacaa atccaaactg gcgcacttca ccagttccat ttatctgccg 4560
ggcaacgctc gtaatatcaa cgtgtacgcg aaagaatgca ccggtctggc ctgggaatgg 4620
tggcgtacgg tgattgatga ccgcaacctg ccgctggtta aaaatcgcaa catctccatc 4680
tggggcacca ccctgtaccc gaaatatagt aacaaagttg ataacccgat tgaataataa 4740
ggatccccta ggggcgcgcc tggtagtgtg gggtctcccc atgcgagagt agggaactgc 4800
caggcatcaa ataaaacgaa aggctcagtc gaaagactgg gcctttcgtt ttatctgttg 4860
tttgtcggtg aacgctctcc tgagtaggac aaatccgccg ggagcggatt tgaacgttgc 4920
gaagcaacgg cccggagggt ggcgggcagg acgcccgcca taaactgcca ggcatcaaat 4980
taagcagaag gccatcctga cggatggcct ttttgcgttt ctacaaactc gagctcgaat 5040
tcgtaatcat ggtcatagct gtttcctgtg tgaaattgtt atccgctcac aattccacac 5100
aacatacgag ccggaagcat aaagtgtaaa gcctggggtg cctaatgagt gagctaactc 5160
acattaattg cgttgcgctc actgcccgct ttccagtcgg gaaacctgtc gtgccagctg 5220
cattaatgaa tcggccaacg cgcggggaga ggcggtttgc gtattgggcg ctcttccgct 5280
tcctcgctca ctgactcgct gcgctcggtc gttcggctgc ggcgagcggt atcagctcac 5340
tcaaaggcgg taatacggtt atccacagaa tcaggggata acgcaggaaa gaacatgtga 5400
gcaaaaggcc agcaaaagcc caggaaccgt aaaaaggccg cgttgctggc gtttttccat 5460
aggctccgcc cccctgacga gcatcacaaa aatcgacgct caagtcagag gtggcgaaac 5520
ccgacaggac tataaagata ccaggcgttt ccccctggaa gctccctcgt gcgctctcct 5580
gttccgaccc tgccgcttac cggatacctg tccgcctttc tcccttcggg aagcgtggcg 5640
ctttctcata gctcacgctg taggtatctc agttcggtgt aggtcgttcg ctccaagctg 5700
ggctgtgtgc acgaaccccc cgttcagccc gaccgctgcg ccttatccgg taactatcgt 5760
cttgagtcca acccggtaag acacgactta tcgccactgg cagcagccac tggtaacagg 5820
attagcagag cgaggtatgt aggcggtgct acagagttct tgaagtggtg gcctaactac 5880
ggctacacta gaaggacagt atttggtatc tgcgctctgc tgaagccagt taccttcgga 5940
aaaagagttg gtagctcttg atccggcaaa caaaccaccg ctggtagcgg tggttttttt 6000
gtttgcaagc agcagattac gcgcagaaaa aaaggatctc aagaagatcc tttgatcttt 6060
tctacggggt ctgacgctca gtggaacgaa aactcacgtt aagggatttt ggtcatgaga 6120
ttatcaaaaa ggatcttcac ctagatcctt ttaaattaaa aatgaagttt tagcacgtgc 6180
tattattgaa gcatttatca gggttattgt ctcatgagcg gatacatatt tgaatgtatt 6240
tagaaaaata aacaaatagg ggttccgcgc acatttcccc gaaaagtgcc acctgtatgc 6300
ggtgtgaaat accgcacaga tgcgtaagga gaaaataccg catcaggaaa ttgtaagcgt 6360
taataattca gaagaactcg tcaagaaggc gatagaaggc gatgcgctgc gaatcgggag 6420
cggcgatacc gtaaagcacg aggaagcggt cagcccattc gccgccaagc tcttcagcaa 6480

```
tatcacgggt agccaacgct atgtcctgat agcggtccgc cacacccagc cggccacagt   6540

cgatgaatcc agaaaagcgg ccattttcca ccatgatatt cggcaagcag gcatcgccat   6600

gggtcacgac gagatcctcg ccgtcgggca tgctcgcctt gagcctggcg aacagttcgg   6660

ctggcgcgag cccctgatgc tcttcgtcca gatcatcctg atcgacaaga ccggcttcca   6720

tccgagtacg tgctcgctcg atgcgatgtt tcgcttggtg gtcgaatggg caggtagccg   6780

gatcaagcgt atgcagccgc cgcattgcat cagccatgat ggatactttc tcggcaggag   6840

caaggtgaga tgacaggaga tcctgccccg gcacttcgcc caatagcagc cagtcccttc   6900

ccgcttcagt gacaacgtcg agcacagctg cgcaaggaac gcccgtcgtg gccagccacg   6960

atagccgcgc tgcctcgtct tgcagttcat tcagggcacc ggacaggtcg gtcttgacaa   7020

aaagaaccgg gcgcccctgc gctgacagcc ggaacacggc ggcatcagag cagccgattg   7080

tctgttgtgc ccagtcatag ccgaatagcc tctccaccca agcggccgga gaacctgcgt   7140

gcaatccatc ttgttcaatc atgcgaaacg atcctcatcc tgtctcttga tcagagcttg   7200

atcccctgcg ccatcagatc cttggcggcg agaaagccat ccagtttact ttgcagggct   7260

tcccaacctt accagagggc gccccagctg gcaattccgg ttcgcttgct gtccataaaa   7320

ccgcccagta gaagcatatg                                                7340
```

<210> SEQ ID NO 5
<211> LENGTH: 7340
<212> TYPE: DNA
<213> ORGANISM: Artificial Sequence
<220> FEATURE:
<223> OTHER INFORMATION: pVX-176

<400> SEQUENCE: 5

```
aagcttaatt aatctttctg cgaattgaga tgacgccact ggctgggcgt catcccggtt     60

tcccgggtaa acaccaccga aaaatagtta ctatcttcaa agccacattc ggtcgaaata    120

tcactgatta acaggcggct atgctggaga agatattgcg catgacacac tctgacctgt    180

cgcagatatt gattgatggt cattccagtc tgctggcgaa attgctgacg caaaacgcgc    240

tcactgcacg atgcctcatc acaaaattta tccagcgcaa agggactttt caggctagcc    300

gccagccggg taatcagctt atccagcaac gtttcgctgg atgttggcgg caacgaatca    360

ctggtgtaac gatggcgatt cagcaacatc accaactgcc cgaacagcaa ctcagccatt    420

tcgttagcaa acggcacatg ctgactactt tcatgctcaa gctgaccgat aacctgccgc    480

gcctgcgcca tccccatgct acctaagcgc cagtgtggtt gccctgcgct ggcgttaaat    540

cccggaatcg cccccctgcca gtcaagattc agcttcagac gctccgggca ataaataata    600

ttctgcaaaa ccagatcgtt aacggaagcg taggagtgtt tatcgtcagc atgaatgtaa    660

aagagatcgc cacgggtaat gcgataaggg cgatcgttga gtacatgcag gccattaccg    720

cgccagacaa tcaccagctc acaaaaatca tgtgtatgtt cagcaaagac atcttgcgga    780

taacggtcag ccacagcgac tgcctgctgg tcgctggcaa aaaaatcatc tttgagaagt    840

tttaactgat gcgccaccgt ggctacctcg gccagagaac gaagttgatt attcgcaata    900

tggcgtacaa atacgttgag aagattcgcg ttattgcaga aagccatccc gtccctggcg    960

aatatcacgc ggtgaccagt taaactctcg gcgaaaaagc gtcgaaaagt ggttactgtc   1020

gctgaatcca cagcgatagg cgatgtcagt aacgctggcc tcgctgtggc gtagcagatg   1080

tcgggctttc atcagtcgca ggcggttcag gtatcgctga ggcgtcagtc ccgtttgctg   1140
```

-continued

```
cttaagctgc cgatgtagcg tacgcagtga aagagaaaat tgatccgcca cggcatccca   1200
attcacctca tcggcaaaat ggtcctccag ccaggccaga agcaagttga gacgtgatgc   1260
gctgttttcc aggttctcct gcaaactgct tttacgcagc aagagcagta attgcataaa   1320
caagatctcg cgactggcgg tcgagggtaa atcattttcc ccttcctgct gttccatctg   1380
tgcaaccagc tgtcgcacct gctgcaatac gctgtggtta acgcgccagt gagacggata   1440
ctgcccatcc agctcttgtg gcagcaactg attcagcccg gcgagaaact gaaatcgatc   1500
cggcgagcga tacagcacat tggtcagaca cagattatcg gtatgttcat acagatgccg   1560
atcatgatcg cgtacgaaac agaccgtgcc accggtgatg gtatagggct gcccattaaa   1620
cacatgaata cccgtgccat gttcgacaat cacaatttca tgaaaatcat gatgatgttc   1680
aggaaaatcc gcctgcggga gccggggttc tatcgccacg gacgcgttac cagacggaaa   1740
aaaatccaca ctatgtaata cggtcatact ggcctcctga tgtcgtcaac acggcgaaat   1800
agtaatcacg aggtcaggtt cttaccttaa attttcgacg gaaaaccacg taaaaaacgt   1860
cgatttttca agatacagcg tgaattttca ggaaatgcgg tgagcatcac atcaccacaa   1920
ttcagcaaat tgtgaacatc atcacgttca tctttccctg gttgccaatg gcccattttc   1980
ctgtcagtaa cgagaaggtc gcgaattcag gcgcttttta gactggtcgt aatgaaattc   2040
aggaggatgg tcgacatgaa agccacgaaa ctggttctgg gtgctgttat cctgggttcc   2100
acgctgctgg cgggttgttc ctctaatgcg aaaatcgatc aaggcatcaa cccgtatgtg   2160
ggctttgaaa tgggttacga ttggctgggt cgtatgccgt ataaaggcag cgttgaaaat   2220
ggtgcataca aagctcaggg cgtccaactg accgcgaaac tgggttatcc gatcacggat   2280
gacctggata tttacacccg tctgggcggt atggtctggc gtgcagatac gaaaagcaac   2340
gtgtatggca aaaatcatga caccggtgtg tctccggttt tcgcgggcgg tgttgaatat   2400
gccatcacgc cggaaattgc aacccgtctg gaataccagt ggaccaacaa tatcggcgat   2460
gcacacacga ttggtacccg cccggataac ggcattccgg gtatcgacga aattctggcg   2520
gccctgccga aaacggatac ctataaactg attctgaatg gcaaaacgct gaaaggtgaa   2580
accacgaccg aagctgttga cgcagctacc gcggaaaaag tcttcaaaca atacgctaac   2640
gataatggcg tggacggtga atggacctac gatgacgcga cgaaaacctt cacggtcacc   2700
gaaaaaccgg aagtgatcga tgccagtgaa ctgacgccgg cagttacgac ctataaactg   2760
gtcattaacg gcaaaaccct gaaaggtgaa acgaccacgg aagctgtgga tgcagcaacc   2820
gcagaaaaag ttttcaaaca gtacgccaat gacaacggtg tggacggcga atggacgtac   2880
gatgacgcaa cgaaaacctt cacggtgacc gaaaaaccgg aagttatcga tgcctccgaa   2940
ctgaccccgg cagtcaccac gtataaactg gtgatcaatg gtaaaacgct gaaaggcgaa   3000
accacgacca aagcggttga tgccgaaacc gcagaaaaag cttttaaaca atacgcgaat   3060
gacaatggcg tggatggcgt gtggacctac gatgatgcga ccaaaacctt taccgttacc   3120
gaataataat ctagaaggag gaacaatatg aaaaagatta tgctggtctt tattaccctg   3180
attctggtgt ccctgccgat tgcacaacaa accgaagcgg gcgatgcgag cgccttcaac   3240
aaagaaaaca gcatcagctc tatggcaccg ccggcttcac cgccggcatc gccgaaaacc   3300
ccgatcgaga aaaaacatgc tgatgaaatc gacaaataca tccagggcct ggactacaat   3360
aaaaacaatg tgctggttta tcacggtgat gccgttacga atgtcccgcc gcgtaaaggc   3420
tataaagacg gtaacgaata catcgtggtt gaaaagaaaa agaaaagcat caaccagaac   3480
aatgctgata ttcaagtcgt gaacgcgatc agttccctga cctatccggg cgcactggtc   3540
```

aaagctaata gcgaactggt ggaaaaccag ccggatgtgc tgccggttaa acgtgacagc 3600
ctgaccctgt ctattgatct gccgggtatg acgaaccaag ataacaaaat cgttgtcaaa 3660
aacgcaacca aaagtaacgt caacaatgct gtgaatacgc tggttgaacg ctggaacgaa 3720
aaatatgcgc aggcctaccc gaatgtgtcc gccaaaattg attatgatga cgaaatggcg 3780
tactcagaat cgcaactgat cgccaaattt ggcaccgcgt tcaaagccgt taacaatagc 3840
ctgaacgtca attttggcgc gatttctgaa ggtaaaatgc aggaaatggt gatctcattc 3900
aaacaaatct actacaacgt caacgtgaac gaaccgaccc gtccgtcgcg ctttttcggc 3960
aaagccgtca cgaaagaaca gctgcaagcg ctgggtgtga atgccgaaaa cccgccggca 4020
tatatttcat cggtggcgta tggtcgccag gtttacctga aactgagcac caacagccat 4080
tctacgaaag ttaaagcggc ctttaaagca gctgtctctg gcaaaagtgt ctccggtgat 4140
gtggaactga ccaacatcat caaaaacagc tctttcaaag ccgttattta tggcggttct 4200
gcaaaagatg aagtccagat tatcgacggc aatctgggtg atctgcgtga cattctgaaa 4260
aaaggcgcga cctttaaccg cgaaacgccg ggtgtgccga tcgcctacac cacgaatttc 4320
ctgaaagata acgaactggc agttatcaaa aacaactcag aatacatcga aaccacgtcg 4380
aaagcttaca ccgatggcaa aattaatatc gaccacagtg gcggttatgt tgcacagttt 4440
aacatttcct gggatgaagt gaattacgac ccggagggta acgaaatcgt tcaacataaa 4500
aactggagtg aaaacaacaa atccaaaacc gcgcacttca cgagttccat ttatctgccg 4560
ggcaacgctc gtaatatcaa cgtgtacgcg aaagaatgca ccggtctggc ctgggaatgg 4620
tggcgtacgg tgattgatga ccgcaacctg ccgctggtta aaaatcgcaa catctccatc 4680
tggggcacca ccctgtaccc gaaatactcc aacaaagttg ataacccgat tgaataataa 4740
ggatccccta ggggcgcgcc tggtagtgtg gggtctcccc atgcgagagt agggaactgc 4800
caggcatcaa ataaaacgaa aggctcagtc gaaagactgg gcctttcgtt ttatctgttg 4860
tttgtcggtg aacgctctcc tgagtaggac aaatccgccg ggagcggatt tgaacgttgc 4920
gaagcaacgg cccggagggt ggcgggcagg acgcccgcca taaactgcca ggcatcaaat 4980
taagcagaag gccatcctga cggatggcct ttttgcgttt ctacaaactc gagctcgaat 5040
tcgtaatcat ggtcatagct gtttcctgtg tgaaattgtt atccgctcac aattccacac 5100
aacatacgag ccggaagcat aaagtgtaaa gcctggggtg cctaatgagt gagctaactc 5160
acattaattg cgttgcgctc actgcccgct ttccagtcgg gaaacctgtc gtgccagctg 5220
cattaatgaa tcggccaacg cgcggggaga ggcggtttgc gtattgggcg ctcttccgct 5280
tcctcgctca ctgactcgct gcgctcggtc gttcggctgc ggcgagcggt atcagctcac 5340
tcaaaggcgg taatacggtt atccacagaa tcaggggata acgcaggaaa gaacatgtga 5400
gcaaaaggcc agcaaaagcc caggaaccgt aaaaaggccg cgttgctggc gtttttccat 5460
aggctccgcc cccctgacga gcatcacaaa aatcgacgct caagtcagag gtggcgaaac 5520
ccgacaggac tataaagata ccaggcgttt ccccctggaa gctccctcgt gcgctctcct 5580
gttccgaccc tgccgcttac cggatacctg tccgcctttc tcccttcggg aagcgtggcg 5640
ctttctcata gctcacgctg taggtatctc agttcggtgt aggtcgttcg ctccaagctg 5700
ggctgtgtgc acgaaccccc cgttcagccc gaccgctgcg ccttatccgg taactatcgt 5760
cttgagtcca acccggtaag acacgactta tcgccactgg cagcagccac tggtaacagg 5820
attagcagag cgaggtatgt aggcggtgct acagagttct tgaagtggtg gcctaactac 5880

```
ggctacacta gaaggacagt atttggtatc tgcgctctgc tgaagccagt taccttcgga   5940

aaaagagttg gtagctcttg atccggcaaa caaaccaccg ctggtagcgg tggttttttt   6000

gtttgcaagc agcagattac gcgcagaaaa aaaggatctc aagaagatcc tttgatcttt   6060

tctacggggt ctgacgctca gtggaacgaa aactcacgtt aagggatttt ggtcatgaga   6120

ttatcaaaaa ggatcttcac ctagatcctt ttaaattaaa aatgaagttt tagcacgtgc   6180

tattattgaa gcatttatca gggttattgt ctcatgagcg gatacatatt tgaatgtatt   6240

tagaaaaata aacaaatagg ggttccgcgc acatttcccc gaaaagtgcc acctgtatgc   6300

ggtgtgaaat accgcacaga tgcgtaagga gaaaataccg catcaggaaa ttgtaagcgt   6360

taataattca gaagaactcg tcaagaaggc gatagaaggc gatgcgctgc gaatcgggag   6420

cggcgatacc gtaaagcacg aggaagcggt cagcccattc gccgccaagc tcttcagcaa   6480

tatcacgggt agccaacgct atgtcctgat agcggtccgc cacacccagc cggccacagt   6540

cgatgaatcc agaaaagcgg ccattttcca ccatgatatt cggcaagcag gcatcgccat   6600

gggtcacgac gagatcctcg ccgtcgggca tgctcgcctt gagcctggcg aacagttcgg   6660

ctggcgcgag cccctgatgc tcttcgtcca gatcatcctg atcgacaaga ccggcttcca   6720

tccgagtacg tgctcgctcg atgcgatgtt tcgcttggtg gtcgaatggg caggtagccg   6780

gatcaagcgt atgcagccgc cgcattgcat cagccatgat ggatactttc tcggcaggag   6840

caaggtgaga tgacaggaga tcctgccccg gcacttcgcc caatagcagc cagtcccttc   6900

ccgcttcagt gacaacgtcg agcacagctg cgcaaggaac gcccgtcgtg gccagccacg   6960

atagccgcgc tgcctcgtct tgcagttcat tcagggcacc ggacaggtcg gtcttgacaa   7020

aaagaaccgg gcgcccctgc gctgacagcc ggaacacggc ggcatcagag cagccgattg   7080

tctgttgtgc ccagtcatag ccgaatagcc tctccaccca agcggccgga gaacctgcgt   7140

gcaatccatc ttgttcaatc atgcgaaacg atcctcatcc tgtctcttga tcagagcttg   7200

atcccctgcg ccatcagatc cttggcggcg agaaagccat ccagtttact ttgcagggct   7260

tcccaacctt accagagggc gccccagctg gcaattccgg ttcgcttgct gtccataaaa   7320

ccgcccagta gaagcatatg                                               7340
```

<210> SEQ ID NO 6
<211> LENGTH: 7253
<212> TYPE: DNA
<213> ORGANISM: Artificial Sequence
<220> FEATURE:
<223> OTHER INFORMATION: pVX-177

<400> SEQUENCE: 6

```
atatgaagct taattaatct ttctgcgaat tgagatgacg ccactggctg ggcgtcatcc     60

cggtttcccg ggtaaacacc accgaaaaat agttactatc ttcaaagcca cattcggtcg    120

aaatatcact gattaacagg cggctatgct ggagaagata ttgcgcatga cacactctga    180

cctgtcgcag atattgattg atggtcattc cagtctgctg gcgaaattgc tgacgcaaaa    240

cgcgctcact gcacgatgcc tcatcacaaa atttatccag cgcaaaggga cttttcaggc    300

tagccgccag ccgggtaatc agcttatcca gcaacgtttc gctggatgtt ggcggcaacg    360

aatcactggt gtaacgatgg cgattcagca acatcaccaa ctgcccgaac agcaactcag    420

ccatttcgtt agcaaacggc acatgctgac tactttcatg ctcaagctga ccgataacct    480

gccgcgcctg cgccatcccc atgctaccta agcgccagtg tggttgccct gcgctggcgt    540

taaatcccgg aatcgccccc tgccagtcaa gattcagctt cagacgctcc gggcaataaa    600
```

```
taatattctg caaaaccaga tcgttaacgg aagcgtagga gtgtttatcg tcagcatgaa    660
tgtaaaagag atcgccacgg gtaatgcgat aagggcgatc gttgagtaca tgcaggccat    720
taccgcgcca gacaatcacc agctcacaaa aatcatgtgt atgttcagca aagacatctt    780
gcggataacg gtcagccaca gcgactgcct gctggtcgct ggcaaaaaaa tcatctttga    840
gaagttttaa ctgatgcgcc accgtggcta cctcggccag agaacgaagt tgattattcg    900
caatatggcg tacaaatacg ttgagaagat tcgcgttatt gcagaaagcc atcccgtccc    960
tggcgaatat cacgcggtga ccagttaaac tctcggcgaa aaagcgtcga aaagtggtta   1020
ctgtcgctga atccacagcg ataggcgatg tcagtaacgc tggcctcgct gtggcgtagc   1080
agatgtcggg ctttcatcag tcgcaggcgg ttcaggtatc gctgaggcgt cagtcccgtt   1140
tgctgcttaa gctgccgatg tagcgtacgc agtgaaagag aaaattgatc cgccacggca   1200
tcccaattca cctcatcggc aaaatggtcc tccagccagg ccagaagcaa gttgagacgt   1260
gatgcgctgt tttccaggtt ctcctgcaaa ctgcttttac gcagcaagag cagtaattgc   1320
ataaacaaga tctcgcgact ggcggtcgag ggtaaatcat ttccccttc ctgctgttcc   1380
atctgtgcaa ccagctgtcg cacctgctgc aatacgctgt ggttaacgcg ccagtgagac   1440
ggatactgcc catccagctc ttgtggcagc aactgattca gcccggcgag aaactgaaat   1500
cgatccggcg agcgatacag cacattggtc agacacagat tatcggtatg ttcatacaga   1560
tgccgatcat gatcgcgtac gaaacagacc gtgccaccgg tgatggtata gggctgccca   1620
ttaaacacat gaatacccgt gccatgttcg acaatcacaa tttcatgaaa atcatgatga   1680
tgttcaggaa aatccgcctg cgggagccgg ggttctatcg ccacggacgc gttaccagac   1740
ggaaaaaaat ccacactatg taatacggtc atactggcct cctgatgtcg tcaacacggc   1800
gaaatagtaa tcacgaggtc aggttcttac cttaaatttt cgacggaaaa ccacgtaaaa   1860
aacgtcgatt tttcaagata cagcgtgaat tttcaggaaa tgcggtgagc atcacatcac   1920
cacaattcag caaattgtga acatcatcac gttcatcttt ccctggttgc caatggccca   1980
ttttcctgtc agtaacgaga aggtcgcgaa ttcaggcgct ttttagactg gtcgtaatga   2040
aattcaggag gatggtcgac atgaaagcca cgaaactggt tctgggtgct gttatcctgg   2100
gttccacgct gctggcgggt tgttcctcta atgcgaaaat cgatcaaggc atcaacccgt   2160
atgtgggctt tgaaatgggt tacgattggc tgggtcgtat gccgtataaa ggcagcgttg   2220
aaaatggtgc atacaaagct cagggcgtcc aactgaccgc gaaactgggt tatccgatca   2280
cggatgacct ggatatttac acccgtctgg gcggtatggt ctggcgtgca gatacgaaaa   2340
gcaacgtgta tggcaaaaat catgacaccg gtgtgtctcc ggttttcgcg ggcggtgttg   2400
aatatgccat cacgccggaa attgcaaccc gtctggaata ccagtggacc aacaatatcg   2460
gcgatgcaca cacgattggt acccgcccgg ataacggcat tccgggtatc gacgaaattc   2520
tggcggccct gccgaaaacg gatacctata aactgattct gaatggcaaa acgctgaaag   2580
gtgaaaccac gaccgaagct gttgacgcag ctaccgcgga aaaagtcttc aaacaatacg   2640
ctaacgataa tggcgtggac ggtgaatgga cctacgatga cgcgacgaaa accttcacgg   2700
tcaccgaaaa accggaagtg atcgatgcca gtgaactgac gccggcagtt acgacctata   2760
aactggtcat taacggcaaa accctgaaag gtgaaacgac cacggaagct gtggatgcag   2820
caaccgcaga aaaagttttc aaacagtacg ccaatgacaa cggtgtggac ggcgaatgga   2880
cgtacgatga cgcaacgaaa accttcacgg tgaccgaaaa accggaagtt atcgatgcct   2940
```

-continued ccgaactgac cccggcagtc accacgtata aactggtgat caatggtaaa acgctgaaag 3000
gcgaaaccac gaccaaagcg gttgatgccg aaaccgcaga aaaagctttt aaacaatacg 3060
cgaatgacaa tggcgtggat ggcgtgtgga cctacgatga tgcgaccaaa acctttaccg 3120
ttaccgaata ataatctaga aggaggaaca atatgatccg cttcaaaaag accaaactga 3180
ttgcgagcat tgcgatggca ctgtgtctgt tctcccagcc ggtgatttcg ttctcaaaag 3240
atattaccga caaaaatcag tccatcgatt caggcattag ctctctgtct tataaccgta 3300
atgaagtgct ggcgtccaat ggtgacaaaa tcgaatcatt tgttccgaaa gaaggcaaaa 3360
aagccggtaa caaattcatt gtggttgaac gtcagaaacg ctctctgacc acgagtccgg 3420
ttgatatctc cattatcgat tcagtcaatg accgtaccta tccgggtgca ctgcaactgg 3480
cagacaaagc atttgtggaa aaccgtccga cgattctgat ggttaaacgc aaaccgatta 3540
acatcaatat tgatctgccg ggcctgaaag gtgaaaatag tatcaaagtg gatgacccga 3600
cctatggcaa agtttcgggt gcaattgatg aactggtcag caaatggaac gaaaaataca 3660
gttccaccca tacgctgccg gcgcgtaccc agtattcgga aagcatggtg tactctaaaa 3720
gtcaaatctc atcggcgctg aacgttaatg ccaaagtcct ggaaaactct ctgggtgtgg 3780
attttaatgc ggttgccaac aatgagaaaa aagtgatgat cctggcatat aaacagattt 3840
tctacaccgt tagtgctgat ctgccgaaaa acccgtctga cctgtttgat gacagtgtca 3900
cgttcaacga tctgaaacaa aaaggcgtgt ctaatgaagc gccgccgctg atggtgtcta 3960
acgttgccta tggtcgtacc atttacgtta aactggaaac cacgagctct agtaaagatg 4020
tccaggcggc ctttaaagcc ctgatcaaaa acaccgatat caaaaatagc cagcaataca 4080
aagacatcta cgaaaattcc tcattcaccg cagtcgtgct gggcggtgat gctcaggaac 4140
acaacaaagt tgtcacgaaa gattttgacg aaatccgcaa agtgattaaa gataacgcaa 4200
ccttctcgac gaaaaatccg gcttatccga tttcgtacac cagcgttttt ctgaaagata 4260
acagcgtcgc agctgtgcat aataaaaccg actatatcga aaccaccagc accgaataca 4320
gcaaaggcaa aattaatctg gatcactccg gtgcatatgt cgctcagttc gaagtggcct 4380
gggatgaagt ttcatacgac aaagaaggca atgaagtgct gacccataaa acgtgggatg 4440
gtaactatca agacaaaacc gcacactact ccacggttat tccgctggaa gcaaacgctc 4500
gtaatatccg cattaaagcg cgtgaatgca ccggtctggc atgggaatgg tggcgtgatg 4560
tcatcagcga atatgacgtg ccgctgacga acaatatcaa tgtgtcaatc tggggcacca 4620
cgctgtatcc gggtagttcc atcacctata attaataagg atcccctagg ggcgcgcctg 4680
gtagtgtggg gtctccccat gcgagagtag ggaactgcca ggcatcaaat aaaacgaaag 4740
gctcagtcga aagactgggc ctttcgtttt atctgttgtt tgtcggtgaa cgctctcctg 4800
agtaggacaa atccgccggg agcggatttg aacgttgcga agcaacggcc cggagggtgg 4860
cgggcaggac gcccgccata aactgccagg catcaaatta agcagaaggc catcctgacg 4920
gatggccttt ttgcgtttct acaaactcga gctcgaattc gtaatcatgg tcatagctgt 4980
ttcctgtgtg aaattgttat ccgctcacaa ttccacacaa catacgagcc ggaagcataa 5040
agtgtaaagc ctggggtgcc taatgagtga gctaactcac attaattgcg ttgcgctcac 5100
tgcccgcttt ccagtcggga aacctgtcgt gccagctgca ttaatgaatc ggccaacgcg 5160
cggggagagg cggtttgcgt attgggcgct cttccgcttc ctcgctcact gactcgctgc 5220
gctcggtcgt tcggctgcgg cgagcggtat cagctcactc aaaggcggta atacggttat 5280
ccacagaatc aggggataac gcaggaaaga acatgtgagc aaaaggccag caaaagccca 5340
ggaaccgtaa aaaggccgcg ttgctggcgt ttttccatag gctccgcccc cctgacgagc 5400
atcacaaaaa tcgacgctca agtcagaggt ggcgaaaccc gacaggacta taaagatacc 5460
aggcgtttcc ccctggaagc tccctcgtgc gctctcctgt tccgaccctg ccgcttaccg 5520
gatacctgtc cgcctttctc ccttcgggaa gcgtggcgct ttctcatagc tcacgctgta 5580
ggtatctcag ttcggtgtag gtcgttcgct ccaagctggg ctgtgtgcac gaacccccccg 5640 ttcagcccga ccgctgcgcc ttatccggta actatcgtct tgagtccaac ccggtaagac 5700
acgacttatc gccactggca gcagccactg gtaacaggat tagcagagcg aggtatgtag 5760
gcggtgctac agagttcttg aagtggtggc ctaactacgg ctacactaga aggacagtat 5820
ttggtatctg cgctctgctg aagccagtta ccttcggaaa aagagttggt agctcttgat 5880
ccggcaaaca aaccaccgct ggtagcggtg gtttttttgt ttgcaagcag cagattacgc 5940
gcagaaaaaa aggatctcaa gaagatcctt tgatcttttc tacggggtct gacgctcagt 6000
ggaacgaaaa ctcacgttaa gggattttgg tcatgagatt atcaaaaagg atcttcacct 6060
agatcctttt aaattaaaaa tgaagtttta gcacgtgcta ttattgaagc atttatcagg 6120
gttattgtct catgagcgga tacatatttg aatgtattta gaaaaataaa caaatagggg 6180
ttccgcgcac atttccccga aaagtgccac ctgtatgcgg tgtgaaatac cgcacagatg 6240
cgtaaggaga aaataccgca tcaggaaatt gtaagcgtta ataattcaga agaactcgtc 6300
aagaaggcga tagaaggcga tgcgctgcga atcgggagcg gcgataccgt aaagcacgag 6360
gaagcggtca gcccattcgc cgccaagctc ttcagcaata tcacgggtag ccaacgctat 6420
gtcctgatag cggtccgcca cacccagccg gccacagtcg atgaatccag aaaagcggcc 6480
attttccacc atgatattcg gcaagcaggc atcgccatgg gtcacgacga gatcctcgcc 6540
gtcgggcatg ctcgccttga gcctggcgaa cagttcggct ggcgcgagcc cctgatgctc 6600
ttcgtccaga tcatcctgat cgacaagacc ggcttccatc cgagtacgtg ctcgctcgat 6660
gcgatgtttc gcttggtggt cgaatgggca ggtagccgga tcaagcgtat gcagccgccg 6720
cattgcatca gccatgatgg atactttctc ggcaggagca aggtgagatg acaggagatc 6780
ctgccccggc acttcgccca atagcagcca gtcccttccc gcttcagtga caacgtcgag 6840
cacagctgcg caaggaacgc ccgtcgtggc cagccacgat agccgcgctg cctcgtcttg 6900
cagttcattc agggcaccgg acaggtcggt cttgacaaaa agaaccgggc gcccctgcgc 6960
tgacagccgg aacacggcgg catcagagca gccgattgtc tgttgtgccc agtcatagcc 7020
gaatagcctc tccacccaag cggccggaga acctgcgtgc aatccatctt gttcaatcat 7080
gcgaaacgat cctcatcctg tctcttgatc agagcttgat cccctgcgcc atcagatcct 7140
tggcggcgag aaagccatcc agtttacttt gcagggcttc ccaaccttac cagagggcgc 7200
cccagctggc aattccggtt cgcttgctgt ccataaaacc gcccagtaga agc 7253

<210> SEQ ID NO 7
<211> LENGTH: 6398
<212> TYPE: DNA
<213> ORGANISM: Artificial Sequence
<220> FEATURE:
<223> OTHER INFORMATION: pVX-199

<400> SEQUENCE: 7
aagcttaatt aatctttctg cgaattgaga tgacgccact ggctgggcgt catcccggtt 60
tcccgggtaa acaccaccga aaaatagtta ctatcttcaa agccacattc ggtcgaaata 120

```
tcactgatta acaggcggct atgctggaga agatattgcg catgacacac tctgacctgt    180
cgcagatatt gattgatggt cattccagtc tgctggcgaa attgctgacg caaaacgcgc    240
tcactgcacg atgcctcatc acaaaattta tccagcgcaa agggactttt caggctagcc    300
gccagccggg taatcagctt atccagcaac gtttcgctgg atgttggcgg caacgaatca    360
ctggtgtaac gatggcgatt cagcaacatc accaactgcc cgaacagcaa ctcagccatt    420
tcgttagcaa acggcacatg ctgactactt tcatgctcaa gctgaccgat aacctgccgc    480
gcctgcgcca tccccatgct acctaagcgc cagtgtggtt gccctgcgct ggcgttaaat    540
cccggaatcg ccccctgcca gtcaagattc agcttcagac gctccgggca ataaataata    600
ttctgcaaaa ccagatcgtt aacggaagcg taggagtgtt tatcgtcagc atgaatgtaa    660
aagagatcgc cacgggtaat gcgataaggg cgatcgttga gtacatgcag gccattaccg    720
cgccagacaa tcaccagctc acaaaaatca tgtgtatgtt cagcaaagac atcttgcgga    780
taacggtcag ccacagcgac tgcctgctgg tcgctggcaa aaaaatcatc tttgagaagt    840
tttaactgat gcgccaccgt ggctacctcg gccagagaac gaagttgatt attcgcaata    900
tggcgtacaa atacgttgag aagattcgcg ttattgcaga aagccatccc gtccctggcg    960
aatatcacgc ggtgaccagt taaactctcg gcgaaaaagc gtcgaaaagt ggttactgtc   1020
gctgaatcca cagcgatagg cgatgtcagt aacgctggcc tcgctgtggc gtagcagatg   1080
tcgggctttc atcagtcgca ggcggttcag gtatcgctga ggcgtcagtc ccgtttgctg   1140
cttaagctgc cgatgtagcg tacgcagtga aagagaaaat tgatccgcca cggcatccca   1200
attcacctca tcggcaaaat ggtcctccag ccaggccaga agcaagttga gacgtgatgc   1260
gctgttttcc aggttctcct gcaaactgct tttacgcagc aagagcagta attgcataaa   1320
caagatctcg cgactggcgg tcgagggtaa atcattttcc ccttcctgct gttccatctg   1380
tgcaaccagc tgtcgcacct gctgcaatac gctgtggtta acgcgccagt gagacggata   1440
ctgcccatcc agctcttgtg gcagcaactg attcagcccg gcgagaaact gaaatcgatc   1500
cggcgagcga tacagcacat tggtcagaca cagattatcg gtatgttcat acagatgccg   1560
atcatgatcg cgtacgaaac agaccgtgcc accggtgatg gtatagggct gcccattaaa   1620
cacatgaata cccgtgccat gttcgacaat cacaatttca tgaaaatcat gatgatgttc   1680
aggaaaatcc gcctgcggga gccggggttc tatcgccacg gacgcgttac cagacggaaa   1740
aaaatccaca ctatgtaata cggtcatact ggcctcctga tgtcgtcaac acggcgaaat   1800
agtaatcacg aggtcaggtt cttaccttaa attttcgacg gaaaaccacg taaaaaacgt   1860
cgatttttca agatacagcg tgaattttca ggaaatgcgg tgagcatcac atcaccacaa   1920
ttcagcaaat tgtgaacatc atcacgttca tctttccctg gttgccaatg gcccattttc   1980
ctgtcagtaa cgagaaggtc gcgaattcag gcgcttttta gactggtcgt aatgaaattc   2040
aggaggatgg tcgacatgaa agccacgaaa ctggttctgg gtgctgttat cctgggttcc   2100
acgctgctgg cgggttgttc ctctaatgcg aaaatcgatc aaggcatcaa cccgtatgtg   2160
ggctttgaaa tgggttacga ttggctgggt cgtatgccgt ataaaggcag cgttgaaaat   2220
ggtgcataca aagctcaggg cgtccaactg accgcgaaac tgggttatcc gatcacggat   2280
gacctggata tttacacccg tctgggcggt atggtctggc gtgcagatac gaaaagcaac   2340
gtgtatggca aaaatcatga caccggtgtg tctccggttt tcgcgggcgg tgttgaatat   2400
gccatcacgc cggaaattgc aacccgtctg gaataccagt ggaccaacaa tatcggcgat   2460
gcacacacga ttggtacccg cccggataac ggcattccgg gtatcgacga aattctggcg   2520
```

gccctgccga aaacggatac ctataaactg attctgaatg gcaaaacgct gaaaggtgaa 2580
accacgaccg aagctgttga cgcagctacc gcggaaaaag tcttcaaaca atacgctaac 2640
gataatggcg tggacggtga atggacctac gatgacgcga cgaaaacctt cacggtcacc 2700
gaaaaaccgg aagtgatcga tgccagtgaa ctgacgccgg cagttacgac ctataaactg 2760
gtcattaacg gcaaaaccct gaaaggtgaa acgaccacgg aagctgtgga tgcagcaacc 2820
gcagaaaaag ttttcaaaca gtacgccaat gacaacggtg tggacggcga atggacgtac 2880
gatgacgcaa cgaaaacctt cacggtgacc gaaaaaccgg aagttatcga tgcctccgaa 2940
ctgaccccgg cagtcaccac gtataaactg gtgatcaatg gtaaaacgct gaaaggcgaa 3000
accacgacca aagcggttga tgccgaaacc gcagaaaaag cttttaaaca atacgcgaat 3060
gacaatggcg tggatggcgt gtggacctac gatgatgcga ccaaaacctt taccgttacc 3120
gaataataat ctagaggatc caggaggaac aatatgtccc gcaaactgtt cgctagtatt 3180
ctgattggtg ctctgctggg tatcggtgct ccgccgtctg ctcacgctgg tgctgatgac 3240
gtggttgaca gctctaaatc ttttgttatg gaaaacttca gttcctatca tggcaccaaa 3300
ccgggttacg tcgattcgat tcagaaaggc atccaaaaac cgaaaagcgg cacccagggt 3360
aactatgatg acgattggaa aggtttctac tcaacggaca acaaatacga tgcggccggc 3420
tactccgtgg acaacgaaaa tccgctgagc ggtaaagcag gcggtgtcgt gaaagttacc 3480
tatccgggcc tgacgaaagt gctggcgctg aaagttgata acgccgaaac catcaaaaaa 3540
gaactgggcc tgtccctgac cgaaccgctg atggaacaag tgggtacgga agaatttatc 3600
aaacgtttcg gcgatggtgc atctcgcgtt gtcctgagtc tgccgtttgc tgaaggctca 3660
tcgagcgtcg aatacattaa caattgggaa caagcaaaag ctctgagcgt ggaactggaa 3720
atcaatttcg aaacgcgtgg taaacgtggt caagatgcaa tgtatgaata tatggctcaa 3780
gcgtgtgcgg gtaaccgtgt tcgctaataa ggcgcgcctg gtagtgtggg gtctccccat 3840
gcgagagtag ggaactgcca ggcatcaaat aaaacgaaag gctcagtcga aagactgggc 3900
ctttcgtttt atctgttgtt tgtcggtgaa cgctctcctg agtaggacaa atccgccggg 3960
agcggatttg aacgttgcga agcaacggcc cggagggtgg cgggcaggac gcccgccata 4020
aactgccagg catcaaatta agcagaaggc catcctgacg gatggccttt ttgcgtttct 4080
acaaactcga gctcgaattc gtaatcatgg tcatagctgt ttcctgtgtg aaattgttat 4140
ccgctcacaa ttccacacaa catacgagcc ggaagcataa agtgtaaagc ctggggtgcc 4200
taatgagtga gctaactcac attaattgcg ttgcgctcac tgcccgcttt ccagtcggga 4260
aacctgtcgt gccagctgca ttaatgaatc ggccaacgcg cggggagagg cggtttgcgt 4320
attgggcgct cttccgcttc ctcgctcact gactcgctgc gctcggtcgt tcggctgcgg 4380
cgagcggtat cagctcactc aaaggcggta atacggttat ccacagaatc aggggataac 4440
gcaggaaaga acatgtgagc aaaaggccag caaaagccca ggaaccgtaa aaaggccgcg 4500
ttgctggcgt ttttccatag gctccgcccc cctgacgagc atcacaaaaa tcgacgctca 4560
agtcagaggt ggcgaaaccc gacaggacta taaagatacc aggcgtttcc ccctggaagc 4620
tccctcgtgc gctctcctgt tccgaccctg ccgcttaccg gatacctgtc cgcctttctc 4680
ccttcgggaa gcgtggcgct ttctcatagc tcacgctgta ggtatctcag ttcggtgtag 4740
gtcgttcgct ccaagctggg ctgtgtgcac gaaccccccg ttcagcccga ccgctgcgcc 4800
ttatccggta actatcgtct tgagtccaac ccggtaagac acgacttatc gccactggca 4860
gcagccactg gtaacaggat tagcagagcg aggtatgtag gcggtgctac agagttcttg 4920
aagtggtggc ctaactacgg ctacactaga aggacagtat ttggtatctg cgctctgctg 4980
aagccagtta ccttcggaaa aagagttggt agctcttgat ccggcaaaca aaccaccgct 5040
ggtagcggtg gtttttttgt ttgcaagcag cagattacgc gcagaaaaaa aggatctcaa 5100
gaagatcctt tgatcttttc tacggggtct gacgctcagt ggaacgaaaa ctcacgttaa 5160
gggattttgg tcatgagatt atcaaaaagg atcttcacct agatcctttt aaattaaaaa 5220
tgaagtttta gcacgtgcta ttattgaagc atttatcagg gttattgtct catgagcgga 5280
tacatatttg aatgtattta gaaaaataaa caaatagggg ttccgcgcac atttccccga 5340
aaagtgccac ctgtatgcgg tgtgaaatac cgcacagatg cgtaaggaga aaataccgca 5400
tcaggaaatt gtaagcgtta ataattcaga agaactcgtc aagaaggcga tagaaggcga 5460
tgcgctgcga atcgggagcg gcgataccgt aaagcacgag gaagcggtca gcccattcgc 5520
cgccaagctc ttcagcaata tcacgggtag ccaacgctat gtcctgatag cggtccgcca 5580
cacccagccg gccacagtcg atgaatccag aaaagcggcc attttccacc atgatattcg 5640
gcaagcaggc atcgccatgg gtcacgacga gatcctcgcc gtcgggcatg ctcgccttga 5700
gcctggcgaa cagttcggct ggcgcgagcc cctgatgctc ttcgtccaga tcatcctgat 5760
cgacaagacc ggcttccatc cgagtacgtg ctcgctcgat gcgatgtttc gcttggtggt 5820
cgaatgggca ggtagccgga tcaagcgtat gcagccgccg cattgcatca gccatgatgg 5880
atactttctc ggcaggagca aggtgagatg acaggagatc ctgccccggc acttcgccca 5940
atagcagcca gtcccttccc gcttcagtga caacgtcgag cacagctgcg caaggaacgc 6000
ccgtcgtggc cagccacgat agccgcgctg cctcgtcttg cagttcattc agggcaccgg 6060
acaggtcggt cttgacaaaa agaaccgggc gcccctgcgc tgacagccgg aacacggcgg 6120
catcagagca gccgattgtc tgttgtgccc agtcatagcc gaatagcctc tccacccaag 6180
cggccggaga acctgcgtgc aatccatctt gttcaatcat gcgaaacgat cctcatcctg 6240
tctcttgatc agagcttgat cccctgcgcc atcagatcct tggcggcgag aaagccatcc 6300
agtttacttt gcagggcttc ccaaccttac cagagggcgc cccagctggc aattccggtt 6360
cgcttgctgt ccataaaacc gcccagtaga agcatatg 6398

<210> SEQ ID NO 8
<211> LENGTH: 6326
<212> TYPE: DNA
<213> ORGANISM: Artificial Sequence
<220> FEATURE:
<223> OTHER INFORMATION: pVX-198

<400> SEQUENCE: 8
aagcttaatt aatctttctg cgaattgaga tgacgccact ggctgggcgt catcccggtt 60
tcccgggtaa acaccaccga aaaatagtta ctatcttcaa agccacattc ggtcgaaata 120
tcactgatta acaggcggct atgctggaga agatattgcg catgacacac tctgacctgt 180
cgcagatatt gattgatggt cattccagtc tgctggcgaa attgctgacg caaaacgcgc 240
tcactgcacg atgcctcatc acaaaattta tccagcgcaa agggactttt caggctagcc 300
gccagccggg taatcagctt atccagcaac gtttcgctgg atgttggcgg caacgaatca 360
ctggtgtaac gatggcgatt cagcaacatc accaactgcc cgaacagcaa ctcagccatt 420
tcgttagcaa acggcacatg ctgactactt tcatgctcaa gctgaccgat aacctgccgc 480
gcctgcgcca tccccatgct acctaagcgc cagtgtggtt gccctgcgct ggcgttaaat 540

```
cccggaatcg cccoctgcca gtcaagattc agcttcagac gctccgggca ataaataata    600
ttctgcaaaa ccagatcgtt aacggaagcg taggagtgtt tatcgtcagc atgaatgtaa    660
aagagatcgc cacgggtaat gcgataaggg cgatcgttga gtacatgcag gccattaccg    720
cgccagacaa tcaccagctc acaaaaatca tgtgtatgtt cagcaaagac atcttgcgga    780
taacggtcag ccacagcgac tgcctgctgg tcgctggcaa aaaaatcatc tttgagaagt    840
tttaactgat gcgccaccgt ggctacctcg gccagagaac gaagttgatt attcgcaata    900
tggcgtacaa atacgttgag aagattcgcg ttattgcaga aagccatccc gtccctggcg    960
aatatcacgc ggtgaccagt taaactctcg gcgaaaaagc gtcgaaaagt ggttactgtc   1020
gctgaatcca cagcgatagg cgatgtcagt aacgctggcc tcgctgtggc gtagcagatg   1080
tcgggctttc atcagtcgca ggcggttcag gtatcgctga ggcgtcagtc ccgtttgctg   1140
cttaagctgc cgatgtagcg tacgcagtga aagagaaaat tgatccgcca cggcatccca   1200
attcacctca tcggcaaaat ggtcctccag ccaggccaga agcaagttga gacgtgatgc   1260
gctgttttcc aggttctcct gcaaactgct tttacgcagc aagagcagta attgcataaa   1320
caagatctcg cgactggcgg tcgagggtaa atcattttcc ccttcctgct gttccatctg   1380
tgcaaccagc tgtcgcacct gctgcaatac gctgtggtta acgcgccagt gagacggata   1440
ctgcccatcc agctcttgtg gcagcaactg attcagcccg gcgagaaact gaaatcgatc   1500
cggcgagcga tacagcacat tggtcagaca cagattatcg gtatgttcat acagatgccg   1560
atcatgatcg cgtacgaaac agaccgtgcc accggtgatg gtatagggct gcccattaaa   1620
cacatgaata cccgtgccat gttcgacaat cacaatttca tgaaaatcat gatgatgttc   1680
aggaaaatcc gcctgcggga gccggggttc tatcgccacg gacgcgttac cagacggaaa   1740
aaaatccaca ctatgtaata cggtcatact ggcctcctga tgtcgtcaac acggcgaaat   1800
agtaatcacg aggtcaggtt cttaccttaa attttcgacg gaaaaccacg taaaaaacgt   1860
cgatttttca agatacagcg tgaattttca ggaaatgcgg tgagcatcac atcaccacaa   1920
ttcagcaaat tgtgaacatc atcacgttca tctttccctg gttgccaatg gcccattttc   1980
ctgtcagtaa cgagaaggtc gcgaattcag gcgcttttta gactggtcgt aatgaaattc   2040
aggaggatgg tcgacatgaa agccacgaaa ctggttctgg gtgctgttat cctgggttcc   2100
acgctgctgg cgggttgttc ctctaatgcg aaaatcgatc aaggcatcaa cccgtatgtg   2160
ggctttgaaa tgggttacga ttggctgggt cgtatgccgt ataaaggcag cgttgaaaat   2220
ggtgcataca aagctcaggg cgtccaactg accgcgaaac tgggttatcc gatcacggat   2280
gacctggata tttacacccg tctgggcggt atggtctggc gtgcagatac gaaaagcaac   2340
gtgtatggca aaaatcatga caccggtgtg tctccggttt tcgcgggcgg tgttgaatat   2400
gccatcacgc cggaaattgc aacccgtctg gaataccagt ggaccaacaa tatcggcgat   2460
gcacacacga ttggtacccg cccggataac ggcattccgg gtatcgacga aattctggcg   2520
gccctgccga aaacggatac ctataaactg attctgaatg gcaaaacgct gaaaggtgaa   2580
accacgaccg aagctgttga cgcagctacc gcggaaaaag tcttcaaaca atacgctaac   2640
gataatggcg tggacggtga atggacctac gatgacgcga cgaaaacctt cacggtcacc   2700
gaaaaaccgg aagtgatcga tgccagtgaa ctgacgccgg cagttacgac ctataaactg   2760
gtcattaacg gcaaaaccct gaaaggtgaa acgaccacgg aagctgtgga tgcagcaacc   2820
gcagaaaaag ttttcaaaca gtacgccaat gacaacggtg tggacggcga atggacgtac   2880
```

gatgacgcaa cgaaaacctt cacggtgacc gaaaaaccgg aagttatcga tgcctccgaa 2940
ctgaccccgg cagtcaccac gtataaactg gtgatcaatg gtaaaacgct gaaaggcgaa 3000
accacgacca aagcggttga tgccgaaacc gcagaaaaag cttttaaaca atacgcgaat 3060
gacaatggcg tggatggcgt gtggacctac gatgatgcga ccaaaacctt taccgttacc 3120
gaataataat ctagaggatc caggaggaac aatatgggcg cagacgacgt tgttgacagc 3180
agcaaatctt tcgttatgga aaacttcagc agctatcacg gcaccaaacc gggctatgtg 3240
gactctattc agaaaggcat ccaaaaaccg aaaagtggca cccagggtaa ctatgatgac 3300
gattggaaag gtttttactc cacggacaat aaatatgatg cggccggcta ctcggtcgac 3360
aacgaaaatc cgctgagcgg taaagcaggc ggtgtggtta aagttaccta tccgggcctg 3420
acgaaagttc tggcgctgaa agtcgataac gccgaaacca tcaaaaaaga actgggcctg 3480
tcactgaccg aaccgctgat ggaacaagtg ggtacggaag aatttatcaa acgtttcggc 3540
gatggtgcat cccgcgtcgt gctgtcactg ccgtttgctg aaggcagctc tagtgtggaa 3600
tacattaaca attgggaaca agcaaaagct ctgagcgttg aactggaaat caatttcgaa 3660
acgcgtggta aacgtggtca agatgcgatg tatgaatata tggctcaagc gtgtgcgggt 3720
aaccgtgtgc gttaataagg cgcgcctggt agtgtggggt ctccccatgc gagagtaggg 3780
aactgccagg catcaaataa aacgaaaggc tcagtcgaaa gactgggcct ttcgttttat 3840
ctgttgtttg tcggtgaacg ctctcctgag taggacaaat ccgccgggag cggatttgaa 3900
cgttgcgaag caacggcccg gagggtggcg ggcaggacgc ccgccataaa ctgccaggca 3960
tcaaattaag cagaaggcca tcctgacgga tggccttttt gcgtttctac aaactcgagc 4020
tcgaattcgt aatcatggtc atagctgttt cctgtgtgaa attgttatcc gctcacaatt 4080
ccacacaaca tacgagccgg aagcataaag tgtaaagcct ggggtgccta atgagtgagc 4140
taactcacat taattgcgtt gcgctcactg cccgctttcc agtcgggaaa cctgtcgtgc 4200
cagctgcatt aatgaatcgg ccaacgcgcg gggagaggcg gtttgcgtat tgggcgctct 4260
tccgcttcct cgctcactga ctcgctgcgc tcggtcgttc ggctgcggcg agcggtatca 4320
gctcactcaa aggcggtaat acggttatcc acagaatcag gggataacgc aggaaagaac 4380
atgtgagcaa aaggccagca aaagcccagg aaccgtaaaa aggccgcgtt gctggcgttt 4440
ttccataggc tccgcccccc tgacgagcat cacaaaaatc gacgctcaag tcagaggtgg 4500
cgaaacccga caggactata aagataccag gcgtttcccc ctggaagctc cctcgtgcgc 4560
tctcctgttc cgaccctgcc gcttaccgga tacctgtccg cctttctccc ttcgggaagc 4620
gtggcgcttt ctcatagctc acgctgtagg tatctcagtt cggtgtaggt cgttcgctcc 4680
aagctgggct gtgtgcacga accccccgtt cagcccgacc gctgcgcctt atccggtaac 4740
tatcgtcttg agtccaaccc ggtaagacac gacttatcgc cactggcagc agccactggt 4800
aacaggatta gcagagcgag gtatgtaggc ggtgctacag agttcttgaa gtggtggcct 4860
aactacggct acactagaag gacagtattt ggtatctgcg ctctgctgaa gccagttacc 4920
ttcggaaaaa gagttggtag ctcttgatcc ggcaaacaaa ccaccgctgg tagcggtggt 4980
tttttgtttg caagcagcag attacgcgca gaaaaaaagg atctcaagaa gatcctttga 5040
tcttttctac ggggtctgac gctcagtgga acgaaaactc acgttaaggg attttggtca 5100
tgagattatc aaaaaggatc ttcacctaga tccttttaaa ttaaaaatga agttttaaat 5160
acgtgctatt attgaagcat ttatcagggt tattgtctca tgagcggata catatttgaa 5220
tgtatttaga aaaataaaca aataggggtt ccgcgcacat ttccccgaaa agtgccacct 5280
gtatgcggtg tgaaataccg cacagatgcg taaggagaaa ataccgcatc aggaaattgt 5340
aagcgttaat aattcagaag aactcgtcaa gaaggcgata gaaggcgatg cgctgcgaat 5400
cgggagcggc gataccgtaa agcacgagga agcggtcagc ccattcgccg ccaagctctt 5460
cagcaatatc acgggtagcc aacgctatgt cctgatagcg gtccgccaca cccagccggc 5520
cacagtcgat gaatccagaa aagcggccat tttccaccat gatattcggc aagcaggcat 5580
cgccatgggt cacgacgaga tcctcgccgt cgggcatgct cgccttgagc ctggcgaaca 5640
gttcggctgg cgcgagcccc tgatgctctt cgtccagatc atcctgatcg acaagaccgg 5700
cttccatccg agtacgtgct cgctcgatgc gatgtttcgc ttggtggtcg aatgggcagg 5760
tagccggatc aagcgtatgc agccgccgca ttgcatcagc catgatggat actttctcgg 5820
caggagcaag gtgagatgac aggagatcct gccccggcac ttcgcccaat agcagccagt 5880
cccttcccgc ttcagtgaca acgtcgagca cagctgcgca aggaacgccc gtcgtggcca 5940
gccacgatag ccgcgctgcc tcgtcttgca gttcattcag ggcaccggac aggtcggtct 6000
tgacaaaaag aaccgggcgc ccctgcgctg acagccggaa cacggcggca tcagagcagc 6060
cgattgtctg ttgtgcccag tcatagccga atagcctctc cacccaagcg gccggagaac 6120
ctgcgtgcaa tccatcttgt tcaatcatgc gaaacgatcc tcatcctgtc tcttgatcag 6180
agcttgatcc cctgcgccat cagatccttg gcggcgagaa agccatccag tttactttgc 6240
agggcttccc aaccttacca gagggcgccc cagctggcaa ttccggttcg cttgctgtcc 6300
ataaaaccgc ccagtagaag catatg 6326

<210> SEQ ID NO 9
<211> LENGTH: 6517
<212> TYPE: DNA
<213> ORGANISM: Artificial Sequence
<220> FEATURE:
<223> OTHER INFORMATION: pVX-200

<400> SEQUENCE: 9
aagcttaatt aatctttctg cgaattgaga tgacgccact ggctgggcgt catcccggtt 60
tcccgggtaa acaccaccga aaaatagtta ctatcttcaa agccacattc ggtcgaaata 120
tcactgatta acaggcggct atgctggaga agatattgcg catgacacac tctgacctgt 180
cgcagatatt gattgatggt cattccagtc tgctggcgaa attgctgacg caaaacgcgc 240
tcactgcacg atgcctcatc acaaaattta tccagcgcaa agggactttt caggctagcc 300
gccagccggg taatcagctt atccagcaac gtttcgctgg atgttggcgg caacgaatca 360
ctggtgtaac gatggcgatt cagcaacatc accaactgcc cgaacagcaa ctcagccatt 420
tcgttagcaa acggcacatg ctgactactt tcatgctcaa gctgaccgat aacctgccgc 480
gcctgcgcca tccccatgct acctaagcgc cagtgtggtt gccctgcgct ggcgttaaat 540
cccggaatcg ccccctgcca gtcaagattc agcttcagac gctccgggca ataaataata 600
ttctgcaaaa ccagatcgtt aacggaagcg taggagtgtt tatcgtcagc atgaatgtaa 660
aagagatcgc cacgggtaat gcgataaggg cgatcgttga gtacatgcag gccattaccg 720
cgccagacaa tcaccagctc acaaaaaatca tgtgtatgtt cagcaaagac atcttgcgga 780
taacggtcag ccacagcgac tgcctgctgg tcgctggcaa aaaaatcatc tttgagaagt 840
tttaactgat gcgccaccgt ggctacctcg gccagagaac gaagttgatt attcgcaata 900
tggcgtacaa atacgttgag aagattcgcg ttattgcaga aagccatccc gtccctggcg 960

```
aatatcacgc ggtgaccagt taaactctcg gcgaaaaagc gtcgaaaagt ggttactgtc   1020
gctgaatcca cagcgatagg cgatgtcagt aacgctggcc tcgctgtggc gtagcagatg   1080
tcgggctttc atcagtcgca ggcggttcag gtatcgctga ggcgtcagtc ccgtttgctg   1140
cttaagctgc cgatgtagcg tacgcagtga aagagaaaat tgatccgcca cggcatccca   1200
attcacctca tcggcaaaat ggtcctccag ccaggccaga agcaagttga gacgtgatgc   1260
gctgttttcc aggttctcct gcaaactgct tttacgcagc aagagcagta attgcataaa   1320
caagatctcg cgactggcgg tcgagggtaa atcattttcc ccttcctgct gttccatctg   1380
tgcaaccagc tgtcgcacct gctgcaatac gctgtggtta acgcgccagt gagacggata   1440
ctgcccatcc agctcttgtg gcagcaactg attcagcccg gcgagaaact gaaatcgatc   1500
cggcgagcga tacagcacat tggtcagaca cagattatcg gtatgttcat acagatgccg   1560
atcatgatcg cgtacgaaac agaccgtgcc accggtgatg gtatagggct gcccattaaa   1620
cacatgaata cccgtgccat gttcgacaat cacaatttca tgaaaatcat gatgatgttc   1680
aggaaaatcc gcctgcggga gccggggttc tatcgccacg gacgcgttac cagacggaaa   1740
aaaatccaca ctatgtaata cggtcatact ggcctcctga tgtcgtcaac acggcgaaat   1800
agtaatcacg aggtcaggtt cttaccttaa attttcgacg gaaaaccacg taaaaaacgt   1860
cgatttttca agatacagcg tgaattttca ggaaatgcgg tgagcatcac atcaccacaa   1920
ttcagcaaat tgtgaacatc atcacgttca tctttccctg gttgccaatg gcccattttc   1980
ctgtcagtaa cgagaaggtc gcgaattcag gcgcttttta gactggtcgt aatgaaattc   2040
aggaggatgg tcgacatgaa agccacgaaa ctggttctgg gtgctgttat cctgggttcc   2100
acgctgctgg cgggttgttc ctctaatgcg aaaatcgatc aaggcatcaa cccgtatgtg   2160
ggctttgaaa tgggttacga ttggctgggt cgtatgccgt ataaaggcag cgttgaaaat   2220
ggtgcataca aagctcaggg cgtccaactg accgcgaaac tgggttatcc gatcacggat   2280
gacctggata tttacacccg tctgggcggt atggtctggc gtgcagatac gaaaagcaac   2340
gtgtatggca aaaatcatga caccggtgtg tctccggttt tcgcgggcgg tgttgaatat   2400
gccatcacgc cggaaattgc aacccgtctg gaataccagt ggaccaacaa tatcggcgat   2460
gcacacacga ttggtacccg cccggataac ggcattccgg gtatcgacga aattctggcg   2520
gccctgccga aaacggatac ctataaactg attctgaatg gcaaaacgct gaaaggtgaa   2580
accacgaccg aagctgttga cgcagctacc gcggaaaaag tcttcaaaca atacgctaac   2640
gataatggcg tggacggtga atggacctac gatgacgcga cgaaaacctt cacggtcacc   2700
gaaaaaccgg aagtgatcga tgccagtgaa ctgacgccgg cagttacgac ctataaactg   2760
gtcattaacg gcaaaaccct gaaaggtgaa acgaccacgg aagctgtgga tgcagcaacc   2820
gcagaaaaag ttttcaaaca gtacgccaat gacaacggtg tggacggcga atggacgtac   2880
gatgacgcaa cgaaaacctt cacggtgacc gaaaaaccgg aagttatcga tgcctccgaa   2940
ctgaccccgg cagtcaccac gtataaactg gtgatcaatg gtaaaacgct gaaaggcgaa   3000
accacgacca aagcggttga tgccgaaacc gcagaaaaag cttttaaaca atacgcgaat   3060
gacaatggcg tggatggcgt gtggacctac gatgatgcga ccaaaacctt taccgttacc   3120
gaataataat ctagaggatc caggaggatt actatatggg tctggatacc gtgagcttct   3180
cgacgaaagg cgcaacctac attacctacg tgaacttcct gaacgaactg cgtgtgaaac   3240
tgaaaccgga aggcaacagc catggtatcc cgctgctgcg taaaaaatgc gatgacccgg   3300
gcaaatgttt tgttctggtc gcactgagta acgataatgg tcagctggca gaaattgcta   3360
```

-continued

```
tcgacgtgac ctcagtttat gtggttggct accaagtccg taaccgctcg tatttcttta   3420
aagatgcacc ggacgcggcc tacgaaggtc tgtttaaaaa taccatcaaa acgcgcctgc   3480
acttcggcgg tagttatccg tccctggaag gcgaaaaagc gtatcgtgaa accacggatc   3540
tgggcattga accgctgcgc attggtatca aaaaactgga tgaaaacgcg attgacaatt   3600
ataaaccgac ggaaatcgcc agctctctgc tggtcgtgat tcagatggtg tcagaagccg   3660
ctcgttttac ctttatcgaa aatcaaatcc gcaacaactt tcaacaaaga attcgcccgg   3720
ctaataatac gatctcgctg gaaaataaat ggggtaaact gagctttcaa atccgcacct   3780
cgggcgctaa cggcatgttc tccgaagcgg tggaactgga acgtgccaac ggcaaaaaat   3840
attacgttac cgctgtggac caggtgaaac cgaaaatcgc tctgctgaaa ttcgttgata   3900
aagacccgaa ataataagga tcccctaggg gcgcgcctgg tagtgtgggg tctccccatg   3960
cgagagtagg gaactgccag gcatcaaata aaacgaaagg ctcagtcgaa agactgggcc   4020
tttcgtttta tctgttgttt gtcggtgaac gctctcctga gtaggacaaa tccgccggga   4080
gcggatttga acgttgcgaa gcaacggccc ggagggtggc gggcaggacg cccgccataa   4140
actgccaggc atcaaattaa gcagaaggcc atcctgacgg atggcctttt tgcgtttcta   4200
caaactcgag ctcgaattcg taatcatggt catagctgtt tcctgtgtga aattgttatc   4260
cgctcacaat tccacacaac atacgagccg gaagcataaa gtgtaaagcc tggggtgcct   4320
aatgagtgag ctaactcaca ttaattgcgt tgcgctcact gcccgctttc cagtcgggaa   4380
acctgtcgtg ccagctgcat taatgaatcg gccaacgcgc ggggagaggc ggtttgcgta   4440
ttgggcgctc ttccgcttcc tcgctcactg actcgctgcg ctcggtcgtt cggctgcggc   4500
gagcggtatc agctcactca aaggcggtaa tacggttatc cacagaatca ggggataacg   4560
caggaaagaa catgtgagca aaaggccagc aaaagcccag gaaccgtaaa aaggccgcgt   4620
tgctggcgtt tttccatagg ctccgccccc ctgacgagca tcacaaaaat cgacgctcaa   4680
gtcagaggtg gcgaaacccg acaggactat aaagatacca ggcgtttccc cctggaagct   4740
ccctcgtgcg ctctcctgtt ccgaccctgc cgcttaccgg atacctgtcc gcctttctcc   4800
cttcgggaag cgtggcgctt tctcatagct cacgctgtag gtatctcagt tcggtgtagg   4860
tcgttcgctc caagctgggc tgtgtgcacg aaccccccgt tcagcccgac cgctgcgcct   4920
tatccggtaa ctatcgtctt gagtccaacc cggtaagaca cgacttatcg ccactggcag   4980
cagccactgg taacaggatt agcagagcga ggtatgtagg cggtgctaca gagttcttga   5040
agtggtggcc taactacggc tacactagaa ggacagtatt tggtatctgc gctctgctga   5100
agccagttac cttcggaaaa agagttggta gctcttgatc cggcaaacaa accaccgctg   5160
gtagcggtgg tttttttgtt tgcaagcagc agattacgcg cagaaaaaaa ggatctcaag   5220
aagatccttt gatcttttct acggggtctg acgctcagtg gaacgaaaac tcacgttaag   5280
ggattttggt catgagatta tcaaaaagga tcttcaccta gatcctttta aattaaaaat   5340
gaagttttag cacgtgctat tattgaagca tttatcaggg ttattgtctc atgagcggat   5400
acatatttga atgtatttag aaaaataaac aaataggggt tccgcgcaca tttccccgaa   5460
aagtgccacc tgtatgcggt gtgaaatacc gcacagatgc gtaaggagaa aataccgcat   5520
caggaaattg taagcgttaa taattcagaa gaactcgtca agaaggcgat agaaggcgat   5580
gcgctgcgaa tcgggagcgg cgataccgta aagcacgagg aagcggtcag cccattcgcc   5640
gccaagctct tcagcaatat cacgggtagc caacgctatg tcctgatagc ggtccgccac   5700
```

acccagccgg ccacagtcga tgaatccaga aaagcggcca ttttccacca tgatattcgg 5760
caagcaggca tcgccatggg tcacgacgag atcctcgccg tcgggcatgc tcgccttgag 5820
cctggcgaac agttcggctg gcgcgagccc ctgatgctct tcgtccagat catcctgatc 5880
gacaagaccg gcttccatcc gagtacgtgc tcgctcgatg cgatgtttcg cttggtggtc 5940
gaatgggcag gtagccggat caagcgtatg cagccgccgc attgcatcag ccatgatgga 6000
tactttctcg gcaggagcaa ggtgagatga caggagatcc tgccccggca cttcgcccaa 6060
tagcagccag tcccttcccg cttcagtgac aacgtcgagc acagctgcgc aaggaacgcc 6120
cgtcgtggcc agccacgata gccgcgctgc ctcgtcttgc agttcattca gggcaccgga 6180
caggtcggtc ttgacaaaaa gaaccgggcg cccctgcgct gacagccgga acacggcggc 6240
atcagagcag ccgattgtct gttgtgccca gtcatagccg aatagcctct ccacccaagc 6300
ggccggagaa cctgcgtgca atccatcttg ttcaatcatg cgaaacgatc ctcatcctgt 6360
ctcttgatca gagcttgatc ccctgcgcca tcagatcctt ggcggcgaga aagccatcca 6420
gtttactttg cagggcttcc caaccttacc agagggcgcc ccagctggca attccggttc 6480
gcttgctgtc cataaaaccg cccagtagaa gcatatg 6517

<210> SEQ ID NO 10
<211> LENGTH: 7965
<212> TYPE: DNA
<213> ORGANISM: Artificial Sequence
<220> FEATURE:
<223> OTHER INFORMATION: pVX-195

<400> SEQUENCE: 10
aagcttaatt aatctttctg cgaattgaga tgacgccact ggctgggcgt catcccggtt 60
tcccgggtaa acaccaccga aaaatagtta ctatcttcaa agccacattc ggtcgaaata 120
tcactgatta acaggcggct atgctggaga agatattgcg catgacacac tctgacctgt 180
cgcagatatt gattgatggt cattccagtc tgctggcgaa attgctgacg caaaacgcgc 240
tcactgcacg atgcctcatc acaaaattta tccagcgcaa agggactttt caggctagcc 300
gccagccggg taatcagctt atccagcaac gtttcgctgg atgttggcgg caacgaatca 360
ctggtgtaac gatggcgatt cagcaacatc accaactgcc cgaacagcaa ctcagccatt 420
tcgttagcaa acggcacatg ctgactactt tcatgctcaa gctgaccgat aacctgccgc 480
gcctgcgcca tccccatgct acctaagcgc cagtgtggtt gccctgcgct ggcgttaaat 540
cccggaatcg ccccctgcca gtcaagattc agcttcagac gctccgggca ataaataata 600
ttctgcaaaa ccagatcgtt aacggaagcg taggagtgtt tatcgtcagc atgaatgtaa 660
aagagatcgc cacgggtaat gcgataaggg cgatcgttga gtacatgcag gccattaccg 720
cgccagacaa tcaccagctc acaaaaatca tgtgtatgtt cagcaaagac atcttgcgga 780
taacggtcag ccacagcgac tgcctgctgg tcgctggcaa aaaaatcatc tttgagaagt 840
tttaactgat gcgccaccgt ggctacctcg gccagagaac gaagttgatt attcgcaata 900
tggcgtacaa atacgttgag aagattcgcg ttattgcaga aagccatccc gtccctggcg 960
aatatcacgc ggtgaccagt taaactctcg gcgaaaaagc gtcgaaaagt ggttactgtc 1020
gctgaatcca cagcgatagg cgatgtcagt aacgctggcc tcgctgtggc gtagcagatg 1080
tcgggctttc atcagtcgca ggcggttcag gtatcgctga ggcgtcagtc ccgtttgctg 1140
cttaagctgc cgatgtagcg tacgcagtga aagagaaaat tgatccgcca cggcatccca 1200
attcacctca tcggcaaaat ggtcctccag ccaggccaga agcaagttga gacgtgatgc 1260

```
gctgttttcc aggttctcct gcaaactgct tttacgcagc aagagcagta attgcataaa   1320
caagatctcg cgactggcgg tcgagggtaa atcattttcc ccttcctgct gttccatctg   1380
tgcaaccagc tgtcgcacct gctgcaatac gctgtggtta acgcgccagt gagacggata   1440
ctgcccatcc agctcttgtg gcagcaactg attcagcccg gcgagaaact gaaatcgatc   1500
cggcgagcga tacagcacat tggtcagaca cagattatcg gtatgttcat acagatgccg   1560
atcatgatcg cgtacgaaac agaccgtgcc accggtgatg gtatagggct gcccattaaa   1620
cacatgaata cccgtgccat gttcgacaat cacaatttca tgaaaatcat gatgatgttc   1680
aggaaaatcc gcctgcggga gccggggttc tatcgccacg gacgcgttac cagacggaaa   1740
aaaatccaca ctatgtaata cggtcatact ggcctcctga tgtcgtcaac acggcgaaat   1800
agtaatcacg aggtcaggtt cttaccttaa attttcgacg gaaaaccacg taaaaaacgt   1860
cgatttttca agatacagcg tgaattttca ggaaatgcgg tgagcatcac atcaccacaa   1920
ttcagcaaat tgtgaacatc atcacgttca tctttccctg gttgccaatg gcccattttc   1980
ctgtcagtaa cgagaaggtc gcgaattcag gcgcttttta gactggtcgt aatgaaattc   2040
aggaggatgg tcgacatgaa agccacgaaa ctggttctgg gtgctgttat cctgggttcc   2100
acgctgctgg cgggttgttc ctctaatgcg aaaatcgatc aaggcatcaa cccgtatgtg   2160
ggctttgaaa tgggttacga ttggctgggt cgtatgccgt ataaaggcag cgttgaaaat   2220
ggtgcataca aagctcaggg cgtccaactg accgcgaaac tgggttatcc gatcacggat   2280
gacctggata tttacacccg tctgggcggt atggtctggc gtgcagatac gaaaagcaac   2340
gtgtatggca aaaatcatga caccggtgtg tctccggttt tcgcgggcgg tgttgaatat   2400
gccatcacgc cggaaattgc aacccgtctg gaataccagt ggaccaacaa tatcggcgat   2460
gcacacacga ttggtacccg cccggataac ggcattccgg gtatcgacga aattctggcg   2520
gccctgccga aaacggatac ctataaactg attctgaatg gcaaaacgct gaaaggtgaa   2580
accacgaccg aagctgttga cgcagctacc gcggaaaaag tcttcaaaca atacgctaac   2640
gataatggcg tggacggtga atggacctac gatgacgcga cgaaaacctt cacggtcacc   2700
gaaaaaccgg aagtgatcga tgccagtgaa ctgacgccgg cagttacgac ctataaactg   2760
gtcattaacg gcaaaaccct gaaaggtgaa acgaccacgg aagctgtgga tgcagcaacc   2820
gcagaaaaag ttttcaaaca gtacgccaat gacaacggtg tggacggcga atggacgtac   2880
gatgacgcaa cgaaaacctt cacggtgacc gaaaaaccgg aagttatcga tgcctccgaa   2940
ctgaccccgg cagtcaccac gtataaactg gtgatcaatg gtaaaacgct gaaaggcgaa   3000
accacgacca aagcggttga tgccgaaacc gcagaaaaag cttttaaaca atacgcgaat   3060
gacaatggcg tggatggcgt gtggacctac gatgatgcga ccaaaacctt taccgttacc   3120
gaataataat ctagagctga ggagggattg agcgatgtct gcattcaata aagaaaattc   3180
aatttcatcc atggcaccac cagcatctcc gcctgcaagt cctaagacgc caatcgaaaa   3240
gaaacacgcg gatgaaatcg ataagtatat acaaggattg gattacaata aaaacaatgt   3300
attagtatac cacggagatg cagtgacaaa tgtgccgcca agaaaaggtt acaaagatgg   3360
aaatgaatat attgttgtgg agaaaaagaa gaaatccatc aatcaaaata atgcagacat   3420
tcaagttgtg aatgcaattt cgagcctaac ctatccaggt gctctcgtaa aagcgaattc   3480
ggaattagta gaaaatcaac cagatgttct ccctgtaaaa cgtgattcat taacactcag   3540
cattgatttg ccaggtatga ctaatcaaga caataaaata gttgtaaaaa atgccactaa   3600
```

-continued

```
atcaaacgtt aacaacgcag taaatacatt agtggaaaga tggaatgaaa aatatgctca   3660
agcttatcca aatgtaagtg caaaaattga ttatgatgac gaaatggctt acagtgaatc   3720
acaattaatt gcgaaatttg gtacagcatt taaagctgta aataatagct tgaatgtaaa   3780
cttcggcgca atcagtgaag ggaaaatgca agaagaagtc attagtttta aacaaattta   3840
ctataacgtg aatgttaatg aacctacaag accttccaga tttttcggca aagctgttac   3900
taaagagcag ttgcaagcgc ttggagtgaa tgcagaaaat cctcctgcat atatctcaag   3960
tgtggcgtat ggccgtcaag tttatttgaa attatcaact aattcccata gtactaaagt   4020
aaaagctgct tttgatgctg ccgtaagcgg aaaatctgtc tcaggtgatg tagaactaac   4080
aaatatcatc aaaaattctt ccttcaaagc cgtaatttac ggaggttccg caaaagatga   4140
agttcaaatc atcgacggca acctcggaga cttacgcgat attttgaaaa aaggcgctac   4200
ttttaatcga gaaacaccag gagttcccat tgcttataca acaaacttcc taaaagacaa   4260
tgaattagct gttattaaaa acaactcaga atatattgaa acaacttcaa aagcttatac   4320
agatggaaaa attaacatcg atcactctgg aggatacgtt gctcaattca acatttcttg   4380
ggatgaagta aattatgatc ctgaaggtaa cgaaattgtt caacataaaa actggagcga   4440
aaacaataaa agcaagctag ctcatttcac atcgtccatc tatttgcctg gtaacgcgag   4500
aaatattaat gtttacgcta aagaatgcac tggtttagct tgggaatggt ggagaacggt   4560
aattgatgac cggaacttac cacttgtgaa aaatagaaat atctccatct ggggcaccac   4620
gctttatccg aaatatagta ataaagtaga taatccaatc gaatatgatt ataaagatga   4680
cgatgacaaa taataatcta gaggatccag gaggaacaat atgtcccgca aactgttcgc   4740
tagtattctg attggtgctc tgctgggtat cggtgctccg ccgtctgctc acgctggtgc   4800
tgatgacgtg gttgacagct ctaaatcttt tgttatggaa aacttcagtt cctatcatgg   4860
caccaaaccg ggttacgtcg attcgattca gaaaggcatc caaaaaccga aaagcggcac   4920
ccagggtaac tatgatgacg attggaaagg tttctactca acggacaaca aatacgatgc   4980
ggccggctac tccgtggaca acgaaaatcc gctgagcggt aaagcaggcg gtgtcgtgaa   5040
agttacctat ccgggcctga cgaaagtgct ggcgctgaaa gttgataacg ccgaaaccat   5100
caaaaaagaa ctgggcctgt ccctgaccga accgctgatg gaacaagtgg gtacggaaga   5160
atttatcaaa cgtttcggcg atggtgcatc tcgcgttgtc ctgagtctgc cgtttgctga   5220
aggctcatcg agcgtcgaat acattaacaa ttgggaacaa gcaaaagctc tgagcgtgga   5280
actggaaatc aatttcgaaa cgcgtggtaa acgtggtcaa gatgcaatgt atgaatatat   5340
ggctcaagcg tgtgcgggta accgtgttcg ctaataaggc gcgcctggta gtgtggggtc   5400
tccccatgcg agagtaggga actgccaggc atcaaataaa acgaaaggct cagtcgaaag   5460
actgggcctt tcgttttatc tgttgtttgt cggtgaacgc tctcctgagt aggacaaatc   5520
cgccgggagc ggatttgaac gttgcgaagc aacggcccgg agggtggcgg gcaggacgcc   5580
cgccataaac tgccaggcat caaattaagc agaaggccat cctgacggat ggcctttttg   5640
cgtttctaca aactcgagct cgaattcgta atcatggtca tagctgtttc ctgtgtgaaa   5700
ttgttatccg ctcacaattc cacacaacat acgagccgga agcataaagt gtaaagcctg   5760
gggtgcctaa tgagtgagct aactcacatt aattgcgttg cgctcactgc ccgctttcca   5820
gtcgggaaac ctgtcgtgcc agctgcatta atgaatcggc caacgcgcgg ggagaggcgg   5880
tttgcgtatt gggcgctctt ccgcttcctc gctcactgac tcgctgcgct cggtcgttcg   5940
gctgcggcga gcggtatcag ctcactcaaa ggcggtaata cggttatcca cagaatcagg   6000
```

ggataacgca ggaaagaaca tgtgagcaaa aggccagcaa aagcccagga accgtaaaaa 6060
ggccgcgttg ctggcgtttt tccataggct ccgcccccct gacgagcatc acaaaaatcg 6120
acgctcaagt cagaggtggc gaaacccgac aggactataa agataccagg cgtttccccc 6180
tggaagctcc ctcgtgcgct ctcctgttcc gaccctgccg cttaccggat acctgtccgc 6240
ctttctccct tcgggaagcg tggcgctttc tcatagctca cgctgtaggt atctcagttc 6300
ggtgtaggtc gttcgctcca agctgggctg tgtgcacgaa ccccccgttc agcccgaccg 6360
ctgcgcctta tccggtaact atcgtcttga gtccaacccg gtaagacacg acttatcgcc 6420
actggcagca gccactggta acaggattag cagagcgagg tatgtaggcg gtgctacaga 6480
gttcttgaag tggtggccta actacggcta cactagaagg acagtatttg gtatctgcgc 6540
tctgctgaag ccagttacct tcggaaaaag agttggtagc tcttgatccg gcaaacaaac 6600
caccgctggt agcggtggtt tttttgtttg caagcagcag attacgcgca gaaaaaaagg 6660
atctcaagaa gatcctttga tcttttctac ggggtctgac gctcagtgga acgaaaactc 6720
acgttaaggg attttggtca tgagattatc aaaaaggatc ttcacctaga tccttttaaa 6780
ttaaaaatga agttttagca cgtgctatta ttgaagcatt tatcagggtt attgtctcat 6840
gagcggatac atatttgaat gtatttagaa aaataaacaa ataggggttc cgcgcacatt 6900
tccccgaaaa gtgccacctg tatgcggtgt gaaataccgc acagatgcgt aaggagaaaa 6960
taccgcatca ggaaattgta agcgttaata attcagaaga actcgtcaag aaggcgatag 7020
aaggcgatgc gctgcgaatc gggagcggcg ataccgtaaa gcacgaggaa gcggtcagcc 7080
cattcgccgc caagctcttc agcaatatca cgggtagcca acgctatgtc ctgatagcgg 7140
tccgccacac ccagccggcc acagtcgatg aatccagaaa agcggccatt ttccaccatg 7200
atattcggca agcaggcatc gccatgggtc acgacgagat cctcgccgtc gggcatgctc 7260
gccttgagcc tggcgaacag ttcggctggc gcgagcccct gatgctcttc gtccagatca 7320
tcctgatcga caagaccggc ttccatccga gtacgtgctc gctcgatgcg atgtttcgct 7380
tggtggtcga atgggcaggt agccggatca agcgtatgca gccgccgcat tgcatcagcc 7440
atgatggata ctttctcggc aggagcaagg tgagatgaca ggagatcctg ccccggcact 7500
tcgcccaata gcagccagtc ccttcccgct tcagtgacaa cgtcgagcac agctgcgcaa 7560
ggaacgcccg tcgtggccag ccacgatagc cgcgctgcct cgtcttgcag ttcattcagg 7620
gcaccggaca ggtcggtctt gacaaaaaga accgggcgcc cctgcgctga cagccggaac 7680
acggcggcat cagagcagcc gattgtctgt tgtgcccagt catagccgaa tagcctctcc 7740
acccaagcgg ccggagaacc tgcgtgcaat ccatcttgtt caatcatgcg aaacgatcct 7800
catcctgtct cttgatcaga gcttgatccc ctgcgccatc agatccttgg cggcgagaaa 7860
gccatccagt ttactttgca gggcttccca accttaccag agggcgcccc agctggcaat 7920
tccggttcgc ttgctgtcca taaaaccgcc cagtagaagc atatg 7965

<210> SEQ ID NO 11
<211> LENGTH: 8003
<212> TYPE: DNA
<213> ORGANISM: Artificial Sequence
<220> FEATURE:
<223> OTHER INFORMATION: pVX-180

<400> SEQUENCE: 11
aagcttaatt aatctttctg cgaattgaga tgacgccact ggctgggcgt catcccggtt 60

-continued

```
tcccgggtaa acaccaccga aaaatagtta ctatcttcaa agccacattc ggtcgaaata    120
tcactgatta acaggcggct atgctggaga agatattgcg catgacacac tctgacctgt    180
cgcagatatt gattgatggt cattccagtc tgctggcgaa attgctgacg caaaacgcgc    240
tcactgcacg atgcctcatc acaaaattta tccagcgcaa agggactttt caggctagcc    300
gccagccggg taatcagctt atccagcaac gtttcgctgg atgttggcgg caacgaatca    360
ctggtgtaac gatggcgatt cagcaacatc accaactgcc cgaacagcaa ctcagccatt    420
tcgttagcaa acggcacatg ctgactactt tcatgctcaa gctgaccgat aacctgccgc    480
gcctgcgcca tccccatgct acctaagcgc cagtgtggtt gccctgcgct ggcgttaaat    540
cccggaatcg ccccctgcca gtcaagattc agcttcagac gctccgggca ataaataata    600
ttctgcaaaa ccagatcgtt aacggaagcg taggagtgtt tatcgtcagc atgaatgtaa    660
aagagatcgc cacgggtaat gcgataaggg cgatcgttga gtacatgcag gccattaccg    720
cgccagacaa tcaccagctc acaaaaatca tgtgtatgtt cagcaaagac atcttgcgga    780
taacggtcag ccacagcgac tgcctgctgg tcgctggcaa aaaaatcatc tttgagaagt    840
tttaactgat gcgccaccgt ggctacctcg gccagagaac gaagttgatt attcgcaata    900
tggcgtacaa atacgttgag aagattcgcg ttattgcaga aagccatccc gtccctggcg    960
aatatcacgc ggtgaccagt taaactctcg gcgaaaaagc gtcgaaaagt ggttactgtc   1020
gctgaatcca cagcgatagg cgatgtcagt aacgctggcc tcgctgtggc gtagcagatg   1080
tcgggctttc atcagtcgca ggcggttcag gtatcgctga ggcgtcagtc ccgtttgctg   1140
cttaagctgc cgatgtagcg tacgcagtga aagagaaaat tgatccgcca cggcatccca   1200
attcacctca tcggcaaaat ggtcctccag ccaggccaga agcaagttga gacgtgatgc   1260
gctgttttcc aggttctcct gcaaactgct tttacgcagc aagagcagta attgcataaa   1320
caagatctcg cgactggcgg tcgagggtaa atcattttcc ccttcctgct gttccatctg   1380
tgcaaccagc tgtcgcacct gctgcaatac gctgtggtta acgcgccagt gagacggata   1440
ctgcccatcc agctcttgtg gcagcaactg attcagcccg gcgagaaact gaaatcgatc   1500
cggcgagcga tacagcacat tggtcagaca cagattatcg gtatgttcat acagatgccg   1560
atcatgatcg cgtacgaaac agaccgtgcc accggtgatg gtatagggct gcccattaaa   1620
cacatgaata cccgtgccat gttcgacaat cacaatttca tgaaaatcat gatgatgttc   1680
aggaaaatcc gcctgcggga gccggggttc tatcgccacg gacgcgttac cagacggaaa   1740
aaaatccaca ctatgtaata cggtcatact ggcctcctga tgtcgtcaac acggcgaaat   1800
agtaatcacg aggtcaggtt cttaccttaa attttcgacg gaaaaccacg taaaaaacgt   1860
cgatttttca agatacagcg tgaattttca ggaaatgcgg tgagcatcac atcaccacaa   1920
ttcagcaaat tgtgaacatc atcacgttca tctttccctg gttgccaatg gcccattttc   1980
ctgtcagtaa cgagaaggtc gcgaattcag gcgcttttta gactggtcgt aatgaaattc   2040
aggaggatgg tcgacatgaa agccacgaaa ctggttctgg gtgctgttat cctgggttcc   2100
acgctgctgg cgggttgttc ctctaatgcg aaaatcgatc aaggcatcaa cccgtatgtg   2160
ggctttgaaa tgggttacga ttggctgggt cgtatgccgt ataaaggcag cgttgaaaat   2220
ggtgcataca aagctcaggg cgtccaactg accgcgaaac tgggttatcc gatcacggat   2280
gacctggata tttacacccg tctgggcggt atggtctggc gtgcagatac gaaaagcaac   2340
gtgtatggca aaaatcatga caccggtgtg tctccggttt tcgcgggcgg tgttgaatat   2400
gccatcacgc cggaaattgc aacccgtctg gaataccagt ggaccaacaa tatcggcgat   2460
```

```
gcacacacga ttggtacccg cccggataac ggcattccgg gtatcgacga aattctggcg   2520
gccctgccga aaacggatac ctataaactg attctgaatg gcaaaacgct gaaaggtgaa   2580
accacgaccg aagctgttga cgcagctacc gcggaaaaag tcttcaaaca atacgctaac   2640
gataatggcg tggacggtga atggacctac gatgacgcga cgaaaacctt cacggtcacc   2700
gaaaaaccgg aagtgatcga tgccagtgaa ctgacgccgg cagttacgac ctataaactg   2760
gtcattaacg gcaaaaccct gaaaggtgaa acgaccacgg aagctgtgga tgcagcaacc   2820
gcagaaaaag ttttcaaaca gtacgccaat gacaacggtg tggacggcga atggacgtac   2880
gatgacgcaa cgaaaacctt cacggtgacc gaaaaaccgg aagttatcga tgcctccgaa   2940
ctgaccccgg cagtcaccac gtataaactg gtgatcaatg gtaaaacgct gaaaggcgaa   3000
accacgacca aagcggttga tgccgaaacc gcagaaaaag cttttaaaca atacgcgaat   3060
gacaatggcg tggatggcgt gtggacctac gatgatgcga ccaaaacctt taccgttacc   3120
gaataataat ctagaaggag gaacaatatg aaaaagatta tgctggtctt tattaccctg   3180
attctggtct ctctgccgat tgctcaacaa acggaagctg gcgacgcaag cgcattcaac   3240
aaagaaaaca gcatcagctc tatggcaccg ccggcttcac cgccggcatc gccgaaaacc   3300
ccgatcgaga aaaaacatgc tgatgaaatc gacaaataca tccagggcct ggactacaat   3360
aaaaacaatg tgctggttta tcacggtgat gccgttacga atgtcccgcc gcgtaaaggc   3420
tataaagacg gtaacgaata catcgtggtt gaaaagaaaa agaaaagcat caaccagaac   3480
aatgctgata ttcaagtcgt gaacgcgatc agttccctga cctatccggg cgcactggtc   3540
aaagctaata gcgaactggt ggaaaaccag ccggatgtgc tgccggttaa acgtgacagc   3600
ctgaccctgt ctattgatct gccgggtatg acgaaccaag ataacaaaat cgttgtcaaa   3660
aacgcaacca aaagtaacgt caacaatgct gtgaatacgc tggttgaacg ctggaacgaa   3720
aaatatgcgc aggcctaccc gaatgtgtcc gccaaaattg attatgatga cgaaatggcg   3780
tactcagaat cgcaactgat cgccaaattt ggcaccgcgt tcaaagccgt taacaatagc   3840
ctgaacgtca attttggcgc gatttctgaa ggtaaaatgc aggaaatggt gatctcattc   3900
aaacaaatct actacaacgt caacgtgaac gaaccgaccc gtccgtcgcg ctttttcggc   3960
aaagccgtca cgaaagaaca gctgcaagcg ctgggtgtga atgccgaaaa cccgccggca   4020
tatatttcat cggtggcgta tggtcgccag gtttacctga aactgagcac caacagccat   4080
tctacgaaag ttaaagcggc ctttaaagca gctgtctctg gcaaaagtgt ctccggtgat   4140
gtggaactga ccaacatcat caaaaacagc tctttcaaag ccgttattta tggcggttct   4200
gcaaaagatg aagtccagat tatcgacggc aatctgggtg atctgcgtga cattctgaaa   4260
aaaggcgcga cctttaaccg cgaaacgccg ggtgtgccga tcgcctacac cacgaatttc   4320
ctgaaagata acgaactggc agttatcaaa aacaactcag aatacatcga aaccacgtcg   4380
aaagcttaca ccgatggcaa aattaatatc gaccacagtg gcggttatgt tgcacagttt   4440
aacatttcct gggatgaagt gaattacgac ccggagggta acgaaatcgt tcaacataaa   4500
aactggagtg aaaacaacaa atccaaactg gcgcacttca ccagttccat ttatctgccg   4560
ggcaacgctc gtaatatcaa cgtgtacgcg aaagaatgca ccggtctggc ctgggaatgg   4620
tggcgtacgg tgattgatga ccgcaacctg ccgctggtta aaaatcgcaa catctccatc   4680
tggggcacca ccctgtaccc gaaatatagt aacaaagttg ataacccgat tgaataataa   4740
ggatccagga ggaacaatat gtcccgcaaa ctgttcgcta gtattctgat tggtgctctg   4800
```

-continued

```
ctgggtatcg gtgctccgcc gtctgctcac gctggtgctg atgacgtggt tgacagctct   4860
aaatcttttg ttatggaaaa cttcagttcc tatcatggca ccaaaccggg ttacgtcgat   4920
tcgattcaga aaggcatcca aaaaccgaaa agcggcaccc agggtaacta tgatgacgat   4980
tggaaaggtt tctactcaac ggacaacaaa tacgatgcgg ccggctactc cgtggacaac   5040
gaaaatccgc tgagcggtaa agcaggcggt gtcgtgaaag ttacctatcc gggcctgacg   5100
aaagtgctgg cgctgaaagt tgataacgcc gaaaccatca aaaaagaact gggcctgtcc   5160
ctgaccgaac cgctgatgga acaagtgggt acggaagaat ttatcaaacg tttcggcgat   5220
ggtgcatctc gcgttgtcct gagtctgccg tttgctgaag gctcatcgag cgtcgaatac   5280
attaacaatt gggaacaagc aaaagctctg agcgtggaac tggaaatcaa tttcgaaacg   5340
cgtggtaaac gtggtcaaga tgcaatgtat gaatatatgg ctcaagcgtg tgcgggtaac   5400
cgtgttcgct aataaggcgc gcctggtagt gtggggtctc cccatgcgag agtagggaac   5460
tgccaggcat caaataaaac gaaaggctca gtcgaaagac tgggcctttc gttttatctg   5520
ttgtttgtcg gtgaacgctc tcctgagtag gacaaatccg ccgggagcgg atttgaacgt   5580
tgcgaagcaa cggcccggag ggtggcgggc aggacgcccg ccataaactg ccaggcatca   5640
aattaagcag aaggccatcc tgacggatgg cctttttgcg tttctacaaa ctcgagctcg   5700
aattcgtaat catggtcata gctgtttcct gtgtgaaatt gttatccgct cacaattcca   5760
cacaacatac gagccggaag cataaagtgt aaagcctggg gtgcctaatg agtgagctaa   5820
ctcacattaa ttgcgttgcg ctcactgccc gctttccagt cgggaaacct gtcgtgccag   5880
ctgcattaat gaatcggcca acgcgcgggg agaggcggtt tgcgtattgg gcgctcttcc   5940
gcttcctcgc tcactgactc gctgcgctcg gtcgttcggc tgcggcgagc ggtatcagct   6000
cactcaaagg cggtaatacg gttatccaca gaatcagggg ataacgcagg aaagaacatg   6060
tgagcaaaag gccagcaaaa gcccaggaac cgtaaaaagg ccgcgttgct ggcgtttttc   6120
cataggctcc gcccccctga cgagcatcac aaaaatcgac gctcaagtca gaggtggcga   6180
aacccgacag gactataaag ataccaggcg tttccccctg gaagctccct cgtgcgctct   6240
cctgttccga ccctgccgct taccggatac ctgtccgcct ttctcccttc gggaagcgtg   6300
gcgctttctc atagctcacg ctgtaggtat ctcagttcgg tgtaggtcgt tcgctccaag   6360
ctgggctgtg tgcacgaacc ccccgttcag cccgaccgct gcgccttatc cggtaactat   6420
cgtcttgagt ccaacccggt aagacacgac ttatcgccac tggcagcagc cactggtaac   6480
aggattagca gagcgaggta tgtaggcggt gctacagagt tcttgaagtg gtggcctaac   6540
tacggctaca ctagaaggac agtatttggt atctgcgctc tgctgaagcc agttaccttc   6600
ggaaaaagag ttggtagctc ttgatccggc aaacaaacca ccgctggtag cggtggtttt   6660
tttgtttgca agcagcagat tacgcgcaga aaaaaaggat ctcaagaaga tcctttgatc   6720
ttttctacgg ggtctgacgc tcagtggaac gaaaactcac gttaagggat tttggtcatg   6780
agattatcaa aaaggatctt cacctagatc cttttaaatt aaaaatgaag ttttagcacg   6840
tgctattatt gaagcattta tcagggttat tgtctcatga gcggatacat atttgaatgt   6900
atttagaaaa ataaacaaat aggggttccg cgcacatttc cccgaaaagt gccacctgta   6960
tgcggtgtga aataccgcac agatgcgtaa ggagaaaata ccgcatcagg aaattgtaag   7020
cgttaataat tcagaagaac tcgtcaagaa ggcgatagaa ggcgatgcgc tgcgaatcgg   7080
gagcggcgat accgtaaagc acgaggaagc ggtcagccca ttcgccgcca agctcttcag   7140
caatatcacg ggtagccaac gctatgtcct gatagcggtc cgccacaccc agccggccac   7200
```

```
agtcgatgaa tccagaaaag cggccatttt ccaccatgat attcggcaag caggcatcgc   7260

catgggtcac gacgagatcc tcgccgtcgg gcatgctcgc cttgagcctg gcgaacagtt   7320

cggctggcgc gagcccctga tgctcttcgt ccagatcatc ctgatcgaca agaccggctt   7380

ccatccgagt acgtgctcgc tcgatgcgat gtttcgcttg gtggtcgaat gggcaggtag   7440

ccggatcaag cgtatgcagc cgccgcattg catcagccat gatggatact ttctcggcag   7500

gagcaaggtg agatgacagg agatcctgcc ccggcacttc gcccaatagc agccagtccc   7560

ttcccgcttc agtgacaacg tcgagcacag ctgcgcaagg aacgcccgtc gtggccagcc   7620

acgatagccg cgctgcctcg tcttgcagtt cattcagggc accggacagg tcggtcttga   7680

caaaaagaac cgggcgcccc tgcgctgaca gccggaacac ggcggcatca gagcagccga   7740

ttgtctgttg tgcccagtca tagccgaata gcctctccac ccaagcggcc ggagaacctg   7800

cgtgcaatcc atcttgttca atcatgcgaa acgatcctca tcctgtctct tgatcagagc   7860

ttgatcccct gcgccatcag atccttggcg gcgagaaagc catccagttt actttgcagg   7920

gcttcccaac cttaccagag ggcgccccag ctggcaattc cggttcgctt gctgtccata   7980

aaaccgccca gtagaagcat atg                                           8003
```

<210> SEQ ID NO 12
<211> LENGTH: 8003
<212> TYPE: DNA
<213> ORGANISM: Artificial Sequence
<220> FEATURE:
<223> OTHER INFORMATION: pVX-192

<400> SEQUENCE: 12

```
aagcttaatt aatctttctg cgaattgaga tgacgccact ggctgggcgt catcccggtt     60

tcccgggtaa acaccaccga aaaatagtta ctatcttcaa agccacattc ggtcgaaata    120

tcactgatta acaggcggct atgctggaga agatattgcg catgacacac tctgacctgt    180

cgcagatatt gattgatggt cattccagtc tgctggcgaa attgctgacg caaaacgcgc    240

tcactgcacg atgcctcatc acaaaattta tccagcgcaa agggactttt caggctagcc    300

gccagccggg taatcagctt atccagcaac gtttcgctgg atgttggcgg caacgaatca    360

ctggtgtaac gatggcgatt cagcaacatc accaactgcc cgaacagcaa ctcagccatt    420

tcgttagcaa acggcacatg ctgactactt tcatgctcaa gctgaccgat aacctgccgc    480

gcctgcgcca tccccatgct acctaagcgc cagtgtggtt gccctgcgct ggcgttaaat    540

cccggaatcg ccccctgcca gtcaagattc agcttcagac gctccgggca ataaataata    600

ttctgcaaaa ccagatcgtt aacggaagcg taggagtgtt tatcgtcagc atgaatgtaa    660

aagagatcgc cacgggtaat gcgataaggg cgatcgttga gtacatgcag gccattaccg    720

cgccagacaa tcaccagctc acaaaaatca tgtgtatgtt cagcaaagac atcttgcgga    780

taacggtcag ccacagcgac tgcctgctgg tcgctggcaa aaaaatcatc tttgagaagt    840

tttaactgat gcgccaccgt ggctacctcg gccagagaac gaagttgatt attcgcaata    900

tggcgtacaa atacgttgag aagattcgcg ttattgcaga aagccatccc gtccctggcg    960

aatatcacgc ggtgaccagt taaactctcg gcgaaaaagc gtcgaaaagt ggttactgtc   1020

gctgaatcca cagcgatagg cgatgtcagt aacgctggcc tcgctgtggc gtagcagatg   1080

tcgggctttc atcagtcgca ggcggttcag gtatcgctga ggcgtcagtc ccgtttgctg   1140

cttaagctgc cgatgtagcg tacgcagtga aagagaaaat tgatccgcca cggcatccca   1200
```

-continued

```
attcacctca tcggcaaaat ggtcctccag ccaggccaga agcaagttga gacgtgatgc   1260
gctgttttcc aggttctcct gcaaactgct tttacgcagc aagagcagta attgcataaa   1320
caagatctcg cgactggcgg tcgagggtaa atcattttcc ccttcctgct gttccatctg   1380
tgcaaccagc tgtcgcacct gctgcaatac gctgtggtta acgcgccagt gagacggata   1440
ctgcccatcc agctcttgtg gcagcaactg attcagcccg gcgagaaact gaaatcgatc   1500
cggcgagcga tacagcacat tggtcagaca cagattatcg gtatgttcat acagatgccg   1560
atcatgatcg cgtacgaaac agaccgtgcc accggtgatg gtatagggct gcccattaaa   1620
cacatgaata cccgtgccat gttcgacaat cacaatttca tgaaaatcat gatgatgttc   1680
aggaaaatcc gcctgcggga gccggggttc tatcgccacg gacgcgttac cagacggaaa   1740
aaaatccaca ctatgtaata cggtcatact ggcctcctga tgtcgtcaac acggcgaaat   1800
agtaatcacg aggtcaggtt cttaccttaa attttcgacg gaaaaccacg taaaaaacgt   1860
cgatttttca agatacagcg tgaattttca ggaaatgcgg tgagcatcac atcaccacaa   1920
ttcagcaaat tgtgaacatc atcacgttca tctttccctg gttgccaatg gcccattttc   1980
ctgtcagtaa cgagaaggtc gcgaattcag gcgcttttta gactggtcgt aatgaaattc   2040
aggaggatgg tcgacatgaa agccacgaaa ctggttctgg gtgctgttat cctgggttcc   2100
acgctgctgg cgggttgttc ctctaatgcg aaaatcgatc aaggcatcaa cccgtatgtg   2160
ggctttgaaa tgggttacga ttggctgggt cgtatgccgt ataaaggcag cgttgaaaat   2220
ggtgcataca aagctcaggg cgtccaactg accgcgaaac tgggttatcc gatcacggat   2280
gacctggata tttacacccg tctgggcggt atggtctggc gtgcagatac gaaaagcaac   2340
gtgtatggca aaaatcatga caccggtgtg tctccggttt tcgcgggcgg tgttgaatat   2400
gccatcacgc cggaaattgc aacccgtctg gaataccagt ggaccaacaa tatcggcgat   2460
gcacacacga ttggtacccg cccggataac ggcattccgg gtatcgacga aattctggcg   2520
gccctgccga aaacggatac ctataaactg attctgaatg gcaaaacgct gaaaggtgaa   2580
accacgaccg aagctgttga cgcagctacc gcggaaaaag tcttcaaaca atacgctaac   2640
gataatggcg tggacggtga atggacctac gatgacgcga cgaaaacctt cacggtcacc   2700
gaaaaaccgg aagtgatcga tgccagtgaa ctgacgccgg cagttacgac ctataaactg   2760
gtcattaacg gcaaaaccct gaaaggtgaa acgaccacgg aagctgtgga tgcagcaacc   2820
gcagaaaaag ttttcaaaca gtacgccaat gacaacggtg tggacggcga atggacgtac   2880
gatgacgcaa cgaaaacctt cacggtgacc gaaaaaccgg aagttatcga tgcctccgaa   2940
ctgaccccgg cagtcaccac gtataaactg gtgatcaatg gtaaaacgct gaaaggcgaa   3000
accacgacca aagcggttga tgccgaaacc gcagaaaaag cttttaaaca atacgcgaat   3060
gacaatggcg tggatggcgt gtggacctac gatgatgcga ccaaaacctt taccgttacc   3120
gaataataat ctagaaggag gaacaatatg aaaaagatta tgctggtctt tattaccctg   3180
attctggtgt ccctgccgat tgcacacaa accgaagcgg gcgatgcgag cgccttcaac   3240
aaagaaaaca gcatcagctc tatggcaccg ccggcttcac cgccggcatc gccgaaaacc   3300
ccgatcgaga aaaaacatgc tgatgaaatc gacaaataca tccagggcct ggactacaat   3360
aaaaacaatg tgctggttta tcacggtgat gccgttacga atgtcccgcc gcgtaaaggc   3420
tataaagacg gtaacgaata catcgtggtt gaaaagaaaa agaaaagcat caaccagaac   3480
aatgctgata ttcaagtcgt gaacgcgatc agttccctga cctatccggg cgcactggtc   3540
aaagctaata gcgaactggt ggaaaaccag ccggatgtgc tgccggttaa acgtgacagc   3600
```

```
ctgaccctgt ctattgatct gccgggtatg acgaaccaag ataacaaaat cgttgtcaaa   3660
aacgcaacca aaagtaacgt caacaatgct gtgaatacgc tggttgaacg ctggaacgaa   3720
aaatatgcgc aggcctaccc gaatgtgtcc gccaaaattg attatgatga cgaaatggcg   3780
tactcagaat cgcaactgat cgccaaattt ggcaccgcgt tcaaagccgt taacaatagc   3840
ctgaacgtca attttggcgc gatttctgaa ggtaaaatgc aggaaatggt gatctcattc   3900
aaacaaatct actacaacgt caacgtgaac gaaccgaccc gtccgtcgcg ctttttcggc   3960
aaagccgtca cgaaagaaca gctgcaagcg ctgggtgtga atgccgaaaa cccgccggca   4020
tatatttcat cggtggcgta tggtcgccag gtttacctga aactgagcac caacagccat   4080
tctacgaaag ttaaagcggc ctttaaagca gctgtctctg gcaaaagtgt ctccggtgat   4140
gtggaactga ccaacatcat caaaaacagc tctttcaaag ccgttattta tggcggttct   4200
gcaaaagatg aagtccagat tatcgacggc aatctgggtg atctgcgtga cattctgaaa   4260
aaaggcgcga cctttaaccg cgaaacgccg ggtgtgccga tcgcctacac cacgaatttc   4320
ctgaaagata acgaactggc agttatcaaa aacaactcag aatacatcga aaccacgtcg   4380
aaagcttaca ccgatggcaa aattaatatc gaccacagtg gcggttatgt tgcacagttt   4440
aacatttcct gggatgaagt gaattacgac ccggagggta acgaaatcgt tcaacataaa   4500
aactggagtg aaaacaacaa atccaaaacc gcgcacttca cgagttccat ttatctgccg   4560
ggcaacgctc gtaatatcaa cgtgtacgcg aaagaatgca ccggtctggc ctgggaatgg   4620
tggcgtacgg tgattgatga ccgcaacctg ccgctggtta aaaatcgcaa catctccatc   4680
tggggcacca ccctgtaccc gaaatactcc aacaaagttg ataacccgat tgaataataa   4740
ggatccagga ggaacaatat gtcccgcaaa ctgttcgcta gtattctgat tggtgctctg   4800
ctgggtatcg gtgctccgcc gtctgctcac gctggtgctg atgacgtggt tgacagctct   4860
aaatcttttg ttatggaaaa cttcagttcc tatcatggca ccaaaccggg ttacgtcgat   4920
tcgattcaga aaggcatcca aaaaccgaaa agcggcaccc agggtaacta tgatgacgat   4980
tggaaaggtt tctactcaac ggacaacaaa tacgatgcgg ccggctactc cgtggacaac   5040
gaaaatccgc tgagcggtaa agcaggcggt gtcgtgaaag ttacctatcc gggcctgacg   5100
aaagtgctgg cgctgaaagt tgataacgcc gaaaccatca aaaaagaact gggcctgtcc   5160
ctgaccgaac cgctgatgga acaagtgggt acggaagaat ttatcaaacg tttcggcgat   5220
ggtgcatctc gcgttgtcct gagtctgccg tttgctgaag gctcatcgag cgtcgaatac   5280
attaacaatt gggaacaagc aaaagctctg agcgtggaac tggaaatcaa tttcgaaacg   5340
cgtggtaaac gtggtcaaga tgcaatgtat gaatatatgg ctcaagcgtg tgcgggtaac   5400
cgtgttcgct aataaggcgc gcctggtagt gtggggtctc cccatgcgag agtagggaac   5460
tgccaggcat caaataaaac gaaaggctca gtcgaaagac tgggcctttc gttttatctg   5520
ttgtttgtcg gtgaacgctc tcctgagtag gacaaatccg ccgggagcgg atttgaacgt   5580
tgcgaagcaa cggcccggag ggtggcgggc aggacgcccg ccataaactg ccaggcatca   5640
aattaagcag aaggccatcc tgacggatgg cctttttgcg tttctacaaa ctcgagctcg   5700
aattcgtaat catggtcata gctgtttcct gtgtgaaatt gttatccgct cacaattcca   5760
cacaacatac gagccggaag cataaagtgt aaagcctggg gtgcctaatg agtgagctaa   5820
ctcacattaa ttgcgttgcg ctcactgccc gctttccagt cgggaaacct gtcgtgccag   5880
ctgcattaat gaatcggcca acgcgcgggg agaggcggtt tgcgtattgg gcgctcttcc   5940
```

gcttcctcgc tcactgactc gctgcgctcg gtcgttcggc tgcggcgagc ggtatcagct 6000
cactcaaagg cggtaatacg gttatccaca gaatcagggg ataacgcagg aaagaacatg 6060
tgagcaaaag gccagcaaaa gcccaggaac cgtaaaaagg ccgcgttgct ggcgtttttc 6120
cataggctcc gcccccctga cgagcatcac aaaaatcgac gctcaagtca gaggtggcga 6180
aacccgacag gactataaag ataccaggcg tttccccctg gaagctccct cgtgcgctct 6240
cctgttccga ccctgccgct taccggatac ctgtccgcct ttctcccttc gggaagcgtg 6300
gcgctttctc atagctcacg ctgtaggtat ctcagttcgg tgtaggtcgt tcgctccaag 6360
ctgggctgtg tgcacgaacc ccccgttcag cccgaccgct gcgccttatc cggtaactat 6420
cgtcttgagt ccaacccggt aagacacgac ttatcgccac tggcagcagc cactggtaac 6480
aggattagca gagcgaggta tgtaggcggt gctacagagt tcttgaagtg gtggcctaac 6540
tacggctaca ctagaaggac agtatttggt atctgcgctc tgctgaagcc agttaccttc 6600
ggaaaaagag ttggtagctc ttgatccggc aaacaaacca ccgctggtag cggtggtttt 6660
tttgtttgca agcagcagat tacgcgcaga aaaaaaggat ctcaagaaga tcctttgatc 6720
ttttctacgg ggtctgacgc tcagtggaac gaaaactcac gttaagggat tttggtcatg 6780
agattatcaa aaaggatctt cacctagatc cttttaaatt aaaaatgaag ttttagcacg 6840
tgctattatt gaagcattta tcagggttat tgtctcatga gcggatacat atttgaatgt 6900
atttagaaaa ataaacaaat aggggttccg cgcacatttc cccgaaaagt gccacctgta 6960
tgcggtgtga aataccgcac agatgcgtaa ggagaaaata ccgcatcagg aaattgtaag 7020
cgttaataat tcagaagaac tcgtcaagaa ggcgatagaa ggcgatgcgc tgcgaatcgg 7080
gagcggcgat accgtaaagc acgaggaagc ggtcagccca ttcgccgcca agctcttcag 7140
caatatcacg ggtagccaac gctatgtcct gatagcggtc cgccacaccc agccggccac 7200
agtcgatgaa tccagaaaag cggccatttt ccaccatgat attcggcaag caggcatcgc 7260
catgggtcac gacgagatcc tcgccgtcgg gcatgctcgc cttgagcctg gcgaacagtt 7320
cggctggcgc gagcccctga tgctcttcgt ccagatcatc ctgatcgaca agaccggctt 7380
ccatccgagt acgtgctcgc tcgatgcgat gtttcgcttg gtggtcgaat gggcaggtag 7440
ccggatcaag cgtatgcagc cgccgcattg catcagccat gatggatact ttctcggcag 7500
gagcaaggtg agatgacagg agatcctgcc ccggcacttc gcccaatagc agccagtccc 7560
ttcccgcttc agtgacaacg tcgagcacag ctgcgcaagg aacgcccgtc gtggccagcc 7620
acgatagccg cgctgcctcg tcttgcagtt cattcagggc accggacagg tcggtcttga 7680
caaaaagaac cgggcgcccc tgcgctgaca gccggaacac ggcggcatca gagcagccga 7740
ttgtctgttg tgcccagtca tagccgaata gcctctccac ccaagcggcc ggagaacctg 7800
cgtgcaatcc atcttgttca atcatgcgaa acgatcctca tcctgtctct tgatcagagc 7860
ttgatcccct gcgccatcag atccttggcg gcgagaaagc catccagttt actttgcagg 7920
gcttcccaac cttaccagag ggcgccccag ctggcaattc cggttcgctt gctgtccata 7980
aaaccgccca gtagaagcat atg 8003

<210> SEQ ID NO 13
<211> LENGTH: 7916
<212> TYPE: DNA
<213> ORGANISM: Artificial Sequence
<220> FEATURE:
<223> OTHER INFORMATION: pVX-184

<400> SEQUENCE: 13

```
aagcttaatt aatctttctg cgaattgaga tgacgccact ggctgggcgt catcccggtt     60
tcccgggtaa acaccaccga aaaatagtta ctatcttcaa agccacattc ggtcgaaata    120
tcactgatta acaggcggct atgctggaga agatattgcg catgacacac tctgacctgt    180
cgcagatatt gattgatggt cattccagtc tgctggcgaa attgctgacg caaaacgcgc    240
tcactgcacg atgcctcatc acaaaattta tccagcgcaa agggactttt caggctagcc    300
gccagccggg taatcagctt atccagcaac gtttcgctgg atgttggcgg caacgaatca    360
ctggtgtaac gatggcgatt cagcaacatc accaactgcc cgaacagcaa ctcagccatt    420
tcgttagcaa acggcacatg ctgactactt tcatgctcaa gctgaccgat aacctgccgc    480
gcctgcgcca tccccatgct acctaagcgc cagtgtggtt gccctgcgct ggcgttaaat    540
cccggaatcg ccccctgcca gtcaagattc agcttcagac gctccgggca ataaataata    600
ttctgcaaaa ccagatcgtt aacggaagcg taggagtgtt tatcgtcagc atgaatgtaa    660
aagagatcgc cacgggtaat gcgataaggg cgatcgttga gtacatgcag gccattaccg    720
cgccagacaa tcaccagctc acaaaaatca tgtgtatgtt cagcaaagac atcttgcgga    780
taacggtcag ccacagcgac tgcctgctgg tcgctggcaa aaaaatcatc tttgagaagt    840
tttaactgat gcgccaccgt ggctacctcg gccagagaac gaagttgatt attcgcaata    900
tggcgtacaa atacgttgag aagattcgcg ttattgcaga aagccatccc gtccctggcg    960
aatatcacgc ggtgaccagt taaactctcg gcgaaaaagc gtcgaaaagt ggttactgtc   1020
gctgaatcca cagcgatagg cgatgtcagt aacgctggcc tcgctgtggc gtagcagatg   1080
tcgggctttc atcagtcgca ggcggttcag gtatcgctga ggcgtcagtc ccgtttgctg   1140
cttaagctgc cgatgtagcg tacgcagtga aagagaaaat tgatccgcca cggcatccca   1200
attcacctca tcggcaaaat ggtcctccag ccaggccaga agcaagttga gacgtgatgc   1260
gctgttttcc aggttctcct gcaaactgct tttacgcagc aagagcagta attgcataaa   1320
caagatctcg cgactggcgg tcgagggtaa atcattttcc ccttcctgct gttccatctg   1380
tgcaaccagc tgtcgcacct gctgcaatac gctgtggtta acgcgccagt gagacggata   1440
ctgcccatcc agctcttgtg gcagcaactg attcagcccg gcgagaaact gaaatcgatc   1500
cggcgagcga tacagcacat tggtcagaca cagattatcg gtatgttcat acagatgccg   1560
atcatgatcg cgtacgaaac agaccgtgcc accggtgatg gtatagggct gcccattaaa   1620
cacatgaata cccgtgccat gttcgacaat cacaatttca tgaaaatcat gatgatgttc   1680
aggaaaatcc gcctgcggga gccggggttc tatcgccacg gacgcgttac cagacggaaa   1740
aaaatccaca ctatgtaata cggtcatact ggcctcctga tgtcgtcaac acggcgaaat   1800
agtaatcacg aggtcaggtt cttaccttaa attttcgacg gaaaaccacg taaaaaacgt   1860
cgatttttca agatacagcg tgaattttca ggaaatgcgg tgagcatcac atcaccacaa   1920
ttcagcaaat tgtgaacatc atcacgttca tctttccctg gttgccaatg gcccattttc   1980
ctgtcagtaa cgagaaggtc gcgaattcag gcgcttttta gactggtcgt aatgaaattc   2040
aggaggatgg tcgacatgaa agccacgaaa ctggttctgg gtgctgttat cctgggttcc   2100
acgctgctgg cgggttgttc ctctaatgcg aaaatcgatc aaggcatcaa cccgtatgtg   2160
ggctttgaaa tgggttacga ttggctgggt cgtatgccgt ataaaggcag cgttgaaaat   2220
ggtgcataca aagctcaggg cgtccaactg accgcgaaac tgggttatcc gatcacggat   2280
gacctggata tttacacccg tctgggcggt atggtctggc gtgcagatac gaaaagcaac   2340
```

-continued

```
gtgtatggca aaaatcatga caccggtgtg tctccggttt tcgcgggcgg tgttgaatat   2400
gccatcacgc cggaaattgc aacccgtctg gaataccagt ggaccaacaa tatcggcgat   2460
gcacacacga ttggtacccg cccggataac ggcattccgg gtatcgacga aattctggcg   2520
gccctgccga aaacggatac ctataaactg attctgaatg gcaaaacgct gaaaggtgaa   2580
accacgaccg aagctgttga cgcagctacc gcggaaaaag tcttcaaaca atacgctaac   2640
gataatggcg tggacggtga atggacctac gatgacgcga cgaaaacctt cacggtcacc   2700
gaaaaaccgg aagtgatcga tgccagtgaa ctgacgccgg cagttacgac ctataaactg   2760
gtcattaacg gcaaaaccct gaaaggtgaa acgaccacgg aagctgtgga tgcagcaacc   2820
gcagaaaaag ttttcaaaca gtacgccaat gacaacggtg tggacggcga atggacgtac   2880
gatgacgcaa cgaaaacctt cacggtgacc gaaaaaccgg aagttatcga tgcctccgaa   2940
ctgaccccgg cagtcaccac gtataaactg gtgatcaatg gtaaaacgct gaaaggcgaa   3000
accacgacca aagcggttga tgccgaaacc gcagaaaaag cttttaaaca atacgcgaat   3060
gacaatggcg tggatggcgt gtggacctac gatgatgcga ccaaaacctt taccgttacc   3120
gaataataat ctagaaggag gaacaatatg atccgcttca aaaagaccaa actgattgcg   3180
agcattgcga tggcactgtg tctgttctcc cagccggtga tttcgttctc aaaagatatt   3240
accgacaaaa atcagtccat cgattcaggc attagctctc tgtcttataa ccgtaatgaa   3300
gtgctggcgt ccaatggtga caaaatcgaa tcatttgttc cgaaagaagg caaaaaagcc   3360
ggtaacaaat tcattgtggt tgaacgtcag aaacgctctc tgaccacgag tccggttgat   3420
atctccatta tcgattcagt caatgaccgt acctatccgg gtgcactgca actggcagac   3480
aaagcatttg tggaaaaccg tccgacgatt ctgatggtta aacgcaaacc gattaacatc   3540
aatattgatc tgccgggcct gaaaggtgaa aatagtatca aagtggatga cccgacctat   3600
ggcaaagttt cgggtgcaat tgatgaactg gtcagcaaat ggaacgaaaa atacagttcc   3660
acccatacgc tgccggcgcg tacccagtat tcggaaagca tggtgtactc taaaagtcaa   3720
atctcatcgg cgctgaacgt taatgccaaa gtcctggaaa actctctggg tgtggatttt   3780
aatgcggttg ccaacaatga gaaaaaagtg atgatcctgg catataaaca gatttctac    3840
accgttagtg ctgatctgcc gaaaaacccg tctgacctgt ttgatgacag tgtcacgttc   3900
aacgatctga aacaaaaagg cgtgtctaat gaagcgccgc cgctgatggt gtctaacgtt   3960
gcctatggtc gtaccattta cgttaaactg gaaaccacga gctctagtaa agatgtccag   4020
gcggccttta aagccctgat caaaaacacc gatatcaaaa atagccagca atacaaagac   4080
atctacgaaa attcctcatt caccgcagtc gtgctgggcg gtgatgctca ggaacacaac   4140
aaagttgtca cgaaagattt tgacgaaatc cgcaaagtga ttaaagataa cgcaaccttc   4200
tcgacgaaaa atccggctta tccgatttcg tacaccagcg tttttctgaa agataacagc   4260
gtcgcagctg tgcataataa aaccgactat atcgaaacca ccagcaccga atacagcaaa   4320
ggcaaaatta atctggatca ctccggtgca tatgtcgctc agttcgaagt ggcctgggat   4380
gaagtttcat acgacaaaga aggcaatgaa gtgctgaccc ataaaacgtg ggatggtaac   4440
tatcaagaca aaaccgcaca ctactccacg gttattccgc tggaagcaaa cgctcgtaat   4500
atccgcatta aagcgcgtga atgcaccggt ctggcatggg aatggtggcg tgatgtcatc   4560
agcgaatatg acgtgccgct gacgaacaat atcaatgtgt caatctgggg caccacgctg   4620
tatccgggta gttccatcac ctataattaa taaggatcca ggaggaacaa tatgtcccgc   4680
aaactgttcg ctagtattct gattggtgct ctgctgggta tcggtgctcc gccgtctgct   4740
```

```
cacgctggtg ctgatgacgt ggttgacagc tctaaatctt ttgttatgga aaacttcagt   4800
tcctatcatg gcaccaaacc gggttacgtc gattcgattc agaaaggcat ccaaaaaccg   4860
aaaagcggca cccagggtaa ctatgatgac gattggaaag gtttctactc aacggacaac   4920
aaatacgatg cggccggcta ctccgtggac aacgaaaatc cgctgagcgg taaagcaggc   4980
ggtgtcgtga aagttaccta tccgggcctg acgaaagtgc tggcgctgaa agttgataac   5040
gccgaaacca tcaaaaaaga actgggcctg tccctgaccg aaccgctgat ggaacaagtg   5100
ggtacggaag aatttatcaa acgtttcggc gatggtgcat ctcgcgttgt cctgagtctg   5160
ccgtttgctg aaggctcatc gagcgtcgaa tacattaaca attgggaaca agcaaaagct   5220
ctgagcgtgg aactggaaat caatttcgaa acgcgtggta aacgtggtca agatgcaatg   5280
tatgaatata tggctcaagc gtgtgcgggt aaccgtgttc gctaataagg cgcgcctggt   5340
agtgtggggt ctccccatgc gagagtaggg aactgccagg catcaaataa aacgaaaggc   5400
tcagtcgaaa gactgggcct ttcgttttat ctgttgtttg tcggtgaacg ctctcctgag   5460
taggacaaat ccgccgggag cggatttgaa cgttgcgaag caacggcccg gagggtggcg   5520
ggcaggacgc ccgccataaa ctgccaggca tcaaattaag cagaaggcca tcctgacgga   5580
tggccttttt gcgtttctac aaactcgagc tcgaattcgt aatcatggtc atagctgttt   5640
cctgtgtgaa attgttatcc gctcacaatt ccacacaaca tacgagccgg aagcataaag   5700
tgtaaagcct ggggtgccta atgagtgagc taactcacat taattgcgtt gcgctcactg   5760
cccgctttcc agtcgggaaa cctgtcgtgc cagctgcatt aatgaatcgg ccaacgcgcg   5820
gggagaggcg gtttgcgtat tgggcgctct tccgcttcct cgctcactga ctcgctgcgc   5880
tcggtcgttc ggctgcggcg agcggtatca gctcactcaa aggcggtaat acggttatcc   5940
acagaatcag gggataacgc aggaaagaac atgtgagcaa aaggccagca aaagcccagg   6000
aaccgtaaaa aggccgcgtt gctggcgttt ttccataggc tccgcccccc tgacgagcat   6060
cacaaaaatc gacgctcaag tcagaggtgg cgaaacccga caggactata aagataccag   6120
gcgtttcccc ctggaagctc cctcgtgcgc tctcctgttc cgaccctgcc gcttaccgga   6180
tacctgtccg cctttctccc ttcgggaagc gtggcgcttt ctcatagctc acgctgtagg   6240
tatctcagtt cggtgtaggt cgttcgctcc aagctgggct gtgtgcacga acccccccgtt   6300
cagcccgacc gctgcgcctt atccggtaac tatcgtcttg agtccaaccc ggtaagacac   6360
gacttatcgc cactggcagc agccactggt aacaggatta gcagagcgag gtatgtaggc   6420
ggtgctacag agttcttgaa gtggtggcct aactacggct acactagaag gacagtattt   6480
ggtatctgcg ctctgctgaa gccagttacc ttcggaaaaa gagttggtag ctcttgatcc   6540
ggcaaacaaa ccaccgctgg tagcggtggt ttttttgttt gcaagcagca gattacgcgc   6600
agaaaaaaag gatctcaaga agatcctttg atcttttcta cggggtctga cgctcagtgg   6660
aacgaaaact cacgttaagg gattttggtc atgagattat caaaaaggat cttcacctag   6720
atccttttaa attaaaaatg aagttttagc acgtgctatt attgaagcat ttatcagggt   6780
tattgtctca tgagcggata catatttgaa tgtatttaga aaaataaaca aataggggtt   6840
ccgcgcacat ttccccgaaa agtgccacct gtatgcggtg tgaaataccg cacagatgcg   6900
taaggagaaa ataccgcatc aggaaattgt aagcgttaat aattcagaag aactcgtcaa   6960
gaaggcgata gaaggcgatg cgctgcgaat cgggagcggc gataccgtaa agcacgagga   7020
agcggtcagc ccattcgccg ccaagctctt cagcaatatc acgggtagcc aacgctatgt   7080
```

-continued

```
cctgatagcg gtccgccaca cccagccggc cacagtcgat gaatccagaa aagcggccat   7140

tttccaccat gatattcggc aagcaggcat cgccatgggt cacgacgaga tcctcgccgt   7200

cgggcatgct cgccttgagc ctggcgaaca gttcggctgg cgcgagcccc tgatgctctt   7260

cgtccagatc atcctgatcg acaagaccgg cttccatccg agtacgtgct cgctcgatgc   7320

gatgtttcgc ttggtggtcg aatgggcagg tagccggatc aagcgtatgc agccgccgca   7380

ttgcatcagc catgatggat actttctcgg caggagcaag gtgagatgac aggagatcct   7440

gccccggcac ttcgcccaat agcagccagt cccttcccgc ttcagtgaca acgtcgagca   7500

cagctgcgca aggaacgccc gtcgtggcca gccacgatag ccgcgctgcc tcgtcttgca   7560

gttcattcag ggcaccggac aggtcggtct tgacaaaaag aaccgggcgc ccctgcgctg   7620

acagccggaa cacggcggca tcagagcagc cgattgtctg ttgtgcccag tcatagccga   7680

atagcctctc cacccaagcg gccggagaac ctgcgtgcaa tccatcttgt tcaatcatgc   7740

gaaacgatcc tcatcctgtc tcttgatcag agcttgatcc cctgcgccat cagatccttg   7800

gcggcgagaa agccatccag tttactttgc agggcttccc aaccttacca gagggcgccc   7860

cagctggcaa ttccggttcg cttgctgtcc ataaaaccgc ccagtagaag catatg       7916
```

<210> SEQ ID NO 14
<211> LENGTH: 7662
<212> TYPE: DNA
<213> ORGANISM: Artificial Sequence
<220> FEATURE:
<223> OTHER INFORMATION: pVX-158

<400> SEQUENCE: 14

```
aagcttaatt aatctttctg cgaattgaga tgacgccact ggctgggcgt catcccggtt     60

tcccgggtaa acaccaccga aaaatagtta ctatcttcaa agccacattc ggtcgaaata    120

tcactgatta acaggcggct atgctggaga agatattgcg catgacacac tctgacctgt    180

cgcagatatt gattgatggt cattccagtc tgctggcgaa attgctgacg caaaacgcgc    240

tcactgcacg atgcctcatc acaaaattta tccagcgcaa agggactttt caggctagcc    300

gccagccggg taatcagctt atccagcaac gtttcgctgg atgttggcgg caacgaatca    360

ctggtgtaac gatggcgatt cagcaacatc accaactgcc cgaacagcaa ctcagccatt    420

tcgttagcaa acggcacatg ctgactactt tcatgctcaa gctgaccgat aacctgccgc    480

gcctgcgcca tccccatgct acctaagcgc cagtgtggtt gccctgcgct ggcgttaaat    540

cccggaatcg ccccctgcca gtcaagattc agcttcagac gctccgggca ataaataata    600

ttctgcaaaa ccagatcgtt aacggaagcg taggagtgtt tatcgtcagc atgaatgtaa    660

aagagatcgc cacgggtaat gcgataaggg cgatcgttga gtacatgcag gccattaccg    720

cgccagacaa tcaccagctc acaaaaatca tgtgtatgtt cagcaaagac atcttgcgga    780

taacggtcag ccacagcgac tgcctgctgg tcgctggcaa aaaaatcatc tttgagaagt    840

tttaactgat gcgccaccgt ggctacctcg gccagagaac gaagttgatt attcgcaata    900

tggcgtacaa atacgttgag aagattcgcg ttattgcaga aagccatccc gtccctggcg    960

aatatcacgc ggtgaccagt taaactctcg gcgaaaaagc gtcgaaaagt ggttactgtc   1020

gctgaatcca cagcgatagg cgatgtcagt aacgctggcc tcgctgtggc gtagcagatg   1080

tcgggctttc atcagtcgca ggcggttcag gtatcgctga ggcgtcagtc ccgtttgctg   1140

cttaagctgc cgatgtagcg tacgcagtga aagagaaaat tgatccgcca cggcatccca   1200

attcacctca tcggcaaaat ggtcctccag ccaggccaga agcaagttga gacgtgatgc   1260
```

```
gctgttttcc aggttctcct gcaaactgct tttacgcagc aagagcagta attgcataaa   1320
caagatctcg cgactggcgg tcgagggtaa atcattttcc ccttcctgct gttccatctg   1380
tgcaaccagc tgtcgcacct gctgcaatac gctgtggtta acgcgccagt gagacggata   1440
ctgcccatcc agctcttgtg gcagcaactg attcagcccg gcgagaaact gaaatcgatc   1500
cggcgagcga tacagcacat tggtcagaca cagattatcg gtatgttcat acagatgccg   1560
atcatgatcg cgtacgaaac agaccgtgcc accggtgatg gtatagggct gcccattaaa   1620
cacatgaata cccgtgccat gttcgacaat cacaatttca tgaaaatcat gatgatgttc   1680
aggaaaatcc gcctgcggga gccggggttc tatcgccacg gacgcgttac cagacggaaa   1740
aaaatccaca ctatgtaata cggtcatact ggcctcctga tgtcgtcaac acggcgaaat   1800
agtaatcacg aggtcaggtt cttaccttaa attttcgacg gaaaaccacg taaaaaacgt   1860
cgatttttca agatacagcg tgaattttca ggaaatgcgg tgagcatcac atcaccacaa   1920
ttcagcaaat tgtgaacatc atcacgttca tctttccctg gttgccaatg gcccattttc   1980
ctgtcagtaa cgagaaggtc gcgaattcag gcgcttttta gactggtcgt aatgaaattc   2040
aggaggatgg tcgacatgaa agccacgaaa ctggttctgg gtgctgttat cctgggttcc   2100
acgctgctgg cgggttgttc ctctaatgcg aaaatcgatc aaggcatcaa cccgtatgtg   2160
ggctttgaaa tgggttacga ttggctgggt cgtatgccgt ataaaggcag cgttgaaaat   2220
ggtgcataca aagctcaggg cgtccaactg accgcgaaac tgggttatcc gatcacggat   2280
gacctggata tttacacccg tctgggcggt atggtctggc gtgcagatac gaaaagcaac   2340
gtgtatggca aaaatcatga caccggtgtg tctccggttt tcgcgggcgg tgttgaatat   2400
gccatcacgc cggaaattgc aacccgtctg gaataccagt ggaccaacaa tatcggcgat   2460
gcacacacga ttggtacccg cccggataac ggcattccgg gtatcgacga aattctggcg   2520
gccctgccga aaacggatac ctataaactg attctgaatg gcaaaacgct gaaaggtgaa   2580
accacgaccg aagctgttga cgcagctacc gcggaaaaag tcttcaaaca atacgctaac   2640
gataatggcg tggacggtga atggacctac gatgacgcga cgaaaacctt cacggtcacc   2700
gaaaaaccgg aagtgatcga tgccagtgaa ctgacgccgg cagttacgac ctataaactg   2760
gtcattaacg gcaaaaccct gaaaggtgaa acgaccacgg aagctgtgga tgcagcaacc   2820
gcagaaaaag ttttcaaaca gtacgccaat gacaacggtg tggacggcga atggacgtac   2880
gatgacgcaa cgaaaacctt cacggtgacc gaaaaaccgg aagttatcga tgcctccgaa   2940
ctgaccccgg cagtcaccac gtataaactg gtgatcaatg gtaaaacgct gaaaggcgaa   3000
accacgacca aagcggttga tgccgaaacc gcagaaaaag cttttaaaca atacgcgaat   3060
gacaatggcg tggatggcgt gtggacctac gatgatgcga ccaaaacctt taccgttacc   3120
gaataataat ctagagctga ggagggattg agcgatgtct gcattcaata aagaaaattc   3180
aatttcatcc atggcaccac cagcatctcc gcctgcaagt cctaagacgc caatcgaaaa   3240
gaaacacgcg gatgaaatcg ataagtatat acaaggattg gattacaata aaaacaatgt   3300
attagtatac cacggagatg cagtgacaaa tgtgccgcca agaaaaggtt acaaagatgg   3360
aaatgaatat attgttgtgg agaaaaagaa gaaatccatc aatcaaaata atgcagacat   3420
tcaagttgtg aatgcaattt cgagcctaac ctatccaggt gctctcgtaa aagcgaattc   3480
ggaattagta gaaaatcaac cagatgttct ccctgtaaaa cgtgattcat taacactcag   3540
cattgatttg ccaggtatga ctaatcaaga caataaaata gttgtaaaaa atgccactaa   3600
```

-continued

```
atcaaacgtt aacaacgcag taaatacatt agtggaaaga tggaatgaaa aatatgctca   3660
agcttatcca aatgtaagtg caaaaattga ttatgatgac gaaatggctt acagtgaatc   3720
acaattaatt gcgaaatttg gtacagcatt taaagctgta aataatagct tgaatgtaaa   3780
cttcggcgca atcagtgaag ggaaaatgca agaagaagtc attagtttta aacaaattta   3840
ctataacgtg aatgttaatg aacctacaag accttccaga tttttcggca aagctgttac   3900
taaagagcag ttgcaagcgc ttggagtgaa tgcagaaaat cctcctgcat atatctcaag   3960
tgtggcgtat ggccgtcaag tttatttgaa attatcaact aattcccata gtactaaagt   4020
aaaagctgct tttgatgctg ccgtaagcgg aaaatctgtc tcaggtgatg tagaactaac   4080
aaatatcatc aaaaattctt ccttcaaagc cgtaatttac ggaggttccg caaaagatga   4140
agttcaaatc atcgacggca acctcggaga cttacgcgat attttgaaaa aaggcgctac   4200
ttttaatcga gaaacaccag gagttcccat tgcttataca acaaacttcc taaaagacaa   4260
tgaattagct gttattaaaa acaactcaga atatattgaa acaacttcaa aagcttatac   4320
agatggaaaa attaacatcg atcactctgg aggatacgtt gctcaattca acatttcttg   4380
ggatgaagta aattatgatc ctgaaggtaa cgaaattgtt caacataaaa actggagcga   4440
aaacaataaa agcaagctag ctcatttcac atcgtccatc tatttgcctg gtaacgcgag   4500
aaatattaat gtttacgcta aagaatgcac tggtttagct tgggaatggt ggagaacggt   4560
aattgatgac cggaacttac cacttgtgaa aaatagaaat atctccatct ggggcaccac   4620
gctttatccg aaatatagta ataaagtaga taatccaatc gaatatgatt ataaagatga   4680
cgatgacaaa taataatcta gaggatccag gaggaacaat atgggcgcag acgacgttgt   4740
tgacagcagc aaatctttcg ttatggaaaa cttcagcagc tatcacggca ccaaaccggg   4800
ctatgtggac tctattcaga aaggcatcca aaaaccgaaa agtggcaccc agggtaacta   4860
tgatgacgat tggaaaggtt tttactccac ggacaataaa tatgatgcgg ccggctactc   4920
ggtcgacaac gaaaatccgc tgagcggtaa agcaggcggt gtggttaaag ttacctatcc   4980
gggcctgacg aaagttctgg cgctgaaagt cgataacgcc gaaaccatca aaaaagaact   5040
gggcctgtca ctgaccgaac cgctgatgga acaagtgggt acggaagaat ttatcaaacg   5100
tttcggcgat ggtgcatccc gcgtcgtgct gtcactgccg tttgctgaag gcagctctag   5160
tgtggaatac attaacaatt gggaacaagc aaaagctctg agcgttgaac tggaaatcaa   5220
tttcgaaacg cgtggtaaac gtggtcaaga tgcgatgtat gaatatatgg ctcaagcgtg   5280
tgcgggtaac cgtgtgcgtt aataaggcgc gccggatccc cgcgccctca tccgaaaggg   5340
cgtatgggta ccgagctcga attcgtaatc atggtcatag ctgtttcctg tgtgaaattg   5400
ttatccgctc acaattccac acaacatacg agccggaagc ataaagtgta aagcctgggg   5460
tgcctaatga gtgagctaac tcacattaat tgcgttgcgc tcactgcccg ctttccagtc   5520
gggaaacctg tcgtgccagc tgcattaatg aatcggccaa cgcgcgggga gaggcggttt   5580
gcgtattggg cgctcttccg cttcctcgct cactgactcg ctgcgctcgg tcgttcggct   5640
gcggcgagcg gtatcagctc actcaaaggc ggtaatacgg ttatccacag aatcagggga   5700
taacgcagga aagaacatgt gagcaaaagg ccagcaaaag cccaggaacc gtaaaaaggc   5760
cgcgttgctg gcgtttttcc ataggctccg cccccctgac gagcatcaca aaaatcgacg   5820
ctcaagtcag aggtggcgaa acccgacagg actataaaga taccaggcgt ttccccctgg   5880
aagctccctc gtgcgctctc ctgttccgac cctgccgctt accggatacc tgtccgcctt   5940
tctcccttcg ggaagcgtgg cgctttctca tagctcacgc tgtaggtatc tcagttcggt   6000
```

gtaggtcgtt cgctccaagc tgggctgtgt gcacgaaccc cccgttcagc ccgaccgctg 6060
cgccttatcc ggtaactatc gtcttgagtc caacccggta agacacgact tatcgccact 6120
ggcagcagcc actggtaaca ggattagcag agcgaggtat gtaggcggtg ctacagagtt 6180
cttgaagtgg tggcctaact acggctacac tagaaggaca gtatttggta tctgcgctct 6240
gctgaagcca gttaccttcg gaaaaagagt tggtagctct tgatccggca aacaaaccac 6300
cgctggtagc ggtggttttt ttgtttgcaa gcagcagatt acgcgcagaa aaaaaggatc 6360
tcaagaagat cctttgatct tttctacggg gtctgacgct cagtggaacg aaaactcacg 6420
ttaagggatt ttggtcatga gattatcaaa aaggatcttc acctagatcc ttttaaatta 6480
aaaatgaagt tttagcacgt gctattattg aagcatttat cagggttatt gtctcatgag 6540
cggatacata tttgaatgta tttagaaaaa taaacaaata ggggttccgc gcacatttcc 6600
ccgaaaagtg ccacctgtat gcggtgtgaa ataccgcaca gatgcgtaag gagaaaatac 6660
cgcatcagga aattgtaagc gttaataatt cagaagaact cgtcaagaag gcgatagaag 6720
gcgatgcgct gcgaatcggg agcggcgata ccgtaaagca cgaggaagcg gtcagcccat 6780
tcgccgccaa gctcttcagc aatatcacgg gtagccaacg ctatgtcctg atagcggtcc 6840
gccacaccca gccggccaca gtcgatgaat ccagaaaagc ggccattttc caccatgata 6900
ttcggcaagc aggcatcgcc atgggtcacg acgagatcct cgccgtcggg catgctcgcc 6960
ttgagcctgg cgaacagttc ggctggcgcg agcccctgat gctcttcgtc cagatcatcc 7020
tgatcgacaa gaccggcttc catccgagta cgtgctcgct cgatgcgatg tttcgcttgg 7080
tggtcgaatg ggcaggtagc cggatcaagc gtatgcagcc gccgcattgc atcagccatg 7140
atggatactt tctcggcagg agcaaggtga gatgacagga gatcctgccc cggcacttcg 7200
cccaatagca gccagtccct tcccgcttca gtgacaacgt cgagcacagc tgcgcaagga 7260
acgcccgtcg tggccagcca cgatagccgc gctgcctcgt cttgcagttc attcagggca 7320
ccggacaggt cggtcttgac aaaaagaacc gggcgcccct gcgctgacag ccggaacacg 7380
gcggcatcag agcagccgat tgtctgttgt gcccagtcat agccgaatag cctctccacc 7440
caagcggccg gagaacctgc gtgcaatcca tcttgttcaa tcatgcgaaa cgatcctcat 7500
cctgtctctt gatcagagct tgatcccctg cgccatcaga tccttggcgg cgagaaagcc 7560
atccagttta ctttgcaggg cttcccaacc ttaccagagg gcgccccagc tggcaattcc 7620
ggttcgcttg ctgtccataa aaccgcccag tagaagcata tg 7662

<210> SEQ ID NO 15
<211> LENGTH: 7931
<212> TYPE: DNA
<213> ORGANISM: Artificial Sequence
<220> FEATURE:
<223> OTHER INFORMATION: pVX-179

<400> SEQUENCE: 15
aagcttaatt aatctttctg cgaattgaga tgacgccact ggctgggcgt catcccggtt 60
tcccgggtaa acaccaccga aaaatagtta ctatcttcaa agccacattc ggtcgaaata 120
tcactgatta acaggcggct atgctggaga agatattgcg catgacacac tctgacctgt 180
cgcagatatt gattgatggt cattccagtc tgctggcgaa attgctgacg caaaacgcgc 240
tcactgcacg atgcctcatc acaaaattta tccagcgcaa agggactttt caggctagcc 300
gccagccggg taatcagctt atccagcaac gtttcgctgg atgttggcgg caacgaatca 360

-continued ctggtgtaac gatggcgatt cagcaacatc accaactgcc cgaacagcaa ctcagccatt 420
tcgttagcaa acggcacatg ctgactactt tcatgctcaa gctgaccgat aacctgccgc 480
gcctgcgcca tccccatgct acctaagcgc cagtgtggtt gccctgcgct ggcgttaaat 540
cccggaatcg ccccctgcca gtcaagattc agcttcagac gctccgggca ataaataata 600
ttctgcaaaa ccagatcgtt aacggaagcg taggagtgtt tatcgtcagc atgaatgtaa 660
aagagatcgc cacgggtaat gcgataaggg cgatcgttga gtacatgcag gccattaccg 720
cgccagacaa tcaccagctc acaaaaatca tgtgtatgtt cagcaaagac atcttgcgga 780
taacggtcag ccacagcgac tgcctgctgg tcgctggcaa aaaaatcatc tttgagaagt 840
tttaactgat gcgccaccgt ggctacctcg gccagagaac gaagttgatt attcgcaata 900
tggcgtacaa atacgttgag aagattcgcg ttattgcaga aagccatccc gtccctggcg 960
aatatcacgc ggtgaccagt taaactctcg gcgaaaaagc gtcgaaaagt ggttactgtc 1020
gctgaatcca cagcgatagg cgatgtcagt aacgctggcc tcgctgtggc gtagcagatg 1080
tcgggctttc atcagtcgca ggcggttcag gtatcgctga ggcgtcagtc ccgtttgctg 1140
cttaagctgc cgatgtagcg tacgcagtga aagagaaaat tgatccgcca cggcatccca 1200
attcacctca tcggcaaaat ggtcctccag ccaggccaga agcaagttga gacgtgatgc 1260
gctgttttcc aggttctcct gcaaactgct tttacgcagc aagagcagta attgcataaa 1320
caagatctcg cgactggcgg tcgagggtaa atcattttcc ccttcctgct gttccatctg 1380
tgcaaccagc tgtcgcacct gctgcaatac gctgtggtta acgcgccagt gagacggata 1440
ctgcccatcc agctcttgtg gcagcaactg attcagcccg gcgagaaact gaaatcgatc 1500
cggcgagcga tacagcacat tggtcagaca cagattatcg gtatgttcat acagatgccg 1560
atcatgatcg cgtacgaaac agaccgtgcc accggtgatg gtatagggct gcccattaaa 1620
cacatgaata cccgtgccat gttcgacaat cacaatttca tgaaaatcat gatgatgttc 1680
aggaaaatcc gcctgcggga gccggggttc tatcgccacg gacgcgttac cagacggaaa 1740
aaaatccaca ctatgtaata cggtcatact ggcctcctga tgtcgtcaac acggcgaaat 1800
agtaatcacg aggtcaggtt cttaccttaa attttcgacg gaaaaccacg taaaaaacgt 1860
cgatttttca agatacagcg tgaattttca ggaaatgcgg tgagcatcac atcaccacaa 1920
ttcagcaaat tgtgaacatc atcacgttca tctttccctg gttgccaatg gcccattttc 1980
ctgtcagtaa cgagaaggtc gcgaattcag gcgcttttta gactggtcgt aatgaaattc 2040
aggaggatgg tcgacatgaa agccacgaaa ctggttctgg gtgctgttat cctgggttcc 2100
acgctgctgg cgggttgttc ctctaatgcg aaaatcgatc aaggcatcaa cccgtatgtg 2160
ggctttgaaa tgggttacga ttggctgggt cgtatgccgt ataaaggcag cgttgaaaat 2220
ggtgcataca aagctcaggg cgtccaactg accgcgaaac tgggttatcc gatcacggat 2280
gacctggata tttacacccg tctgggcggt atggtctggc gtgcagatac gaaaagcaac 2340
gtgtatggca aaaatcatga caccggtgtg tctccggttt tcgcgggcgg tgttgaatat 2400
gccatcacgc cggaaattgc aacccgtctg gaataccagt ggaccaacaa tatcggcgat 2460
gcacacacga ttggtacccg cccggataac ggcattccgg gtatcgacga aattctggcg 2520
gccctgccga aaacggatac ctataaactg attctgaatg gcaaaacgct gaaaggtgaa 2580
accacgaccg aagctgttga cgcagctacc gcggaaaaag tcttcaaaca atacgctaac 2640
gataatggcg tggacggtga atggacctac gatgacgcga cgaaaacctt cacggtcacc 2700
gaaaaaccgg aagtgatcga tgccagtgaa ctgacgccgg cagttacgac ctataaactg 2760

-continued

```
gtcattaacg gcaaaaccct gaaaggtgaa acgaccacgg aagctgtgga tgcagcaacc   2820
gcagaaaaag ttttcaaaca gtacgccaat gacaacggtg tggacggcga atggacgtac   2880
gatgacgcaa cgaaaacctt cacggtgacc gaaaaaccgg aagttatcga tgcctccgaa   2940
ctgaccccgg cagtcaccac gtataaactg gtgatcaatg gtaaaacgct gaaaggcgaa   3000
accacgacca aagcggttga tgccgaaacc gcagaaaaag cttttaaaca atacgcgaat   3060
gacaatggcg tggatggcgt gtggacctac gatgatgcga ccaaaacctt taccgttacc   3120
gaataataat ctagaaggag gaacaatatg aaaaagatta tgctggtctt tattaccctg   3180
attctggtct ctctgccgat tgctcaacaa acggaagctg gcgacgcaag cgcattcaac   3240
aaagaaaaca gcatcagctc tatggcaccg ccggcttcac cgccggcatc gccgaaaacc   3300
ccgatcgaga aaaaacatgc tgatgaaatc gacaaataca tccagggcct ggactacaat   3360
aaaaacaatg tgctggttta tcacggtgat gccgttacga atgtcccgcc gcgtaaaggc   3420
tataaagacg gtaacgaata catcgtggtt gaaaagaaaa agaaaagcat caaccagaac   3480
aatgctgata ttcaagtcgt gaacgcgatc agttccctga cctatccggg cgcactggtc   3540
aaagctaata gcgaactggt ggaaaaccag ccggatgtgc tgccggttaa acgtgacagc   3600
ctgaccctgt ctattgatct gccgggtatg acgaaccaag ataacaaaat cgttgtcaaa   3660
aacgcaacca aaagtaacgt caacaatgct gtgaatacgc tggttgaacg ctggaacgaa   3720
aaatatgcgc aggcctaccc gaatgtgtcc gccaaaattg attatgatga cgaaatggcg   3780
tactcagaat cgcaactgat cgccaaattt ggcaccgcgt tcaaagccgt taacaatagc   3840
ctgaacgtca attttggcgc gatttctgaa ggtaaaatgc aggaaatggt gatctcattc   3900
aaacaaatct actacaacgt caacgtgaac gaaccgaccc gtccgtcgcg ctttttcggc   3960
aaagccgtca cgaaagaaca gctgcaagcg ctgggtgtga atgccgaaaa cccgccggca   4020
tatatttcat cggtggcgta tggtcgccag gtttacctga aactgagcac caacagccat   4080
tctacgaaag ttaaagcggc ctttaaagca gctgtctctg gcaaaagtgt ctccggtgat   4140
gtggaactga ccaacatcat caaaaacagc tctttcaaag ccgttattta tggcggttct   4200
gcaaaagatg aagtccagat tatcgacggc aatctgggtg atctgcgtga cattctgaaa   4260
aaaggcgcga cctttaaccg cgaaacgccg ggtgtgccga tcgcctacac cacgaatttc   4320
ctgaaagata acgaactggc agttatcaaa aacaactcag aatacatcga aaccacgtcg   4380
aaagcttaca ccgatggcaa aattaatatc gaccacagtg gcggttatgt tgcacagttt   4440
aacatttcct gggatgaagt gaattacgac ccggagggta acgaaatcgt tcaacataaa   4500
aactggagtg aaaacaacaa atccaaactg gcgcacttca ccagttccat ttatctgccg   4560
ggcaacgctc gtaatatcaa cgtgtacgcg aaagaatgca ccggtctggc ctgggaatgg   4620
tggcgtacgg tgattgatga ccgcaacctg ccgctggtta aaaatcgcaa catctccatc   4680
tggggcacca ccctgtaccc gaaatatagt aacaaagttg ataacccgat tgaataataa   4740
ggatccagga ggaacaatat gggcgcagac gacgttgttg acagcagcaa atctttcgtt   4800
atggaaaact tcagcagcta tcacggcacc aaaccgggct atgtggactc tattcagaaa   4860
ggcatccaaa aaccgaaaag tggcacccag ggtaactatg atgacgattg gaaaggtttt   4920
tactccacgg acaataaata tgatgcggcc ggctactcgg tcgacaacga aaatccgctg   4980
agcggtaaag caggcggtgt ggttaaagtt acctatccgg gcctgacgaa agttctggcg   5040
ctgaaagtcg ataacgccga aaccatcaaa aaagaactgg gcctgtcact gaccgaaccg   5100
```

-continued

```
ctgatggaac aagtgggtac ggaagaattt atcaaacgtt tcggcgatgg tgcatcccgc   5160
gtcgtgctgt cactgccgtt tgctgaaggc agctctagtg tggaatacat taacaattgg   5220
gaacaagcaa aagctctgag cgttgaactg gaaatcaatt tcgaaacgcg tggtaaacgt   5280
ggtcaagatg cgatgtatga atatatggct caagcgtgtg cgggtaaccg tgtgcgttaa   5340
taaggcgcgc ctggtagtgt ggggtctccc catgcgagag tagggaactg ccaggcatca   5400
aataaaacga aaggctcagt cgaaagactg ggcctttcgt tttatctgtt gtttgtcggt   5460
gaacgctctc ctgagtagga caaatccgcc gggagcggat ttgaacgttg cgaagcaacg   5520
gcccggaggg tggcgggcag gacgcccgcc ataaactgcc aggcatcaaa ttaagcagaa   5580
ggccatcctg acggatggcc tttttgcgtt tctacaaact cgagctcgaa ttcgtaatca   5640
tggtcatagc tgtttcctgt gtgaaattgt tatccgctca caattccaca caacatacga   5700
gccggaagca taaagtgtaa agcctggggt gcctaatgag tgagctaact cacattaatt   5760
gcgttgcgct cactgcccgc tttccagtcg ggaaacctgt cgtgccagct gcattaatga   5820
atcggccaac gcgcggggag aggcggtttg cgtattgggc gctcttccgc ttcctcgctc   5880
actgactcgc tgcgctcggt cgttcggctg cggcgagcgg tatcagctca ctcaaaggcg   5940
gtaatacggt tatccacaga atcaggggat aacgcaggaa agaacatgtg agcaaaaggc   6000
cagcaaaagc ccaggaaccg taaaaaggcc gcgttgctgg cgtttttcca taggctccgc   6060
cccccctgacg agcatcacaa aaatcgacgc tcaagtcaga ggtggcgaaa cccgacagga   6120
ctataaagat accaggcgtt tccccctgga agctccctcg tgcgctctcc tgttccgacc   6180
ctgccgctta ccggatacct gtccgccttt ctcccttcgg gaagcgtggc gctttctcat   6240
agctcacgct gtaggtatct cagttcggtg taggtcgttc gctccaagct gggctgtgtg   6300
cacgaacccc ccgttcagcc cgaccgctgc gccttatccg gtaactatcg tcttgagtcc   6360
aacccggtaa gacacgactt atcgccactg gcagcagcca ctggtaacag gattagcaga   6420
gcgaggtatg taggcggtgc tacagagttc ttgaagtggt ggcctaacta cggctacact   6480
agaaggacag tatttggtat ctgcgctctg ctgaagccag ttaccttcgg aaaaagagtt   6540
ggtagctctt gatccggcaa acaaaccacc gctggtagcg gtggtttttt tgtttgcaag   6600
cagcagatta cgcgcagaaa aaaaggatct caagaagatc ctttgatctt ttctacgggg   6660
tctgacgctc agtggaacga aaactcacgt taagggattt tggtcatgag attatcaaaa   6720
aggatcttca cctagatcct tttaaattaa aaatgaagtt ttagcacgtg ctattattga   6780
agcatttatc agggttattg tctcatgagc ggatacatat ttgaatgtat ttagaaaaat   6840
aaacaaatag gggttccgcg cacatttccc cgaaaagtgc cacctgtatg cggtgtgaaa   6900
taccgcacag atgcgtaagg agaaaatacc gcatcaggaa attgtaagcg ttaataattc   6960
agaagaactc gtcaagaagg cgatagaagg cgatgcgctg cgaatcggga gcggcgatac   7020
cgtaaagcac gaggaagcgg tcagcccatt cgccgccaag ctcttcagca atatcacggg   7080
tagccaacgc tatgtcctga tagcggtccg ccacacccag ccggccacag tcgatgaatc   7140
cagaaaagcg gccattttcc accatgatat tcggcaagca ggcatcgcca tgggtcacga   7200
cgagatcctc gccgtcgggc atgctcgcct tgagcctggc gaacagttcg gctggcgcga   7260
gcccctgatg ctcttcgtcc agatcatcct gatcgacaag accggcttcc atccgagtac   7320
gtgctcgctc gatgcgatgt ttcgcttggt ggtcgaatgg gcaggtagcc ggatcaagcg   7380
tatgcagccg ccgcattgca tcagccatga tggatacttt ctcggcagga gcaaggtgag   7440
atgacaggag atcctgcccc ggcacttcgc ccaatagcag ccagtccctt cccgcttcag   7500
```

```
tgacaacgtc gagcacagct gcgcaaggaa cgcccgtcgt ggccagccac gatagccgcg   7560

ctgcctcgtc ttgcagttca ttcagggcac cggacaggtc ggtcttgaca aaaagaaccg   7620

ggcgcccctg cgctgacagc cggaacacgg cggcatcaga gcagccgatt gtctgttgtg   7680

cccagtcata gccgaatagc ctctccaccc aagcggccgg agaacctgcg tgcaatccat   7740

cttgttcaat catgcgaaac gatcctcatc ctgtctcttg atcagagctt gatcccctgc   7800

gccatcagat ccttggcggc gagaaagcca tccagtttac tttgcagggc ttcccaacct   7860

taccagaggg cgccccagct ggcaattccg gttcgcttgc tgtccataaa accgcccagt   7920

agaagcatat g                                                         7931
```

<210> SEQ ID NO 16
<211> LENGTH: 7931
<212> TYPE: DNA
<213> ORGANISM: Artificial Sequence
<220> FEATURE:
<223> OTHER INFORMATION: pVX-191

<400> SEQUENCE: 16

```
aagcttaatt aatctttctg cgaattgaga tgacgccact ggctgggcgt catcccggtt     60

tcccgggtaa acaccaccga aaaatagtta ctatcttcaa agccacattc ggtcgaaata    120

tcactgatta acaggcggct atgctggaga agatattgcg catgacacac tctgacctgt    180

cgcagatatt gattgatggt cattccagtc tgctggcgaa attgctgacg caaaacgcgc    240

tcactgcacg atgcctcatc acaaaattta tccagcgcaa agggactttt caggctagcc    300

gccagccggg taatcagctt atccagcaac gtttcgctgg atgttggcgg caacgaatca    360

ctggtgtaac gatggcgatt cagcaacatc accaactgcc cgaacagcaa ctcagccatt    420

tcgttagcaa acggcacatg ctgactactt tcatgctcaa gctgaccgat aacctgccgc    480

gcctgcgcca tccccatgct acctaagcgc cagtgtggtt gccctgcgct ggcgttaaat    540

cccggaatcg ccccctgcca gtcaagattc agcttcagac gctccgggca ataaataata    600

ttctgcaaaa ccagatcgtt aacggaagcg taggagtgtt tatcgtcagc atgaatgtaa    660

aagagatcgc cacgggtaat gcgataaggg cgatcgttga gtacatgcag gccattaccg    720

cgccagacaa tcaccagctc acaaaaatca tgtgtatgtt cagcaaagac atcttgcgga    780

taacggtcag ccacagcgac tgcctgctgg tcgctggcaa aaaaatcatc tttgagaagt    840

tttaactgat gcgccaccgt ggctacctcg gccagagaac gaagttgatt attcgcaata    900

tggcgtacaa atacgttgag aagattcgcg ttattgcaga aagccatccc gtccctggcg    960

aatatcacgc ggtgaccagt taaactctcg gcgaaaaagc gtcgaaaagt ggttactgtc   1020

gctgaatcca cagcgatagg cgatgtcagt aacgctggcc tcgctgtggc gtagcagatg   1080

tcgggctttc atcagtcgca ggcggttcag gtatcgctga ggcgtcagtc ccgtttgctg   1140

cttaagctgc cgatgtagcg tacgcagtga aagagaaaat tgatccgcca cggcatccca   1200

attcacctca tcggcaaaat ggtcctccag ccaggccaga agcaagttga gacgtgatgc   1260

gctgttttcc aggttctcct gcaaactgct tttacgcagc aagagcagta attgcataaa   1320

caagatctcg cgactggcgg tcgagggtaa atcattttcc ccttcctgct gttccatctg   1380

tgcaaccagc tgtcgcacct gctgcaatac gctgtggtta acgcgccagt gagacggata   1440

ctgcccatcc agctcttgtg gcagcaactg attcagcccg gcgagaaact gaaatcgatc   1500

cggcgagcga tacagcacat tggtcagaca cagattatcg gtatgttcat acagatgccg   1560
```

-continued

```
atcatgatcg cgtacgaaac agaccgtgcc accggtgatg gtatagggct gcccattaaa   1620
cacatgaata cccgtgccat gttcgacaat cacaatttca tgaaaatcat gatgatgttc   1680
aggaaaatcc gcctgcggga gccggggttc tatcgccacg gacgcgttac cagacggaaa   1740
aaaatccaca ctatgtaata cggtcatact ggcctcctga tgtcgtcaac acggcgaaat   1800
agtaatcacg aggtcaggtt cttaccttaa attttcgacg gaaaaccacg taaaaaacgt   1860
cgatttttca agatacagcg tgaattttca ggaaatgcgg tgagcatcac atcaccacaa   1920
ttcagcaaat tgtgaacatc atcacgttca tctttccctg gttgccaatg gcccattttc   1980
ctgtcagtaa cgagaaggtc gcgaattcag gcgcttttta gactggtcgt aatgaaattc   2040
aggaggatgg tcgacatgaa agccacgaaa ctggttctgg gtgctgttat cctgggttcc   2100
acgctgctgg cgggttgttc ctctaatgcg aaaatcgatc aaggcatcaa cccgtatgtg   2160
ggctttgaaa tgggttacga ttggctgggt cgtatgccgt ataaaggcag cgttgaaaat   2220
ggtgcataca aagctcaggg cgtccaactg accgcgaaac tgggttatcc gatcacggat   2280
gacctggata tttacacccg tctgggcggt atggtctggc gtgcagatac gaaaagcaac   2340
gtgtatggca aaaatcatga caccggtgtg tctccggttt tcgcgggcgg tgttgaatat   2400
gccatcacgc cggaaattgc aacccgtctg gaataccagt ggaccaacaa tatcggcgat   2460
gcacacacga ttggtacccg cccggataac ggcattccgg gtatcgacga aattctggcg   2520
gccctgccga aaacggatac ctataaactg attctgaatg gcaaaacgct gaaaggtgaa   2580
accacgaccg aagctgttga cgcagctacc gcggaaaaag tcttcaaaca atacgctaac   2640
gataatggcg tggacggtga atggacctac gatgacgcga cgaaaacctt cacggtcacc   2700
gaaaaaccgg aagtgatcga tgccagtgaa ctgacgccgg cagttacgac ctataaactg   2760
gtcattaacg gcaaaaccct gaaaggtgaa acgaccacgg aagctgtgga tgcagcaacc   2820
gcagaaaaag ttttcaaaca gtacgccaat gacaacggtg tggacggcga atggacgtac   2880
gatgacgcaa cgaaaacctt cacggtgacc gaaaaaccgg aagttatcga tgcctccgaa   2940
ctgaccccgg cagtcaccac gtataaactg gtgatcaatg gtaaaacgct gaaaggcgaa   3000
accacgacca aagcggttga tgccgaaacc gcagaaaaag cttttaaaca atacgcgaat   3060
gacaatggcg tggatggcgt gtggacctac gatgatgcga ccaaaacctt taccgttacc   3120
gaataataat ctagaaggag gaacaatatg aaaaagatta tgctggtctt tattaccctg   3180
attctggtgt ccctgccgat tgcacaacaa accgaagcgg gcgatgcgag cgccttcaac   3240
aaagaaaaca gcatcagctc tatggcaccg ccggcttcac cgccggcatc gccgaaaacc   3300
ccgatcgaga aaaaacatgc tgatgaaatc gacaaataca tccagggcct ggactacaat   3360
aaaaacaatg tgctggttta tcacggtgat gccgttacga atgtcccgcc gcgtaaaggc   3420
tataaagacg gtaacgaata catcgtggtt gaaaagaaaa agaaaagcat caaccagaac   3480
aatgctgata ttcaagtcgt gaacgcgatc agttccctga cctatccggg cgcactggtc   3540
aaagctaata gcgaactggt ggaaaaccag ccggatgtgc tgccggttaa acgtgacagc   3600
ctgaccctgt ctattgatct gccgggtatg acgaaccaag ataacaaaat cgttgtcaaa   3660
aacgcaacca aaagtaacgt caacaatgct gtgaatacgc tggttgaacg ctggaacgaa   3720
aaatatgcgc aggcctaccc gaatgtgtcc gccaaaattg attatgatga cgaaatggcg   3780
tactcagaat cgcaactgat cgccaaattt ggcaccgcgt tcaaagccgt taacaatagc   3840
ctgaacgtca attttggcgc gatttctgaa ggtaaaatgc aggaaatggt gatctcattc   3900
aaacaaatct actacaacgt caacgtgaac gaaccgaccc gtccgtcgcg ctttttcggc   3960
```

-continued

```
aaagccgtca cgaaagaaca gctgcaagcg ctgggtgtga atgccgaaaa cccgccggca   4020
tatatttcat cggtggcgta tggtcgccag gtttacctga aactgagcac caacagccat   4080
tctacgaaag ttaaagcggc ctttaaagca gctgtctctg gcaaaagtgt ctccggtgat   4140
gtggaactga ccaacatcat caaaaacagc tctttcaaag ccgttattta tggcggttct   4200
gcaaaagatg aagtccagat tatcgacggc aatctgggtg atctgcgtga cattctgaaa   4260
aaaggcgcga cctttaaccg cgaaacgccg ggtgtgccga tcgcctacac cacgaatttc   4320
ctgaaagata acgaactggc agttatcaaa aacaactcag aatacatcga aaccacgtcg   4380
aaagcttaca ccgatggcaa aattaatatc gaccacagtg gcggttatgt tgcacagttt   4440
aacatttcct gggatgaagt gaattacgac ccggagggta acgaaatcgt tcaacataaa   4500
aactggagtg aaaacaacaa atccaaaacc gcgcacttca cgagttccat ttatctgccg   4560
ggcaacgctc gtaatatcaa cgtgtacgcg aaagaatgca ccggtctggc ctgggaatgg   4620
tggcgtacgg tgattgatga ccgcaacctg ccgctggtta aaaatcgcaa catctccatc   4680
tggggcacca ccctgtaccc gaaatactcc aacaaagttg ataacccgat tgaataataa   4740
ggatccagga ggaacaatat gggcgcagac gacgttgttg acagcagcaa atctttcgtt   4800
atggaaaact tcagcagcta tcacggcacc aaaccgggct atgtggactc tattcagaaa   4860
ggcatccaaa aaccgaaaag tggcacccag ggtaactatg atgacgattg gaaaggtttt   4920
tactccacgg acaataaata tgatgcggcc ggctactcgg tcgacaacga aaatccgctg   4980
agcggtaaag caggcggtgt ggttaaagtt acctatccgg gcctgacgaa agttctggcg   5040
ctgaaagtcg ataacgccga aaccatcaaa aaagaactgg gcctgtcact gaccgaaccg   5100
ctgatggaac aagtgggtac ggaagaattt atcaaacgtt tcggcgatgg tgcatcccgc   5160
gtcgtgctgt cactgccgtt tgctgaaggc agctctagtg tggaatacat taacaattgg   5220
gaacaagcaa aagctctgag cgttgaactg gaaatcaatt tcgaaacgcg tggtaaacgt   5280
ggtcaagatg cgatgtatga atatatggct caagcgtgtg cgggtaaccg tgtgcgttaa   5340
taaggcgcgc ctggtagtgt ggggtctccc catgcgagag tagggaactg ccaggcatca   5400
aataaaacga aaggctcagt cgaaagactg ggcctttcgt tttatctgtt gtttgtcggt   5460
gaacgctctc ctgagtagga caaatccgcc gggagcggat ttgaacgttg cgaagcaacg   5520
gcccggaggg tggcgggcag gacgcccgcc ataaactgcc aggcatcaaa ttaagcagaa   5580
ggccatcctg acggatggcc tttttgcgtt tctacaaact cgagctcgaa ttcgtaatca   5640
tggtcatagc tgtttcctgt gtgaaattgt tatccgctca caattccaca caacatacga   5700
gccggaagca taaagtgtaa agcctggggt gcctaatgag tgagctaact cacattaatt   5760
gcgttgcgct cactgcccgc tttccagtcg ggaaacctgt cgtgccagct gcattaatga   5820
atcggccaac gcgcggggag aggcggtttg cgtattgggc gctcttccgc ttcctcgctc   5880
actgactcgc tgcgctcggt cgttcggctg cggcgagcgg tatcagctca ctcaaaggcg   5940
gtaatacggt tatccacaga atcaggggat aacgcaggaa agaacatgtg agcaaaaggc   6000
cagcaaaagc ccaggaaccg taaaaaggcc gcgttgctgg cgtttttcca taggctccgc   6060
ccccctgacg agcatcacaa aaatcgacgc tcaagtcaga ggtggcgaaa cccgacagga   6120
ctataaagat accaggcgtt tccccctgga agctccctcg tgcgctctcc tgttccgacc   6180
ctgccgctta ccggatacct gtccgccttt ctcccttcgg gaagcgtggc gctttctcat   6240
agctcacgct gtaggtatct cagttcggtg taggtcgttc gctccaagct gggctgtgtg   6300
```

cacgaacccc ccgttcagcc cgaccgctgc gccttatccg gtaactatcg tcttgagtcc 6360
aacccggtaa gacacgactt atcgccactg gcagcagcca ctggtaacag gattagcaga 6420
gcgaggtatg taggcggtgc tacagagttc ttgaagtggt ggcctaacta cggctacact 6480
agaaggacag tatttggtat ctgcgctctg ctgaagccag ttaccttcgg aaaaagagtt 6540
ggtagctctt gatccggcaa acaaaccacc gctggtagcg gtggtttttt tgtttgcaag 6600
cagcagatta cgcgcagaaa aaaaggatct caagaagatc ctttgatctt ttctacgggg 6660
tctgacgctc agtggaacga aaactcacgt taagggattt tggtcatgag attatcaaaa 6720
aggatcttca cctagatcct tttaaattaa aaatgaagtt ttagcacgtg ctattattga 6780
agcatttatc agggttattg tctcatgagc ggatacatat ttgaatgtat ttagaaaaat 6840
aaacaaatag gggttccgcg cacatttccc cgaaaagtgc cacctgtatg cggtgtgaaa 6900
taccgcacag atgcgtaagg agaaaatacc gcatcaggaa attgtaagcg ttaataattc 6960
agaagaactc gtcaagaagg cgatagaagg cgatgcgctg cgaatcggga gcggcgatac 7020
cgtaaagcac gaggaagcgg tcagcccatt cgccgccaag ctcttcagca atatcacggg 7080
tagccaacgc tatgtcctga tagcggtccg ccacacccag ccggccacag tcgatgaatc 7140
cagaaaagcg gccattttcc accatgatat tcggcaagca ggcatcgcca tgggtcacga 7200
cgagatcctc gccgtcgggc atgctcgcct tgagcctggc gaacagttcg gctggcgcga 7260
gcccctgatg ctcttcgtcc agatcatcct gatcgacaag accggcttcc atccgagtac 7320
gtgctcgctc gatgcgatgt ttcgcttggt ggtcgaatgg gcaggtagcc ggatcaagcg 7380
tatgcagccg ccgcattgca tcagccatga tggatacttt ctcggcagga gcaaggtgag 7440
atgacaggag atcctgcccc ggcacttcgc ccaatagcag ccagtccctt cccgcttcag 7500
tgacaacgtc gagcacagct gcgcaaggaa cgcccgtcgt ggccagccac gatagccgcg 7560
ctgcctcgtc ttgcagttca ttcagggcac cggacaggtc ggtcttgaca aaaagaaccg 7620
ggcgcccctg cgctgacagc cggaacacgg cggcatcaga gcagccgatt gtctgttgtg 7680
cccagtcata gccgaatagc ctctccaccc aagcggccgg agaacctgcg tgcaatccat 7740
cttgttcaat catgcgaaac gatcctcatc ctgtctcttg atcagagctt gatcccctgc 7800
gccatcagat ccttggcggc gagaaagcca tccagtttac tttgcagggc ttcccaacct 7860
taccagaggg cgccccagct ggcaattccg gttcgcttgc tgtccataaa accgcccagt 7920
agaagcatat g 7931

<210> SEQ ID NO 17
<211> LENGTH: 7844
<212> TYPE: DNA
<213> ORGANISM: Artificial Sequence
<220> FEATURE:
<223> OTHER INFORMATION: pVX-183

<400> SEQUENCE: 17
aagcttaatt aatctttctg cgaattgaga tgacgccact ggctgggcgt catcccggtt 60
tcccgggtaa acaccaccga aaaatagtta ctatcttcaa agccacattc ggtcgaaata 120
tcactgatta acaggcggct atgctggaga agatattgcg catgacacac tctgacctgt 180
cgcagatatt gattgatggt cattccagtc tgctggcgaa attgctgacg caaaacgcgc 240
tcactgcacg atgcctcatc acaaaattta tccagcgcaa agggactttt caggctagcc 300
gccagccggg taatcagctt atccagcaac gtttcgctgg atgttggcgg caacgaatca 360
ctggtgtaac gatggcgatt cagcaacatc accaactgcc cgaacagcaa ctcagccatt 420

-continued

```
tcgttagcaa acggcacatg ctgactactt tcatgctcaa gctgaccgat aacctgccgc    480
gcctgcgcca tccccatgct acctaagcgc cagtgtggtt gccctgcgct ggcgttaaat    540
cccggaatcg ccccctgcca gtcaagattc agcttcagac gctccgggca ataaataata    600
ttctgcaaaa ccagatcgtt aacggaagcg taggagtgtt tatcgtcagc atgaatgtaa    660
aagagatcgc cacgggtaat gcgataaggg cgatcgttga gtacatgcag gccattaccg    720
cgccagacaa tcaccagctc acaaaaatca tgtgtatgtt cagcaaagac atcttgcgga    780
taacggtcag ccacagcgac tgcctgctgg tcgctggcaa aaaaatcatc tttgagaagt    840
tttaactgat gcgccaccgt ggctacctcg gccagagaac gaagttgatt attcgcaata    900
tggcgtacaa atacgttgag aagattcgcg ttattgcaga aagccatccc gtccctggcg    960
aatatcacgc ggtgaccagt taaactctcg gcgaaaaagc gtcgaaaagt ggttactgtc   1020
gctgaatcca cagcgatagg cgatgtcagt aacgctggcc tcgctgtggc gtagcagatg   1080
tcgggctttc atcagtcgca ggcggttcag gtatcgctga ggcgtcagtc ccgtttgctg   1140
cttaagctgc cgatgtagcg tacgcagtga aagagaaaat tgatccgcca cggcatccca   1200
attcacctca tcggcaaaat ggtcctccag ccaggccaga agcaagttga gacgtgatgc   1260
gctgttttcc aggttctcct gcaaactgct tttacgcagc aagagcagta attgcataaa   1320
caagatctcg cgactggcgg tcgagggtaa atcattttcc ccttcctgct gttccatctg   1380
tgcaaccagc tgtcgcacct gctgcaatac gctgtggtta acgcgccagt gagacggata   1440
ctgcccatcc agctcttgtg gcagcaactg attcagcccg gcgagaaact gaaatcgatc   1500
cggcgagcga tacagcacat tggtcagaca cagattatcg gtatgttcat acagatgccg   1560
atcatgatcg cgtacgaaac agaccgtgcc accggtgatg gtatagggct gcccattaaa   1620
cacatgaata cccgtgccat gttcgacaat cacaatttca tgaaaatcat gatgatgttc   1680
aggaaaatcc gcctgcggga gccggggttc tatcgccacg gacgcgttac cagacggaaa   1740
aaaatccaca ctatgtaata cggtcatact ggcctcctga tgtcgtcaac acggcgaaat   1800
agtaatcacg aggtcaggtt cttaccttaa attttcgacg gaaaaccacg taaaaaacgt   1860
cgatttttca agatacagcg tgaattttca ggaaatgcgg tgagcatcac atcaccacaa   1920
ttcagcaaat tgtgaacatc atcacgttca tctttccctg gttgccaatg gcccattttc   1980
ctgtcagtaa cgagaaggtc gcgaattcag gcgcttttta gactggtcgt aatgaaattc   2040
aggaggatgg tcgacatgaa agccacgaaa ctggttctgg gtgctgttat cctgggttcc   2100
acgctgctgg cgggttgttc ctctaatgcg aaaatcgatc aaggcatcaa cccgtatgtg   2160
ggctttgaaa tgggttacga ttggctgggt cgtatgccgt ataaaggcag cgttgaaaat   2220
ggtgcataca aagctcaggg cgtccaactg accgcgaaac tgggttatcc gatcacggat   2280
gacctggata tttacacccg tctgggcggt atggtctggc gtgcagatac gaaaagcaac   2340
gtgtatggca aaaatcatga caccggtgtg tctccggttt tcgcgggcgg tgttgaatat   2400
gccatcacgc cggaaattgc aacccgtctg gaataccagt ggaccaacaa tatcggcgat   2460
gcacacacga ttggtacccg cccggataac ggcattccgg gtatcgacga aattctggcg   2520
gccctgccga aaacggatac ctataaactg attctgaatg gcaaaacgct gaaaggtgaa   2580
accacgaccg aagctgttga cgcagctacc gcggaaaaag tcttcaaaca atacgctaac   2640
gataatggcg tggacggtga atggacctac gatgacgcga cgaaaacctt cacggtcacc   2700
gaaaaaccgg aagtgatcga tgccagtgaa ctgacgccgg cagttacgac ctataaactg   2760
```

-continued

```
gtcattaacg gcaaaaccct gaaaggtgaa acgaccacgg aagctgtgga tgcagcaacc   2820

gcagaaaaag ttttcaaaca gtacgccaat gacaacggtg tggacggcga atggacgtac   2880

gatgacgcaa cgaaaacctt cacggtgacc gaaaaaccgg aagttatcga tgcctccgaa   2940

ctgaccccgg cagtcaccac gtataaactg gtgatcaatg gtaaaacgct gaaaggcgaa   3000

accacgacca aagcggttga tgccgaaacc gcagaaaaag cttttaaaca atacgcgaat   3060

gacaatggcg tggatggcgt gtggacctac gatgatgcga ccaaaacctt taccgttacc   3120

gaataataat ctagaaggag gaacaatatg atccgcttca aaaagaccaa actgattgcg   3180

agcattgcga tggcactgtg tctgttctcc cagccggtga tttcgttctc aaaagatatt   3240

accgacaaaa atcagtccat cgattcaggc attagctctc tgtcttataa ccgtaatgaa   3300

gtgctggcgt ccaatggtga caaaatcgaa tcatttgttc cgaaagaagg caaaaaagcc   3360

ggtaacaaat tcattgtggt tgaacgtcag aaacgctctc tgaccacgag tccggttgat   3420

atctccatta tcgattcagt caatgaccgt acctatccgg gtgcactgca actggcagac   3480

aaagcatttg tggaaaaccg tccgacgatt ctgatggtta aacgcaaacc gattaacatc   3540

aatattgatc tgccgggcct gaaaggtgaa aatagtatca aagtggatga cccgacctat   3600

ggcaaagttt cgggtgcaat tgatgaactg gtcagcaaat ggaacgaaaa atacagttcc   3660

acccatacgc tgccggcgcg tacccagtat tcggaaagca tggtgtactc taaaagtcaa   3720

atctcatcgg cgctgaacgt taatgccaaa gtcctggaaa actctctggg tgtggatttt   3780

aatgcggttg ccaacaatga gaaaaaagtg atgatcctgg catataaaca gattttctac   3840

accgttagtg ctgatctgcc gaaaaacccg tctgacctgt ttgatgacag tgtcacgttc   3900

aacgatctga aacaaaaagg cgtgtctaat gaagcgccgc cgctgatggt gtctaacgtt   3960

gcctatggtc gtaccattta cgttaaactg gaaaccacga gctctagtaa agatgtccag   4020

gcggccttta aagccctgat caaaaacacc gatatcaaaa atagccagca atacaaagac   4080

atctacgaaa attcctcatt caccgcagtc gtgctgggcg gtgatgctca ggaacacaac   4140

aaagttgtca cgaaagattt tgacgaaatc cgcaaagtga ttaaagataa cgcaaccttc   4200

tcgacgaaaa atccggctta tccgatttcg tacaccagcg tttttctgaa agataacagc   4260

gtcgcagctg tgcataataa aaccgactat atcgaaacca ccagcaccga atacagcaaa   4320

ggcaaaatta atctggatca ctccggtgca tatgtcgctc agttcgaagt ggcctgggat   4380

gaagtttcat acgacaaaga aggcaatgaa gtgctgaccc ataaaacgtg ggatggtaac   4440

tatcaagaca aaaccgcaca ctactccacg gttattccgc tggaagcaaa cgctcgtaat   4500

atccgcatta aagcgcgtga atgcaccggt ctggcatggg aatggtggcg tgatgtcatc   4560

agcgaatatg acgtgccgct gacgaacaat atcaatgtgt caatctgggg caccacgctg   4620

tatccgggta gttccatcac ctataattaa taaggatcca ggaggaacaa tatgggcgca   4680

gacgacgttg ttgacagcag caaatctttc gttatggaaa acttcagcag ctatcacggc   4740

accaaaccgg gctatgtgga ctctattcag aaaggcatcc aaaaaccgaa aagtggcacc   4800

cagggtaact atgatgacga ttggaaaggt ttttactcca cggacaataa atatgatgcg   4860

gccggctact cggtcgacaa cgaaaatccg ctgagcggta aagcaggcgg tgtggttaaa   4920

gttacctatc cgggcctgac gaaagttctg gcgctgaaag tcgataacgc cgaaaccatc   4980

aaaaaagaac tgggcctgtc actgaccgaa ccgctgatgg aacaagtggg tacggaagaa   5040

tttatcaaac gtttcggcga tggtgcatcc cgcgtcgtgc tgtcactgcc gtttgctgaa   5100

ggcagctcta gtgtggaata cattaacaat tgggaacaag caaaagctct gagcgttgaa   5160
```

-continued

```
ctggaaatca atttcgaaac gcgtggtaaa cgtggtcaag atgcgatgta tgaatatatg   5220
gctcaagcgt gtgcgggtaa ccgtgtgcgt taataaggcg cgcctggtag tgtggggtct   5280
ccccatgcga gagtagggaa ctgccaggca tcaaataaaa cgaaaggctc agtcgaaaga   5340
ctgggccttt cgttttatct gttgtttgtc ggtgaacgct ctcctgagta ggacaaatcc   5400
gccgggagcg gatttgaacg ttgcgaagca acggcccgga gggtggcggg caggacgccc   5460
gccataaact gccaggcatc aaattaagca gaaggccatc ctgacggatg gcctttttgc   5520
gtttctacaa actcgagctc gaattcgtaa tcatggtcat agctgtttcc tgtgtgaaat   5580
tgttatccgc tcacaattcc acacaacata cgagccggaa gcataaagtg taaagcctgg   5640
ggtgcctaat gagtgagcta actcacatta attgcgttgc gctcactgcc cgctttccag   5700
tcgggaaacc tgtcgtgcca gctgcattaa tgaatcggcc aacgcgcggg gagaggcggt   5760
ttgcgtattg ggcgctcttc cgcttcctcg ctcactgact cgctgcgctc ggtcgttcgg   5820
ctgcggcgag cggtatcagc tcactcaaag gcggtaatac ggttatccac agaatcaggg   5880
gataacgcag gaaagaacat gtgagcaaaa ggccagcaaa agcccaggaa ccgtaaaaag   5940
gccgcgttgc tggcgttttt ccataggctc cgcccccctg acgagcatca caaaaatcga   6000
cgctcaagtc agaggtggcg aaacccgaca ggactataaa gataccaggc gtttccccct   6060
ggaagctccc tcgtgcgctc tcctgttccg accctgccgc ttaccggata cctgtccgcc   6120
tttctccctt cgggaagcgt ggcgctttct catagctcac gctgtaggta tctcagttcg   6180
gtgtaggtcg ttcgctccaa gctgggctgt gtgcacgaac cccccgttca gcccgaccgc   6240
tgcgccttat ccggtaacta tcgtcttgag tccaacccgg taagacacga cttatcgcca   6300
ctggcagcag ccactggtaa caggattagc agagcgaggt atgtaggcgg tgctacagag   6360
ttcttgaagt ggtggcctaa ctacggctac actagaagga cagtatttgg tatctgcgct   6420
ctgctgaagc cagttacctt cggaaaaaga gttggtagct cttgatccgg caaacaaacc   6480
accgctggta gcggtggttt ttttgtttgc aagcagcaga ttacgcgcag aaaaaaagga   6540
tctcaagaag atcctttgat cttttctacg gggtctgacg ctcagtggaa cgaaaactca   6600
cgttaaggga ttttggtcat gagattatca aaaaggatct tcacctagat ccttttaaat   6660
taaaaatgaa gttttagcac gtgctattat tgaagcattt atcagggtta ttgtctcatg   6720
agcggataca tatttgaatg tatttagaaa aataaacaaa taggggttcc gcgcacattt   6780
ccccgaaaag tgccacctgt atgcggtgtg aaataccgca cagatgcgta aggagaaaat   6840
accgcatcag gaaattgtaa gcgttaataa ttcagaagaa ctcgtcaaga aggcgataga   6900
aggcgatgcg ctgcgaatcg ggagcggcga taccgtaaag cacgaggaag cggtcagccc   6960
attcgccgcc aagctcttca gcaatatcac gggtagccaa cgctatgtcc tgatagcggt   7020
ccgccacacc cagccggcca cagtcgatga atccagaaaa gcggccattt tccaccatga   7080
tattcggcaa gcaggcatcg ccatgggtca cgacgagatc ctcgccgtcg ggcatgctcg   7140
ccttgagcct ggcgaacagt tcggctggcg cgagcccctg atgctcttcg tccagatcat   7200
cctgatcgac aagaccggct tccatccgag tacgtgctcg ctcgatgcga tgtttcgctt   7260
ggtggtcgaa tgggcaggta gccggatcaa gcgtatgcag ccgccgcatt gcatcagcca   7320
tgatggatac tttctcggca ggagcaaggt gagatgacag gagatcctgc cccggcactt   7380
cgcccaatag cagccagtcc cttcccgctt cagtgacaac gtcgagcaca gctgcgcaag   7440
gaacgcccgt cgtggccagc cacgatagcc gcgctgcctc gtcttgcagt tcattcaggg   7500
```

caccggacag gtcggtcttg acaaaaagaa ccgggcgccc ctgcgctgac agccggaaca 7560
cggcggcatc agagcagccg attgtctgtt gtgcccagtc atagccgaat agcctctcca 7620
cccaagcggc cggagaacct gcgtgcaatc catcttgttc aatcatgcga aacgatcctc 7680
atcctgtctc ttgatcagag cttgatcccc tgcgccatca gatccttggc ggcgagaaag 7740
ccatccagtt tactttgcag ggcttcccaa ccttaccaga gggcgcccca gctggcaatt 7800
ccggttcgct tgctgtccat aaaaccgccc agtagaagca tatg 7844

<210> SEQ ID NO 18
<211> LENGTH: 8084
<212> TYPE: DNA
<213> ORGANISM: Artificial Sequence
<220> FEATURE:
<223> OTHER INFORMATION: pVX-196

<400> SEQUENCE: 18
aagcttaatt aatctttctg cgaattgaga tgacgccact ggctgggcgt catcccggtt 60
tcccgggtaa acaccaccga aaaatagtta ctatcttcaa agccacattc ggtcgaaata 120
tcactgatta acaggcggct atgctggaga agatattgcg catgacacac tctgacctgt 180
cgcagatatt gattgatggt cattccagtc tgctggcgaa attgctgacg caaaacgcgc 240
tcactgcacg atgcctcatc acaaaattta tccagcgcaa agggactttt caggctagcc 300
gccagccggg taatcagctt atccagcaac gtttcgctgg atgttggcgg caacgaatca 360
ctggtgtaac gatggcgatt cagcaacatc accaactgcc cgaacagcaa ctcagccatt 420
tcgttagcaa acggcacatg ctgactactt tcatgctcaa gctgaccgat aacctgccgc 480
gcctgcgcca tccccatgct acctaagcgc cagtgtggtt gccctgcgct ggcgttaaat 540
cccggaatcg ccccctgcca gtcaagattc agcttcagac gctccgggca ataaataata 600
ttctgcaaaa ccagatcgtt aacggaagcg taggagtgtt tatcgtcagc atgaatgtaa 660
aagagatcgc cacgggtaat gcgataaggg cgatcgttga gtacatgcag gccattaccg 720
cgccagacaa tcaccagctc acaaaaatca tgtgtatgtt cagcaaagac atcttgcgga 780
taacggtcag ccacagcgac tgcctgctgg tcgctggcaa aaaaatcatc tttgagaagt 840
tttaactgat gcgccaccgt ggctacctcg gccagagaac gaagttgatt attcgcaata 900
tggcgtacaa atacgttgag aagattcgcg ttattgcaga aagccatccc gtccctggcg 960
aatatcacgc ggtgaccagt taaactctcg gcgaaaaagc gtcgaaaagt ggttactgtc 1020
gctgaatcca cagcgatagg cgatgtcagt aacgctggcc tcgctgtggc gtagcagatg 1080
tcgggctttc atcagtcgca ggcggttcag gtatcgctga ggcgtcagtc ccgtttgctg 1140
cttaagctgc cgatgtagcg tacgcagtga aagagaaaat tgatccgcca cggcatccca 1200
attcacctca tcggcaaaat ggtcctccag ccaggccaga agcaagttga gacgtgatgc 1260
gctgttttcc aggttctcct gcaaactgct tttacgcagc aagagcagta attgcataaa 1320
caagatctcg cgactggcgg tcgagggtaa atcattttcc ccttcctgct gttccatctg 1380
tgcaaccagc tgtcgcacct gctgcaatac gctgtggtta acgcgccagt gagacggata 1440
ctgcccatcc agctcttgtg gcagcaactg attcagcccg gcgagaaact gaaatcgatc 1500
cggcgagcga tacagcacat tggtcagaca cagattatcg gtatgttcat acagatgccg 1560
atcatgatcg cgtacgaaac agaccgtgcc accggtgatg gtatagggct gcccattaaa 1620
cacatgaata cccgtgccat gttcgacaat cacaatttca tgaaaatcat gatgatgttc 1680
aggaaaatcc gcctgcggga gccggggttc tatcgccacg gacgcgttac cagacggaaa 1740
aaaatccaca ctatgtaata cggtcatact ggcctcctga tgtcgtcaac acggcgaaat 1800
agtaatcacg aggtcaggtt cttaccttaa attttcgacg gaaaaccacg taaaaaacgt 1860
cgatttttca agatacagcg tgaattttca ggaaatgcgg tgagcatcac atcaccacaa 1920
ttcagcaaat tgtgaacatc atcacgttca tctttccctg gttgccaatg gcccattttc 1980
ctgtcagtaa cgagaaggtc gcgaattcag gcgcttttta gactggtcgt aatgaaattc 2040
aggaggatgg tcgacatgaa agccacgaaa ctggttctgg gtgctgttat cctgggttcc 2100
acgctgctgg cgggttgttc ctctaatgcg aaaatcgatc aaggcatcaa cccgtatgtg 2160
ggctttgaaa tgggttacga ttggctgggt cgtatgccgt ataaaggcag cgttgaaaat 2220
ggtgcataca aagctcaggg cgtccaactg accgcgaaac tgggttatcc gatcacggat 2280
gacctggata tttacacccg tctgggcggt atggtctggc gtgcagatac gaaaagcaac 2340
gtgtatggca aaaatcatga caccggtgtg tctccggttt tcgcgggcgg tgttgaatat 2400
gccatcacgc cggaaattgc aacccgtctg gaataccagt ggaccaacaa tatcggcgat 2460
gcacacacga ttggtacccg cccggataac ggcattccgg gtatcgacga aattctggcg 2520
gccctgccga aaacggatac ctataaactg attctgaatg gcaaaacgct gaaaggtgaa 2580
accacgaccg aagctgttga cgcagctacc gcggaaaaag tcttcaaaca atacgctaac 2640
gataatggcg tggacggtga atggacctac gatgacgcga cgaaaacctt cacggtcacc 2700
gaaaaaccgg aagtgatcga tgccagtgaa ctgacgccgg cagttacgac ctataaactg 2760
gtcattaacg gcaaaaccct gaaaggtgaa acgaccacgg aagctgtgga tgcagcaacc 2820
gcagaaaaag ttttcaaaca gtacgccaat gacaacggtg tggacggcga atggacgtac 2880
gatgacgcaa cgaaaacctt cacggtgacc gaaaaaccgg aagttatcga tgcctccgaa 2940
ctgaccccgg cagtcaccac gtataaactg gtgatcaatg gtaaaacgct gaaaggcgaa 3000
accacgacca aagcggttga tgccgaaacc gcagaaaaag cttttaaaca atacgcgaat 3060
gacaatggcg tggatggcgt gtggacctac gatgatgcga ccaaaacctt taccgttacc 3120
gaataataat ctagagctga ggagggattg agcgatgtct gcattcaata aagaaaattc 3180
aatttcatcc atggcaccac cagcatctcc gcctgcaagt cctaagacgc caatcgaaaa 3240
gaaacacgcg gatgaaatcg ataagtatat acaaggattg gattacaata aaaacaatgt 3300
attagtatac cacggagatg cagtgacaaa tgtgccgcca agaaaaggtt acaaagatgg 3360
aaatgaatat attgttgtgg agaaaaagaa gaaatccatc aatcaaaata atgcagacat 3420
tcaagttgtg aatgcaattt cgagcctaac ctatccaggt gctctcgtaa aagcgaattc 3480
ggaattagta gaaaatcaac cagatgttct ccctgtaaaa cgtgattcat taacactcag 3540
cattgatttg ccaggtatga ctaatcaaga caataaaata gttgtaaaaa atgccactaa 3600
atcaaacgtt aacaacgcag taaatacatt agtggaaaga tggaatgaaa aatatgctca 3660
agcttatcca aatgtaagtg caaaaattga ttatgatgac gaaatggctt acagtgaatc 3720
acaattaatt gcgaaatttg gtacagcatt taaagctgta aataatagct tgaatgtaaa 3780
cttcggcgca atcagtgaag ggaaaatgca agaagaagtc attagtttta aacaaattta 3840
ctataacgtg aatgttaatg aacctacaag accttccaga tttttcggca aagctgttac 3900
taaagagcag ttgcaagcgc ttggagtgaa tgcagaaaat cctcctgcat atatctcaag 3960
tgtggcgtat ggccgtcaag tttatttgaa attatcaact aattcccata gtactaaagt 4020
aaaagctgct tttgatgctg ccgtaagcgg aaaatctgtc tcaggtgatg tagaactaac 4080

-continued

```
aaatatcatc aaaaattctt ccttcaaagc cgtaatttac ggaggttccg caaaagatga   4140
agttcaaatc atcgacggca acctcggaga cttacgcgat attttgaaaa aaggcgctac   4200
ttttaatcga gaaacaccag gagttcccat tgcttataca acaaacttcc taaaagacaa   4260
tgaattagct gttattaaaa acaactcaga atatattgaa acaacttcaa aagcttatac   4320
agatggaaaa attaacatcg atcactctgg aggatacgtt gctcaattca acatttcttg   4380
ggatgaagta aattatgatc ctgaaggtaa cgaaattgtt caacataaaa actggagcga   4440
aaacaataaa agcaagctag ctcatttcac atcgtccatc tatttgcctg gtaacgcgag   4500
aaatattaat gtttacgcta aagaatgcac tggtttagct tgggaatggt ggagaacggt   4560
aattgatgac cggaacttac cacttgtgaa aaatagaaat atctccatct ggggcaccac   4620
gctttatccg aaatatagta ataaagtaga taatccaatc gaatatgatt ataaagatga   4680
cgatgacaaa taataatcta gaggatccag gaggattact atatgggtct ggataccgtg   4740
agcttctcga cgaaaggcgc aacctacatt acctacgtga acttcctgaa cgaactgcgt   4800
gtgaaactga aaccggaagg caacagccat ggtatcccgc tgctgcgtaa aaaatgcgat   4860
gacccgggca aatgttttgt tctggtcgca ctgagtaacg ataatggtca gctggcagaa   4920
attgctatcg acgtgacctc agtttatgtg gttggctacc aagtccgtaa ccgctcgtat   4980
ttctttaaag atgcaccgga cgcggcctac gaaggtctgt ttaaaaatac catcaaaacg   5040
cgcctgcact tcggcggtag ttatccgtcc ctggaaggcg aaaaagcgta tcgtgaaacc   5100
acggatctgg gcattgaacc gctgcgcatt ggtatcaaaa aactggatga aaacgcgatt   5160
gacaattata aaccgacgga aatcgccagc tctctgctgg tcgtgattca gatggtgtca   5220
gaagccgctc gttttacctt tatcgaaaat caaatccgca acaactttca acaaagaatt   5280
cgcccggcta ataatacgat ctcgctggaa aataaatggg gtaaactgag ctttcaaatc   5340
cgcacctcgg gcgctaacgg catgttctcc gaagcggtgg aactggaacg tgccaacggc   5400
aaaaaatatt acgttaccgc tgtggaccag gtgaaaccga aaatcgctct gctgaaattc   5460
gttgataaag acccgaaata ataaggatcc cctaggggcg cgcctggtag tgtggggtct   5520
ccccatgcga gagtagggaa ctgccaggca tcaaataaaa cgaaaggctc agtcgaaaga   5580
ctgggccttt cgttttatct gttgtttgtc ggtgaacgct ctcctgagta ggacaaatcc   5640
gccgggagcg gatttgaacg ttgcgaagca acggcccgga gggtggcggg caggacgccc   5700
gccataaact gccaggcatc aaattaagca gaaggccatc ctgacggatg gcctttttgc   5760
gtttctacaa actcgagctc gaattcgtaa tcatggtcat agctgtttcc tgtgtgaaat   5820
tgttatccgc tcacaattcc acacaacata cgagccggaa gcataaagtg taaagcctgg   5880
ggtgcctaat gagtgagcta actcacatta attgcgttgc gctcactgcc cgctttccag   5940
tcgggaaacc tgtcgtgcca gctgcattaa tgaatcggcc aacgcgcggg gagaggcggt   6000
ttgcgtattg ggcgctcttc cgcttcctcg ctcactgact cgctgcgctc ggtcgttcgg   6060
ctgcggcgag cggtatcagc tcactcaaag gcggtaatac ggttatccac agaatcaggg   6120
gataacgcag gaaagaacat gtgagcaaaa ggccagcaaa agcccaggaa ccgtaaaaag   6180
gccgcgttgc tggcgttttt ccataggctc cgcccccctg acgagcatca caaaaatcga   6240
cgctcaagtc agaggtggcg aaacccgaca ggactataaa gataccaggc gtttccccct   6300
ggaagctccc tcgtgcgctc tcctgttccg accctgccgc ttaccggata cctgtccgcc   6360
tttctccctt cgggaagcgt ggcgctttct catagctcac gctgtaggta tctcagttcg   6420
gtgtaggtcg ttcgctccaa gctgggctgt gtgcacgaac cccccgttca gcccgaccgc   6480
```

tgcgccttat ccggtaacta tcgtcttgag tccaacccgg taagacacga cttatcgcca 6540
ctggcagcag ccactggtaa caggattagc agagcgaggt atgtaggcgg tgctacagag 6600
ttcttgaagt ggtggcctaa ctacggctac actagaagga cagtatttgg tatctgcgct 6660
ctgctgaagc cagttacctt cggaaaaaga gttggtagct cttgatccgg caaacaaacc 6720
accgctggta gcggtggttt ttttgtttgc aagcagcaga ttacgcgcag aaaaaaagga 6780
tctcaagaag atcctttgat cttttctacg gggtctgacg ctcagtggaa cgaaaactca 6840
cgttaaggga ttttggtcat gagattatca aaaaggatct tcacctagat ccttttaaat 6900
taaaaatgaa gttttagcac gtgctattat tgaagcattt atcagggtta ttgtctcatg 6960
agcggataca tatttgaatg tatttagaaa aataaacaaa taggggttcc gcgcacattt 7020
ccccgaaaag tgccacctgt atgcggtgtg aaataccgca cagatgcgta aggagaaaat 7080
accgcatcag gaaattgtaa gcgttaataa ttcagaagaa ctcgtcaaga aggcgataga 7140
aggcgatgcg ctgcgaatcg ggagcggcga taccgtaaag cacgaggaag cggtcagccc 7200
attcgccgcc aagctcttca gcaatatcac gggtagccaa cgctatgtcc tgatagcggt 7260
ccgccacacc cagccggcca cagtcgatga atccagaaaa gcggccattt tccaccatga 7320
tattcggcaa gcaggcatcg ccatgggtca cgacgagatc ctcgccgtcg ggcatgctcg 7380
ccttgagcct ggcgaacagt tcggctggcg cgagcccctg atgctcttcg tccagatcat 7440
cctgatcgac aagaccggct tccatccgag tacgtgctcg ctcgatgcga tgtttcgctt 7500
ggtggtcgaa tgggcaggta gccggatcaa gcgtatgcag ccgccgcatt gcatcagcca 7560
tgatggatac tttctcggca ggagcaaggt gagatgacag gagatcctgc cccggcactt 7620
cgcccaatag cagccagtcc cttcccgctt cagtgacaac gtcgagcaca gctgcgcaag 7680
gaacgcccgt cgtggccagc cacgatagcc gcgctgcctc gtcttgcagt tcattcaggg 7740
caccggacag gtcggtcttg acaaaaagaa ccgggcgccc ctgcgctgac agccggaaca 7800
cggcggcatc agagcagccg attgtctgtt gtgcccagtc atagccgaat agcctctcca 7860
cccaagcggc cggagaacct gcgtgcaatc catcttgttc aatcatgcga aacgatcctc 7920
atcctgtctc ttgatcagag cttgatcccc tgcgccatca gatccttggc ggcgagaaag 7980
ccatccagtt tactttgcag ggcttcccaa ccttaccaga gggcgcccca gctggcaatt 8040
ccggttcgct tgctgtccat aaaaccgccc agtagaagca tatg 8084

<210> SEQ ID NO 19
<211> LENGTH: 8122
<212> TYPE: DNA
<213> ORGANISM: Artificial Sequence
<220> FEATURE:
<223> OTHER INFORMATION: pVX-181

<400> SEQUENCE: 19
aagcttaatt aatctttctg cgaattgaga tgacgccact ggctgggcgt catcccggtt 60
tcccgggtaa acaccaccga aaaatagtta ctatcttcaa agccacattc ggtcgaaata 120
tcactgatta acaggcggct atgctggaga agatattgcg catgacacac tctgacctgt 180
cgcagatatt gattgatggt cattccagtc tgctggcgaa attgctgacg caaaacgcgc 240
tcactgcacg atgcctcatc acaaaattta tccagcgcaa agggactttt caggctagcc 300
gccagccggg taatcagctt atccagcaac gtttcgctgg atgttggcgg caacgaatca 360
ctggtgtaac gatggcgatt cagcaacatc accaactgcc cgaacagcaa ctcagccatt 420

```
tcgttagcaa acggcacatg ctgactactt tcatgctcaa gctgaccgat aacctgccgc    480
gcctgcgcca tccccatgct acctaagcgc cagtgtggtt gccctgcgct ggcgttaaat    540
cccggaatcg ccccctgcca gtcaagattc agcttcagac gctccgggca ataaataata    600
ttctgcaaaa ccagatcgtt aacggaagcg taggagtgtt tatcgtcagc atgaatgtaa    660
aagagatcgc cacgggtaat gcgataaggg cgatcgttga gtacatgcag gccattaccg    720
cgccagacaa tcaccagctc acaaaaatca tgtgtatgtt cagcaaagac atcttgcgga    780
taacggtcag ccacagcgac tgcctgctgg tcgctggcaa aaaaatcatc tttgagaagt    840
tttaactgat gcgccaccgt ggctacctcg gccagagaac gaagttgatt attcgcaata    900
tggcgtacaa atacgttgag aagattcgcg ttattgcaga aagccatccc gtccctggcg    960
aatatcacgc ggtgaccagt taaactctcg gcgaaaaagc gtcgaaaagt ggttactgtc   1020
gctgaatcca cagcgatagg cgatgtcagt aacgctggcc tcgctgtggc gtagcagatg   1080
tcgggctttc atcagtcgca ggcggttcag gtatcgctga ggcgtcagtc ccgtttgctg   1140
cttaagctgc cgatgtagcg tacgcagtga aagagaaaat tgatccgcca cggcatccca   1200
attcacctca tcggcaaaat ggtcctccag ccaggccaga agcaagttga gacgtgatgc   1260
gctgttttcc aggttctcct gcaaactgct tttacgcagc aagagcagta attgcataaa   1320
caagatctcg cgactggcgg tcgagggtaa atcattttcc ccttcctgct gttccatctg   1380
tgcaaccagc tgtcgcacct gctgcaatac gctgtggtta acgcgccagt gagacggata   1440
ctgcccatcc agctcttgtg gcagcaactg attcagcccg gcgagaaact gaaatcgatc   1500
cggcgagcga tacagcacat tggtcagaca cagattatcg gtatgttcat acagatgccg   1560
atcatgatcg cgtacgaaac agaccgtgcc accggtgatg gtatagggct gcccattaaa   1620
cacatgaata cccgtgccat gttcgacaat cacaatttca tgaaaatcat gatgatgttc   1680
aggaaaatcc gcctgcggga gccggggttc tatcgccacg gacgcgttac cagacggaaa   1740
aaaatccaca ctatgtaata cggtcatact ggcctcctga tgtcgtcaac acggcgaaat   1800
agtaatcacg aggtcaggtt cttaccttaa attttcgacg gaaaaccacg taaaaaacgt   1860
cgatttttca agatacagcg tgaattttca ggaaatgcgg tgagcatcac atcaccacaa   1920
ttcagcaaat tgtgaacatc atcacgttca tctttccctg gttgccaatg gcccattttc   1980
ctgtcagtaa cgagaaggtc gcgaattcag gcgcttttta gactggtcgt aatgaaattc   2040
aggaggatgg tcgacatgaa agccacgaaa ctggttctgg gtgctgttat cctgggttcc   2100
acgctgctgg cgggttgttc ctctaatgcg aaaatcgatc aaggcatcaa cccgtatgtg   2160
ggctttgaaa tgggttacga ttggctgggt cgtatgccgt ataaaggcag cgttgaaaat   2220
ggtgcataca aagctcaggg cgtccaactg accgcgaaac tgggttatcc gatcacggat   2280
gacctggata tttacacccg tctgggcggt atggtctggc gtgcagatac gaaaagcaac   2340
gtgtatggca aaaatcatga caccggtgtg tctccggttt tcgcgggcgg tgttgaatat   2400
gccatcacgc cggaaattgc aacccgtctg gaataccagt ggaccaacaa tatcggcgat   2460
gcacacacga ttggtacccg cccggataac ggcattccgg gtatcgacga aattctggcg   2520
gccctgccga aaacggatac ctataaactg attctgaatg gcaaaacgct gaaaggtgaa   2580
accacgaccg aagctgttga cgcagctacc gcggaaaaag tcttcaaaca atacgctaac   2640
gataatggcg tggacggtga atggacctac gatgacgcga cgaaaacctt cacggtcacc   2700
gaaaaaccgg aagtgatcga tgccagtgaa ctgacgccgg cagttacgac ctataaactg   2760
gtcattaacg gcaaaaccct gaaaggtgaa acgaccacgg aagctgtgga tgcagcaacc   2820
```

gcagaaaaag ttttcaaaca gtacgccaat gacaacggtg tggacggcga atggacgtac 2880
gatgacgcaa cgaaaacctt cacggtgacc gaaaaaccgg aagttatcga tgcctccgaa 2940
ctgaccccgg cagtcaccac gtataaactg gtgatcaatg gtaaaacgct gaaaggcgaa 3000
accacgacca aagcggttga tgccgaaacc gcagaaaaag cttttaaaca atacgcgaat 3060
gacaatggcg tggatggcgt gtggacctac gatgatgcga ccaaaacctt taccgttacc 3120
gaataataat ctagaaggag gaacaatatg aaaaagatta tgctggtctt tattaccctg 3180
attctggtct ctctgccgat tgctcaacaa acggaagctg gcgacgcaag cgcattcaac 3240
aaagaaaaca gcatcagctc tatggcaccg ccggcttcac cgccggcatc gccgaaaacc 3300
ccgatcgaga aaaaacatgc tgatgaaatc gacaaataca tccagggcct ggactacaat 3360
aaaaacaatg tgctggttta tcacggtgat gccgttacga atgtcccgcc gcgtaaaggc 3420
tataaagacg gtaacgaata catcgtggtt gaaaagaaaa agaaaagcat caaccagaac 3480
aatgctgata ttcaagtcgt gaacgcgatc agttccctga cctatccggg cgcactggtc 3540
aaagctaata gcgaactggt ggaaaaccag ccggatgtgc tgccggttaa acgtgacagc 3600
ctgaccctgt ctattgatct gccgggtatg acgaaccaag ataacaaaat cgttgtcaaa 3660
aacgcaacca aaagtaacgt caacaatgct gtgaatacgc tggttgaacg ctggaacgaa 3720
aaatatgcgc aggcctaccc gaatgtgtcc gccaaaattg attatgatga cgaaatggcg 3780
tactcagaat cgcaactgat cgccaaattt ggcaccgcgt tcaaagccgt taacaatagc 3840
ctgaacgtca attttggcgc gatttctgaa ggtaaaatgc aggaaatggt gatctcattc 3900
aaacaaatct actacaacgt caacgtgaac gaaccgaccc gtccgtcgcg ctttttcggc 3960
aaagccgtca cgaaagaaca gctgcaagcg ctgggtgtga atgccgaaaa cccgccggca 4020
tatatttcat cggtggcgta tggtcgccag gtttacctga aactgagcac caacagccat 4080
tctacgaaag ttaaagcggc ctttaaagca gctgtctctg gcaaaagtgt ctccggtgat 4140
gtggaactga ccaacatcat caaaaacagc tctttcaaag ccgttattta tggcggttct 4200
gcaaaagatg aagtccagat tatcgacggc aatctgggtg atctgcgtga cattctgaaa 4260
aaaggcgcga cctttaaccg cgaaacgccg ggtgtgccga tcgcctacac cacgaatttc 4320
ctgaaagata acgaactggc agttatcaaa aacaactcag aatacatcga aaccacgtcg 4380
aaagcttaca ccgatggcaa aattaatatc gaccacagtg gcggttatgt tgcacagttt 4440
aacatttcct gggatgaagt gaattacgac ccggagggta acgaaatcgt tcaacataaa 4500
aactggagtg aaaacaacaa atccaaactg gcgcacttca ccagttccat ttatctgccg 4560
ggcaacgctc gtaatatcaa cgtgtacgcg aaagaatgca ccggtctggc ctgggaatgg 4620
tggcgtacgg tgattgatga ccgcaacctg ccgctggtta aaaatcgcaa catctccatc 4680
tggggcacca ccctgtaccc gaaatatagt aacaaagttg ataacccgat tgaataataa 4740
ggatccagga ggattactat atgggtctgg ataccgtgag cttctcgacg aaaggcgcaa 4800
cctacattac ctacgtgaac ttcctgaacg aactgcgtgt gaaactgaaa ccggaaggca 4860
acagccatgg tatcccgctg ctgcgtaaaa aatgcgatga cccgggcaaa tgttttgttc 4920
tggtcgcact gagtaacgat aatggtcagc tggcagaaat tgctatcgac gtgacctcag 4980
tttatgtggt tggctaccaa gtccgtaacc gctcgtattt ctttaaagat gcaccggacg 5040
cggcctacga aggtctgttt aaaaatacca tcaaaacgcg cctgcacttc ggcggtagtt 5100
atccgtccct ggaaggcgaa aaagcgtatc gtgaaaccac ggatctgggc attgaaccgc 5160

-continued

```
tgcgcattgg tatcaaaaaa ctggatgaaa acgcgattga caattataaa ccgacggaaa   5220
tcgccagctc tctgctggtc gtgattcaga tggtgtcaga agccgctcgt tttaccttta   5280
tcgaaaatca aatccgcaac aactttcaac aaagaattcg cccggctaat aatacgatct   5340
cgctggaaaa taaatggggt aaactgagct ttcaaatccg cacctcgggc gctaacggca   5400
tgttctccga agcggtggaa ctggaacgtg ccaacggcaa aaaatattac gttaccgctg   5460
tggaccaggt gaaaccgaaa atcgctctgc tgaaattcgt tgataaagac ccgaaataat   5520
aaggatcccc taggggcgcg cctggtagtg tggggtctcc ccatgcgaga gtagggaact   5580
gccaggcatc aaataaaacg aaaggctcag tcgaaagact gggcctttcg ttttatctgt   5640
tgtttgtcgg tgaacgctct cctgagtagg acaaatccgc cgggagcgga tttgaacgtt   5700
gcgaagcaac ggcccggagg gtggcgggca ggacgcccgc cataaactgc caggcatcaa   5760
attaagcaga aggccatcct gacggatggc ctttttgcgt ttctacaaac tcgagctcga   5820
attcgtaatc atggtcatag ctgtttcctg tgtgaaattg ttatccgctc acaattccac   5880
acaacatacg agccggaagc ataaagtgta aagcctgggg tgcctaatga gtgagctaac   5940
tcacattaat tgcgttgcgc tcactgcccg ctttccagtc gggaaacctg tcgtgccagc   6000
tgcattaatg aatcggccaa cgcgcgggga gaggcggttt gcgtattggg cgctcttccg   6060
cttcctcgct cactgactcg ctgcgctcgg tcgttcggct gcggcgagcg gtatcagctc   6120
actcaaaggc ggtaatacgg ttatccacag aatcagggga taacgcagga aagaacatgt   6180
gagcaaaagg ccagcaaaag cccaggaacc gtaaaaaggc cgcgttgctg gcgtttttcc   6240
ataggctccg cccccctgac gagcatcaca aaaatcgacg ctcaagtcag aggtggcgaa   6300
acccgacagg actataaaga taccaggcgt ttccccctgg aagctccctc gtgcgctctc   6360
ctgttccgac cctgccgctt accggatacc tgtccgcctt tctcccttcg ggaagcgtgg   6420
cgctttctca tagctcacgc tgtaggtatc tcagttcggt gtaggtcgtt cgctccaagc   6480
tgggctgtgt gcacgaaccc cccgttcagc ccgaccgctg cgccttatcc ggtaactatc   6540
gtcttgagtc caacccggta agacacgact tatcgccact ggcagcagcc actggtaaca   6600
ggattagcag agcgaggtat gtaggcggtg ctacagagtt cttgaagtgg tggcctaact   6660
acggctacac tagaaggaca gtatttggta tctgcgctct gctgaagcca gttaccttcg   6720
gaaaaagagt tggtagctct tgatccggca aacaaaccac cgctggtagc ggtggttttt   6780
ttgtttgcaa gcagcagatt acgcgcagaa aaaaaggatc tcaagaagat cctttgatct   6840
tttctacggg gtctgacgct cagtggaacg aaaactcacg ttaagggatt ttggtcatga   6900
gattatcaaa aaggatcttc acctagatcc ttttaaatta aaaatgaagt tttagcacgt   6960
gctattattg aagcatttat cagggttatt gtctcatgag cggatacata tttgaatgta   7020
tttagaaaaa taaacaaata ggggttccgc gcacatttcc ccgaaaagtg ccacctgtat   7080
gcggtgtgaa ataccgcaca gatgcgtaag gagaaaatac cgcatcagga aattgtaagc   7140
gttaataatt cagaagaact cgtcaagaag gcgatagaag gcgatgcgct gcgaatcggg   7200
agcggcgata ccgtaaagca cgaggaagcg gtcagcccat tcgccgccaa gctcttcagc   7260
aatatcacgg gtagccaacg ctatgtcctg atagcggtcc gccacaccca gccggccaca   7320
gtcgatgaat ccagaaaagc ggccattttc caccatgata ttcggcaagc aggcatcgcc   7380
atgggtcacg acgagatcct cgccgtcggg catgctcgcc ttgagcctgg cgaacagttc   7440
ggctggcgcg agcccctgat gctcttcgtc cagatcatcc tgatcgacaa gaccggcttc   7500
catccgagta cgtgctcgct cgatgcgatg tttcgcttgg tggtcgaatg ggcaggtagc   7560
```

cggatcaagc gtatgcagcc gccgcattgc atcagccatg atggatactt tctcggcagg 7620
agcaaggtga gatgacagga gatcctgccc cggcacttcg cccaatagca gccagtccct 7680
tcccgcttca gtgacaacgt cgagcacagc tgcgcaagga acgcccgtcg tggccagcca 7740
cgatagccgc gctgcctcgt cttgcagttc attcagggca ccggacaggt cggtcttgac 7800
aaaaagaacc gggcgcccct gcgctgacag ccggaacacg gcggcatcag agcagccgat 7860
tgtctgttgt gcccagtcat agccgaatag cctctccacc caagcggccg gagaacctgc 7920
gtgcaatcca tcttgttcaa tcatgcgaaa cgatcctcat cctgtctctt gatcagagct 7980
tgatcccctg cgccatcaga tccttggcgg cgagaaagcc atccagttta ctttgcaggg 8040
cttcccaacc ttaccagagg gcgccccagc tggcaattcc ggttcgcttg ctgtccataa 8100
aaccgcccag tagaagcata tg 8122

<210> SEQ ID NO 20
<211> LENGTH: 8122
<212> TYPE: DNA
<213> ORGANISM: Artificial Sequence
<220> FEATURE:
<223> OTHER INFORMATION: pVX-193

<400> SEQUENCE: 20
aagcttaatt aatctttctg cgaattgaga tgacgccact ggctgggcgt catcccggtt 60
tcccgggtaa acaccaccga aaaatagtta ctatcttcaa agccacattc ggtcgaaata 120
tcactgatta acaggcggct atgctggaga agatattgcg catgacacac tctgacctgt 180
cgcagatatt gattgatggt cattccagtc tgctggcgaa attgctgacg caaaacgcgc 240
tcactgcacg atgcctcatc acaaaattta tccagcgcaa agggactttt caggctagcc 300
gccagccggg taatcagctt atccagcaac gtttcgctgg atgttggcgg caacgaatca 360
ctggtgtaac gatggcgatt cagcaacatc accaactgcc cgaacagcaa ctcagccatt 420
tcgttagcaa acggcacatg ctgactactt tcatgctcaa gctgaccgat aacctgccgc 480
gcctgcgcca tccccatgct acctaagcgc cagtgtggtt gccctgcgct ggcgttaaat 540
cccggaatcg ccccctgcca gtcaagattc agcttcagac gctccgggca ataaataata 600
ttctgcaaaa ccagatcgtt aacggaagcg taggagtgtt tatcgtcagc atgaatgtaa 660
aagagatcgc cacgggtaat gcgataaggg cgatcgttga gtacatgcag gccattaccg 720
cgccagacaa tcaccagctc acaaaaatca tgtgtatgtt cagcaaagac atcttgcgga 780
taacggtcag ccacagcgac tgcctgctgg tcgctggcaa aaaaatcatc tttgagaagt 840
tttaactgat gcgccaccgt ggctacctcg gccagagaac gaagttgatt attcgcaata 900
tggcgtacaa atacgttgag aagattcgcg ttattgcaga aagccatccc gtccctggcg 960
aatatcacgc ggtgaccagt taaactctcg gcgaaaaagc gtcgaaaagt ggttactgtc 1020
gctgaatcca cagcgatagg cgatgtcagt aacgctggcc tcgctgtggc gtagcagatg 1080
tcgggctttc atcagtcgca ggcggttcag gtatcgctga ggcgtcagtc ccgtttgctg 1140
cttaagctgc cgatgtagcg tacgcagtga aagagaaaat tgatccgcca cggcatccca 1200
attcacctca tcggcaaaat ggtcctccag ccaggccaga agcaagttga gacgtgatgc 1260
gctgttttcc aggttctcct gcaaactgct tttacgcagc aagagcagta attgcataaa 1320
caagatctcg cgactggcgg tcgagggtaa atcattttcc ccttcctgct gttccatctg 1380
tgcaaccagc tgtcgcacct gctgcaatac gctgtggtta acgcgccagt gagacggata 1440

-continued

```
ctgcccatcc agctcttgtg gcagcaactg attcagcccg gcgagaaact gaaatcgatc   1500
cggcgagcga tacagcacat tggtcagaca cagattatcg gtatgttcat acagatgccg   1560
atcatgatcg cgtacgaaac agaccgtgcc accggtgatg gtatagggct gcccattaaa   1620
cacatgaata cccgtgccat gttcgacaat cacaatttca tgaaaatcat gatgatgttc   1680
aggaaaatcc gcctgcggga gccggggttc tatcgccacg gacgcgttac cagacggaaa   1740
aaaatccaca ctatgtaata cggtcatact ggcctcctga tgtcgtcaac acggcgaaat   1800
agtaatcacg aggtcaggtt cttaccttaa attttcgacg gaaaaccacg taaaaaacgt   1860
cgatttttca agatacagcg tgaattttca ggaaatgcgg tgagcatcac atcaccacaa   1920
ttcagcaaat tgtgaacatc atcacgttca tctttccctg gttgccaatg gcccattttc   1980
ctgtcagtaa cgagaaggtc gcgaattcag gcgcttttta gactggtcgt aatgaaattc   2040
aggaggatgg tcgacatgaa agccacgaaa ctggttctgg gtgctgttat cctgggttcc   2100
acgctgctgg cgggttgttc ctctaatgcg aaaatcgatc aaggcatcaa cccgtatgtg   2160
ggctttgaaa tgggttacga ttggctgggt cgtatgccgt ataaaggcag cgttgaaaat   2220
ggtgcataca aagctcaggg cgtccaactg accgcgaaac tgggttatcc gatcacggat   2280
gacctggata tttacacccg tctgggcggt atggtctggc gtgcagatac gaaaagcaac   2340
gtgtatggca aaaatcatga caccggtgtg tctccggttt tcgcgggcgg tgttgaatat   2400
gccatcacgc cggaaattgc aacccgtctg gaataccagt ggaccaacaa tatcggcgat   2460
gcacacacga ttggtacccg cccggataac ggcattccgg gtatcgacga aattctggcg   2520
gccctgccga aaacggatac ctataaactg attctgaatg gcaaaacgct gaaaggtgaa   2580
accacgaccg aagctgttga cgcagctacc gcggaaaaag tcttcaaaca atacgctaac   2640
gataatggcg tggacggtga atggacctac gatgacgcga cgaaaacctt cacggtcacc   2700
gaaaaaccgg aagtgatcga tgccagtgaa ctgacgccgg cagttacgac ctataaactg   2760
gtcattaacg gcaaaaccct gaaaggtgaa acgaccacgg aagctgtgga tgcagcaacc   2820
gcagaaaaag ttttcaaaca gtacgccaat gacaacggtg tggacggcga atggacgtac   2880
gatgacgcaa cgaaaacctt cacggtgacc gaaaaaccgg aagttatcga tgcctccgaa   2940
ctgaccccgg cagtcaccac gtataaactg gtgatcaatg gtaaaacgct gaaaggcgaa   3000
accacgacca aagcggttga tgccgaaacc gcagaaaaag cttttaaaca atacgcgaat   3060
gacaatggcg tggatggcgt gtggacctac gatgatgcga ccaaaacctt taccgttacc   3120
gaataataat ctagaaggag gaacaatatg aaaaagatta tgctggtctt tattaccctg   3180
attctggtgt ccctgccgat tgcacaacaa accgaagcgg gcgatgcgag cgccttcaac   3240
aaagaaaaca gcatcagctc tatggcaccg ccggcttcac cgccggcatc gccgaaaacc   3300
ccgatcgaga aaaaacatgc tgatgaaatc gacaaataca tccagggcct ggactacaat   3360
aaaaacaatg tgctggttta tcacggtgat gccgttacga atgtcccgcc gcgtaaaggc   3420
tataaagacg gtaacgaata catcgtggtt gaaaagaaaa agaaaagcat caaccagaac   3480
aatgctgata ttcaagtcgt gaacgcgatc agttccctga cctatccggg cgcactggtc   3540
aaagctaata gcgaactggt ggaaaaccag ccggatgtgc tgccggttaa acgtgacagc   3600
ctgaccctgt ctattgatct gccgggtatg acgaaccaag ataacaaaat cgttgtcaaa   3660
aacgcaacca aaagtaacgt caacaatgct gtgaatacgc tggttgaacg ctggaacgaa   3720
aaatatgcgc aggcctaccc gaatgtgtcc gccaaaattg attatgatga cgaaatggcg   3780
tactcagaat cgcaactgat cgccaaattt ggcaccgcgt tcaaagccgt taacaatagc   3840
```

-continued

```
ctgaacgtca attttggcgc gatttctgaa ggtaaaatgc aggaaatggt gatctcattc   3900
aaacaaatct actacaacgt caacgtgaac gaaccgaccc gtccgtcgcg ctttttcggc   3960
aaagccgtca cgaaagaaca gctgcaagcg ctgggtgtga atgccgaaaa cccgccggca   4020
tatatttcat cggtggcgta tggtcgccag gtttacctga aactgagcac caacagccat   4080
tctacgaaag ttaaagcggc ctttaaagca gctgtctctg gcaaaagtgt ctccggtgat   4140
gtggaactga ccaacatcat caaaaacagc tctttcaaag ccgttattta tggcggttct   4200
gcaaaagatg aagtccagat tatcgacggc aatctgggtg atctgcgtga cattctgaaa   4260
aaaggcgcga cctttaaccg cgaaacgccg ggtgtgccga tcgcctacac cacgaatttc   4320
ctgaaagata acgaactggc agttatcaaa aacaactcag aatacatcga aaccacgtcg   4380
aaagcttaca ccgatggcaa aattaatatc gaccacagtg gcggttatgt tgcacagttt   4440
aacatttcct gggatgaagt gaattacgac ccggagggta acgaaatcgt tcaacataaa   4500
aactggagtg aaaacaacaa atccaaaacc gcgcacttca cgagttccat ttatctgccg   4560
ggcaacgctc gtaatatcaa cgtgtacgcg aaagaatgca ccggtctggc ctgggaatgg   4620
tggcgtacgg tgattgatga ccgcaacctg ccgctggtta aaaatcgcaa catctccatc   4680
tggggcacca ccctgtaccc gaaatactcc aacaaagttg ataacccgat tgaataataa   4740
ggatccagga ggattactat atgggtctgg ataccgtgag cttctcgacg aaaggcgcaa   4800
cctacattac ctacgtgaac ttcctgaacg aactgcgtgt gaaactgaaa ccggaaggca   4860
acagccatgg tatcccgctg ctgcgtaaaa aatgcgatga cccgggcaaa tgttttgttc   4920
tggtcgcact gagtaacgat aatggtcagc tggcagaaat tgctatcgac gtgacctcag   4980
tttatgtggt tggctaccaa gtccgtaacc gctcgtattt ctttaaagat gcaccggacg   5040
cggcctacga aggtctgttt aaaaatacca tcaaaacgcg cctgcacttc ggcggtagtt   5100
atccgtccct ggaaggcgaa aaagcgtatc gtgaaaccac ggatctgggc attgaaccgc   5160
tgcgcattgg tatcaaaaaa ctggatgaaa acgcgattga caattataaa ccgacggaaa   5220
tcgccagctc tctgctggtc gtgattcaga tggtgtcaga agccgctcgt tttaccttta   5280
tcgaaaatca aatccgcaac aactttcaac aaagaattcg cccggctaat aatacgatct   5340
cgctggaaaa taaatggggt aaactgagct ttcaaatccg cacctcgggc gctaacggca   5400
tgttctccga agcggtggaa ctggaacgtg ccaacggcaa aaaatattac gttaccgctg   5460
tggaccaggt gaaaccgaaa atcgctctgc tgaaattcgt tgataaagac ccgaaataat   5520
aaggatcccc tagggggcgcg cctggtagtg tggggtctcc ccatgcgaga gtagggaact   5580
gccaggcatc aaataaaacg aaaggctcag tcgaaagact gggcctttcg ttttatctgt   5640
tgtttgtcgg tgaacgctct cctgagtagg acaaatccgc cgggagcgga tttgaacgtt   5700
gcgaagcaac ggcccggagg gtggcgggca ggacgcccgc cataaactgc caggcatcaa   5760
attaagcaga aggccatcct gacggatggc ctttttgcgt ttctacaaac tcgagctcga   5820
attcgtaatc atggtcatag ctgtttcctg tgtgaaattg ttatccgctc acaattccac   5880
acaacatacg agccggaagc ataaagtgta aagcctgggg tgcctaatga gtgagctaac   5940
tcacattaat tgcgttgcgc tcactgcccg ctttccagtc gggaaacctg tcgtgccagc   6000
tgcattaatg aatcggccaa cgcgcgggga gaggcggttt gcgtattggg cgctcttccg   6060
cttcctcgct cactgactcg ctgcgctcgg tcgttcggct gcggcgagcg gtatcagctc   6120
actcaaaggc ggtaatacgg ttatccacag aatcagggga taacgcagga aagaacatgt   6180
```

gagcaaaagg ccagcaaaag cccaggaacc gtaaaaaggc cgcgttgctg gcgtttttcc 6240
ataggctccg cccccctgac gagcatcaca aaaatcgacg ctcaagtcag aggtggcgaa 6300
acccgacagg actataaaga taccaggcgt ttccccctgg aagctccctc gtgcgctctc 6360
ctgttccgac cctgccgctt accggatacc tgtccgcctt tctcccttcg ggaagcgtgg 6420
cgctttctca tagctcacgc tgtaggtatc tcagttcggt gtaggtcgtt cgctccaagc 6480
tgggctgtgt gcacgaaccc cccgttcagc ccgaccgctg cgccttatcc ggtaactatc 6540
gtcttgagtc caacccggta agacacgact tatcgccact ggcagcagcc actggtaaca 6600
ggattagcag agcgaggtat gtaggcggtg ctacagagtt cttgaagtgg tggcctaact 6660
acggctacac tagaaggaca gtatttggta tctgcgctct gctgaagcca gttaccttcg 6720
gaaaaagagt tggtagctct tgatccggca aacaaaccac cgctggtagc ggtggttttt 6780
ttgtttgcaa gcagcagatt acgcgcagaa aaaaaggatc tcaagaagat cctttgatct 6840
tttctacggg gtctgacgct cagtggaacg aaaactcacg ttaagggatt ttggtcatga 6900
gattatcaaa aaggatcttc acctagatcc ttttaaatta aaaatgaagt tttagcacgt 6960
gctattattg aagcatttat cagggttatt gtctcatgag cggatacata tttgaatgta 7020
tttagaaaaa taaacaaata ggggttccgc gcacatttcc ccgaaaagtg ccacctgtat 7080
gcggtgtgaa ataccgcaca gatgcgtaag gagaaaatac cgcatcagga aattgtaagc 7140
gttaataatt cagaagaact cgtcaagaag gcgatagaag gcgatgcgct gcgaatcggg 7200
agcggcgata ccgtaaagca cgaggaagcg gtcagcccat tcgccgccaa gctcttcagc 7260
aatatcacgg gtagccaacg ctatgtcctg atagcggtcc gccacaccca gccggccaca 7320
gtcgatgaat ccagaaaagc ggccattttc caccatgata ttcggcaagc aggcatcgcc 7380
atgggtcacg acgagatcct cgccgtcggg catgctcgcc ttgagcctgg cgaacagttc 7440
ggctggcgcg agcccctgat gctcttcgtc cagatcatcc tgatcgacaa gaccggcttc 7500
catccgagta cgtgctcgct cgatgcgatg tttcgcttgg tggtcgaatg ggcaggtagc 7560
cggatcaagc gtatgcagcc gccgcattgc atcagccatg atggatactt tctcggcagg 7620
agcaaggtga gatgacagga gatcctgccc cggcacttcg cccaatagca gccagtccct 7680
tcccgcttca gtgacaacgt cgagcacagc tgcgcaagga acgcccgtcg tggccagcca 7740
cgatagccgc gctgcctcgt cttgcagttc attcagggca ccggacaggt cggtcttgac 7800
aaaaagaacc gggcgcccct gcgctgacag ccggaacacg gcggcatcag agcagccgat 7860
tgtctgttgt gcccagtcat agccgaatag cctctccacc caagcggccg gagaacctgc 7920
gtgcaatcca tcttgttcaa tcatgcgaaa cgatcctcat cctgtctctt gatcagagct 7980
tgatcccctg cgccatcaga tccttggcgg cgagaaagcc atccagttta ctttgcaggg 8040
cttcccaacc ttaccagagg gcgccccagc tggcaattcc ggttcgcttg ctgtccataa 8100
aaccgcccag tagaagcata tg 8122

<210> SEQ ID NO 21
<211> LENGTH: 8035
<212> TYPE: DNA
<213> ORGANISM: Artificial Sequence
<220> FEATURE:
<223> OTHER INFORMATION: pVX-185

<400> SEQUENCE: 21
aagcttaatt aatctttctg cgaattgaga tgacgccact ggctgggcgt catcccggtt 60
tcccgggtaa acaccaccga aaaatagtta ctatcttcaa agccacattc ggtcgaaata 120

```
tcactgatta acaggcggct atgctggaga agatattgcg catgacacac tctgacctgt    180
cgcagatatt gattgatggt cattccagtc tgctggcgaa attgctgacg caaaacgcgc    240
tcactgcacg atgcctcatc acaaaattta tccagcgcaa agggactttt caggctagcc    300
gccagccggg taatcagctt atccagcaac gtttcgctgg atgttggcgg caacgaatca    360
ctggtgtaac gatggcgatt cagcaacatc accaactgcc cgaacagcaa ctcagccatt    420
tcgttagcaa acggcacatg ctgactactt tcatgctcaa gctgaccgat aacctgccgc    480
gcctgcgcca tccccatgct acctaagcgc cagtgtggtt gccctgcgct ggcgttaaat    540
cccggaatcg ccccctgcca gtcaagattc agcttcagac gctccgggca ataaataata    600
ttctgcaaaa ccagatcgtt aacggaagcg taggagtgtt tatcgtcagc atgaatgtaa    660
aagagatcgc cacgggtaat gcgataaggg cgatcgttga gtacatgcag gccattaccg    720
cgccagacaa tcaccagctc acaaaaatca tgtgtatgtt cagcaaagac atcttgcgga    780
taacggtcag ccacagcgac tgcctgctgg tcgctggcaa aaaaatcatc tttgagaagt    840
tttaactgat gcgccaccgt ggctacctcg gccagagaac gaagttgatt attcgcaata    900
tggcgtacaa atacgttgag aagattcgcg ttattgcaga aagccatccc gtccctggcg    960
aatatcacgc ggtgaccagt taaactctcg gcgaaaaagc gtcgaaaagt ggttactgtc   1020
gctgaatcca cagcgatagg cgatgtcagt aacgctggcc tcgctgtggc gtagcagatg   1080
tcgggctttc atcagtcgca ggcggttcag gtatcgctga ggcgtcagtc ccgtttgctg   1140
cttaagctgc cgatgtagcg tacgcagtga aagagaaaat tgatccgcca cggcatccca   1200
attcacctca tcggcaaaat ggtcctccag ccaggccaga agcaagttga gacgtgatgc   1260
gctgttttcc aggttctcct gcaaactgct tttacgcagc aagagcagta attgcataaa   1320
caagatctcg cgactggcgg tcgagggtaa atcattttcc ccttcctgct gttccatctg   1380
tgcaaccagc tgtcgcacct gctgcaatac gctgtggtta acgcgccagt gagacggata   1440
ctgcccatcc agctcttgtg gcagcaactg attcagcccg gcgagaaact gaaatcgatc   1500
cggcgagcga tacagcacat tggtcagaca cagattatcg gtatgttcat acagatgccg   1560
atcatgatcg cgtacgaaac agaccgtgcc accggtgatg gtatagggct gcccattaaa   1620
cacatgaata cccgtgccat gttcgacaat cacaatttca tgaaaatcat gatgatgttc   1680
aggaaaatcc gcctgcggga gccggggttc tatcgccacg gacgcgttac cagacggaaa   1740
aaaatccaca ctatgtaata cggtcatact ggcctcctga tgtcgtcaac acggcgaaat   1800
agtaatcacg aggtcaggtt cttaccttaa attttcgacg gaaaaccacg taaaaaacgt   1860
cgatttttca agatacagcg tgaattttca ggaaatgcgg tgagcatcac atcaccacaa   1920
ttcagcaaat tgtgaacatc atcacgttca tctttccctg gttgccaatg gcccattttc   1980
ctgtcagtaa cgagaaggtc gcgaattcag gcgcttttta gactggtcgt aatgaaattc   2040
aggaggatgg tcgacatgaa agccacgaaa ctggttctgg gtgctgttat cctgggttcc   2100
acgctgctgg cgggttgttc ctctaatgcg aaaatcgatc aaggcatcaa cccgtatgtg   2160
ggctttgaaa tgggttacga ttggctgggt cgtatgccgt ataaaggcag cgttgaaaat   2220
ggtgcataca aagctcaggg cgtccaactg accgcgaaac tgggttatcc gatcacggat   2280
gacctggata tttacacccg tctgggcggt atggtctggc gtgcagatac gaaaagcaac   2340
gtgtatggca aaaatcatga caccggtgtg tctccggttt tcgcgggcgg tgttgaatat   2400
gccatcacgc cggaaattgc aacccgtctg gaataccagt ggaccaacaa tatcggcgat   2460
```

-continued gcacacacga ttggtacccg cccggataac ggcattccgg gtatcgacga aattctggcg 2520
gccctgccga aaacggatac ctataaactg attctgaatg gcaaaacgct gaaaggtgaa 2580
accacgaccg aagctgttga cgcagctacc gcggaaaaag tcttcaaaca atacgctaac 2640
gataatggcg tggacggtga atggacctac gatgacgcga cgaaaacctt cacggtcacc 2700
gaaaaaccgg aagtgatcga tgccagtgaa ctgacgccgg cagttacgac ctataaactg 2760
gtcattaacg gcaaaaccct gaaaggtgaa acgaccacgg aagctgtgga tgcagcaacc 2820
gcagaaaaag ttttcaaaca gtacgccaat gacaacggtg tggacggcga atggacgtac 2880
gatgacgcaa cgaaaacctt cacggtgacc gaaaaaccgg aagttatcga tgcctccgaa 2940
ctgaccccgg cagtcaccac gtataaactg gtgatcaatg gtaaaacgct gaaaggcgaa 3000
accacgacca aagcggttga tgccgaaacc gcagaaaaag cttttaaaca atacgcgaat 3060
gacaatggcg tggatggcgt gtggacctac gatgatgcga ccaaaacctt taccgttacc 3120
gaataataat ctagaaggag gaacaatatg atccgcttca aaaagaccaa actgattgcg 3180
agcattgcga tggcactgtg tctgttctcc cagccggtga tttcgttctc aaaagatatt 3240
accgacaaaa atcagtccat cgattcaggc attagctctc tgtcttataa ccgtaatgaa 3300
gtgctggcgt ccaatggtga caaaatcgaa tcatttgttc cgaaagaagg caaaaaagcc 3360
ggtaacaaat tcattgtggt tgaacgtcag aaacgctctc tgaccacgag tccggttgat 3420
atctccatta tcgattcagt caatgaccgt acctatccgg gtgcactgca actggcagac 3480
aaagcatttg tggaaaaccg tccgacgatt ctgatggtta aacgcaaacc gattaacatc 3540
aatattgatc tgccgggcct gaaaggtgaa aatagtatca aagtggatga cccgacctat 3600
ggcaaagttt cgggtgcaat tgatgaactg gtcagcaaat ggaacgaaaa atacagttcc 3660
acccatacgc tgccggcgcg tacccagtat tcggaaagca tggtgtactc taaaagtcaa 3720
atctcatcgg cgctgaacgt taatgccaaa gtcctggaaa actctctggg tgtggatttt 3780
aatgcggttg ccaacaatga gaaaaaagtg atgatcctgg catataaaca gattttctac 3840
accgttagtg ctgatctgcc gaaaaacccg tctgacctgt ttgatgacag tgtcacgttc 3900
aacgatctga aacaaaaagg cgtgtctaat gaagcgccgc cgctgatggt gtctaacgtt 3960
gcctatggtc gtaccattta cgttaaactg gaaaccacga gctctagtaa agatgtccag 4020
gcggccttta aagccctgat caaaaacacc gatatcaaaa atagccagca atacaaagac 4080
atctacgaaa attcctcatt caccgcagtc gtgctgggcg gtgatgctca ggaacacaac 4140
aaagttgtca cgaaagattt tgacgaaatc cgcaaagtga ttaaagataa cgcaaccttc 4200
tcgacgaaaa atccggctta tccgatttcg tacaccagcg tttttctgaa agataacagc 4260
gtcgcagctg tgcataataa aaccgactat atcgaaacca ccagcaccga atacagcaaa 4320
ggcaaaatta atctggatca ctccggtgca tatgtcgctc agttcgaagt ggcctgggat 4380
gaagtttcat acgacaaaga aggcaatgaa gtgctgaccc ataaaacgtg ggatggtaac 4440
tatcaagaca aaaccgcaca ctactccacg gttattccgc tggaagcaaa cgctcgtaat 4500
atccgcatta aagcgcgtga atgcaccggt ctggcatggg aatggtggcg tgatgtcatc 4560
agcgaatatg acgtgccgct gacgaacaat atcaatgtgt caatctgggg caccacgctg 4620
tatccgggta gttccatcac ctataattaa taaggatcca ggaggattac tatatgggtc 4680
tggataccgt gagcttctcg acgaaaggcg caacctacat tacctacgtg aacttcctga 4740
acgaactgcg tgtgaaactg aaaccggaag gcaacagcca tggtatcccg ctgctgcgta 4800
aaaaatgcga tgacccgggc aaatgttttg ttctggtcgc actgagtaac gataatggtc 4860
agctggcaga aattgctatc gacgtgacct cagtttatgt ggttggctac caagtccgta 4920
accgctcgta tttctttaaa gatgcaccgg acgcggccta cgaaggtctg tttaaaaata 4980
ccatcaaaac gcgcctgcac ttcggcggta gttatccgtc cctggaaggc gaaaaagcgt 5040
atcgtgaaac cacggatctg ggcattgaac cgctgcgcat tggtatcaaa aaactggatg 5100
aaaacgcgat tgacaattat aaaccgacgg aaatcgccag ctctctgctg gtcgtgattc 5160
agatggtgtc agaagccgct cgttttacct ttatcgaaaa tcaaatccgc aacaactttc 5220
aacaaagaat tcgcccggct aataatacga tctcgctgga aaataaatgg ggtaaactga 5280
gctttcaaat ccgcacctcg ggcgctaacg gcatgttctc cgaagcggtg gaactggaac 5340
gtgccaacgg caaaaaatat tacgttaccg ctgtggacca ggtgaaaccg aaaatcgctc 5400
tgctgaaatt cgttgataaa gacccgaaat aataaggatc ccctaggggc gcgcctggta 5460
gtgtggggtc tccccatgcg agagtaggga actgccaggc atcaaataaa acgaaaggct 5520
cagtcgaaag actgggcctt tcgttttatc tgttgtttgt cggtgaacgc tctcctgagt 5580
aggacaaatc cgccgggagc ggatttgaac gttgcgaagc aacggcccgg agggtggcgg 5640
gcaggacgcc cgccataaac tgccaggcat caaattaagc agaaggccat cctgacggat 5700
ggcctttttg cgtttctaca aactcgagct cgaattcgta atcatggtca tagctgtttc 5760
ctgtgtgaaa ttgttatccg ctcacaattc cacacaacat acgagccgga agcataaagt 5820
gtaaagcctg gggtgcctaa tgagtgagct aactcacatt aattgcgttg cgctcactgc 5880
ccgctttcca gtcgggaaac ctgtcgtgcc agctgcatta atgaatcggc caacgcgcgg 5940
ggagaggcgg tttgcgtatt gggcgctctt ccgcttcctc gctcactgac tcgctgcgct 6000
cggtcgttcg gctgcggcga gcggtatcag ctcactcaaa ggcggtaata cggttatcca 6060
cagaatcagg ggataacgca ggaaagaaca tgtgagcaaa aggccagcaa aagcccagga 6120
accgtaaaaa ggccgcgttg ctggcgtttt tccataggct ccgcccccct gacgagcatc 6180
acaaaaatcg acgctcaagt cagaggtggc gaaacccgac aggactataa agataccagg 6240
cgtttccccc tggaagctcc ctcgtgcgct ctcctgttcc gaccctgccg cttaccggat 6300
acctgtccgc ctttctccct tcgggaagcg tggcgctttc tcatagctca cgctgtaggt 6360
atctcagttc ggtgtaggtc gttcgctcca agctgggctg tgtgcacgaa ccccccgttc 6420
agcccgaccg ctgcgcctta tccggtaact atcgtcttga gtccaacccg gtaagacacg 6480
acttatcgcc actggcagca gccactggta acaggattag cagagcgagg tatgtaggcg 6540
gtgctacaga gttcttgaag tggtggccta actacggcta cactagaagg acagtatttg 6600
gtatctgcgc tctgctgaag ccagttacct tcggaaaaag agttggtagc tcttgatccg 6660
gcaaacaaac caccgctggt agcggtggtt tttttgtttg caagcagcag attacgcgca 6720
gaaaaaaagg atctcaagaa gatcctttga tcttttctac ggggtctgac gctcagtgga 6780
acgaaaactc acgttaaggg attttggtca tgagattatc aaaaaggatc ttcacctaga 6840
tccttttaaa ttaaaaatga agttttagca cgtgctatta ttgaagcatt tatcagggtt 6900
attgtctcat gagcggatac atatttgaat gtatttagaa aaataaacaa ataggggttc 6960
cgcgcacatt tccccgaaaa gtgccacctg tatgcggtgt gaaataccgc acagatgcgt 7020
aaggagaaaa taccgcatca ggaaattgta agcgttaata attcagaaga actcgtcaag 7080
aaggcgatag aaggcgatgc gctgcgaatc gggagcggcg ataccgtaaa gcacgaggaa 7140
gcggtcagcc cattcgccgc caagctcttc agcaatatca cgggtagcca acgctatgtc 7200

-continued

```
ctgatagcgg tccgccacac ccagccggcc acagtcgatg aatccagaaa agcggccatt   7260

ttccaccatg atattcggca agcaggcatc gccatgggtc acgacgagat cctcgccgtc   7320

gggcatgctc gccttgagcc tggcgaacag ttcggctggc gcgagcccct gatgctcttc   7380

gtccagatca tcctgatcga caagaccggc ttccatccga gtacgtgctc gctcgatgcg   7440

atgtttcgct tggtggtcga atgggcaggt agccggatca agcgtatgca gccgccgcat   7500

tgcatcagcc atgatggata ctttctcggc aggagcaagg tgagatgaca ggagatcctg   7560

ccccggcact tcgcccaata gcagccagtc ccttcccgct tcagtgacaa cgtcgagcac   7620

agctgcgcaa ggaacgcccg tcgtggccag ccacgatagc cgcgctgcct cgtcttgcag   7680

ttcattcagg gcaccggaca ggtcggtctt gacaaaaaga accgggcgcc cctgcgctga   7740

cagccggaac acggcggcat cagagcagcc gattgtctgt tgtgcccagt catagccgaa   7800

tagcctctcc acccaagcgg ccggagaacc tgcgtgcaat ccatcttgtt caatcatgcg   7860

aaacgatcct catcctgtct cttgatcaga gcttgatccc ctgcgccatc agatccttgg   7920

cggcgagaaa gccatccagt ttactttgca gggcttccca accttaccag agggcgcccc   7980

agctggcaat tccggttcgc ttgctgtcca taaaaccgcc cagtagaagc atatg        8035
```

```
<210> SEQ ID NO 22
<211> LENGTH: 444
<212> TYPE: PRT
<213> ORGANISM: Artificial Sequence
<220> FEATURE:
<223> OTHER INFORMATION: Lpp-OmpA-Protein G

<400> SEQUENCE: 22

Met Lys Ala Thr Lys Leu Val Leu Gly Ala Val Ile Leu Gly Ser Thr
 1               5                  10                  15

Leu Leu Ala Gly Cys Ser Ser Asn Ala Lys Ile Asp Gln Gly Ile Asn
            20                  25                  30

Pro Tyr Val Gly Phe Glu Met Gly Tyr Asp Trp Leu Gly Arg Met Pro
        35                  40                  45

Tyr Lys Gly Ser Val Glu Asn Gly Ala Tyr Lys Ala Gln Gly Val Gln
    50                  55                  60

Leu Thr Ala Lys Leu Gly Tyr Pro Ile Thr Asp Asp Leu Asp Ile Tyr
65                  70                  75                  80

Thr Arg Leu Gly Gly Met Val Trp Arg Ala Asp Thr Lys Ser Asn Val
                85                  90                  95

Tyr Gly Lys Asn His Asp Thr Gly Val Ser Pro Val Phe Ala Gly Gly
            100                 105                 110

Val Glu Tyr Ala Ile Thr Pro Glu Ile Ala Thr Arg Leu Glu Tyr Gln
        115                 120                 125

Trp Thr Asn Asn Ile Gly Asp Ala His Thr Ile Gly Thr Arg Pro Asp
    130                 135                 140

Asn Gly Ile Pro Gly Ala Ala Asn Ala Ala Gln His Asp Glu Ala Gln
145                 150                 155                 160

Gln Asn Ala Phe Tyr Gln Val Leu Asn Met Pro Asn Leu Asn Ala Asp
                165                 170                 175

Gln Arg Asn Gly Phe Ile Gln Ser Leu Lys Asp Asp Pro Ser Gln Ser
            180                 185                 190

Ala Asn Val Leu Gly Glu Ala Gln Lys Leu Asn Asp Ser Gln Ala Pro
        195                 200                 205

Lys Ala Asp Ala Gln Gln Asn Asn Phe Asn Lys Asp Gln Gln Ser Ala
    210                 215                 220
```

Phe Tyr Glu Ile Leu Asn Met Pro Asn Leu Asn Glu Ala Gln Arg Asn
225 230 235 240

Gly Phe Ile Gln Ser Leu Lys Asp Asp Pro Ser Gln Ser Thr Asn Val
245 250 255

Leu Gly Glu Ala Lys Lys Leu Asn Glu Ser Gln Ala Pro Lys Ala Asp
260 265 270

Asn Asn Phe Asn Lys Glu Gln Gln Asn Ala Phe Tyr Glu Ile Leu Asn
275 280 285

Met Pro Asn Leu Asn Glu Glu Gln Arg Asn Gly Phe Ile Gln Ser Leu
290 295 300

Lys Asp Asp Pro Ser Gln Ser Ala Asn Leu Leu Ser Glu Ala Lys Lys
305 310 315 320

Leu Asn Glu Ser Gln Ala Pro Lys Ala Asp Asn Lys Phe Asn Lys Glu
325 330 335

Gln Gln Asn Ala Phe Tyr Glu Ile Leu His Leu Pro Asn Leu Asn Glu
340 345 350

Glu Gln Arg Asn Gly Phe Ile Gln Ser Leu Lys Asp Asp Pro Ser Gln
355 360 365

Ser Ala Asn Leu Leu Ala Glu Ala Lys Lys Leu Asn Asp Ala Gln Ala
370 375 380

Pro Lys Ala Asp Asn Lys Phe Asn Lys Glu Gln Gln Asn Ala Phe Tyr
385 390 395 400

Glu Ile Leu His Leu Pro Asn Leu Thr Glu Glu Gln Arg Asn Gly Phe
405 410 415

Ile Gln Ser Leu Lys Asp Asp Pro Ser Val Ser Lys Glu Ile Leu Ala
420 425 430

Glu Ala Lys Lys Leu Asn Asp Ala Gln Ala Pro Lys
435 440

<210> SEQ ID NO 23
<211> LENGTH: 356
<212> TYPE: PRT
<213> ORGANISM: Artificial Sequence
<220> FEATURE:
<223> OTHER INFORMATION: Lpp-OmpA-Protein G

<400> SEQUENCE: 23

Met Lys Ala Thr Lys Leu Val Leu Gly Ala Val Ile Leu Gly Ser Thr
1 5 10 15

Leu Leu Ala Gly Cys Ser Ser Asn Ala Lys Ile Asp Gln Gly Ile Asn
20 25 30

Pro Tyr Val Gly Phe Glu Met Gly Tyr Asp Trp Leu Gly Arg Met Pro
35 40 45

Tyr Lys Gly Ser Val Glu Asn Gly Ala Tyr Lys Ala Gln Gly Val Gln
50 55 60

Leu Thr Ala Lys Leu Gly Tyr Pro Ile Thr Asp Asp Leu Asp Ile Tyr
65 70 75 80

Thr Arg Leu Gly Gly Met Val Trp Arg Ala Asp Thr Lys Ser Asn Val
85 90 95

Tyr Gly Lys Asn His Asp Thr Gly Val Ser Pro Val Phe Ala Gly Gly
100 105 110

Val Glu Tyr Ala Ile Thr Pro Glu Ile Ala Thr Arg Leu Glu Tyr Gln
115 120 125

Trp Thr Asn Asn Ile Gly Asp Ala His Thr Ile Gly Thr Arg Pro Asp
130 135 140

Asn Gly Ile Pro Gly Ile Asp Glu Ile Leu Ala Ala Leu Pro Lys Thr
145 150 155 160

Asp Thr Tyr Lys Leu Ile Leu Asn Gly Lys Thr Leu Lys Gly Glu Thr
165 170 175

Thr Thr Glu Ala Val Asp Ala Ala Thr Ala Glu Lys Val Phe Lys Gln
180 185 190

Tyr Ala Asn Asp Asn Gly Val Asp Gly Glu Trp Thr Tyr Asp Asp Ala
195 200 205

Thr Lys Thr Phe Thr Val Thr Glu Lys Pro Glu Val Ile Asp Ala Ser
210 215 220

Glu Leu Thr Pro Ala Val Thr Thr Tyr Lys Leu Val Ile Asn Gly Lys
225 230 235 240

Thr Leu Lys Gly Glu Thr Thr Thr Glu Ala Val Asp Ala Ala Thr Ala
245 250 255

Glu Lys Val Phe Lys Gln Tyr Ala Asn Asp Asn Gly Val Asp Gly Glu
260 265 270

Trp Thr Tyr Asp Asp Ala Thr Lys Thr Phe Thr Val Thr Glu Lys Pro
275 280 285

Glu Val Ile Asp Ala Ser Glu Leu Thr Pro Ala Val Thr Thr Tyr Lys
290 295 300

Leu Val Ile Asn Gly Lys Thr Leu Lys Gly Glu Thr Thr Thr Lys Ala
305 310 315 320

Val Asp Ala Glu Thr Ala Glu Lys Ala Phe Lys Gln Tyr Ala Asn Asp
325 330 335

Asn Gly Val Asp Gly Val Trp Thr Tyr Asp Asp Ala Thr Lys Thr Phe
340 345 350

Thr Val Thr Glu
355

<210> SEQ ID NO 24
<211> LENGTH: 252
<212> TYPE: PRT
<213> ORGANISM: Artificial Sequence
<220> FEATURE:
<223> OTHER INFORMATION: Gelonin

<400> SEQUENCE: 24

Met Gly Leu Asp Thr Val Ser Phe Ser Thr Lys Gly Ala Thr Tyr Ile
1 5 10 15

Thr Tyr Val Asn Phe Leu Asn Glu Leu Arg Val Lys Leu Lys Pro Glu
20 25 30

Gly Asn Ser His Gly Ile Pro Leu Leu Arg Lys Lys Cys Asp Asp Pro
35 40 45

Gly Lys Cys Phe Val Leu Val Ala Leu Ser Asn Asp Asn Gly Gln Leu
50 55 60

Ala Glu Ile Ala Ile Asp Val Thr Ser Val Tyr Val Val Gly Tyr Gln
65 70 75 80

Val Arg Asn Arg Ser Tyr Phe Phe Lys Asp Ala Pro Asp Ala Ala Tyr
85 90 95

Glu Gly Leu Phe Lys Asn Thr Ile Lys Thr Arg Leu His Phe Gly Gly
100 105 110

Ser Tyr Pro Ser Leu Glu Gly Glu Lys Ala Tyr Arg Glu Thr Thr Asp
115 120 125

Leu Gly Ile Glu Pro Leu Arg Ile Gly Ile Lys Lys Leu Asp Glu Asn
130 135 140

Ala Ile Asp Asn Tyr Lys Pro Thr Glu Ile Ala Ser Ser Leu Leu Val
145 150 155 160

Val Ile Gln Met Val Ser Glu Ala Ala Arg Phe Thr Phe Ile Glu Asn
165 170 175

Gln Ile Arg Asn Asn Phe Gln Gln Arg Ile Arg Pro Ala Asn Asn Thr
180 185 190

Ile Ser Leu Glu Asn Lys Trp Gly Lys Leu Ser Phe Gln Ile Arg Thr
195 200 205

Ser Gly Ala Asn Gly Met Phe Ser Glu Ala Val Glu Leu Glu Arg Ala
210 215 220

Asn Gly Lys Lys Tyr Tyr Val Thr Ala Val Asp Gln Val Lys Pro Lys
225 230 235 240

Ile Ala Leu Leu Lys Phe Val Asp Lys Asp Pro Lys
245 250

<210> SEQ ID NO 25
<211> LENGTH: 217
<212> TYPE: PRT
<213> ORGANISM: Artificial Sequence
<220> FEATURE:
<223> OTHER INFORMATION: Diphtheria toxin Fragment A with native signal sequence

<400> SEQUENCE: 25

Met Ser Arg Lys Leu Phe Ala Ser Ile Leu Ile Gly Ala Leu Leu Gly
1 5 10 15

Ile Gly Ala Pro Pro Ser Ala His Ala Gly Ala Asp Asp Val Val Asp
20 25 30

Ser Ser Lys Ser Phe Val Met Glu Asn Phe Ser Ser Tyr His Gly Thr
35 40 45

Lys Pro Gly Tyr Val Asp Ser Ile Gln Lys Gly Ile Gln Lys Pro Lys
50 55 60

Ser Gly Thr Gln Gly Asn Tyr Asp Asp Asp Trp Lys Gly Phe Tyr Ser
65 70 75 80

Thr Asp Asn Lys Tyr Asp Ala Ala Gly Tyr Ser Val Asp Asn Glu Asn
85 90 95

Pro Leu Ser Gly Lys Ala Gly Gly Val Val Lys Val Thr Tyr Pro Gly
100 105 110

Leu Thr Lys Val Leu Ala Leu Lys Val Asp Asn Ala Glu Thr Ile Lys
115 120 125

Lys Glu Leu Gly Leu Ser Leu Thr Glu Pro Leu Met Glu Gln Val Gly
130 135 140

Thr Glu Glu Phe Ile Lys Arg Phe Gly Asp Gly Ala Ser Arg Val Val
145 150 155 160

Leu Ser Leu Pro Phe Ala Glu Gly Ser Ser Ser Val Glu Tyr Ile Asn
165 170 175

Asn Trp Glu Gln Ala Lys Ala Leu Ser Val Glu Leu Glu Ile Asn Phe
180 185 190

Glu Thr Arg Gly Lys Arg Gly Gln Asp Ala Met Tyr Glu Tyr Met Ala
195 200 205

Gln Ala Cys Ala Gly Asn Arg Val Arg
210 215

<210> SEQ ID NO 26
<211> LENGTH: 193
<212> TYPE: PRT

<213> ORGANISM: Artificial Sequence
<220> FEATURE:
<223> OTHER INFORMATION: Diphtheria toxin Fragment A lacking the native signal sequence

<400> SEQUENCE: 26

Met Gly Ala Asp Asp Val Val Asp Ser Ser Lys Ser Phe Val Met Glu
1 5 10 15

Asn Phe Ser Ser Tyr His Gly Thr Lys Pro Gly Tyr Val Asp Ser Ile
20 25 30

Gln Lys Gly Ile Gln Lys Pro Lys Ser Gly Thr Gln Gly Asn Tyr Asp
35 40 45

Asp Asp Trp Lys Gly Phe Tyr Ser Thr Asp Asn Lys Tyr Asp Ala Ala
50 55 60

Gly Tyr Ser Val Asp Asn Glu Asn Pro Leu Ser Gly Lys Ala Gly Gly
65 70 75 80

Val Val Lys Val Thr Tyr Pro Gly Leu Thr Lys Val Leu Ala Leu Lys
85 90 95

Val Asp Asn Ala Glu Thr Ile Lys Lys Glu Leu Gly Leu Ser Leu Thr
100 105 110

Glu Pro Leu Met Glu Gln Val Gly Thr Glu Glu Phe Ile Lys Arg Phe
115 120 125

Gly Asp Gly Ala Ser Arg Val Val Leu Ser Leu Pro Phe Ala Glu Gly
130 135 140

Ser Ser Ser Val Glu Tyr Ile Asn Asn Trp Glu Gln Ala Lys Ala Leu
145 150 155 160

Ser Val Glu Leu Glu Ile Asn Phe Glu Thr Arg Gly Lys Arg Gly Gln
165 170 175

Asp Ala Met Tyr Glu Tyr Met Ala Gln Ala Cys Ala Gly Asn Arg Val
180 185 190

Arg

<210> SEQ ID NO 27
<211> LENGTH: 500
<212> TYPE: PRT
<213> ORGANISM: Artificial Sequence
<220> FEATURE:
<223> OTHER INFORMATION: Perfringolysin O

<400> SEQUENCE: 27

Met Ile Arg Phe Lys Lys Thr Lys Leu Ile Ala Ser Ile Ala Met Ala
1 5 10 15

Leu Cys Leu Phe Ser Gln Pro Val Ile Ser Phe Ser Lys Asp Ile Thr
20 25 30

Asp Lys Asn Gln Ser Ile Asp Ser Gly Ile Ser Ser Leu Ser Tyr Asn
35 40 45

Arg Asn Glu Val Leu Ala Ser Asn Gly Asp Lys Ile Glu Ser Phe Val
50 55 60

Pro Lys Glu Gly Lys Lys Ala Gly Asn Lys Phe Ile Val Val Glu Arg
65 70 75 80

Gln Lys Arg Ser Leu Thr Thr Ser Pro Val Asp Ile Ser Ile Ile Asp
85 90 95

Ser Val Asn Asp Arg Thr Tyr Pro Gly Ala Leu Gln Leu Ala Asp Lys
100 105 110

Ala Phe Val Glu Asn Arg Pro Thr Ile Leu Met Val Lys Arg Lys Pro
115 120 125

Ile Asn Ile Asn Ile Asp Leu Pro Gly Leu Lys Gly Glu Asn Ser Ile
130 135 140

Lys Val Asp Asp Pro Thr Tyr Gly Lys Val Ser Gly Ala Ile Asp Glu
145 150 155 160

Leu Val Ser Lys Trp Asn Glu Lys Tyr Ser Ser Thr His Thr Leu Pro
165 170 175

Ala Arg Thr Gln Tyr Ser Glu Ser Met Val Tyr Ser Lys Ser Gln Ile
180 185 190

Ser Ser Ala Leu Asn Val Asn Ala Lys Val Leu Glu Asn Ser Leu Gly
195 200 205

Val Asp Phe Asn Ala Val Ala Asn Asn Glu Lys Lys Val Met Ile Leu
210 215 220

Ala Tyr Lys Gln Ile Phe Tyr Thr Val Ser Ala Asp Leu Pro Lys Asn
225 230 235 240

Pro Ser Asp Leu Phe Asp Asp Ser Val Thr Phe Asn Asp Leu Lys Gln
245 250 255

Lys Gly Val Ser Asn Glu Ala Pro Pro Leu Met Val Ser Asn Val Ala
260 265 270

Tyr Gly Arg Thr Ile Tyr Val Lys Leu Glu Thr Thr Ser Ser Ser Lys
275 280 285

Asp Val Gln Ala Ala Phe Lys Ala Leu Ile Lys Asn Thr Asp Ile Lys
290 295 300

Asn Ser Gln Gln Tyr Lys Asp Ile Tyr Glu Asn Ser Ser Phe Thr Ala
305 310 315 320

Val Val Leu Gly Gly Asp Ala Gln Glu His Asn Lys Val Val Thr Lys
325 330 335

Asp Phe Asp Glu Ile Arg Lys Val Ile Lys Asp Asn Ala Thr Phe Ser
340 345 350

Thr Lys Asn Pro Ala Tyr Pro Ile Ser Tyr Thr Ser Val Phe Leu Lys
355 360 365

Asp Asn Ser Val Ala Ala Val His Asn Lys Thr Asp Tyr Ile Glu Thr
370 375 380

Thr Ser Thr Glu Tyr Ser Lys Gly Lys Ile Asn Leu Asp His Ser Gly
385 390 395 400

Ala Tyr Val Ala Gln Phe Glu Val Ala Trp Asp Glu Val Ser Tyr Asp
405 410 415

Lys Glu Gly Asn Glu Val Leu Thr His Lys Thr Trp Asp Gly Asn Tyr
420 425 430

Gln Asp Lys Thr Ala His Tyr Ser Thr Val Ile Pro Leu Glu Ala Asn
435 440 445

Ala Arg Asn Ile Arg Ile Lys Ala Arg Glu Cys Thr Gly Leu Ala Trp
450 455 460

Glu Trp Trp Arg Asp Val Ile Ser Glu Tyr Asp Val Pro Leu Thr Asn
465 470 475 480

Asn Ile Asn Val Ser Ile Trp Gly Thr Thr Leu Tyr Pro Gly Ser Ser
485 490 495

Ile Thr Tyr Asn
500

<210> SEQ ID NO 28
<211> LENGTH: 499
<212> TYPE: PRT
<213> ORGANISM: Artificial Sequence
<220> FEATURE:
<223> OTHER INFORMATION: Perfringolysin O

<400> SEQUENCE: 28

Met Ile Arg Phe Lys Lys Thr Lys Leu Ile Ala Ser Ile Ala Met Ala
1 5 10 15

Leu Cys Leu Phe Ser Gln Pro Val Ile Ser Phe Ser Lys Asp Ile Thr
20 25 30

Asp Lys Asn Gln Ser Ile Asp Ser Gly Ile Ser Ser Leu Ser Tyr Asn
35 40 45

Arg Asn Glu Val Leu Ala Ser Asn Gly Asp Lys Ile Glu Ser Phe Val
50 55 60

Pro Lys Glu Gly Lys Lys Ala Gly Asn Lys Phe Ile Val Val Glu Arg
65 70 75 80

Gln Lys Arg Ser Leu Thr Thr Ser Pro Val Asp Ile Ser Ile Ile Asp
85 90 95

Ser Val Asn Asp Arg Thr Tyr Pro Gly Ala Leu Gln Leu Ala Asp Lys
100 105 110

Ala Phe Val Glu Asn Arg Pro Thr Ile Leu Met Val Lys Glu Ala Ile
115 120 125

Asn Ile Asn Ile Asp Leu Pro Gly Leu Lys Gly Glu Asn Ser Ile Lys
130 135 140

Val Asp Asp Pro Thr Tyr Gly Lys Val Ser Gly Ala Ile Asp Glu Leu
145 150 155 160

Val Ser Lys Trp Asn Glu Lys Tyr Ser Ser Thr His Thr Leu Pro Ala
165 170 175

Arg Thr Gln Tyr Ser Glu Ser Met Val Tyr Ser Lys Ser Gln Ile Ser
180 185 190

Ser Ala Leu Asn Val Asn Ala Lys Val Leu Glu Asn Ser Leu Gly Val
195 200 205

Asp Phe Asn Ala Val Ala Asn Asn Glu Lys Lys Val Met Ile Leu Ala
210 215 220

Tyr Lys Gln Ile Phe Tyr Thr Val Ser Ala Asp Leu Pro Lys Asn Pro
225 230 235 240

Ser Asp Leu Phe Asp Asp Ser Val Thr Phe Asn Asp Leu Lys Gln Lys
245 250 255

Gly Val Ser Asn Glu Ala Pro Pro Leu Met Val Ser Asn Val Ala Tyr
260 265 270

Gly Arg Thr Ile Tyr Val Lys Leu Glu Thr Thr Ser Ser Ser Lys Asp
275 280 285

Val Gln Ala Ala Phe Lys Ala Leu Ile Lys Asn Thr Asp Ile Lys Asn
290 295 300

Ser Gln Gln Tyr Lys Asp Ile Tyr Glu Asn Ser Ser Phe Thr Ala Val
305 310 315 320

Val Leu Gly Gly Asp Ala Gln Glu His Asn Lys Val Val Thr Lys Asp
325 330 335

Phe Asp Glu Ile Arg Lys Val Ile Lys Asp Asn Ala Thr Phe Ser Thr
340 345 350

Lys Asn Pro Ala Tyr Pro Ile Ser Tyr Thr Ser Val Phe Leu Lys Asp
355 360 365

Asn Ser Val Ala Ala Val His Asn Lys Thr Asp Tyr Ile Glu Thr Thr
370 375 380

Ser Thr Glu Tyr Ser Lys Gly Lys Ile Asn Leu Asp His Ser Gly Ala
385 390 395 400

Tyr Val Ala Gln Phe Glu Val Ala Trp Asp Glu Val Ser Tyr Asp Lys

```
                405                 410                 415

Glu Gly Asn Glu Val Leu Thr His Lys Thr Trp Asp Gly Asn Tyr Gln
            420                 425                 430

Asp Lys Thr Ala His Tyr Ser Thr Val Ile Pro Leu Glu Ala Asn Ala
        435                 440                 445

Arg Asn Ile Arg Ile Lys Ala Arg Glu Cys Thr Gly Leu Ala Trp Glu
    450                 455                 460

Trp Trp Arg Asp Val Ile Ser Glu Tyr Asp Val Pro Leu Thr Asn Asn
465                 470                 475                 480

Ile Asn Val Ser Ile Trp Gly Thr Thr Leu Tyr Pro Gly Ser Ser Ile
                485                 490                 495

Thr Tyr Asn


<210> SEQ ID NO 29
<211> LENGTH: 529
<212> TYPE: PRT
<213> ORGANISM: Listeria monocytogenes
<220> FEATURE:
<223> OTHER INFORMATION: Listeriolysin O

<400> SEQUENCE: 29

Met Lys Lys Leu Met Leu Val Phe Ile Thr Leu Ile Leu Val Ser Leu
 1               5                  10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270
```

Ala Val Thr Lys Glu Gln Leu Gln Ala Leu Gly Val Asn Ala Glu Asn
275 280 285

Pro Pro Ala Tyr Ile Ser Ser Val Ala Tyr Gly Arg Gln Val Tyr Leu
290 295 300

Lys Leu Ser Thr Asn Ser His Ser Thr Lys Val Lys Ala Ala Phe Asp
305 310 315 320

Ala Ala Val Ser Gly Lys Ser Val Ser Gly Asp Val Glu Leu Thr Asn
325 330 335

Ile Ile Lys Asn Ser Ser Phe Lys Ala Val Ile Tyr Gly Gly Ser Ala
340 345 350

Lys Asp Glu Val Gln Ile Ile Asp Gly Asn Leu Gly Asp Leu Arg Asp
355 360 365

Ile Leu Lys Lys Gly Ala Thr Phe Asn Arg Glu Thr Pro Gly Val Pro
370 375 380

Ile Ala Tyr Thr Thr Asn Phe Leu Lys Asp Asn Glu Leu Ala Val Ile
385 390 395 400

Lys Asn Asn Ser Glu Tyr Ile Glu Thr Thr Ser Lys Ala Tyr Thr Asp
405 410 415

Gly Lys Ile Asn Ile Asp His Ser Gly Gly Tyr Val Ala Gln Phe Asn
420 425 430

Ile Ser Trp Asp Glu Val Asn Tyr Asp Pro Glu Gly Asn Glu Ile Val
435 440 445

Gln His Lys Asn Trp Ser Glu Asn Asn Lys Ser Lys Leu Ala His Phe
450 455 460

Thr Ser Ser Ile Tyr Leu Pro Gly Asn Ala Arg Asn Ile Asn Val Tyr
465 470 475 480

Ala Lys Glu Cys Thr Gly Leu Ala Trp Glu Trp Trp Arg Thr Val Ile
485 490 495

Asp Asp Arg Asn Leu Pro Leu Val Lys Asn Arg Asn Ile Ser Ile Trp
500 505 510

Gly Thr Thr Leu Tyr Pro Lys Tyr Ser Asn Lys Val Asp Asn Pro Ile
515 520 525

Glu

<210> SEQ ID NO 30
<211> LENGTH: 504
<212> TYPE: PRT
<213> ORGANISM: Listeria monocytogenes
<220> FEATURE:
<223> OTHER INFORMATION: Listeriolysin O lacking signal sequence

<400> SEQUENCE: 30

Met Ser Ala Phe Asn Lys Glu Asn Ser Ile Ser Ser Met Ala Pro Pro
1 5 10 15

Ala Ser Pro Pro Ala Ser Pro Lys Thr Pro Ile Glu Lys Lys His Ala
20 25 30

Asp Glu Ile Asp Lys Tyr Ile Gln Gly Leu Asp Tyr Asn Lys Asn Asn
35 40 45

Val Leu Val Tyr His Gly Asp Ala Val Thr Asn Val Pro Pro Arg Lys
50 55 60

Gly Tyr Lys Asp Gly Asn Glu Tyr Ile Val Val Glu Lys Lys Lys Lys
65 70 75 80

Ser Ile Asn Gln Asn Asn Ala Asp Ile Gln Val Val Asn Ala Ile Ser
85 90 95

```
Ser Leu Thr Tyr Pro Gly Ala Leu Val Lys Ala Asn Ser Glu Leu Val
            100                 105                 110

Glu Asn Gln Pro Asp Val Leu Pro Val Lys Arg Asp Ser Leu Thr Leu
        115                 120                 125

Ser Ile Asp Leu Pro Gly Met Thr Asn Gln Asp Asn Lys Ile Val Val
    130                 135                 140

Lys Asn Ala Thr Lys Ser Asn Val Asn Asn Ala Val Asn Thr Leu Val
145                 150                 155                 160

Glu Arg Trp Asn Glu Lys Tyr Ala Gln Ala Tyr Pro Asn Val Ser Ala
                165                 170                 175

Lys Ile Asp Tyr Asp Asp Glu Met Ala Tyr Ser Glu Ser Gln Leu Ile
            180                 185                 190

Ala Lys Phe Gly Thr Ala Phe Lys Ala Val Asn Asn Ser Leu Asn Val
        195                 200                 205

Asn Phe Gly Ala Ile Ser Glu Gly Lys Met Gln Glu Glu Val Ile Ser
    210                 215                 220

Phe Lys Gln Ile Tyr Tyr Asn Val Asn Val Asn Glu Pro Thr Arg Pro
225                 230                 235                 240

Ser Arg Phe Phe Gly Lys Ala Val Thr Lys Glu Gln Leu Gln Ala Leu
                245                 250                 255

Gly Val Asn Ala Glu Asn Pro Pro Ala Tyr Ile Ser Ser Val Ala Tyr
            260                 265                 270

Gly Arg Gln Val Tyr Leu Lys Leu Ser Thr Asn Ser His Ser Thr Lys
        275                 280                 285

Val Lys Ala Ala Phe Asp Ala Ala Val Ser Gly Lys Ser Val Ser Gly
    290                 295                 300

Asp Val Glu Leu Thr Asn Ile Ile Lys Asn Ser Ser Phe Lys Ala Val
305                 310                 315                 320

Ile Tyr Gly Gly Ser Ala Lys Asp Glu Val Gln Ile Ile Asp Gly Asn
                325                 330                 335

Leu Gly Asp Leu Arg Asp Ile Leu Lys Lys Gly Ala Thr Phe Asn Arg
            340                 345                 350

Glu Thr Pro Gly Val Pro Ile Ala Tyr Thr Thr Asn Phe Leu Lys Asp
        355                 360                 365

Asn Glu Leu Ala Val Ile Lys Asn Asn Ser Glu Tyr Ile Glu Thr Thr
    370                 375                 380

Ser Lys Ala Tyr Thr Asp Gly Lys Ile Asn Ile Asp His Ser Gly Gly
385                 390                 395                 400

Tyr Val Ala Gln Phe Asn Ile Ser Trp Asp Glu Val Asn Tyr Asp Pro
                405                 410                 415

Glu Gly Asn Glu Ile Val Gln His Lys Asn Trp Ser Glu Asn Asn Lys
            420                 425                 430

Ser Lys Leu Ala His Phe Thr Ser Ser Ile Tyr Leu Pro Gly Asn Ala
        435                 440                 445

Arg Asn Ile Asn Val Tyr Ala Lys Glu Cys Thr Gly Leu Ala Trp Glu
    450                 455                 460

Trp Trp Arg Thr Val Ile Asp Asp Arg Asn Leu Pro Leu Val Lys Asn
465                 470                 475                 480

Arg Asn Ile Ser Ile Trp Gly Thr Thr Leu Tyr Pro Lys Tyr Ser Asn
                485                 490                 495

Lys Val Asp Asn Pro Ile Glu Tyr
            500
```

<210> SEQ ID NO 31
<211> LENGTH: 529
<212> TYPE: PRT
<213> ORGANISM: Artificial Sequence
<220> FEATURE:
<223> OTHER INFORMATION: Listeriolysin O (stabilized; sLLO)

<400> SEQUENCE: 31

```
Met Lys Lys Ile Met Leu Val Phe Ile Thr Leu Ile Leu Val Ser Leu
 1               5                  10                  15

Pro Ile Ala Gln Gln Thr Glu Ala Gly Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Met Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Lys
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
```

```
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp Pro Glu Gly Asn Glu Ile Val
        435                 440                 445

Gln His Lys Asn Trp Ser Glu Asn Asn Lys Ser Lys Leu Ala His Phe
    450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Trp Arg Thr Val Ile
                485                 490                 495

Asp Asp Arg Asn Leu Pro Leu Val Lys Asn Arg Asn Ile Ser Ile Trp
            500                 505                 510

Gly Thr Thr Leu Tyr Pro Lys Tyr Ser Asn Lys Val Asp Asn Pro Ile
        515                 520                 525

Glu


<210> SEQ ID NO 32
<211> LENGTH: 529
<212> TYPE: PRT
<213> ORGANISM: Artificial Sequence
<220> FEATURE:
<223> OTHER INFORMATION: Listeriolysin O (pH-stabilized; sLLOpH)

<400> SEQUENCE: 32

Met Lys Lys Ile Met Leu Val Phe Ile Thr Leu Ile Leu Val Ser Leu
 1               5                  10                  15

Pro Ile Ala Gln Gln Thr Glu Ala Gly Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205
```

-continued

```
Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Met Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Lys
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp Pro Glu Gly Asn Glu Ile Val
        435                 440                 445

Gln His Lys Asn Trp Ser Glu Asn Asn Lys Ser Lys Thr Ala His Phe
    450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Trp Arg Thr Val Ile
                485                 490                 495

Asp Asp Arg Asn Leu Pro Leu Val Lys Asn Arg Asn Ile Ser Ile Trp
            500                 505                 510

Gly Thr Thr Leu Tyr Pro Lys Tyr Ser Asn Lys Val Asp Asn Pro Ile
        515                 520                 525

Glu
```

```
<210> SEQ ID NO 33
<211> LENGTH: 1503
<212> TYPE: DNA
<213> ORGANISM: Artificial Sequence
<220> FEATURE:
<223> OTHER INFORMATION: PFOs L462F (PFOf)

<400> SEQUENCE: 33

atgatccgct tcaaaaagac caaactgatt gcgagcattg cgatggcact gtgtctgttc      60

tcccagccgg tgatttcgtt ctcaaaagat attaccgaca aaaatcagtc catcgattca     120

ggcattagct ctctgtctta taaccgtaat gaagtgctgg cgtccaatgg tgacaaaatc     180
```

-continued

```
gaatcatttg ttccgaaaga aggcaaaaaa gccggtaaca aattcattgt ggttgaacgt    240
cagaaacgct ctctgaccac gagtccggtt gatatctcca ttatcgattc agtcaatgac    300
cgtacctatc cgggtgcact gcaactggca gacaaagcat ttgtggaaaa ccgtccgacg    360
attctgatgg ttaaacgcaa accgattaac atcaatattg atctgccggg cctgaaaggt    420
gaaaatagta tcaaagtgga tgacccgacc tatggcaaag tttcgggtgc aattgatgaa    480
ctggtcagca aatggaacga aaaatacagt tccacccata cgctgccggc gcgtacccag    540
tattcggaaa gcatggtgta ctctaaaagt caaatctcat cggcgctgaa cgttaatgcc    600
aaagtcctgg aaaactctct gggtgtggat tttaatgcgg ttgccaacaa tgagaaaaaa    660
gtgatgatcc tggcatataa acagattttc tacaccgtta gtgctgatct gccgaaaaac    720
ccgtctgacc tgtttgatga cagtgtcacg ttcaacgatc tgaaacaaaa aggcgtgtct    780
aatgaagcgc cgccgctgat ggtgtctaac gttgcctatg gtcgtaccat ttacgttaaa    840
ctggaaacca cgtctagcag taaagatgtc caggcggcct ttaaagccct gatcaaaaac    900
accgatatca aaaatagcca gcaatacaaa gacatctacg aaaattcctc attcaccgca    960
gtcgtgctgg gcggtgatgc tcaggaacac aacaaagttg tcacgaaaga ttttgacgaa   1020
atccgcaaag tgattaaaga taacgcaacc ttctcgacga aaaatccggc ttatccgatt   1080
tcgtacacca gcgtttttct gaaagataac agcgtcgcag ctgtgcataa taaaaccgac   1140
tatatcgaaa ccaccagcac cgaatacagc aaaggcaaaa ttaatctgga tcactccggt   1200
gcatatgtcg ctcagttcga agtggcctgg gatgaagttt catacgacaa agaaggcaat   1260
gaagtgctga cccataaaac gtgggatggt aactatcaag acaaaaccgc acactactcc   1320
acggttattc cgctggaagc aaacgctcgt aatatccgca ttaaagcgcg tgaatgcacc   1380
ggttttgcat gggaatggtg gcgtgatgtc atcagcgaat atgacgtgcc gctgacgaac   1440
aatatcaatg tgtcaatctg ggcaccacg  ctgtatccgg gtagttccat cacctataat   1500
taa                                                                 1503
```

<210> SEQ ID NO 34
<211> LENGTH: 500
<212> TYPE: PRT
<213> ORGANISM: Artificial Sequence
<220> FEATURE:
<223> OTHER INFORMATION: PFOs L462F (PFOf)

<400> SEQUENCE: 34

```
Met Ile Arg Phe Lys Lys Thr Lys Leu Ile Ala Ser Ile Ala Met Ala
1               5                   10                  15

Leu Cys Leu Phe Ser Gln Pro Val Ile Ser Phe Ser Lys Asp Ile Thr
            20                  25                  30

Asp Lys Asn Gln Ser Ile Asp Ser Gly Ile Ser Ser Leu Ser Tyr Asn
        35                  40                  45

Arg Asn Glu Val Leu Ala Ser Asn Gly Asp Lys Ile Glu Ser Phe Val
    50                  55                  60

Pro Lys Glu Gly Lys Lys Ala Gly Asn Lys Phe Ile Val Val Glu Arg
65                  70                  75                  80

Gln Lys Arg Ser Leu Thr Thr Ser Pro Val Asp Ile Ser Ile Ile Asp
                85                  90                  95

Ser Val Asn Asp Arg Thr Tyr Pro Gly Ala Leu Gln Leu Ala Asp Lys
            100                 105                 110

Ala Phe Val Glu Asn Arg Pro Thr Ile Leu Met Val Lys Arg Lys Pro
        115                 120                 125
```

Ile Asn Ile Asn Ile Asp Leu Pro Gly Leu Lys Gly Glu Asn Ser Ile
130 135 140

Lys Val Asp Asp Pro Thr Tyr Gly Lys Val Ser Gly Ala Ile Asp Glu
145 150 155 160

Leu Val Ser Lys Trp Asn Glu Lys Tyr Ser Ser Thr His Thr Leu Pro
165 170 175

Ala Arg Thr Gln Tyr Ser Glu Ser Met Val Tyr Ser Lys Ser Gln Ile
180 185 190

Ser Ser Ala Leu Asn Val Asn Ala Lys Val Leu Glu Asn Ser Leu Gly
195 200 205

Val Asp Phe Asn Ala Val Ala Asn Asn Glu Lys Lys Val Met Ile Leu
210 215 220

Ala Tyr Lys Gln Ile Phe Tyr Thr Val Ser Ala Asp Leu Pro Lys Asn
225 230 235 240

Pro Ser Asp Leu Phe Asp Asp Ser Val Thr Phe Asn Asp Leu Lys Gln
245 250 255

Lys Gly Val Ser Asn Glu Ala Pro Pro Leu Met Val Ser Asn Val Ala
260 265 270

Tyr Gly Arg Thr Ile Tyr Val Lys Leu Glu Thr Thr Ser Ser Ser Lys
275 280 285

Asp Val Gln Ala Ala Phe Lys Ala Leu Ile Lys Asn Thr Asp Ile Lys
290 295 300

Asn Ser Gln Gln Tyr Lys Asp Ile Tyr Glu Asn Ser Ser Phe Thr Ala
305 310 315 320

Val Val Leu Gly Gly Asp Ala Gln Glu His Asn Lys Val Val Thr Lys
325 330 335

Asp Phe Asp Glu Ile Arg Lys Val Ile Lys Asp Asn Ala Thr Phe Ser
340 345 350

Thr Lys Asn Pro Ala Tyr Pro Ile Ser Tyr Thr Ser Val Phe Leu Lys
355 360 365

Asp Asn Ser Val Ala Ala Val His Asn Lys Thr Asp Tyr Ile Glu Thr
370 375 380

Thr Ser Thr Glu Tyr Ser Lys Gly Lys Ile Asn Leu Asp His Ser Gly
385 390 395 400

Ala Tyr Val Ala Gln Phe Glu Val Ala Trp Asp Glu Val Ser Tyr Asp
405 410 415

Lys Glu Gly Asn Glu Val Leu Thr His Lys Thr Trp Asp Gly Asn Tyr
420 425 430

Gln Asp Lys Thr Ala His Tyr Ser Thr Val Ile Pro Leu Glu Ala Asn
435 440 445

Ala Arg Asn Ile Arg Ile Lys Ala Arg Glu Cys Thr Gly Phe Ala Trp
450 455 460

Glu Trp Trp Arg Asp Val Ile Ser Glu Tyr Asp Val Pro Leu Thr Asn
465 470 475 480

Asn Ile Asn Val Ser Ile Trp Gly Thr Thr Leu Tyr Pro Gly Ser Ser
485 490 495

Ile Thr Tyr Asn
500

<210> SEQ ID NO 35
<211> LENGTH: 1503
<212> TYPE: DNA
<213> ORGANISM: Artificial Sequence
<220> FEATURE:

<223> OTHER INFORMATION: PFOsG137Q (PFOq)

<400> SEQUENCE: 35

```
atgatccgct tcaaaaagac caaactgatt gcgagcattg cgatggcact gtgtctgttc     60
tcccagccgg tgatttcgtt ctcaaaagat attaccgaca aaaatcagtc catcgattca    120
ggcattagct ctctgtctta taaccgtaat gaagtgctgg cgtccaatgg tgacaaaatc    180
gaatcatttg ttccgaaaga aggcaaaaaa gccggtaaca aattcattgt ggttgaacgt    240
cagaaacgct ctctgaccac gagtccggtt gatatctcca ttatcgattc agtcaatgac    300
cgtacctatc cgggtgcact gcaactggca gacaaagcat ttgtggaaaa ccgtccgacg    360
attctgatgg ttaaacgcaa accgattaac atcaatattg atctgccgca gctgaaaggt    420
gaaaatagta tcaaagtgga tgacccgacc tatggcaaag tttcgggtgc aattgatgaa    480
ctggtcagca aatggaacga aaaatacagt tccacccata cgctgccggc gcgtacccag    540
tattcggaaa gcatggtgta ctctaaaagt caaatctcat cggcgctgaa cgttaatgcc    600
aaagtcctgg aaaactctct gggtgtggat tttaatgcgg ttgccaacaa tgagaaaaaa    660
gtgatgatcc tggcatataa acagattttc tacaccgtta gtgctgatct gccgaaaaac    720
ccgtctgacc tgtttgatga cagtgtcacg ttcaacgatc tgaaacaaaa aggcgtgtct    780
aatgaagcgc cgccgctgat ggtgtctaac gttgcctatg gtcgtaccat ttacgttaaa    840
ctggaaacca cgtctagcag taaagatgtc caggcggcct ttaaagccct gatcaaaaac    900
accgatatca aaaatagcca gcaatacaaa gacatctacg aaaattcctc attcaccgca    960
gtcgtgctgg gcggtgatgc tcaggaacac aacaaagttg tcacgaaaga ttttgacgaa   1020
atccgcaaag tgattaaaga taacgcaacc ttctcgacga aaaatccggc ttatccgatt   1080
tcgtacacca gcgtttttct gaaagataac agcgtcgcag ctgtgcataa taaaaccgac   1140
tatatcgaaa ccaccagcac cgaatacagc aaaggcaaaa ttaatctgga tcactccggt   1200
gcatatgtcg ctcagttcga agtggcctgg gatgaagttt catacgacaa agaaggcaat   1260
gaagtgctga cccataaaac gtgggatggt aactatcaag acaaaaccgc acactactcc   1320
acggttattc cgctggaagc aaacgctcgt aatatccgca ttaaagcgcg tgaatgcacc   1380
ggtctggcat gggaatggtg gcgtgatgtc atcagcgaat atgacgtgcc gctgacgaac   1440
aatatcaatg tgtcaatctg gggcaccacg ctgtatccgg gtagttccat cacctataat   1500
taa                                                                 1503
```

<210> SEQ ID NO 36
<211> LENGTH: 500
<212> TYPE: PRT
<213> ORGANISM: Artificial Sequence
<220> FEATURE:
<223> OTHER INFORMATION: PFOsG137Q (PFOq)

<400> SEQUENCE: 36

```
Met Ile Arg Phe Lys Lys Thr Lys Leu Ile Ala Ser Ile Ala Met Ala
1               5                   10                  15

Leu Cys Leu Phe Ser Gln Pro Val Ile Ser Phe Ser Lys Asp Ile Thr
            20                  25                  30

Asp Lys Asn Gln Ser Ile Asp Ser Gly Ile Ser Ser Leu Ser Tyr Asn
        35                  40                  45

Arg Asn Glu Val Leu Ala Ser Asn Gly Asp Lys Ile Glu Ser Phe Val
    50                  55                  60

Pro Lys Glu Gly Lys Lys Ala Gly Asn Lys Phe Ile Val Val Glu Arg
```

-continued 65 70 75 80

Gln Lys Arg Ser Leu Thr Thr Ser Pro Val Asp Ile Ser Ile Ile Asp
85 90 95

Ser Val Asn Asp Arg Thr Tyr Pro Gly Ala Leu Gln Leu Ala Asp Lys
100 105 110

Ala Phe Val Glu Asn Arg Pro Thr Ile Leu Met Val Lys Arg Lys Pro
115 120 125

Ile Asn Ile Asn Ile Asp Leu Pro Gln Leu Lys Gly Glu Asn Ser Ile
130 135 140

Lys Val Asp Asp Pro Thr Tyr Gly Lys Val Ser Gly Ala Ile Asp Glu
145 150 155 160

Leu Val Ser Lys Trp Asn Glu Lys Tyr Ser Ser Thr His Thr Leu Pro
165 170 175

Ala Arg Thr Gln Tyr Ser Glu Ser Met Val Tyr Ser Lys Ser Gln Ile
180 185 190

Ser Ser Ala Leu Asn Val Asn Ala Lys Val Leu Glu Asn Ser Leu Gly
195 200 205

Val Asp Phe Asn Ala Val Ala Asn Asn Glu Lys Lys Val Met Ile Leu
210 215 220

Ala Tyr Lys Gln Ile Phe Tyr Thr Val Ser Ala Asp Leu Pro Lys Asn
225 230 235 240

Pro Ser Asp Leu Phe Asp Asp Ser Val Thr Phe Asn Asp Leu Lys Gln
245 250 255

Lys Gly Val Ser Asn Glu Ala Pro Pro Leu Met Val Ser Asn Val Ala
260 265 270

Tyr Gly Arg Thr Ile Tyr Val Lys Leu Glu Thr Thr Ser Ser Ser Lys
275 280 285

Asp Val Gln Ala Ala Phe Lys Ala Leu Ile Lys Asn Thr Asp Ile Lys
290 295 300

Asn Ser Gln Gln Tyr Lys Asp Ile Tyr Glu Asn Ser Ser Phe Thr Ala
305 310 315 320

Val Val Leu Gly Gly Asp Ala Gln Glu His Asn Lys Val Val Thr Lys
325 330 335

Asp Phe Asp Glu Ile Arg Lys Val Ile Lys Asp Asn Ala Thr Phe Ser
340 345 350

Thr Lys Asn Pro Ala Tyr Pro Ile Ser Tyr Thr Ser Val Phe Leu Lys
355 360 365

Asp Asn Ser Val Ala Ala Val His Asn Lys Thr Asp Tyr Ile Glu Thr
370 375 380

Thr Ser Thr Glu Tyr Ser Lys Gly Lys Ile Asn Leu Asp His Ser Gly
385 390 395 400

Ala Tyr Val Ala Gln Phe Glu Val Ala Trp Asp Glu Val Ser Tyr Asp
405 410 415

Lys Glu Gly Asn Glu Val Leu Thr His Lys Thr Trp Asp Gly Asn Tyr
420 425 430

Gln Asp Lys Thr Ala His Tyr Ser Thr Val Ile Pro Leu Glu Ala Asn
435 440 445

Ala Arg Asn Ile Arg Ile Lys Ala Arg Glu Cys Thr Gly Leu Ala Trp
450 455 460

Glu Trp Trp Arg Asp Val Ile Ser Glu Tyr Asp Val Pro Leu Thr Asn
465 470 475 480

Asn Ile Asn Val Ser Ile Trp Gly Thr Thr Leu Tyr Pro Gly Ser Ser
485 490 495

Ile Thr Tyr Asn
500

<210> SEQ ID NO 37
<211> LENGTH: 1503
<212> TYPE: DNA
<213> ORGANISM: Artificial Sequence
<220> FEATURE:
<223> OTHER INFORMATION: PFOsH438Y (PFOy)

<400> SEQUENCE: 37
atgatccgct tcaaaaagac caaactgatt gcgagcattg cgatggcact gtgtctgttc 60
tcccagccgg tgatttcgtt ctcaaaagat attaccgaca aaaatcagtc catcgattca 120
ggcattagct ctctgtctta taaccgtaat gaagtgctgg cgtccaatgg tgacaaaatc 180
gaatcatttg ttccgaaaga aggcaaaaaa gccggtaaca aattcattgt ggttgaacgt 240
cagaaacgct ctctgaccac gagtccggtt gatatctcca ttatcgattc agtcaatgac 300
cgtacctatc cgggtgcact gcaactggca gacaaagcat ttgtggaaaa ccgtccgacg 360
attctgatgg ttaaacgcaa accgattaac atcaatattg atctgccggg cctgaaaggt 420
gaaaatagta tcaaagtgga tgacccgacc tatggcaaag tttcgggtgc aattgatgaa 480
ctggtcagca aatggaacga aaaatacagt tccacccata cgctgccggc gcgtacccag 540
tattcggaaa gcatggtgta ctctaaaagt caaatctcat cggcgctgaa cgttaatgcc 600
aaagtcctgg aaaactctct gggtgtggat tttaatgcgg ttgccaacaa tgagaaaaaa 660
gtgatgatcc tggcatataa acagattttc tacaccgtta gtgctgatct gccgaaaaac 720
ccgtctgacc tgtttgatga cagtgtcacg ttcaacgatc tgaaacaaaa aggcgtgtct 780
aatgaagcgc cgccgctgat ggtgtctaac gttgcctatg gtcgtaccat ttacgttaaa 840
ctggaaacca cgtctagcag taaagatgtc caggcggcct ttaaagccct gatcaaaaac 900
accgatatca aaaatagcca gcaatacaaa gacatctacg aaaattcctc attcaccgca 960
gtcgtgctgg gcggtgatgc tcaggaacac aacaaagttg tcacgaaaga ttttgacgaa 1020
atccgcaaag tgattaaaga taacgcaacc ttctcgacga aaaatccggc ttatccgatt 1080
tcgtacacca gcgtttttct gaaagataac agcgtcgcag ctgtgcataa taaaaccgac 1140
tatatcgaaa ccaccagcac cgaatacagc aaaggcaaaa ttaatctgga tcactccggt 1200
gcatatgtcg ctcagttcga agtggcctgg gatgaagttt catacgacaa agaaggcaat 1260
gaagtgctga cccataaaac gtgggatggt aactatcaag acaaaaccgc atattactcc 1320
acggttattc cgctggaagc aaacgctcgt aatatccgca ttaaagcgcg tgaatgcacc 1380
ggtctggcat gggaatggtg gcgtgatgtc atcagcgaat atgacgtgcc gctgacgaac 1440
aatatcaatg tgtcaatctg gggcaccacg ctgtatccgg gtagttccat cacctataat 1500
taa 1503

<210> SEQ ID NO 38
<211> LENGTH: 500
<212> TYPE: PRT
<213> ORGANISM: Artificial Sequence
<220> FEATURE:
<223> OTHER INFORMATION: PFOsH438Y (PFOy)

<400> SEQUENCE: 38

Met Ile Arg Phe Lys Lys Thr Lys Leu Ile Ala Ser Ile Ala Met Ala
1 5 10 15

```
Leu Cys Leu Phe Ser Gln Pro Val Ile Ser Phe Ser Lys Asp Ile Thr
            20                  25                  30

Asp Lys Asn Gln Ser Ile Asp Ser Gly Ile Ser Ser Leu Ser Tyr Asn
        35                  40                  45

Arg Asn Glu Val Leu Ala Ser Asn Gly Asp Lys Ile Glu Ser Phe Val
    50                  55                  60

Pro Lys Glu Gly Lys Lys Ala Gly Asn Lys Phe Ile Val Val Glu Arg
65                  70                  75                  80

Gln Lys Arg Ser Leu Thr Thr Ser Pro Val Asp Ile Ser Ile Ile Asp
                85                  90                  95

Ser Val Asn Asp Arg Thr Tyr Pro Gly Ala Leu Gln Leu Ala Asp Lys
            100                 105                 110

Ala Phe Val Glu Asn Arg Pro Thr Ile Leu Met Val Lys Arg Lys Pro
        115                 120                 125

Ile Asn Ile Asn Ile Asp Leu Pro Gly Leu Lys Gly Glu Asn Ser Ile
    130                 135                 140

Lys Val Asp Asp Pro Thr Tyr Gly Lys Val Ser Gly Ala Ile Asp Glu
145                 150                 155                 160

Leu Val Ser Lys Trp Asn Glu Lys Tyr Ser Ser Thr His Thr Leu Pro
                165                 170                 175

Ala Arg Thr Gln Tyr Ser Glu Ser Met Val Tyr Ser Lys Ser Gln Ile
            180                 185                 190

Ser Ser Ala Leu Asn Val Asn Ala Lys Val Leu Glu Asn Ser Leu Gly
        195                 200                 205

Val Asp Phe Asn Ala Val Ala Asn Asn Glu Lys Lys Val Met Ile Leu
    210                 215                 220

Ala Tyr Lys Gln Ile Phe Tyr Thr Val Ser Ala Asp Leu Pro Lys Asn
225                 230                 235                 240

Pro Ser Asp Leu Phe Asp Asp Ser Val Thr Phe Asn Asp Leu Lys Gln
                245                 250                 255

Lys Gly Val Ser Asn Glu Ala Pro Pro Leu Met Val Ser Asn Val Ala
            260                 265                 270

Tyr Gly Arg Thr Ile Tyr Val Lys Leu Glu Thr Thr Ser Ser Ser Lys
        275                 280                 285

Asp Val Gln Ala Ala Phe Lys Ala Leu Ile Lys Asn Thr Asp Ile Lys
    290                 295                 300

Asn Ser Gln Gln Tyr Lys Asp Ile Tyr Glu Asn Ser Ser Phe Thr Ala
305                 310                 315                 320

Val Val Leu Gly Gly Asp Ala Gln Glu His Asn Lys Val Val Thr Lys
                325                 330                 335

Asp Phe Asp Glu Ile Arg Lys Val Ile Lys Asp Asn Ala Thr Phe Ser
            340                 345                 350

Thr Lys Asn Pro Ala Tyr Pro Ile Ser Tyr Thr Ser Val Phe Leu Lys
        355                 360                 365

Asp Asn Ser Val Ala Ala Val His Asn Lys Thr Asp Tyr Ile Glu Thr
    370                 375                 380

Thr Ser Thr Glu Tyr Ser Lys Gly Lys Ile Asn Leu Asp His Ser Gly
385                 390                 395                 400

Ala Tyr Val Ala Gln Phe Glu Val Ala Trp Asp Glu Val Ser Tyr Asp
                405                 410                 415

Lys Glu Gly Asn Glu Val Leu Thr His Lys Thr Trp Asp Gly Asn Tyr
            420                 425                 430

Gln Asp Lys Thr Ala Tyr Tyr Ser Thr Val Ile Pro Leu Glu Ala Asn
```

```
        435                 440                 445

Ala Arg Asn Ile Arg Ile Lys Ala Arg Glu Cys Thr Gly Leu Ala Trp
    450                 455                 460

Glu Trp Trp Arg Asp Val Ile Ser Glu Tyr Asp Val Pro Leu Thr Asn
465                 470                 475                 480

Asn Ile Asn Val Ser Ile Trp Gly Thr Thr Leu Tyr Pro Gly Ser Ser
                485                 490                 495

Ile Thr Tyr Asn
            500
```

<210> SEQ ID NO 39
<211> LENGTH: 807
<212> TYPE: DNA
<213> ORGANISM: Artificial Sequence
<220> FEATURE:
<223> OTHER INFORMATION: Lpp-OmpA-Protein A- 2Fc - No F(ab) binding

<400> SEQUENCE: 39

```
atgaaagcta cgaaactggt cctgggtgct gttatcctgg gttctacgct gctggctggc      60

tgttcctcca acgcaaaaat tgatcagggc attaacccgt atgtgggctt tgaaatgggt     120

tacgattggc tgggtcgtat gccgtataaa ggctctgttg aaaatggtgc gtacaaagcc     180

cagggcgtcc aactgaccgc taaactgggt tatccgatta ccgatgacct ggatatctac     240

acgcgtctgg gcggtatggt ctggcgtgcg gataccaaaa gtaacgtgta tggcaaaaat     300

catgacacgg gtgtgtcccc ggttttcgcg ggcggtgttg aatatgccat taccccggaa     360

atcgcaacgc gtctggaata ccagtggacc aacaatattg gcgatgcaca taccatcggt     420

acgcgtccgg acaacggcat cccgggtgca ccgaaagctg ataacaaatt caacaaagaa     480

cagcaaaacg cgttctatga aattctgcac ctgccgaacc tgaatgaaga acagcgtaat     540

gcctttatcc aatcactgaa agatgacccg agccagtctg caaacctgct ggcggaagcc     600

aaaaaactga atgatgcaca ggctccgaaa gctgacaata aatttaataa agaacaacaa     660

aacgcgttct acgaaatcct gcatctgccg aatctgaacg aagaacagcg caatgccttc     720

atccaatcgc tgaaagatga cccgtcacag agtgcgaacc tgctggcgga agctaaaaaa     780

ctgaacgacg ctcaagcccc gaaataa                                         807
```

<210> SEQ ID NO 40
<211> LENGTH: 268
<212> TYPE: PRT
<213> ORGANISM: Artificial Sequence
<220> FEATURE:
<223> OTHER INFORMATION: Lpp-OmpA-Protein A- 2Fc - No F(ab) binding

<400> SEQUENCE: 40

```
Met Lys Ala Thr Lys Leu Val Leu Gly Ala Val Ile Leu Gly Ser Thr
 1               5                  10                  15

Leu Leu Ala Gly Cys Ser Ser Asn Ala Lys Ile Asp Gln Gly Ile Asn
            20                  25                  30

Pro Tyr Val Gly Phe Glu Met Gly Tyr Asp Trp Leu Gly Arg Met Pro
        35                  40                  45

Tyr Lys Gly Ser Val Glu Asn Gly Ala Tyr Lys Ala Gln Gly Val Gln
    50                  55                  60

Leu Thr Ala Lys Leu Gly Tyr Pro Ile Thr Asp Asp Leu Asp Ile Tyr
65                  70                  75                  80

Thr Arg Leu Gly Gly Met Val Trp Arg Ala Asp Thr Lys Ser Asn Val
                85                  90                  95
```

Tyr Gly Lys Asn His Asp Thr Gly Val Ser Pro Val Phe Ala Gly Gly
100 105 110

Val Glu Tyr Ala Ile Thr Pro Glu Ile Ala Thr Arg Leu Glu Tyr Gln
115 120 125

Trp Thr Asn Asn Ile Gly Asp Ala His Thr Ile Gly Thr Arg Pro Asp
130 135 140

Asn Gly Ile Pro Gly Ala Pro Lys Ala Asp Asn Lys Phe Asn Lys Glu
145 150 155 160

Gln Gln Asn Ala Phe Tyr Glu Ile Leu His Leu Pro Asn Leu Asn Glu
165 170 175

Glu Gln Arg Asn Ala Phe Ile Gln Ser Leu Lys Asp Asp Pro Ser Gln
180 185 190

Ser Ala Asn Leu Leu Ala Glu Ala Lys Lys Leu Asn Asp Ala Gln Ala
195 200 205

Pro Lys Ala Asp Asn Lys Phe Asn Lys Glu Gln Gln Asn Ala Phe Tyr
210 215 220

Glu Ile Leu His Leu Pro Asn Leu Asn Glu Glu Gln Arg Asn Ala Phe
225 230 235 240

Ile Gln Ser Leu Lys Asp Asp Pro Ser Gln Ser Ala Asn Leu Leu Ala
245 250 255

Glu Ala Lys Lys Leu Asn Asp Ala Gln Ala Pro Lys
260 265

<210> SEQ ID NO 41
<211> LENGTH: 807
<212> TYPE: DNA
<213> ORGANISM: Artificial Sequence
<220> FEATURE:
<223> OTHER INFORMATION: Lpp-OmpA-Protein A 2Fc-OTR (OmpT resistant) - No F(ab) binding

<400> SEQUENCE: 41
atgaaagcaa cgaaactggt tctgggtgcg gttattctgg gtagtacgct gctggctggc 60
tgtagctcta atgcgaaaat tgatcagggc attaacccgt atgtgggctt tgaaatgggt 120
tacgattggc tgggtcgtat gccgtataaa ggctctgttg aaaatggtgc gtacaaagcc 180
cagggcgtcc aactgaccgc taaactgggt tatccgatta ccgatgacct ggatatctac 240
acgcgtctgg gcggtatggt ctggcgtgcg gataccaaaa gtaacgtgta tggcaaaaat 300
catgacacgg gtgtgtcccc ggttttcgcg ggcggtgttg aatatgccat taccccggaa 360
atcgcaacgc gtctggaata ccagtggacc aacaatattg gcgatgcaca taccatcggt 420
acgcgtccgg acaacggcat cccgggtgca ccgaaagctg ataacaaatt caacaaagaa 480
cagcaaaacg cgttctatga aattctgcac ctgccgaacc tgaatgaaga acagcgtaat 540
gcctttatcc aatcactgaa agatgacccg agccagtctg caaacctgct ggcggaagcc 600
cagaaactga atgatgcaca agctccgaaa gctgacaata aatttaataa agaacaacaa 660
aacgcgttct acgaaatcct gcatctgccg aatctgaacg aagaacagcg caatgccttc 720
atccagtcgc tgaaagatga cccgtcacaa agcgcaaatc tgctggcgga agcccaaaaa 780
ctgaacgacg cacaggcacc gaaataa 807

<210> SEQ ID NO 42
<211> LENGTH: 268
<212> TYPE: PRT
<213> ORGANISM: Artificial Sequence
<220> FEATURE:

-continued

<223> OTHER INFORMATION: Lpp-OmpA-Protein A 2Fc-OTR (OmpT resistant) -
No F(ab) binding

<400> SEQUENCE: 42

Met Lys Ala Thr Lys Leu Val Leu Gly Ala Val Ile Leu Gly Ser Thr
1 5 10 15

Leu Leu Ala Gly Cys Ser Ser Asn Ala Lys Ile Asp Gln Gly Ile Asn
20 25 30

Pro Tyr Val Gly Phe Glu Met Gly Tyr Asp Trp Leu Gly Arg Met Pro
35 40 45

Tyr Lys Gly Ser Val Glu Asn Gly Ala Tyr Lys Ala Gln Gly Val Gln
50 55 60

Leu Thr Ala Lys Leu Gly Tyr Pro Ile Thr Asp Asp Leu Asp Ile Tyr
65 70 75 80

Thr Arg Leu Gly Gly Met Val Trp Arg Ala Asp Thr Lys Ser Asn Val
85 90 95

Tyr Gly Lys Asn His Asp Thr Gly Val Ser Pro Val Phe Ala Gly Gly
100 105 110

Val Glu Tyr Ala Ile Thr Pro Glu Ile Ala Thr Arg Leu Glu Tyr Gln
115 120 125

Trp Thr Asn Asn Ile Gly Asp Ala His Thr Ile Gly Thr Arg Pro Asp
130 135 140

Asn Gly Ile Pro Gly Ala Pro Lys Ala Asp Asn Lys Phe Asn Lys Glu
145 150 155 160

Gln Gln Asn Ala Phe Tyr Glu Ile Leu His Leu Pro Asn Leu Asn Glu
165 170 175

Glu Gln Arg Asn Ala Phe Ile Gln Ser Leu Lys Asp Asp Pro Ser Gln
180 185 190

Ser Ala Asn Leu Leu Ala Glu Ala Gln Lys Leu Asn Asp Ala Gln Ala
195 200 205

Pro Lys Ala Asp Asn Lys Phe Asn Lys Glu Gln Gln Asn Ala Phe Tyr
210 215 220

Glu Ile Leu His Leu Pro Asn Leu Asn Glu Glu Gln Arg Asn Ala Phe
225 230 235 240

Ile Gln Ser Leu Lys Asp Asp Pro Ser Gln Ser Ala Asn Leu Leu Ala
245 250 255

Glu Ala Gln Lys Leu Asn Asp Ala Gln Ala Pro Lys
260 265

THERAPEUTIC COMPOSITIONS AND METHODS FOR ANTIBODY AND FC-CONTAINING TARGETING MOLECULE-BASED TARGETED DELIVERY OF BIOACTIVE MOLECULES BY BACTERIAL MINICELLS

RELATED APPLICATIONS

The present application claims priority under 35 U.S.C. § 119(e) to U.S. Provisional Application Nos. 61/442,999, filed Feb. 15, 2011, and 61/526,219, filed Aug. 22, 2011. The content of these related applications are herein expressly incorporated by reference in their entireties.

REFERENCE TO SEQUENCE LISTING

The present application is being filed along with a Sequence Listing in electronic format. The Sequence Listing is provided as a file entitled SEQLISTING.TXT, created Feb. 14, 2012, which is 248 Kb in size. The information in the electronic format of the Sequence Listing is incorporated herein by reference in its entirety.

BACKGROUND

Field of the Invention

The present application is drawn to compositions and methods for the production, purification, formulation, and use of eubacterial minicells as targeted delivery vehicles for in vivo and in vitro nucleic acid, protein, radionuclide, and small molecule drug delivery for the inhibition or prevention of disease as well as a targeted in vivo imaging and diagnostic technology.

Description of the Related Art

The following description of the background of the invention is provided to aid in understanding the invention, but is not admitted to describe or constitute prior art to the invention. The contents of the articles, patents, and patent applications, and all other documents and electronically available information mentioned or cited in this application, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The need for a robust delivery vehicle capable of encapsulation of a wide array of bioactive molecule species that is also capable of selectively targeting specific cell, organ, and tissue types is significant. Many molecular therapies are hampered by one or more in vivo limitations that include (i) adverse toxic side effects due to on-target or off-target effects on healthy cells, organs, and tissues, (ii) poor pharmacokinetics (PK) and (iii) poor uptake into cells. The targeted delivery of cytotoxic drugs, imaging agents, therapeutic nucleic acids, and other biologically active therapeutic molecules directly into the site(s) and cells that cause disease could relieve many of these deficiencies by decreasing on-target or off-target toxic effects exerted on non-disease tissue, improving the pharmacokinetics of therapeutic agents allowing for more effective administration, and enhancing uptake into cells. Accordingly, it is well recognized that the development of therapies targeted to specific cell, organ, and tissue types represents an important new frontier for clinically relevant therapeutic, diagnostic, theranostic, and imaging technologies.

In the case of chemotherapeutic agents (e.g., small molecule cytotoxic drugs) and protein toxins used in the treatment of most cancers, efficacy of the chemotherapeutic agent or protein toxin is significantly limited by toxicity to normal tissues. In addition, drug pharmacokinetic (PK) parameters contributing to systemic exposure levels frequently are not and cannot be fully optimized to simultaneously maximize anti-tumor activity and minimize side-effects, particularly when the same cellular targets or mechanisms are responsible for anti-tumor activity and normal tissue toxicity. This results in a very narrow therapeutic index, common for most cytotoxic chemotherapeutics and protein toxins.

One way to enhance the therapeutic index of existing drugs is to bind, conjugate, or package them so that a larger percentage of the administered dose ends up in the vicinity of the tumor (passive targeting) and/or inside the tumor cells (active targeting). Many different approaches to targeted delivery have been taken to date although few products are on the market. Popular approaches include the use of liposomal formulations, immunoliposomal formulations, various polymeric nanotechnologies, antibody-drug fusions/conjugates (ADC), antibody or ligand-protein toxin fusions/conjugates, and dendrimers. Liposomal formulations, including "stealth" approaches are limited because (i) they work only by passive targeting, and (ii) they are difficult to manufacture on a large scale. Immunoliposomal formulations overcome the targeting deficiencies of liposomal formulations by adding a targeting component (typically an antibody or antigen binding portion thereof). However, immunoliposomal formulations are even more difficult to manufacture than liposomal formulations, including incorporation of "stealth" technologies. Targeted polymeric nanotechnologies are limited because they require covalent linkage of the payload and targeting moiety. This complicates manufacturing, limits payload size and variety, and also exposes payload to degradation during circulation in the blood. Antibody-drug fusions/conjugates are limited mostly by payload capacity and payload metabolism. Antibody or ligand-protein toxin fusions/conjugates are also limited by off-target toxicity as well as insufficient efficacy, primarily due to the inability of the protein toxin payload to escape the endosomal compartment and effectively reach its cytosolic target following internalization by the target cell. Dendrimers have a larger payload capacity than the antibody-drug fusion/conjugates and can also bind and display targeting moieties, including antibodies. However, dendrimers are also extremely difficult to manufacture because of the complex chemistry and chemical manipulation involved in the construction process. Thus, there is a need for a delivery system to which any antibody (or other targeting moiety such as a soluble receptor ligand such as VEGF-A) can be bound or coupled in a simple non-covalent fashion, which can also encapsulate significant quantities and combinations of bioactive payloads, and is amenable to large scale manufacturing.

SUMMARY OF THE INVENTION

Some embodiments disclosed herein provide a fully intact bacterial minicell, where the minicell comprises: (i) an Fc binding portion of Protein G or an Fc binding portion of Protein A displayed on the surface of the minicell; (ii) one or more bioactive molecules; and (iii) one or more Fc-containing targeting molecules bound to said Fc binding portion, wherein said one or more Fc-containing targeting molecules recognize a eukaryotic antigen.

In some embodiments, the minicell comprises an Fc binding portion of Protein G. In some embodiments, the minicell comprises an Fc binding portion of Protein A.

In some embodiments, at least one of the one or more bioactive molecules is a protein toxin. In some embodiments, the protein toxin is selected from the group consisting of gelonin, diphtheria toxin fragment A, diphtheria toxin fragment A/B, tetanus toxin, *E. coli* heat labile toxin (LTI and/or LTII), cholera toxin, *C. perfringes* iota toxin, *Pseudomonas* exotoxin A, shiga toxin, anthrax toxin, MTX (*B. sphaericus* mosquilicidal toxin), perfringolysin O, streptolysin, barley toxin, mellitin, anthrax toxins LF and EF, adenylate cyclase toxin, botulinolysin B, botulinolysin E3, botulinolysin C, botulinum toxin A, cholera toxin, *clostridium* toxins A, B, and alpha, ricin, shiga A toxin, shiga-like A toxin, cholera A toxin, pertussis S1 toxin, *E. coli* heat labile toxin (LTB), pH stable variants of listeriolysin O (pH-independent; amino acid substitution L461T), thermostable variants of listeriolysin O (amino acid substitutions E247M, D320K), pH and thermostable variants of listeriolysin O (amino acid substitutions E247M, D320K, and L461T), streptolysin O, streptolysin O c, streptolysin O e, sphaericolysin, anthrolysin O, cereolysin, thuringiensilysin O, weihenstephanensilysin, alveolysin, brevilysin, butyriculysin, tetanolysin O, novyilysin, lectinolysin, pneumolysin, mitilysin, pseudopneumolysin, suilysin, intermedilysin, ivanolysin, seeligeriolysin O, vaginolysin, pyolysin, and any combination thereof.

In some embodiments, at least one of the one or more bioactive molecules is a therapeutic small molecule drug. In some embodiments, the therapeutic small molecule drug is selected from the group consisting of DNA damaging agents, agents that inhibit DNA synthesis, microtubule and tubulin binding agents, anti-metabolites, inducers of oxidative damage, anti-angiogenics, endocrine therapies, anti-estrogens, immuno-modulators such as Toll-like receptor agonists or antagonists, histone deacetylase inhibitors, inhibitors of signal transduction such as inhibitors of kinases, inhibitors of heat shock proteins, retinoids, inhibitors of growth factor receptors, anti-mitotic compounds, anti-inflammatories, cell cycle regulators, transcription factor inhibitors, and apoptosis inducers, and any combination thereof.

In some embodiments, at least one of the one or more bioactive molecules is a therapeutic nucleic acid. In some embodiments, at least one of the one or more bioactive molecules is a therapeutic polypeptide. In some embodiments, at least one of the one or more bioactive molecules is a combination of a small molecule drug and a therapeutic nucleic acid.

In some embodiments, at least one of the one or more Fc-containing targeting molecules is specific for a tumor cell surface molecule. In some embodiments, at least one of the one or more Fc-containing targeting molecules is specific for an endothelial cell surface molecule. In some embodiments, at least one of the one or more Fc-containing targeting molecules is specific for a target common to both a tumor cell and an endothelial cell.

In some embodiments, the minicell further comprises an endosomal escape agent.

Some embodiments enclosed herein provide a composition comprising any of the minicells disclosed herein and a pharmaceutically acceptable carrier.

Some embodiments enclosed herein provide a method of treating a disease in a subject, where the method comprises administering any of the compositions disclosed herein to the subject, thereby treating the disease.

In some embodiments, at least one of the one or more bioactive molecule is a protein from an infectious agent.

In some embodiments, at least one of the one or more Fc-containing targeting molecules is specific for a professional antigen presenting cell. In some embodiments, the professional antigen presenting cell is a eukaryotic dendritic cell, eosinophil, neutrophil, basophil, T-cell, B-cell, mast cell, or macrophage.

In some embodiments, at least one of the one or more bioactive molecules is a protein antigen from a tumor. In some embodiments, at least one of the one or more Fc-containing targeting molecules is specific for a eukaryotic dendritic cell or macrophage.

In some embodiments, said minicell further comprises an endosomal escape agent. In some embodiments, said minicell further comprises an immunomodulatory adjuvant.

Some embodimens disclosed herein provide a method of immunization, where the method comprises administering any of the compositions disclosed herein to a subject in need thereof.

DETAILED DESCRIPTION

Definitions

Figure 1:
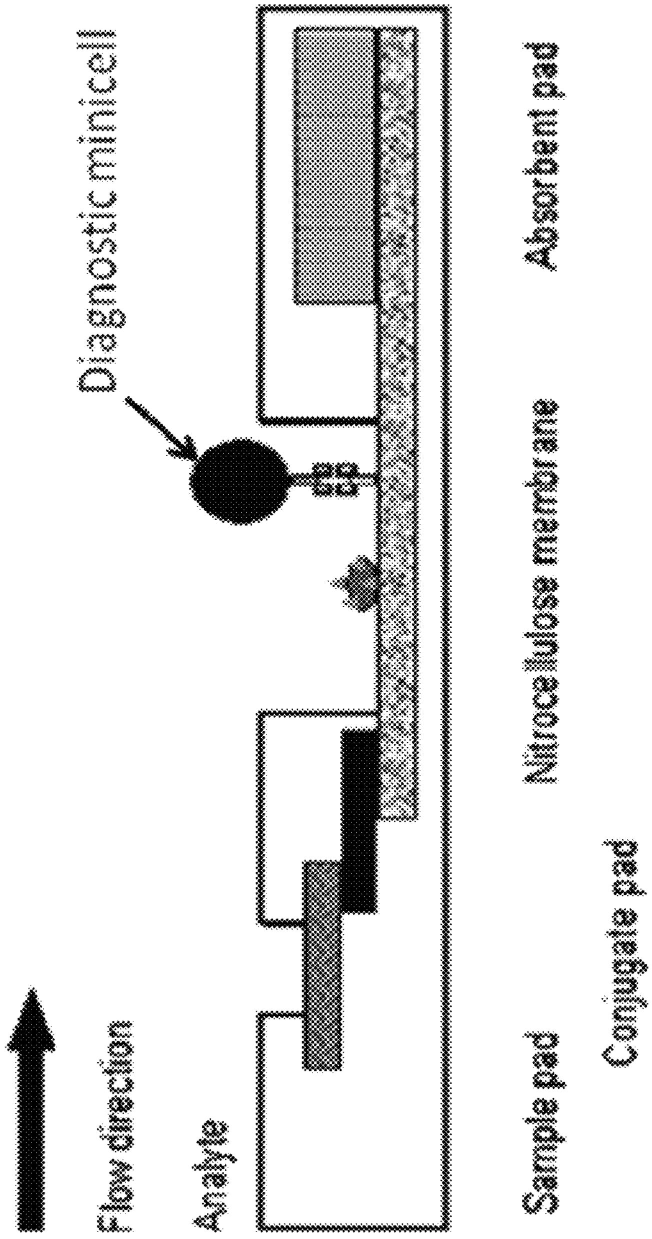
FIG. 1 is a schematic presentation of an illustrative embodiments of a minicell-based Lateral Flow Immunoassay.

As used herein, the term "Fc-binding minicell" refers to a minicell composition in which the minicells and minicell-producing bacterial strain from which the minicells are derived express and display on their cell surface, a fusion protein comprised of (i) an outer membrane export (secretion) signal, (ii) an outer membrane anchoring domain or any functional equivalent thereof, and (iii) one or more of the Fc binding domains of either Protein A or Protein G wherein the minicells are capable of binding to exogenous antibodies, Fc-containing antibody derivatives, or Fc-containing fusion/conjugate molecules through interaction with the Fc regions of the antibodies and/or fusion/conjugate molecules. In some embodiments, minicells express and display an Fc-binding fusion protein comprised of (i) an outer membrane export (secretion) signal, (ii) an outer membrane anchoring domain or any functional equivalent thereof, and (iii) the Fc-binding domain of a mammalian Fc-receptor (and any functional equivalent thereof) wherein the minicells are capable of binding to exogenous antibodies or Fc-containing fusion/conjugate molecules through interaction with the Fc regions of the antibodies and/or fusion/conjugate molecules.

As used herein, the term "targeted therapeutic minicells" refers to bacterial minicells that encapsulate bioactive molecule(s) of choice, display targeting antibodies and/or other Fc-containing fusion/conjugate targeting molecules on the external surface of the minicells by way of interaction with recombinantly expressed surface localized Fc binding regions of Protein G or Protein A such that the antibodies and/or Fc-containing fusion/conjugate targeting molecules are displayed in such a way that they are able to specifically bind to, are bound by, or in some other way specifically recognize and thereby deliver, localize to, or aggregate on or within a specific cell, organ, or tissue type involved in the genesis, progression, and/or maintenance of disease, to deliver the molecular contents of said minicell to the target cell, tissue, and organ type in vitro or in vivo. This specific targeting is intended to use minicells to deliver a therapeutic payload to the targeted cell, organ, and tissue type wherein a therapeutic approach to the treatment of a disease type listed herein is desirable. The targeted therapeutic minicells can also contain an endosomal disruption agent including but not limited to bacterial cytolysins (such as listeriolysin O (LLO) and perfingolysin O (PFO)) and any functional variants or equivalents thereof. Phospholipases, such as PC-PLC or PI-PLC, can also be used as endosomal disrupting agents.

As used herein, the term "targeted diagnostic minicells" refers to bacterial minicells that encapsulate an imaging molecule(s) of choice, displays targeting antibodies and/or Fc-containing fusion/conjugate targeting molecules on the external surface of the minicells by way of interaction with recombinantly expressed surface localized Fc binding regions of Protein G or Protein A such that the antibodies are displayed in such a way that they are able to specifically bind to, are bound by, or in some other way specifically recognize and thereby deliver, localize to, or aggregate on or within a specific cell, organ, or tissue type involved in the genesis, progression, and/or maintenance of disease, to deliver the molecular imaging contents of the minicell to the target cell, tissue, and organ type in vitro or in vivo. This specific targeting, in some embodiments, is intended to use minicells to concentrate molecular imaging agents to the targeted cell, organ, and tissue type wherein a diagnostic approach in whole or in part of a disease type is desirable.

As used herein, the term "targeted minicell vaccine" refers to bacterial minicells that encapsulate a protein antigen and/or a nucleic acid-based vaccine (e.g. DNA or RNA-based vaccine) derived from an infectious disease agent or from a tumor cell of choice, wherein the minicell further displays targeting antibodies and/or Fc-containing fusion/conjugate molecules specific for antigen presenting cells of the immune system on the external surface of the minicells by way of interaction with recombinantly expressed surface localized Fc binding regions of Protein G or Protein A such that antibodies are displayed in such a way that they are able to specifically bind to, are bound by, or in some other way specifically recognize and thereby deliver, localize to, or aggregate within antigen presenting cells, organs, or tissue types involved in the genesis, progression, and/or maintenance of a recipient host immune response, to deliver the antigenic contents of the minicell to the antigen presenting target cell, tissue, and organ type in vitro or in vivo. Antigen presenting cell-specific targeting, in some embodiments, is intended to use targeted minicell vaccines to concentrate protein antigen(s) and/or DNA vaccines and/or adjuvant(s) to antigen presenting cells, organs, and tissue types wherein eliciting a protective recipient host immune response against a particular infectious or autologous disease type listed herein is desirable. The targeted minicell vaccine can include an endosomal disruption agent including but not limited to bacterial cytolysins (such as LLO and PFO) and any functional variants or equivalents thereof. Phospholipases, such as PC-PLC or PI-PLC, can also be used as endosomal disrupting agents.

As used herein, the term "targeting-competent" refers to minicells that express and display one or more Fc binding domains of Protein G or Protein A and are further bound to and display a targeting antibody and/or Fc-containing fusion/conjugate targeting molecule of interest.

As used herein, the term "Integrin-targeted minicells" refers to minicells that express and display the pan-Beta1-integrin-targeting cell surface molecule Invasin from *Yersinia pseudotuberculosis* and any functional equivalents thereof.

As used herein, the term "Integrin-targeted therapeutic minicells" refers to minicells that express and display the pan-Beta1-integrin-targeting cell surface molecule Invasin from *Yersinia pseudotuberculosis* and any functional equivalents thereof wherein the minicells comprising a bioactive molecule(s) including but not limited to therapeutic polypeptides, small molecule drugs, therapeutic nucleic acids, and any combination of the preceding. The integrin-targeted therapeutic minicells can contain an endosomal disruption agent including but not limited to bacterial cytolysins (such as LLO and PFO) and any functional variants or equivalents thereof. Phospholipases, such as PC-PLC or PI-PLC, can also be used as endosomal disrupting agents.

As used herein, the term "cell-specific surface antigen" refers to any protein, peptide, carbohydrate or nucleic acid that is preferentially expressed on the surface of or secreted by any tissue, organ or cell type.

As used herein, the term "prokaryotic cell division gene" refers to a gene that encodes a gene product that participates in the prokaryotic cell division process. Many cell division genes have been discovered and characterized in the art. Examples of cell division genes include, but are not limited to, zipA, sulA, secA, dicA, dicB, dicC, dicF, ftsA, ftsI, ftsN, ftsK, ftsL, ftsQ, ftsW, ftsZ, minC, minD, minE, seqA, ccdB, sfiC, and ddlB.

As used herein, the term "transgene" refers to a gene or genetic material that has been transferred naturally or by any of a number of genetic engineering techniques from one organism to another. In some embodiments, the transgene is a segment of DNA containing a gene sequence that has been isolated from one organism and is introduced into a different organism. This non-native segment of DNA may retain the ability to produce RNA or protein in the transgenic organism, or it may alter the normal function of the transgenic organism's genetic code. In some embodiments, the transgene is an artificially constructed DNA sequence, regardless of whether it contains a gene coding sequence, which is introduced into an organism in which the transgene was previously not found.

As used herein, an agent is said to have been "purified" if its concentration is increased, and/or the concentration of one or more undesirable contaminants is decreased, in a composition relative to the composition from which the agent has been purified. In some embodiments, purification includes enrichment of an agent in a composition and/or isolation of an agent therefrom.

The term "sufficiently devoid of parental cells", synonymous with "sufficiently devoid", as used herein refers to a composition of purified minicells that have a parental cell contamination level that has little or no effect on the toxicity profile and/or therapeutic effect of targeted therapeutic minicells.

The term "domain" or "protein domain" used herein refers to a region of a molecule or structure that shares common physical and/or chemical features. Non-limiting examples of protein domains include hydrophobic transmembrane or peripheral membrane binding regions, globular enzymatic or receptor regions, protein-protein interaction domains, and/or nucleic acid binding domains.

The terms "Eubacteria" and "prokaryote" are used herein as these terms are used by those in the art. The terms "eubacterial" and "prokaryotic" used herein encompass Eubacteria, including both Gram-negative and Gram-positive bacteria, prokaryotic viruses (e.g., bacteriophage), and obligate intracellular parasites (e.g., Richettsia, Chlamydia, etc.).

The term "therapeutic nucleic acid" used herein refers to any collection of diverse nucleic acid molecules that have a therapeutic effect when introduced into a eukaryotic organism (e.g., a mammal such as human). A therapeutic nucleic acid can be a ssDNA, a dsDNA, a ssRNA (including a shRNA), a dsRNA (including siRNA), a tRNA (including a rare codon usage tRNA), a mRNA, a micro RNA (miRNA), a ribosomal RNA (rRNA), a peptide nucleic acid (PNA), a DNA:RNA hybrid, an antisense oligonucleotide, a ribozyme, an aptamer, or any combination thereof.

The term "therapeutic polypeptide" used herein refers to any collection of diverse protein molecule types that have a therapeutic effect when introduced into a eukaryotic organism (e.g., a mammal such as human). A therapeutic polypeptide can be a protein toxin, a cholesterol-dependent cytolysin, a functional enzyme, an activated caspase, a pro-caspase, a cytokine, a chemokine, a cell-penetrating peptide, or any combination and/or plurality of the proceeding.

The term "overexpression" used herein refers to the expression of a functional nucleic acid, polypeptide or protein encoded by DNA in a host cell, wherein the nucleic acid, polypeptide or protein is either not normally present in the host cell, or wherein the nucleic acid, polypeptide or protein is present in the host cell at a higher level than that normally expressed from the endogenous gene encoding the nucleic acid, polypeptide or protein.

The term "modulate" as used herein means to interact with a target either directly or indirectly so as to alter the activity of the target to regulate a biological process. The mode of "modulate" includes, but is not limited to, enhancing the activity of the target, inhibiting the activity of the target, limiting the activity of the target, and extending the activity of the target.

The term "heterologous" as used herein refers to a protein, gene, nucleic acid, imaging agent, buffer component, or any other biologically active or inactive material that is not naturally found in a minicell or minicell-producing bacterial strain and is expressed, transcribed, translated, amplified or otherwise generated by minicell-producing bacterial strains that harbor recombinant genetic material coding for said heterologous material or coding for genes that are capable of producing said heterologous material (e.g., a bioactive metabolite not native to the parent cell).

The term "exogenous" as used herein refers to a protein (including antibodies), gene, nucleic acid, small molecule drug, imaging agent, buffer, radionuclide, or any other biologically active or inactive material that is not native to a cell, or in the case of a minicell, not native to the parent cell of the minicell. Exogenous material differs from heterologous material by virtue of the fact that it is generated, purified, and added separately.

The term "therapeutic" as used herein means having a biological effect or combination of biological effects that prevents, inhibits, eliminates, or prevents progression of a disease or other aberrant biological processes in an animal.

The term "diagnostic" as used herein means having the ability to detect, monitor, follow, and/or identify a disease or condition in an animal (including humans) or from a biological sample including but not limited to blood, urine, saliva, sweat and fecal matters.

The term "theranostic" as used herein means having the combined effects of a therapeutic and a diagnostic composition.

The term "recombinantly expressed" as used herein means the expression of one or more nucleic acid(s) and/or protein(s) from a nucleic acid molecule that is artificially constructed using modern genetic engineering techniques wherein the artificially constructed nucleic acid molecule does not occur naturally in minicells and/or minicell-producing bacterial strains wherein the artificial nucleic acid molecule is present as an episomal nucleic acid molecule or as part of the minicell-producing bacterial chromosome.

The term "episomal" as used herein means a nucleic acid molecule that is independent of the chromosome(s) of a given organism or cell.

The term "detoxified" as used herein refers to a modification made to a composition or component thereof that results in a significant reduction in acute toxicity to the modified composition or component thereof, regardless of what the causative biological basis for toxicity to the composition or component thereof happens to be.

The term "gene silencing" as used herein refers to a specific reduction of the intracellular pool of mRNA for a given protein compared to the normal level of the mRNA as a result of the delivery of a therapeutic nucleic acid delivered by targeted minicells. The therapeutic nucleic acids include, but are not limited to, double stranded RNAs (e.g., siRNA) as well as single stranded RNAs (e.g., shRNA and miRNA) and any eukaryotic expression plasmids encoding the same.

The term "eukaryotic expression plasmid" as used herein refers to a circular double stranded DNA molecule that encodes for one or more gene products operably linked to eukaryotic expression control sequences such that the gene product(s) can be transcribed and translated by a eukaryotic cell from the double stranded DNA molecule.

As used herein, the term "bioactive molecule" refers to a molecule having a biological effect on an eukaryotic organism (e.g., a mammal such as human) when introduced into the eukaryotic organism or cell. Bioactive molecules include, but are not limited to, therapeutic nucleic acids, therapeutic polypeptides (including protein toxins), and therapeutic small molecule drugs.

As used herein, the term “Fc-containing targeting molecule” refers to a molecule that is capable of binding to an Fc binding molecule (e.g., the Fc binding portion of Protein A or Protein G) and contains a recognition site for a target molecule (e.g., an antigen or a receptor). Fc-containing targeting molecules include, but are not limited to, antibodies having an Fc region and soluble receptor ligands engineered to contain an Fc region.

As used herein, the term “eukaryotic antigen” refers to an antigen that of an eukaryotic origin, for example, an antigen displayed on the surface of a eukaryotic cell.

As used herein, the term “protein toxin” refers to a protein that has a toxic effect on eukaryotic cells.

As used herein, the term “small molecule” refers to a molecule that has a biological effect and that has a molecular weight of less than 5000 Daltons. In some embodiments, small molecules have a molecular weight of less than 2500 Daltons. In some embodiments, small molecules have a molecular weight of less than 1000 Daltons. In some embodiments, small molecules have a molecular weight of less than 800 Daltons. In some embodiments, small molecules have a molecular weight of less than 500 Daltons.

As used herein, the term “therapeutic small molecule drug” or “small molecule drug” refers to a small molecule that has a therapeutic effect when introduced into a eukaryotic organism (e.g., a mammal such as human).

Description

The present application relates to the use of bacterial minicells as in vitro and in vivo targeted bioactive molecule delivery and vaccine agents. Eubacterial minicells have a distinct advantage as delivery vehicles, in that they can be engineered to target and deliver large numbers and a large variety of bioactive molecules to specific cell types in vivo. Bacterial minicells are designed to display antibodies and/or other Fc-containing fusions/conjugates on their surfaces that specifically target the minicell to cell types or tissues involved in the initiation, promotion, support, and maintenance of disease or other aberrant biological processes in an animal.

Minicells are achromosomal, membrane-encapsulated biological nanoparticles (approximately 250-500 nm in diameter) that are formed by bacteria following a disruption in the normal division apparatus of bacterial cells. In essence, minicells are small, metabolically active replicas of normal bacterial cells with the exception that they contain no chromosomal DNA and as such, are non-dividing and non-viable. Although minicells do not contain bacterial chromosomes, plasmid DNA molecules (smaller than chromosomes), RNA molecules (of all subtypes), native and/or recombinantly expressed proteins, and other metabolites have all been shown to segregate into minicells. Minicells are uniquely suited as in vivo therapeutic delivery, diagnostic, theranostic, and imaging vehicles because they combine many of the individual advantages of other delivery technologies into a single, versatile delivery vehicle. Minicells can be “engineered” to preferentially encapsulate, be coupled to, or absorb biologically active molecules, including various nucleic acids, proteins, small molecule drugs, and any combination thereof for subsequent delivery in both prophylactic and therapeutic medicinal applications where the detection, prevention, maintenance, and/or inhibition of disease is desirable. As described herein, minicells have the advantage that they can be engineered to selectively target specific cell types responsible for disease through the use of a novel surface display system capable of displaying any Fc region-containing antibody or Fc-region containing antibody derivative, as well as Fc region-containing fusions or conjugates that include but are not limited to polypeptides, nucleic acids, DARPins, radionuclides, carbohydrates, small molecules, and imaging agents.

Another advantage of the use of minicells as delivery vehicles (regardless if they are targeted or non-targeted) is that bioactive molecules can be delivered in combination as described by U.S. Pat. No. 7,183,105, which is incorporated herein by reference in its entirety. For example, it has been demonstrated that minicells can successfully generate humoral immune responses against a heterologous antigen when used as a delivery vehicle for plasmid DNA vaccines. When minicells are used to simultaneously deliver both a DNA vaccine and the corresponding protein antigen, humoral responses were greatly improved, illustrating the benefits of the flexibility of minicells with respect to delivery options. As described herein, minicells have unique features that allow for the loading of small molecule drug and imaging agents as well as the distinct ability to recombinantly express and encapsulate therapeutic nucleic acid delivery molecules, peptides, and proteins for delivery. These unique features allow for a highly flexible delivery system that can deliver multiple payloads of different molecular origins in concert.

Approaches for targeting minicells to eukaryotic cells in vitro and in vivo include (i) random chemical coupling of antibodies, antibody fragments, or other antibody derivates to the surfaces of minicells using myriad chemical coupling techniques known in the art, (ii) using bi-specific antibodies, bi-specific antibody fragments, or bi-specific antibody derivatives to non-covalently attach targeting antibodies to the surfaces of minicells, and (iii) expressing a single chain antibody or other antibody fragment on the surface of the minicells in the context of a contiguous fusion with a minicell membrane-anchoring protein such as a bacterial outer membrane protein. The present application describes a novel approach that provides significant advantages with respect to manufacturing, immunogenicity, and targeting of therapeutic minicells.

In instances where exogenous antibodies existing free in solution are cross-linked to the surfaces of minicells, there is a lack of control over orientation of the antibody or Fc-fusion/conjugate because these molecules will be randomly cross-linked to the surface of minicells in many different orientations. This has two potential effects on the end product that would add to the manufacturing complexity and have the potential to diminish efficacy. The first deleterious effect only applies to the cross-linking of full length antibodies and its exposure of the Fc regions instead of the binding regions, depending on which end of the antibody or other Fc-region containing fusion/conjugate becomes coupled to the minicell surface. The Fc-region has the potential to stimulate the immune system by virtue of the interaction of the Fc-region with various components of the immune system (e.g., the Fc receptor on the surface of Natural Killer cells). The second deleterious effect is that there will be an inherent heterogeneity with respect to the orientation of the antibody (or other Fc-region containing fusion/conjugate) on the surface, such that not all binding regions are exposed. Variable binding portion exposure has the potential to result in diminished and/or variable efficacy as a result of fewer functional binding moieties on the surface of the minicell. Either or both of these limitations have the potential to increase the immunogenicity and/or clearance of minicells, making them less effective therapeutic delivery vehicles. However, when used in the context of the present disclosure, chemical cross-linking of antibodies to the surface of minicells circumvents the issues described above because the Fc-binding minicells of the present disclosure help to orientate the antibodies such that (i) Fc regions of the antibodies are concealed and (ii) the antigen binding sites of bound and cross-linked antibodies are optimally displayed (i.e. pointed outward from the minicell versus a randomized orientation). As used herein, cross-linking reagents can be "homobifunctional" or "heterobifunctional" (having the same or different reactive groups, respectively). Examples of cross-linking reagents include, but are not limited to, those listed in Table 1. In this context, a preferred method with respect to cross-linking include generating and purifying Fc-binding minicells as described herein, incubating the minicells in a solution containing the targeting antibodies of choice, allowing binding to occur, washing excess unbound antibody away, performing the cross-linking reaction, and subsequently removing excess cross-linking reagent using standard methods known in the art.

The compositions and methods disclosed herein are advantageous over some of the compositions and methods where bi-specific antibodies, bi-specific antibody fragments, and bi-specific antibody derivatives are used. For example, it can be costly to make bi-specific antibodies that have specificity for a native minicell surface component on one antibody arm and specificity for a eukaryotic cell surface target on the other. In addition, bi-specific antibodies, much like antibodies chemically conjugated to the surface of minicells, would expose the Fc region, potentially activating complement and/or making the Fc region accessible to Fc-binding cells of the immune system in vivo. Bi-specific antibody fragments that do not include the Fc region can circumvent the issues related to Fc region exposure in vivo, except that these types of molecules require even more genetic engineering than that of a bi-specific antibody. In the case of the construction of bi-specific antibody complexes, there are multiple drawbacks. If the bispecific antibody complex is made using covalent cross-linking methods known in the art, the same limitations apply as in the case where antibodies are cross-linked directly to minicells with respect to having to purify away excess chemical cross-linking agent. As bio-specific antibody complexes are made by mixing equimolar amounts of antibody together followed by the addition of exogenous chemical cross-linking agent to catalyze the reaction, further purification to remove the undesired dually mono-specific species is required. Failure to remove undesired dually mono-specific species would result in crosslinking of minicells to other minicells as a result of the presence of mono-specific antibodies with affinities for minicells. In a related approach obviated by the teachings of U.S. Pat. No. 7,183,105, a hybrid Protein A/G molecule is used as a non-covalent scaffold by which to link two different mono-specific antibodies together to form a "bi-specific ligand" as described in U.S. Pat. Nos. 8,772,013, 8,691,963 and 9,169,495, each of which is hereby incorporated by reference in its entirety. The aggregation problem is amplified with the use of this approach because the Protein A/G molecule used as the scaffold indiscriminately binds six (6) different antibodies per Protein A/G molecule. Again, two separate antibody types are mixed together in equimolar amounts followed by the addition of Protein A/G to non-covalently bind and link the two different antibodies together. In this approach, 720 different permutations of antibody complexes are made, most of which have affinity for two (2) to six (6) minicells. This limitation requires costly and complex manufacturing procedures to be put in place in order to comply with GMP standards. This is in addition to the cost of all of the different components required to manufacture this type of minicell product. An additional problem is the significant potential for toxicity associated with administration of an aggregated product to a patient. As with chemical cross-linking, these limitations also have the potential to increase the immunogenicity and/or clearance of minicells, making them less effective therapeutic delivery vehicles. The Fc-binding minicells disclosed herein reduce immunogenicity when the antibody is derived from the species to which they are administered as a treatment modality. Because Fc-binding minicells bind the Fc regions of antibodies or Fc-containing fusions/conjugates, the Fc regions are thereby masked from the Fc receptor expressing cells of the immune system (e.g., macrophages and NK cells). Further, when the antibody utilized is derived from the species from which the minicell is to be administered as a treatment modality, the minicells become "stealthy" in that the surface is now covered by "self" proteins (antibodies). Immunocompetent organisms do not readily recognize "self" proteins. Minicells that have bound to and display "self" proteins (e.g. antibodies) are thereby further masked from the immune system. Masking targeted therapeutic minicells from the immune system is advantageous because it can increase the in vivo half-life of the minicells providing a longer window for the minicells to reach their intended target.

In the case of the expression and display of a single chain antibody on the surface of the minicell in the context of a contiguous fusion protein to the extracellular domain of a bacterial outer membrane protein, there are two limitations. The first is that not every monoclonal antibody sequence can be converted into a single chain antibody fragment and maintain the same binding properties as the original parent monoclonal antibody molecule. The second limitation is that even in instances where a monoclonal antibody can be converted into a single chain antibody fragment, binding capability sometimes has to be optimized via generation of a variety of fusion sequences and linker constructs. Thus, the single chain antibody display approach is limited only to single chain antibodies that maintain the activity, in whole or in large part, of the parent antibody molecule. While many single chain antibodies exist and can be incorporated into minicell compositions that express and display single chain antibodies or antibody fragments, it is still advantageous to be able to display full length monoclonal antibodies, as taught here, because it further expands the repertoire of antibodies from which the artisan may choose and significantly speeds up the process of selecting potentially successful drug development candidates. In some embodiments, the Fc-binding minicells disclosed herein can be used to "screen" a library of exogenous whole antibodies to select for antibody candidates useful when converted to a single chain for expression and display on the surface of minicells. In other embodiments, the Fc-binding minicells disclosed herein can be employed to screen a library of single chain antibodies as a primary selection process for making determinations as to which single chain antibodies will maintain their binding and internalization properties if converted to a fusion protein designed to be expressed and displayed on the surface of minicells. In yet another example, Fc-binding minicells can be used to screen Fc-containing fusion or conjugated proteins. Such Fc-containing fusions and conjugates are described in more detail herein.

A novel approach for overcoming many of the limitations described above is disclosed herein, in which antibodies or other Fc-region containing fusions/conjugates are non-covalently coupled directly to the surface of minicells that express and display a fusion protein that is comprised of (i)

an outer membrane export (secretion) sequence, (ii) an outer membrane protein or membrane anchoring portion thereof, and (iii) the Fc binding portion(s) of Protein A or Protein G on the minicell surface. Minicells displaying one or more of the Fc binding region(s) of Protein A or Protein G can bind full length antibodies and/or other Fc-region containing fusions/conjugates through the Fc region of the antibodies or fusions/conjugates, with no modification or manipulation of the minicells, antibodies, or Fc-region containing fusions/conjugates by way of co-incubation of the minicells with the antibodies or Fc-region containing fusions/conjugates.

The compositions and methods disclosed herein are advantageous over the coupling approaches listed above, for example, they are designed to display antibodies or other Fc-containing fusions/conjugates such that (i) the Fc region of the antibody is concealed and (ii) the antigen binding/effector domain of the antibodies and/or fusions/conjugates are optimally exposed by virtue of the binding of the antibody or Fc-containing fusion/conjugate to the Protein A or Protein G Fc-binding fusion molecule on the surface of the minicell. The minicells can then be further loaded with one or more species of bioactive payload(s) either by way of exogenous addition of the payload to purified minicells or by recombinant expression of the payload from the minicell-producing parent bacterium prior to or during minicell formation. Bioactive payloads that are expressed or loaded into minicells include but are not limited to small molecule drugs and/or a radionuclide, a therapeutic single stranded short hairpin RNA (ssRNA, a.k.a. shRNA), a therapeutic double stranded RNA molecule (e.g., a siRNA), a ribozyme, an aptamer, a therapeutic polypeptide (e.g., a protein toxin), a eukaryotic expression plasmid encoding for a therapeutic polypeptide or therapeutic nucleic acid, and any combination of the preceding bioactive payloads. In some embodiments, minicells loaded with a bioactive payload or combination thereof and also displaying antibodies or other fusions/conjugates that recognize eukaryotic cell surface molecules are comprised of mutant de-toxified lipopolysaccharide (LPS) molecules as described herein.

In some embodiments, targeted minicells comprising bioactive payload(s) target and engage their cognate eukaryotic cell surface molecule in vivo or in vitro, stimulate endocytosis of the minicell(s), and are degraded, thereby releasing their contents directly into the targeted eukaryotic cell. In some other embodiments, minicells comprising bioactive payload(s) target and engage their cognate eukaryotic cell surface molecule in vivo or in vitro but do not stimulate endocytosis of the minicell(s). These are termed "localized" minicells and are eventually degraded at or near the target cell surface, thereby releasing their contents directly in the vicinity of the targeted eukaryotic cell whereby the payload can exert its therapeutic effect on the target cell. The minicells and minicell-producing bacterial strains disclosed herein have been genetically engineered to express and display one or more of the Fc binding portions of Protein G or Protein A such that they are capable of recognizing and binding to the Fc region of antibodies and/or other Fc-containing fusions/conjugates. Antibodies and/or Fc-containing fusions/conjugates bound by minicells displaying one or more of the Fc binding regions of Protein G or Protein A constitute the targeting component of the targeted minicells disclosed herein.

Protein G is a cell-surface protein expressed by the Gram-positive bacterium Group G *Streptococcus*. Its natural biological function is to prevent opsonization of Group G *Streptococcus* during the infection process by binding the Fc region of antibodies such that the Fc region is masked from the immune system. Normally, anti-bacterial cell surface antigen antibodies bind to the surface of bacterial cells and induce opsonization and/or the activation of complement depending on external exposure of the Fc regions of the bacterial cell surface-bound antibodies. Protein G serves to prevent this in Group G *Streptococcus* by binding the Fc region of antibodies, thereby masking the exposed Fc region from the immune system. Protein G is a 51 kilodalton protein consisting of 13 distinct domains that are commonly further consolidated to include the A/B domains, the S domain, the C/D domains, and the W/M domain. The A/B domains of Protein G consist if three highly related repeats (A1-B1; A2-B2; A3) that have overlapping binding sites for the Fab region of antibodies (moderate affinity) and for serum albumin (high affinity). The S domain is the spacer domain between the A/B and C/D domains. The C/D domain consists of three more highly related repeats (C1-D1; C2-D2; D3) and constitutes the Fc binding region of the molecule. The C/D domain is capable of binding two (2) separate antibodies by the antibody Fc region. Thus, Protein G contains two Fc binding domains, either or both of which can be utilized in the embodiments disclosed herein. The C/D region is commonly used to affinity purify antibodies from serum (or other sources). The W/M domains function to interact with the Gram-positive cell wall and to facilitate export to the outer leaflet of the cell membrane, respectively. The Protein G fusion protein(s) disclosed herein therefore include, but are not limited to, the S and C/D regions of Protein G. In some embodiments, it is advantageous to include only the S and C/D regions in the design of the recombinant fusion proteins disclosed herein to avoid unwanted binding of the Fab regions of antibodies (exposes the Fc region) or to serum albumin. In some embodiments, the serum albumin binding domain of Protein G is included such that minicells can be made into "enhanced stealth minicells" by way of binding serum albumin to the surface of the minicell in addition to an antibody. Minicell surface-bound serum albumin, in addition to the antibody, helps to mask the minicell from the recipient immune system. In these cases, it is preferred to match both species of origin of both the antibody and the serum albumin with that of the recipient.

Protein A is a cell-surface protein expressed by the Gram-positive bacterium *Staphylococcus aureus*. Like Protein G, its natural biological function is also to prevent opsonization of *Staphylococcus aureus* during the infection process. *Staphylococcus aureus* use Protein A to bind to the Fc region of antibodies. Depending on orientation or external exposure, the Fc regions of surface-bound antibodies are capable of activating complement or binding to Fc receptors on phagocytic cells such as neutrophils. Protein A is a 58 kilodalton protein that consists of 7 distinct domains that are commonly referred to as the S, E, D, A, B, C, and X domains. The S domain constitutes the secretion signal. The E domain is not well characterized and has no immunoglobulin binding activity. Domains D, A, B, and C, often grouped together and referred to as the Z domain, contain four (4) consecutive immunoglobulin binding domains, thought to have evolved as a result of gene duplications in *S. aureus*. The D, A, B, and C domains may be uncoupled and each maintains its immunoglobulin binding properties with little or no effect on affinity/specificity. Protein A contains four discreet Fc binding domains, any of which can be utilized in singular or in combination herein. Thus, different Protein A derived Fc-binding fusion proteins can contain 1, 2, 3, or 4 Fc-binding domains and can be incorporated in the compositions and methods disclosed herein at the discretion of a skilled artisan. The X domain has no immunoglobulin binding activity and is responsible for anchoring the C-terminus back into the peptidoglycan wall in the Gram-positive setting. The X domain is dispensable and has no effect on the binding properties of the D, A, B, and C domains. The Protein A fusion protein(s) disclosed herein therefore include, but are not limited to, the D, A, B, and C domains of Protein A or derivatives of one or more of these domains that retain Fc binding capability. Preferred derivatives include domains in which glycine 29 is substituted for alanine, eliminating $F(ab')_2$ binding, and/or derivatives in which putative cleavage sites by OmpT protease have been eliminated by substitution with functionally conserved amino acid residues.

Fc-binding minicells expressing either the Fc binding region of Protein G or that of Protein A can be used to properly display antibodies and/or other Fc-containing fusions/conjugates on the surfaces of minicells which serves to facilitate targeting of minicells to specific cell, tissue, and organ types in vivo. Antibodies, or any Fc containing portion thereof, intended to aid in the targeting of minicells to a specific tissue, organ, and cell type involved in the cause, progression, maintenance, or manifestation of disease can be derived from or be part of any immunoglobulin or immunoglobulin subclass, including but not limited to IgA, IgM, IgD, IgG, and IgE. Antibodies of any subclass intended to facilitate the targeting function of minicells can be "humanized", although any antibody of any subclass against a cell specific antigen can be raised in any animal known to generate antibody responses through adaptive immunity to achieve the same goal. In nature, antibodies are generated such that they contain two separate arms (Fab's), each of which recognizes the same epitope of a particular antigen. However, as described below, advances in molecular biology have enabled researchers to modify the specificity of each arm (or in some cases the Fc region of the molecule) to recognize distinctly different epitopes that may or may not occur in the same or different antigens. These antibody derivatives are referred to as a 'bispecific' antibodies or 'bispecific' targeting moieties.

In the laboratory, antibodies can be engineered to be independently specific for different antigens, such that a single antibody targets two separate antigens simultaneously. By way of non-limiting example, antibodies can be engineered to recognize putative surface components of a given eubacterial minicell (e.g., LPS O-antigens) on one Fab' and the other Fab' of the bispecific antibody can be engineered to recognize a eukaryotic cell-specific surface antigen. In another non-limiting variation on this theme, the Fc region of the heavy chains of the antibody can be genetically engineered to specifically bind to a particular epitope within a given antigen (e.g., LPS) while the Fab' portions of the molecule recognize a different epitope in a separate eukaryotic cell-specific surface antigen or vice versa.

Additionally, those skilled in the art will readily recognize that two separate antibodies, with separate specificities, can be non-covalently attached by coupling them to soluble Protein A, Protein G, or Protein A/G (or any other binding molecule that will recognize and bind two or more antibodies) to form a bispecific antibody derivative capable of adhering to the surface of minicells wherein one antibody within the complex specifically adheres to the surface of the minicell and the other antibody is displayed to specifically recognize and thereby "target" a specific cell, tissue, or organ type expressing an eukaryotic cell-specific surface antigen in vivo. Similarly, one skilled in the art will recognize that two separate antibodies, with separate specificities, can be covalently linked using myriad cross-linking techniques to achieve the same effect.

Other, non-antibody based targeting approaches disclosed in the present application are collectively based on Fc-containing fusions or conjugates. As described herein, examples of molecular targeting moieties includes, but are not limited to, receptor ligands, polypeptides, hormones, carbohydrates, aptamers, antibody-like molecules, nanobodies, affibodies, antibody-like single chain T-cell antigen receptors (STARs), mTCRs, trans-bodies, XmAbs, and DARPins. Fc-conjugation can be achieved using a variety of approaches known in the art. By way of non-limiting example, the soluble EGF or VEGF ligands can be genetically fused or conjugated to an Fc-containing polypeptide (Fc region) and bound to the Fc-binding minicell surface such that the Fc-binding minicells are targeting competent and can selectively localize and be internalized by cells expressing the EGFR or VEGFR2 receptor, respectively. As another non-limiting example, the therapeutic payload itself can be genetically fused or coupled to an Fc-containing polypeptide and bound to the surface of the Fc-binding minicells. For example, Fc-conjugated siRNA molecules can be bound to the surface of Fc-binding minicells in addition to Fc-containing antibodies, Fc-containing antibody derivatives, and/or Fc-containing fusion/conjugate targeting molecules. Fc-containing polypeptide fusions include, but are not limited to, receptor ligand/Fc fusions, Fc-containing peptide fusions, and Fc-containing DARPins. Recombinant expression of the fusion is a preferred method of construction. In the recombinant expression context, Fc regions can be fused to either the amino or carboxy terminus of a given recombinant fusion at the discretion of the skilled artisans such that fusion to the Fc region does not affect ligand activity with respect to receptor binding and stimulation of receptor-mediated endocytosis. Another exemplary approach to making Fc-containing polypeptides, peptides, and DARPins is by chemical conjugation (a.k.a. cross-linking) of purified recombinant Fc region molecules to recombinant polypeptide, peptide, and/or DARPin molecules using any of the cross-linking techniques known in the art. In the context of chemical cross-linking, it is advantageous to include "reactive" amino acid groups on either or both of the purified recombinant Fc-region or the polypeptide, peptide, and/or DARPin molecule to be conjugated. Examples of reactive amino acids include, but are not limited to, those that contain sulfhydryl groups, preferably a cysteine residue. In some embodiments, for use with popular heterobifunctional cross-linking reagents, it is preferable to include a lysine residue at the linkage site of the opposing conjugate (e.g., Fc-region contains a cysteine residue while targeting or payload polypeptide contains a lysine or vice versa). In instances where purified recombinant Fc regions are cross-linked to hormones, carbohydrates, aptamers, and other non-amino acid and/or peptide based molecules, the skilled artisans would recognize that many other cross-linking reagents can be employed to achieve the same. Cross-linking reagents can be "homobifunctional" or "heterobifunctional" (having the same or different reactive groups, respectively). Examples of cross-linking reagents include, but are not limited to, those listed in Table 1. Table 1 also illustrates non-limiting examples of cross-linking reagents that can be used for each conjugate molecule type/approach.

In some preferred embodiments, minicells and minicell-producing bacterial strains are "engineered" to express and display a recombinant Fc binding portion of Protein G or Protein A on their surfaces. Surface localization of recombinant polypeptides has been successfully accomplished in *Salmonella enterica* by using fusion proteins that contain an Antigen 43-α outer membrane anchoring domain fused to a single chain FcV antibody fragment with specificity for Chlam 12 or CTP3. In a similar study, *E. coli* cells expressing and displaying single chain FcV antibody fragments directed towards Coronavirus epitopes fused with the outer membrane localized IgA protease of *Neisseria gonnorhoeae* were shown to neutralize Coronavirus and prevent infection in vitro. Surface localization can also be accomplished by fusing coding sequences of the desired Fc binding protein with the adhesin-involved-in-diffuse-adherance (AIDA-I) autotransporter from *E. coli*. This can also be accomplished with the Lpp-OmpA whole cell display system described in U.S. Pat. No. 5,348,867, which is incorporated herein by reference. In some embodiments, Lpp-OmpA is used to express and display antibody Fc binding moieties including but not limited to the Fc binding region of Protein A or Protein G on the surfaces of minicells. Other native outer membrane proteins that can serve as the outer membrane fusion partner include, but are not limited to, LamB, OmpF, OmpC, OmpD, PhoE, PAL, pilus proteins, and various flagellins in gram negative Enterobacteriacea family members. This approach is used to express and display Fc-binding fragments of Protein A or Protein G on the surface of minicells derived from any Enterobacteriacea or Bacillaceae family member such that the minicells are capable of binding to and displaying antibodies against cell surface antigens thereby becoming specific targeted delivery vehicles for cell surface antigen-expressing cells, tissues, or organs. One skilled in the art will recognize that achieving this goal is a matter of (i) creating a nucleic acid sequence encoding for a fusion protein between a putative or predicted outer membrane protein or outer membrane localization sequence and the Fc binding domain(s) of Protein A or Protein G, (ii) producing and purifying minicells that express the fusion protein (a.k.a. Fc-binding minicells), (iii) loading minicells with a small molecule drug or other bioactive payload (not required when minicells encapsulate a recombinantly expressed payload or payload combinations; e.g., a protein toxin or a protein toxin and an shRNA combination), (iv) incubating payload-loaded minicells with the targeting antibody or other Fc-containing fusion/conjugate to make targeted therapeutic minicells, (v) washing the preparation to remove excess payload (where applicable) and antibody or Fc-containing fusion/conjugate molecules, and (vi) preparing the minicells as a pharmaceutical composition per the intended route of patient administration.

Bacterial minicells have distinct small molecule drug and imaging agent loading advantages over other delivery technologies. Similar to de-energized bacterial cells, targeted minicells can be easily loaded with high concentrations of small molecule drugs and imaging agents by simple co-incubation of purified minicells with a high concentration of the small molecule drug or imaging agent. Optimally, the small molecule drug(s) and/or imaging agent(s) are incubated with minicells in a loading buffer that is devoid of any exogenous energy source so as to maintain the inactive state of conserved multi-drug efflux pumps. Multi-drug efflux pumps are largely proton motive force (PMF) dependent and it is well recognized by the skilled artisan that the PMF and thereby the efflux pumps are dependent upon an exogenous energy source. Thus, loading minicells in an energy source-free buffer ensures the inactivity of the efflux pump system(s) of minicells and serves to diminish drug efflux from minicells even when drug-loaded minicells are restored to a medium that reverses the concentration gradient of the drug (i.e., drugless medium). Targeted minicells can also be used to deliver two or more small molecule drugs or imaging agents simultaneously such that several intracellular targets are addressed in a single delivery event. In addition, targeted minicells can also be used to deliver one or more small molecule drugs in concert with one or more therapeutic nucleic acids.

Effective delivery of small molecules by way of receptor mediated endocytosis can be limited if the small molecule(s) delivered are exposed to the harsh environment of the endosomal or lysosomal compartments for too long prior to being released to the cytosol of the targeted eukaryotic cell. Thus, the skilled artisans will appreciate that enhanced endosomal escape of small molecules delivered by targeted minicells by this route may be desirable. However, this is not always necessary and can be subjected to the discretion of the skilled artisans and may also be employed in the delivery of other targeted minicell-borne payloads including but not limited to nucleic acids, peptides, proteins, and radionucleotides and any combination of the preceding. Intracellular pathogens are faced with the same problem and as a result have evolved sophisticated mechanisms to either modulate the environment of the endosome to make it hospitable or to escape the endosome completely. In the case of the latter, this is typically mediated by a protein component or protein complex made by the invading organism. For example, the listeriolysin O (LLO; SEQ ID NO:29) protein of the intracellular Gram-positive pathogenic bacterium *Listeria monocytogenes* can be used in the methods and compositions disclosed herein. Listeriolysin O is a 58 kilodalton secreted pH and cholesterol-dependent protein encoded by the hlyA gene of *Listeria monocytogenes* that forms oligomeric pores in the endosomal membrane, facilitating the escape of the invading organism into the cytosol of the infected cell. In some embodiments, full length LLO (containing the signal secretion sequence) is used as the endosomal membrane disruption agent. As skilled artisans will appreciate that other useful variants of LLO that have been described can also be used in the present application. For example, in nature, the secretion of LLO by *Listeria monocytogenes* (and other Gram-positive bacterial species) involves the cleavage of the 24 amino acid signal secretion sequence by membrane proteases to form "mature" LLO. Removing the 24 amino acid-long secretion signal from LLO using recombinant methods results in the sequestration of truncated LLO (cLLO; SEQ ID NO 30) in the bacterial cytosol when expressed. Although cLLO is not secreted, it maintains all of the properties of the secreted form, including its pH and cholesterol-dependent endosomal membrane pore forming capabilities. In some embodiments, the signal sequence of LLO is removed at the genetic level using recombinant techniques known in the art. It has been shown that LLO is a heat labile protein that undergoes an irreversible conformational change that abrogates activity at neutral pH and temperatures above 30° C. Thermostability of LLO can be increased when a combination of amino acid substitutions are made (E247M and D320K; SEQ ID NO 31). In some embodiments, a thermostable version of LLO is used. Upon targeting of the minicell(s), receptor mediated endocytosis carries the minicell into the endosome. The harsh environment of the endosome begins to degrade the engulfed minicell, co-releasing the small molecule payload along with LLO. The released LLO component then aids to facilitate release of the small molecule from the endosome into the cytosol where the small molecule can exert its biological effect(s). As disclosed herein, certain temperature and degradation-stabilized (sLLO) and pH stabilized (pH-independent; sLLOpH) variants of LLO (SEQ ID NO:32) can serve as a therapeutic polypeptide payload as well as an endosomal disruption agent. As used herein, the listeriolysin O (LLO) protein include the full length LLO as well as the truncated LLO (cLLO). Various mutations have been reported, which modulate the cytotoxicity of PFO, without significantly compromising endosomal disruption activity. PFO and said mutational variants can be used in place of LLO for the purpose of endosomal membrane disruption.

Minicells have distinct mechanisms and advantages of loading therapeutic nucleic acids and therapeutic polypeptides (e.g. protein toxins) as opposed to other targeted delivery technologies. For example, the minicell-producing parental cells can be used to recombinantly express/produce one or more therapeutic nucleic acid molecules and/or therapeutic polypeptides prior to or at the same time that minicells are being produced. Recombinant therapeutic nucleic acids and/or therapeutic polypeptides are expressed, segregate into and are encapsulated by minicells, and are then delivered to eukaryotic cells by targeted minicells in vivo or in vitro.

Examples of recombinantly expressed/produced therapeutic nucleic acids to be delivered by minicells include, but are not limited to, RNA interference molecule(s), or ribozyme(s), double stranded therapeutic RNA (e.g., dsRNA or siRNA), single stranded therapeutic RNA (e.g., shRNA), aptamers, ribozymes, eukaryotic expression plasmids encoding for therapeutic polypeptide(s) and/or therapeutic nucleic acids, and any combination of the preceding. Recombinant expression of therapeutic nucleic acid(s) can be the result of expression from any of the various episomal recombinant prokaryotic expression vectors known in the art including, but not limited to, plasmids, cosmids, phagemids, and bacterial artificial chromosomes (BACs), and any combination of the preceding. Recombinant expression can also be achieved by a chromosomally located prokaryotic expression cassette present in one or more copies of the minicell-producing parent cell chromosome. In cases where the therapeutic nucleic acid molecule(s) to be delivered exert their therapeutic effects through a "gene silencing" mechanism of action, the therapeutic nucleic acids are specific for one or more different eukaryotic mRNA transcripts. The therapeutic nucleic acids can be delivered by the same minicell such that one or more genes are silenced by a single delivery event. Targeted minicells are also used to deliver any of these therapeutic nucleic acids in combination. In addition, targeted minicells are used to deliver one or more small molecule drugs in concert with one or more therapeutic nucleic acids.

Effective delivery of therapeutic nucleic acids by way of receptor mediated endocytosis can be limited if the nucleic acid(s) delivered are exposed to the nuclease and protease rich environment of the endosomal compartment for too long prior to being released to the cytosol of the targeted eukaryotic cell. Thus, the skilled artisans will appreciate that enhanced endosomal escape of therapeutic nucleic acids delivered by this route may be desirable. However, this is not always necessary and is included per the discretion of the skilled artisan and can also be employed in the delivery of other targeted minicell-borne payloads including, but not limited to, small molecules, peptides, proteins, and radionuclides and any combination of the preceding. Intracellular pathogens are faced with the same problem and as a result have evolved sophisticated mechanisms to either modulate the environment of the endosome to make it hospitable or to escape the endosome completely. In the case of the latter, this is typically mediated by a protein component or protein complex made by the invading organism. The listeriolysin O (LLO; SEQ ID N0:29) protein of the intracellular Gram-positive pathogenic bacterium *Listeria monocytogenes* is of interest and is incorporated into those embodiments of the present application that include but are not limited to a therapeutic nucleic acid payload component. When expressed in an Fc-binding minicell producing bacterial strain that also expresses therapeutic nucleic acid(s), LLO can be co-encapsulated with the therapeutic nucleic acid(s) by the Fc-binding minicells which are subsequently made targeting-competent by addition of an antibody or Fc-containing fusion/conjugate molecule to the surface of the Fc-binding minicells. Upon targeting of the minicell(s), receptor mediated endocytosis carries the minicell into the endosome. The harsh environment of the endosome begins to degrade the engulfed minicell, co-releasing the therapeutic nucleic acid payload along with LLO. The released LLO component then facilitates release of the therapeutic nucleic acid from the endosome into the cytosol where the nucleic acid can exert its biological effect(s).

In cases where the therapeutic nucleic acid molecule(s) is pre-formed by the parental cell by way of recombinant expression from a prokaryotic expression cassette (either chromosomal or episomal in location) and is then packaged inside of the minicells as double stranded RNAs (e.g., siRNA) or single stranded RNAs capable of folding back on themselves to form hairpin structures (e.g., shRNAs), the half-life of the therapeutic RNA(s) within the minicell is increased by use of Fc-binding minicell producing bacterial strains that harbor a deletion or other non-functional mutation in RNase genes (e.g., prokaryotic RNase III) responsible for the degradation of intracellular double stranded and/or hairpin RNA molecules. In the absence of the RNase, the therapeutic RNA molecules accumulate to a higher level, increasing the potency of targeted minicells delivering the therapeutic nucleic acid molecules. In the case of *Escherichia coli* minicell producing strains, mutation or deletions are introduced into the mc gene, which encodes for the only known somatic RNaseIII in this species.

Recombinantly expressed/produced therapeutic polypeptides to be delivered by targeted minicells include but are not limited to protein toxins, cholesterol-dependent cytolysins, functional enzymes, activated caspases, pro-caspases, cytokines, chemokines, cell-penetrating peptides, and any combination of the preceding examples. Recombinant expression of a therapeutic polypeptide(s) can be the result of expression from any of the various episomal recombinant prokaryotic expression vectors known in the art including but not limited to plasmids, cosmids, phagemids, and bacterial artificial chromosomes (BACs), and any combination of the preceding examples. In similar fashion, recombinant expression can be achieved by a chromosomally located prokaryotic expression cassette present in one or more copies of the minicell-producing parent cell chromosome. The delivery of protein toxins using the targeted minicells of the present application is an advantageous approach in applications where selective elimination of cells in vivo is desirable. Protein toxins which can facilitate endosomal delivery of payloads and/or function as toxic payloads include, but are not limited to, fragments A/B of diphtheria toxin, fragment A of diphtheria toxin, anthrax toxins LF and EF, adenylate cyclase toxin, gelonin, botulinolysin B, botulinolysin E3, botulinolysin C, botulinum toxin, cholera toxin, *clostridium* toxins A, B and alpha, ricin, shiga A toxin, shiga-like A toxin, cholera A toxin, pertussis S1 toxin, perfringolysin O, *Pseudomonas* exotoxin A, *E. coli* heat labile toxin (LTB), melittin, pH stable variants of listeriolysin O (pH-independent; amino acid substitution L461T), thermostable variants of listeriolysin O (amino acid substitutions E247M, D320K), pH and thermostable variants of listeriolysin O (amino acid substitutions E247M, D320K, and L461T), streptolysin O, streptolysin O c, streptolysin O e, sphaericolysin, anthrolysin O, cereolysin, thuringiensilysin O, weihenstephanensilysin, alveolysin, brevilysin, butyriculysin, tetanolysin O, novyilysin, lectinolysin, pneumolysin, mitilysin, pseudopneumolysin, suilysin, intermedilysin, ivanolysin, seeligeriolysin O, vaginolysin, and pyolysin. Therapeutic polypeptides can be localized to different subcellular compartments of the minicell at the discretion of the skilled artisans. When targeted minicells disclosed herein are derived from a Gram-negative parental minicell-producing strain, recombinantly expressed therapeutic polypeptides produced therefrom can be localized to the cytosol, the inner leaflet of the inner membrane, the outer leaflet of the inner membrane, the periplasm, the inner leaflet of the outer membrane, the outer membrane of minicells, and any combination of the proceeding. When targeted minicells disclosed herein are derived from a Gram-positive parental minicell-producing strain, recombinantly expressed therapeutic polypeptides produced therefrom can be localized to the cytosol, the cell wall, the inner leaflet of the membrane, the membrane of minicells, and any combination of the proceeding.

Effective delivery of therapeutic polypeptides by way of receptor mediated endocytosis can be limited if the polypeptide(s) delivered are exposed to the protease rich environment of the endosomal compartment for too long prior to being released to the cytosol of the targeted eukaryotic cell. Indeed, most therapeutic polypeptides have no intrinsic ability to escape the endosomal compartment, the exception being the cholesterol dependent cytolysins/toxins (e.g. LLO, perfringolysin O (PFO), and streptolysin O (SLO)) as well as fragment A/B of diphtheria toxin (escape mediated by fragment B), ricin, and *Pseudomonas* exotoxin A. Those protein toxins that do contain intrinsic endosomal escape properties do not necessarily require the co-presence of a separate endosomal disruption component in the targeted minicell to be effective and the decision to include an endosomal disrupting agent is at the discretion of the skilled artisans. Other protein toxins, such as gelonin and fragment A of the diphtheria toxin, have no intrinsic ability to escape the endosomal compartment. Thus, the skilled artisans would recognize that enhanced endosomal escape of many different therapeutic polypeptides delivered by the endosomal route is desirable. As described above, the listeriolysin O (LLO) protein of the intracellular Gram-positive pathogenic bacterium *Listeria monocytogenes* is of interest and is incorporated into those embodiments of the present application that include but are not limited to a therapeutic polypeptide payload component or other therapeutic payload requiring endosomal escape to confer best activity. In some embodiments, full length LLO (containing the signal secretion sequence) is used as the endosomal disruption agent. In some embodiments, the signal sequence of LLO (making cLLO; SEQ ID NO:30) is removed at the genetic level using recombinant techniques known in the art and cLLO is used as the endosomal disruption agent. In some embodiments, thermostable and/or pH-independent versions of LLO (harboring mutations E247M, D320K and/or L461T, sLLOpH; SEQ ID NOs: 31 and 32, respectively) are employed. When expressed in an Fc-binding minicell producing bacterial strain that also expresses therapeutic polypeptide(s), LLO (or any of the LLO variants or other endosomal escape facilitators) can be co-encapsulated with the therapeutic polypeptide(s) within the Fc-binding, minicells which are subsequently made targeting-competent by addition of an antibody and/or an Fc-containing fusion/conjugate targeting molecule to the surface of the Fc-binding minicells. Upon targeting of the minicell(s), receptor mediated endocytosis carries the minicell into the endosome. The harsh environment of the endosome begins to degrade the engulfed minicell, co-releasing the therapeutic payload along with the endosomal disruption agent (e.g., LLO, any of its variants, or other endosomal disrupting agent). The released endosomal disruption agent component then facilitates release of the therapeutic payload from the endosome into the cytosol where the payload can exert its biological effect(s). In addition to LLO, preferred endosomal disruption agents include other cytolysins, such as PFO and SLO and derivatives thereof, and phospholipases, such as PI-PLC or PC-PLC.

In cases where the therapeutic polypeptide(s) is preformed by the parental cell by way of recombinant expression from a prokaryotic expression cassette (either chromosomal or episomal in location) and is then packaged inside of the minicells as the therapeutic payload, the half-life of the therapeutic polypeptide(s) within the minicell is increased by use of Fc-binding minicell producing bacterial strains that harbor a deletion or other non-functional mutation in protease genes (e.g., the Ion protease of *E. coli*) responsible for proteolysis. In the absence of the protease(s), the therapeutic polypeptide(s) molecule accumulates to a higher level, increasing the potency of targeted minicells delivering the therapeutic polypeptide molecules. In the case of *Escherichia coli* minicell producing strains, mutation or deletions can be introduced into one or more of the lon, tonB, abgA, ampA, ampM, pepP, clpP, dcp, ddpX/vanX, elaD, frvX, gcp/b3064, hslV, hchA/b1967, hyaD, hybD, hycH, hycl, iadA, ldcA, ycbZ, pepD, pepE, pepQ, pepT, pmbA, pqqL, prlC, ptrB, sgcX, sprT, tldD, ycaL, yeaZ, yegQ, ygeY, yggG, yhbO, yibG, ydpF, degS, ftsH/hflB, glpG, hofD/hopD, lepB, lspA, pppA, sohB, spa, yaeL, yfbL, dacA, dacB, dacC, degP/htrA, degQ, iap, mepA, nlpC,pbpG, tsp, ptrA, teas, umuD, ydcP, ydgD, ydhO, yebA, yhbU, yhjJ, and nlpD genes.

In addition to being used as targeted small molecule drug and therapeutic nucleic acid vehicles, the minicells disclosed herein can also be used as targeted minicell vaccines. As described in more detail below, protein antigen and/or DNA vaccine loaded minicells are targeted directly to antigen presenting cells of the immune system by utilizing antibodies or Fc-containing fusion/conjugate molecules that are specific for eukaryotic cell surface markers expressed by specific antigen presenting cells. In some embodiments, it can be also desirable but not necessary to include LLO or one of its variants (described above) to facilitate transfer of antigen or DNA vaccine to the eukaryotic cell cytosol to promote MHC class-I loading, which stimulates cellular immunity. It can also be desirable to promote MHC class-II loading to stimulate humoral (antibody mediated) immunity by keeping antigens inside the endosomal compartments where the large majority of MHC class II binding occurs. This can be accomplished by eliminating or decreasing the LLO component of the targeted minicell vaccine. In addition, targeted vaccine minicells are further engineered to either express or be loaded with exogenous adjuvant as deemed appropriate by the skilled artisan. Adjuvants can be general adjuvants (such as Keyhole limpet hemocyanin or complete Freud's adjuvant) or can be targeted molecular adjuvants. Targeted molecular adjuvants include those that are antagonists or agonists of Toll-Like Receptors as well as other cellular constituents that have immunomodulatory properties. Targeted vaccines provide recipient immunity to infectious disease agents including but not limited to those infectious disease agents of bacterial, viral, and parasitic origin(s). Targeted vaccines also provided recipient immunity to tumors and other aberrant disease(s) of autologous nature.

In addition to being utilized as targeted delivery vehicles in vivo and in vitro, the Fc-binding minicells disclosed herein are also utilized as analyte detection reagents for diagnostic assays including but not limited to Lateral Flow Immunoassays (LFIAs). In some embodiments, the analyte-detecting Fc-binding minicells can be comprised of (i) Fc-binding minicells, (ii) an analyte-specific antibody or other analyte-specific Fc-containing fusion/conjugate molecule bound to the Fc-containing minicells, and (iii) a detection reagent including, but not limited to, a small molecule flourophore, a fluorescent protein, an enzyme, a magnetic particle, and colloidal gold wherein the detection reagent is encapsulated, displayed, or otherwise associated with the minicells. In a related permutation, Fc-binding minicells are used as a negative readout detection reagent for use in a competitive LFIA. In some embodiments, negative readout Fc-binding minicells are comprised of (i) Fc-binding minicells, (ii) an Fc/analyte fusion/conjugate bound to the Fc-containing minicells, and (iii) a detection reagent including but not limited to a small molecule flourophore, a fluorescent protein, an enzyme, a magnetic particle, and colloidal gold wherein the detection reagent is encapsulated, displayed, or otherwise associated with the minicells. Minicells can be used as detection reagents in kits used to analyze clinical, veterinary, environmental, solid and liquid foodstuffs, pharmaceutical products, and drinking water for the presence or absence of a given relevant analyte in solution. Lateral Flow Immunoassays are constructed whereby they contain (i) product backing, (ii) a sample pad, (iii) a particle conjugate pad, (iv) a porous membrane (e.g. nitrocellulose), (v) a test line, (vi) a control line, and (vii) a wick material. LFIAs are used as rapid point-of-care diagnostics as well as for in-home use (e.g., pregnancy tests), and various field tests (e.g. determining toxin levels in drinking water or soil). LFIA detection reagents are currently limited to colloidal gold conjugates (10 nm), latex beads (colored or fluorescent; varying sizes), and paramagnetic latex covered beads (colored or fluorescent; varying sizes). Each has its limitations and the need for new and improved detection reagents is a key hurdle in the field at present. Colloidal gold conjugates are limited by their sensitivity and cost, latex beads by their lack of sensitivity, and paramagnetic latex beads by their cost. Thus, there is a need for a cost-effective, highly sensitive class of particle-based detection reagents in the diagnostics field that will enable more quantitative and reliable assays, and/or a reduction in manufacturing cost. Because minicells can be loaded with a wide variety of different detection modalities, including functional enzymes that can amplify detection signals and increase sensitivity (not an option with currently available detection particles), they offer significant advantages over currently utilized detection systems.

In order for targeted minicells to be used as therapeutic and diagnostic agents in humans, minicells should contain few or no contaminants, such as viable parental bacterial cells. Levels of viable contaminating cells and other contaminants must be low enough not to cause adverse side effects in patients or to interfere with minicell activity. The inducible expression of a homing endonuclease gene, referred to as a genetic suicide mechanism, is a preferred mechanism by which to eliminate live contaminating parental cells, especially when used in combination with conventional filtration methods. Because minicells are derived from some bacteria that are pathogenic or opportunistically pathogenic, it is important that any contaminating parental cells be functionally eliminated from a given population before systemic, and particularly intravenous, administration. Consequently, the desired minicell formulation would be one in which the residual live parental cell count would be as low as possible so as not cause adverse side effects or interfere with intended minicell activity. To minimize safety concerns, the minicells disclosed herein are derived from minicell-producing strains that comprise safety features, for example, one or more of the three safety features disclosed below. In some embodiments, the minicell-producing strains comprise at least these three synergistic safety features. The first is a genetic suicide mechanism that kills residual live parental cells without lysing them (and expelling free lipopolysaccharide) after the minicell formation step has been completed. The present application incorporates the use of a regulated genetic suicide mechanism that upon exposure to the appropriate inducer, introduces irreparable damage to the chromosomes of minicell-producing parental cells as described in U.S. Patent Publication No. 20100112670, which is hereby incorporated by reference in its entirety. The suicide mechanism operates to introduce irreparable double-stranded breaks to the chromosome of the parental cells and is used as an adjunct to conventional separation techniques to improve minicell purification. The second safety feature is a defined auxotrophy, preferably but not necessarily in the diaminopimelic acid (DAP) biosynthesis pathway, and most preferably in the dapA gene of an *E. coli* minicell-producing strain. Minicell-producing strains of *E. coli* that exhibit DAP auxotrophy (dapA-) cannot survive outside of the laboratory without supplementation of DAP. Further, DAP is not found in mammals, including humans, and as such any minicell-producing parental cells that happen to escape the genetic suicide mechanism will not be able to survive in the environment or in vivo. Many variations on this theme exist for different Gram-negative and Gram-positive bacteria. For example in *Salmonella*, spp., auxotrophies in the aromatic amino acid biosynthesis pathways (the aro genes) produce in effect, the same result. In the case of *Shigella* spp. auxotrophies in the guanine biosynthesis pathway will produce, in effect, the same result. The third safety feature is optional and entails a deletion of the lpxM gene in *E. coli* minicell-producing strains. Deletion of the lpxM gene can result in the production of de-toxified lipopolysaccharide (LPS) molecules. The lpxM gene (also referred to as the msbB gene) functions to add a terminal myristolic acid group to the lipid A portion of the LPS molecule and removal of this group (by way of elimination of the lpxM gene) results in marked detoxification of LPS. Specifically, detoxification is characterized by a decrease in the production of pro-inflammatory cytokines in response to exposure to LPS. This deletion can be introduced into any functionally equivalent gene of any Gram-negative or Gram-positive minicell-producing strain to achieve the same effect. The enhanced safety profile can reduce the risk of infection and potential for developing sepsis, decrease the possibility of genetic reversion through recombination events with other bacteria, and minimize the risk of insertion events in the host. From a regulatory and manufacturing perspective, it is also preferred that antibiotic resistance markers be eliminated from the bacterial chromosome of the minicell-producing parental cell strain. The use of most antibiotic resistance gene markers in minicell-producing strains of bacteria is undesirable in order to comply with regulatory requirements imposed by the U.S. Food and Drug Administration (FDA) for use in humans. The FDA will only tolerate the use of the kanamycin resistance gene marker for selection purposes for bacteria or bacterial production strains wherein the final product is intended for use in humans.

As described herein, Fc-binding eubacterial minicells are capable of being made targeting competent and delivering several classes of bioactive payload in concert or singular wherein the final preparation of minicells is comprised of detoxified LPS and is sufficiently devoid of any viable contaminating parent cells by virtue of the combined effects of a novel, inducible genetic suicide mechanism used in conjunction with conventional separation techniques.

As described herein, bacterial minicells can be used as targeted in vivo therapeutic delivery, diagnostic, theranostic, and imaging agents. In some embodiments, bacterial minicells are designed to incorporate a bioactive payload, and by way of a novel mechanism, readily display antibodies and/or other Fc-containing molecular targeting fusions/conjugates on their surfaces that specifically target the minicell to cell types involved in the initiation, promotion, support, and maintenance of disease in an animal. Some embodiments provide minicells that express and display the Fc binding region of Protein G on the minicell surface wherein the minicell further comprises an antibody and/or Fc-containing fusion/conjugate targeting molecule specific for a eukaryotic cell surface receptor bound by its Fc region to the Fc binding portion of Protein G on the minicell surface wherein the antibody and/or Fc-containing fusion/conjugate targeting molecule-coated minicell further comprises a bioactive payload(s) including but not limited to a small molecule drug, a therapeutic nucleic acid, a radionuclide, an imaging agent, a protein, and any combination of the preceding bioactive payloads. Some embodiments provide minicells that express and display the Fc binding region of Protein A on the minicell surface wherein the minicell further comprises an antibody and/or Fc-containing fusion/conjugate targeting molecule specific for a eukaryotic cell surface receptor, wherein the antibody or Fc-containing fusion/conjugate targeting molecule is bound by its Fc region to the Fc binding portion of Protein A on the minicell surface wherein the antibody and/or Fc-containing fusion/conjugate targeting molecule-coated minicell further comprises a bioactive payload(s) including but not limited to a small molecule drug, a therapeutic nucleic acid, a radionuclide, an imaging agent, a protein, and any combination of the preceding bioactive payloads.

Some embodiments provide minicells that express and display the Fc binding region of Protein G on the minicell surface wherein the minicell further comprises an antibody and/or Fc-containing fusion/conjugate targeting molecule specific for a eukaryotic cell surface receptor, wherein the antibody or Fc-containing fusion/conjugate targeting molecule is bound by its Fc region to the Fc binding portion of Protein G on the minicell surface wherein the antibody and/or Fc-containing fusion/conjugate targeting molecule-coated minicell further comprises a bioactive payload(s) including but not limited to a small molecule drug, a therapeutic nucleic acid, a radionuclide, an imaging agent, a protein, and any combination of the preceding bioactive payloads.

As described herein, bacterial minicells can be used as diagnostic test detection reagents. Such reagents can be utilized as the detection reagent in a wide variety of point-of-care/point-of-need diagnostic product types including but not limited to Lateral Flow Immunoassays. In some embodiments, bacterial minicells can be designed to incorporate a detection reagent and by way of a novel approach, readily display antibodies and/or Fc-containing fusion/conjugate targeting molecules on their surfaces that confer specificity of the minicell detection reagent for a particular analyte or series of analytes to be tested for. Some embodiments provide minicells that express and display the Fc binding region of Protein A on the minicell surface wherein the minicell further comprises an antibody specific for a eukaryotic cell surface receptor, wherein the antibody or Fc-containing fusion/conjugate targeting molecule is bound by its Fc region to the Fc binding portion of Protein A on the minicell surface wherein the antibody and/or Fc-containing fusion/conjugate targeting molecule coated minicell further comprises a detectable reagent(s) including but not limited to a small molecule flourophore, a magnetic particle(s), a colloidal gold particle(s), an active enzyme, a fluorescent protein, and any combination of the preceding detection reagents.

As described herein, bacterial minicells can be used as diagnostic test detection reagents. Such reagents can be utilized as the detection reagent in a wide variety of point-of-care/point-of-need diagnostic product types including but not limited to Lateral Flow Immunoassays. In some embodiments, bacterial minicells are designed to incorporate a detection reagent and by way of a novel approach, readily display antibodies and/or Fc-containing fusion/conjugate targeting molecules on their surfaces that confer specificity of the minicell detection reagent for a particular analyte or series of analytes to be tested for. Some embodiments provide minicells that express and display the Fc binding region of Protein G on the minicell surface wherein the minicell further comprises an antibody specific for a eukaryotic cell surface receptor, wherein the antibody or Fc-containing fusion/conjugate targeting molecule is bound by its Fc region to the Fc binding portion of Protein G on the minicell surface wherein the antibody and/or Fc-containing fusion/conjugate targeting molecule coated minicell further comprises a detectable reagent(s) including but not limited to a small molecule flourophore, a magnetic particle(s), a colloidal gold particle(s), an active enzyme, a fluorescent protein, and any combination of the preceding detection reagents.

In some preferred embodiments, bacterial minicells are used as targeted bioactive molecule delivery vehicles in vivo. In some embodiments, targeted therapeutic minicells comprise a bioactive (synonymous with biologically active) payload that has a negative and/or therapeutic effect on a cell that is involved in disease or another aberrant process in an animal. In some embodiments, the bioactive payload includes but is not limited to small molecule drugs, bioactive nucleic acids, bioactive proteins, bioactive radionuclides, imaging agents, and bioactive lipopolysaccharides, and any combination of the proceeding to produce a "biological effect" (synonymous with biological response) that negatively impacts diseased cells, tissues, or organs or positively effects the production of signals that indirectly mitigate diseased cells, tissues, or organs in an animal. In some embodiments, targeted minicells have biological effects that negatively impact disease including but not limited to an effect that kills cells responsible for the initiation, promotion, or maintenance of the disease; an effect that positively impacts the production of signals that mitigate disease in an animal; an effect that negatively impacts a biological process responsible for the activation of disease in an animal; an effect that elicits an innate immune response in an animal that negatively effects disease, and an effect that elicits an adaptive (humoral and/or cellular) response that negatively impacts disease in an animal, to treat or prevent a disease in the animal. In some embodiments, targeted minicells have biological effects that synergistically negatively impact disease in an animal by exerting a combination of any of the biological effects listed above. In some embodiments, the targeting moiety is an antibody, Fc-containing antibody derivative, and/or Fc-containing fusion/conjugate targeting molecule that is bound to the Fc-binding region of either Protein A or Protein G that is expressed and displayed on the surface of the minicells in the context of a contiguous fusion protein that comprises (i) an outer membrane export (secretion) sequence (ii) an outer membrane protein or membrane anchoring portion thereof, and (iii) the Fc binding portion(s) of Protein A or Protein G on the minicell surface. Minicells displaying the Fc binding region(s) of Protein A or Protein G can bind full length antibodies, Fc-containing antibody derivatives, and/or Fc-containing fusion/conjugate targeting molecules through interaction with the Fc region of the molecules. In some embodiments, the binding portion(s) of Protein A or Protein G is part of a fusion protein designed to be expressed and displayed on the surfaces of minicells. In some embodiments, the binding portion(s) of Protein A or Protein G is a fusion protein with the Neisseria gonnorehae IgAP autotransporter protein. In some embodiments, the binding portion(s) of Protein A or Protein G is a fusion with a putative or predicted outer membrane protein found in gram negative bacteria as described in more detail herein. In some embodiments, the binding portion(s) of Protein A or Protein G is a fusion with the Lpp-OmpA display system which is described in U.S. Pat. No. 5,348,867 and hereby incorporated by reference in its entirety (SEQ ID NO.22 and SEQ ID NO:23, respectively). The antibody, Fc-containing antibody derivative, and/or Fc-containing fusion/conjugate targeting molecule on the surface of minicells can preferentially recognize but is not limited to recognizing cell-specific surface antigens including α3β1 integrin, α4β1 integrin, α5β1 integrin, $\alpha_v\beta3$ integrin, $\alpha_v\beta1$ integrin, β1 integrin, 5T4, CAIX, CD4, CD13, CD19, CD20, CD22, CD25, CD30, CD31, CD33, CD34, CD40, CD44v6, CD45, CD51, CD52, CD54, CD56, CD64, CD70, CD74, CD79, CD105, CD117, CD123, CD133, CD138, CD144, CD146, CD152, CD174, CD205, CD227, CD326, CD340, Cripto, ED-B, GD2, TMEFF2, VEGFR1, VEGFR2, FGFR, PDGFR, ANGPT1, TIE1, TIE2, NRP1, TEK (CD202B), TGFβR, Death Receptor 5 (Trail-R2), DLL4, EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6, FAP, GPNMB, ICAMs, VCAMs, PSMA, HER-2/neu, IL-13R alpha 2, MUC-1, MUC16, EGFR1 (HER-1), EGFR2 (HER-2/neu), EGFR3 (HER-3), IGF-1R, IGF-2R, c-Met (HGFR), Mesothelin, PDGFR, EDGR, TAG-72, transferrin receptor, EpCAM, CTLA-4, PSMA, tenascin C, alpha-fetoprotein, vimentin, C242 antigen, TRAIL-R1, TRAIL-R2, CA-125, GPNMB, CA-IX, GD3 ganglioside, RANKL, BAFF, IL-6R, TAG-72, HAMA, and CD166. In some embodiments, the targeting moiety is selected, in part, because the binding of the minicell-surface displayed antibody targeting moiety, Fc-containing antibody derivatives, and/or Fc-containing fusion/conjugate targeting molecules specific for the antigen induce internalization of the targeted minicell, facilitating intracellular payload delivery. Previously described target-specific antibodies that are used as the targeting component, in some embodiments, include but are not limited to mAb 3F8, mAb CSL362, mAb CSL360, mAb J591, Abagovomab, Abciximab, Adalimumab, Afelimomab, Afutuzumab, Alacizumab, ALD518, Alemtuzumab, Altumomab, Anatumomab, Anrukinzumab, Apolizumab, Arcitumomab, Aselizumab, Atlizumab, Atorolimumab, Bapineuzmab, Basiliximab, Bavituximab, Bectumomab, Belimumab, Benralizumab, Bertilimumab, Besilesomab, Bevacizumab, Biciromab, Bivatuzumab, Blinatumomab, Brentuximab, Briakinumab, Canakinumab, Cantuzumab, Capromab, Catumaxomab, CC49, Cedelizumab, Certolizumab, Cetuximab, mAb528, Citatuzumab, Cixutumumab, Clenoliximab, Clivatuzumab, Conatumumab, CR6261, Dacetuzumab, Daclizumab, Daratumumab, Denosumab, Detumomab, Dorlimomab, Dorlixizumab, Ecromeximab, Eculizumab, Edobacomab, Edrecolomab, Efalizumab, Efungumab, Elotuzumab, Elsilimomab, Enlimomab, Epitumomab, Epratuzumab, Erlizumab, Ertumaxomab, Etaracizumab, Exbivirumab, Fanolesomab, Faralimomab, Farletuzumab, Felvizumab, Fezakinumab, Figitumumab, Fontolizumab, Foravirumab, Fresolimumab, Galiximab, Gantenerumab, Gavilimomab, Gemtuzumab, Girentuximab, Glembatumumab, Golimumab, Gomiliximab, Ibalizumab, Irbitumomab, Igovomab, Imciromab, Infliximab, Intetumumab, Inolimomab, Inotuzumab, Ipilimumab, Iratumumab, J591, Keliximab, Labetuzumab, Lebrikizumab, Lemalesomab, Lerdelimumab, Lexatumumab, Libivirumab, Lintuzumab, Lorvotuzumab, Lucatumumab, Lumiliximab, Mapatumumab, Maslimomab, Matuzumab, Mepolizomab, Metelimumab, Milatuzumab, Minretumomab, Mitumomab, Morolimumab, Motavizumab, Muromonab, Nacolomab, Naptumomab, Natalizumab, Nebacumab, Necitutumab, Nerelimomab, Nimotuzumab, Nofetumomab, Ocrelizumab, Odulimomab, Ofatumumab, Olaratumab, Omalizumab, Oportuzumab, Oregovomab, Otelixizumab, Pagibaximab, Palivizumab, Panitumumab, Panobacumab, Pascolizumab, Pemtumomab, Pertuzumab, Pexelizumab, Pintumomab, Priliximab, Pritumumab, PRO140, Rafivirumab, Ramucirumab, Ranibizumab, Raxibacumab, Regavirumab, Resilizumab, Rilotumumab, Rituximab, Robatumumab, Rontalizumab, Rovelizumab, Ruplizumab, Satumomab, Sevirumab, Sibrotuzumab, Sifalimumab, Siltuximab, Siplizumab, Solanezumab, Sonepcizumab, Sontuzumab, Stamulumab, Sulesomab, Tacatuzumab, Tadocizumab, Talizumab, Tanezumab, Taplitumomab, Tefibazumab, Telimomab, Tenatumomab, Teplizumab, TGN1412, Ticilimumab, Tigatuzumab, TNX-650, Tocilizumab, Toralizumab, Tositumomab, Trastuzumab, Tremelimumab, Tucotuzumab, Tuvirumab, Urtoxazumab, Ustekinumab, Vapaliximab, Vedolizumab, Veltuzumab, Vepalimomab, Visilizumab, Volociximab, Votumumab, Zalutumumab, Zanolimumab, Ziralimumab, Zolimomab, and any combination of the preceding.

In some preferred embodiments, targeted therapeutic minicells are used as targeted small molecule delivery vehicles in vivo and are used to prevent, inhibit, and/or limit disease progression in an animal. In some embodiments, targeted minicells are (i) derived from Fc-binding minicells wherein the Fc-binding minicells display the Fc binding portion of Protein G on their surfaces, (ii) are loaded with one or more species of small molecule drugs, (iii) further comprise surface localized antibodies and/or Fc-containing fusion/conjugate molecules that are bound to the Fc binding portion of the surface displayed Fc binding region of Protein G wherein the antibodies and/or Fc-containing fusion/conjugate molecules that recognize a eukaryotic cell-specific surface antigen and are capable of stimulating receptor mediated endocytosis upon binding of the targeted minicell to the eukaryotic cell-specific surface antigen, and (iv) further comprise a pharmaceutically acceptable carrier for intravenous administration. The species of small molecule drug(s) are selected from but not limited to (1) DNA damaging agents and agents that inhibit DNA synthesis such as anthracyclines (doxorubicin, daunorubicin, epirubicin), alkylating agents (bendamustine, busulfan, carboplatin, carmustine, cisplatin, chlorambucil, cyclophosphamide, dacarbazine, hexamethylmelamine, ifosphamide, lomustine, mechlorethamine, melphalan, mitotane, mytomycin, pipobroman, procarbazine, streptozocin, thiotepa, and triethylenemelamine), platinum derivatives (cisplatin, carboplatin, cis diamminedichloroplatinum), telomerase and topoisomerase inhibitors (Camptosar), (2) microtubule and tubulin binding agents including but not limited to taxanes and taxane derivatives (paclitaxel, docetaxel, BAY 59-8862), (3) anti-metabolites such as capecitabine, chlorodeoxyadenosine, cytarabine (and its activated form, ara-CMP), cytosine arabinoside, dacarbazine, floxuridine, fludarabine, 5-fluorouracil, 5-DFUR, gemcitabine, hydroxyurea, 6-mercaptopurine, methotrexate, pentostatin, trimetrexate, and 6-thioguanine (4) anti-angiogenics (thalidomide, sunitinib, lenalidomide), vascular disrupting agents (flavonoids/flavones, DMXAA, combretastatin derivatives such as CA4DP, ZD6126, AVE8062A, etc.), (5) endocrine therapy such as aromatase inhibitors (4-hydroandrostendione, exemestane, aminoglutethimide, anastrozole, letrozole), (6) anti-estrogens (Tamoxifen, Toremifene, Raloxifene, Faslodex), steroids such as dexamethasone, (7) immuno-modulators such as Toll-like receptor agonists or antagonists, (8) inhibitors to integrins, other adhesion proteins and matrix metalloproteinases), (9) histone deacetylase inhibitors, (10) inhibitors of signal transduction such as inhibitors of tyrosine kinases like imatinib (Gleevec), (11) inhibitors of heat shock proteins, (12) retinoids such as all trans retinoic acid, (13) inhibitors of growth factor receptors or the growth factors themselves, (14) anti-mitotic compounds such as navelbine, vinblastine, vincristine, vindesine, and vinorelbine, (15) anti-inflammatories such as COX inhibitors and (16) cell cycle regulators such as check point regulators and telomerase inhibitors, (17) transcription factor inhibitors, and apoptosis inducers, such as inhibitors of Bcl-2, Bcl-x and XIAP and any combination of the preceding (1-17). The antibody and/or Fc-containing fusion/conjugate molecules on the surface of minicells can preferentially recognize but is not limited to recognizing cell-specific surface antigens including α3β1 integrin, α4β1 integrin, α5β1 integrin, $\alpha_v\beta3$ integrin, $\alpha_v\beta1$ integrin, β1 integrin, 5T4, CAIX, CD4, CD13, CD19, CD20, CD22, CD25, CD30, CD31, CD33, CD34, CD40, CD44v6, CD45, CD51, CD52, CD54, CD56, CD64, CD70, CD74, CD79, CD105, CD117, CD123, CD133, CD138, CD144, CD146, CD152, CD174, CD205, CD227, CD326, CD340, Cripto, ED-B, GD2, TMEFF2, VEGFR1, VEGFR2, FGFR, PDGFR, ANGPT1, TIE1, TIE2, NRP1, TEK (CD202B), TGFβR, Death Receptor 5 (Trail-R2), DLL4, EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6, FAP, GPNMB, ICAMs, VCAMs, PSMA, HER-2/neu, IL-13R alpha 2, MUC-1, MUC16, EGFR1 (HER-1), EGFR2 (HER-2/neu), EGFR3 (HER-3), IGF-1R, IGF-2R, c-Met (HGFR), Mesothelin, PDGFR, EDGR, TAG-72, transferrin receptor, EpCAM, CTLA-4, PSMA, tenascin C, alpha-fetoprotein, vimentin, C242 antigen, TRAIL-R1, TRAIL-R2, CA-125, GPNMB, CA-IX, GD3 ganglioside, RANKL, BAFF, IL-6R, TAG-72, HAMA, and CD166.

In some preferred embodiments, targeted therapeutic minicells are used as targeted small molecule delivery vehicles in vivo and are used to prevent, inhibit, and/or limit disease progression in an animal. In some embodiments, targeted minicells are (i) derived from Fc-binding minicells wherein the Fc-binding minicells display the Fc binding portion of Protein A on their surfaces, (ii) are loaded with one or more species of small molecule drugs, (iii) further comprise surface localized antibodies and/or Fc-containing fusion/conjugate molecules that are bound to the Fc binding portion of the surface displayed Fc binding region of Protein A wherein the antibodies and/or Fc-containing fusion/conjugate molecules recognize a eukaryotic cell-specific surface antigen and are capable of stimulating receptor mediated endocytosis upon binding of the targeted minicell to the eukaryotic cell-specific surface antigen, and (iv) further comprise a pharmaceutically acceptable carrier for intravenous administration. The species of small molecule drug(s) are selected from but not limited to (1) DNA damaging agents and agents that inhibit DNA synthesis such as anthracyclines (doxorubicin, daunorubicin, epirubicin), alkylating agents (bendamustine, busulfan, carboplatin, carmustine, cisplatin, chlorambucil, cyclophosphamide, dacarbazine, hexamethylmelamine, ifosphamide, lomustine, mechlorethamine, melphalan, mitotane, mytomycin, pipobroman, procarbazine, streptozocin, thiotepa, and triethylenemelamine), platinum derivatives (cisplatin, carboplatin, cis diamminedichloroplatinum), telomerase and topoisomerase inhibitors (Camptosar), (2) microtubule and tubulin binding agents including but not limited to taxanes and taxane derivatives (paclitaxel, docetaxel, BAY 59-8862), (3) anti-metabolites such as capecitabine, chlorodeoxyadenosine, cytarabine (and its activated form, ara-CMP), cytosine arabinoside, dacarbazine, floxuridine, fludarabine, 5-fluorouracil, 5-DFUR, gemcitabine, hydroxyurea, 6-mercaptopurine, methotrexate, pentostatin, trimetrexate, and 6-thioguanine (4) anti-angiogenics (thalidomide, sunitinib, lenalidomide), vascular disrupting agents (flavonoids/flavones, DMXAA, combretastatin derivatives such as CA4DP, ZD6126, AVE8062A, etc.), (5) endocrine therapy such as aromatase inhibitors (4-hydroandrostendione, exemestane, aminoglutethimide, anastrozole, letrozole), (6) anti-estrogens (Tamoxifen, Toremifene, Raloxifene, Faslodex), steroids such as dexamethasone, (7) immuno-modulators such as Toll-like receptor agonists or antagonists, (8) inhibitors to integrins, other adhesion proteins and matrix metalloproteinases), (9) histone deacetylase inhibitors, (10) inhibitors of signal transduction such as inhibitors of tyrosine kinases like imatinib (Gleevec), (11) inhibitors of heat shock proteins, (12) retinoids such as all trans retinoic acid, (13) inhibitors of growth factor receptors or the growth factors themselves, (14) anti-mitotic compounds such as navelbine, vinblastine, vincristine, vindesine, and vinorelbine, (15) anti-inflammatories such as COX inhibitors and (16) cell cycle regulators such as check point regulators and telomerase inhibitors, (17) transcription factor inhibitors, and apoptosis inducers, such as inhibitors of Bcl-2, Bcl-x and XIAP and any combination of the preceding (1-17). The antibody and/or Fc-containing fusion/conjugate molecules on the surface of minicells can preferentially recognize but are not limited to recognizing cell-specific surface antigens including α3β1 integrin, α4β1 integrin, α5β1 integrin, $\alpha_v\beta3$ integrin, $\alpha_v\beta1$ integrin, β1 integrin, 5T4, CAIX, CD4, CD13, CD19, CD20, CD22, CD25, CD30, CD31, CD33, CD34, CD40, CD44v6, CD45, CD51, CD52, CD54, CD56, CD64, CD70, CD74, CD79, CD105, CD117, CD123, CD133, CD138, CD144, CD146, CD152, CD174, CD205, CD227, CD326, CD340, Cripto, ED-B, GD2, TMEFF2, VEGFR1, VEGFR2, FGFR, PDGFR, ANGPT1, TIE1, TIE2, NRP1, TEK (CD202B), TGFβR, Death Receptor 5 (Trail-R2), DLL4, EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6, FAP, GPNMB, ICAMs, VCAMs, PSMA, HER-2/neu, IL-13R alpha 2, MUC-1, MUC16, EGFR1 (HER-1), EGFR2 (HER-2/neu), EGFR3 (HER-3), IGF-1R, IGF-2R, c-Met (HGFR), Mesothelin, PDGFR, EDGR, TAG-72, transferrin receptor, EpCAM, CTLA-4, PSMA, tenascin C, alpha-fetoprotein, vimentin, C242 antigen, TRAIL-R1, TRAIL-R2, CA-125, GPNMB, CA-IX, GD3 ganglioside, RANKL, BAFF, IL-6R, TAG-72, HAMA, and CD166.

In some preferred embodiments, targeted therapeutic minicells are used as targeted therapeutic nucleic acid delivery vehicles in vivo and are used to prevent, inhibit, and/or limit disease progression in an animal. In some embodiments, targeted minicells are (i) derived from Fc-binding minicells wherein the Fc-binding minicells display the Fc binding portion of Protein G on their surfaces, (ii) are loaded with one or more therapeutic nucleic acid molecules, (iii) further comprise surface localized antibodies and/or Fc-containing fusion/conjugate molecules that are bound to the Fc binding portion of the surface displayed Fc binding region of Protein G wherein the antibodies and/or Fc-containing fusion/conjugate molecules recognize a eukaryotic cell-specific surface antigen and are capable of stimulating receptor mediated endocytosis upon binding of the targeted minicell to the eukaryotic cell-specific surface antigen, (iv) further comprise an endosomal disrupting agent, and (v) further comprise a pharmaceutically acceptable carrier for intravenous administration. In some embodiments, therapeutic nucleic acids that exert their effects by way of gene silencing (siRNA and shRNA, or a eukaryotic DNA expression plasmid encoding for the same) include but are not limited to comprising one or more contiguous nucleotide sequences having homology to wild-type gene sequences and/or to one or more contiguous sequences containing germ-line and somatic mutations known to be involved in disease, such as cancer. The therapeutic nucleic acid sequences are preferred to have twenty-two (22) nucleotides of homology to the target gene of interest. The therapeutic nucleic acid molecules can be directed against mRNA transcripts of genes including but not limited to Androgen Receptor (AR), ABCB1/MDR1/PGY1 (P-glycoprotein; Pgp), CHK-1, HIF-1, Mcl-1, PDGFR, Tie-2, ABL1, ABL2, AKT2, ALK, BCL2, BCL3, BCL5, BCL6, BLC7A, BCL9, BCL10, BCL11A, BCL11B, Bcl-x, Bcr-Abl, BRAF, CCND1, CDK4, CHK-1, c-Met, c-myc, CTNNB1, DKC1, EGFR1, EGFR2, ERBB2, ERCC-1, EZH2, FES, FGFR1, FGFR2, FGFR3, FGFR-4, FLT1 (VEGFR1), FLT2, FLT3, FLT4, HER2, HER3, HRAS, IGFR, Interleukin 8 (IL-8), JAK, JAK2, KDR/Flk-1 (VEGFR-2), KIT, KRAS2, MET, MRP, mTOR, MYC, MYCL1, MYCN, NRAS, p53, PARP1, PDGFB, PDGFRA, PDGFRB, PI3KCA, PPAR, Rad51, Rad52, Rad53, RalA, REL, RET, RRM1, RRM2, STAT3, survivin, telomerase, TEP1, TERC, TERT, VEGF-A, VEGF-B, VEGF-C, VEGF-D, VEGF-E, Wnt-1, and XIAP. The antibody and/or Fc-containing fusion/conjugate molecules on the surface of minicells can preferentially recognize but are not limited to recognizing cell-specific surface antigens including α3β1 integrin, α4β1 integrin, α5β1 integrin, $\alpha_v\beta3$ integrin, $\alpha_v\beta1$ integrin, β1 integrin, 5T4, CAIX, CD4, CD13, CD19, CD20, CD22, CD25, CD30, CD31, CD33, CD34, CD40, CD44v6, CD45, CD51, CD52, CD54, CD56, CD64, CD70, CD74, CD79, CD105, CD117, CD123, CD133, CD138, CD144, CD146, CD152, CD174, CD205, CD227, CD326, CD340, Cripto, ED-B, GD2, TMEFF2, VEGFR1, VEGFR2, FGFR, PDGFR, ANGPT1, TIE1, TIE2, NRP1, TEK (CD202B), TGFβR, Death Receptor 5 (Trail-R2), DLL4, EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6, FAP, GPNMB, ICAMs, VCAMs, PSMA, HER-2/neu, IL-13R alpha 2, MUC-1, MUC16, EGFR1 (HER-1), EGFR2 (HER-2/neu), EGFR3 (HER-3), IGF-1R, IGF-2R, c-Met (HGFR), Mesothelin, PDGFR, EDGR, TAG-72, transferrin receptor, EpCAM, CTLA-4, PSMA, tenascin C, alpha-fetoprotein, vimentin, C242 antigen, TRAIL-R1, TRAIL-R2, CA-125, GPNMB, CA-IX, GD3 ganglioside, RANKL, BAFF, IL-6R, TAG-72, HAMA, and CD166.

In some preferred embodiments, targeted therapeutic minicells are used as targeted therapeutic nucleic acid delivery vehicles in vivo and are used to prevent, inhibit, and/or limit disease progression in an animal. In some embodiments, targeted minicells are (i) derived from Fc-binding minicells wherein the Fc-binding minicells display the Fc binding portion of Protein A on their surfaces, (ii) are loaded with one or more therapeutic nucleic acids, (iii) further comprise surface localized antibodies and/or Fc-containing fusion/conjugate molecules that are bound to the Fc binding portion of the surface displayed Fc binding region of Protein A wherein the antibodies and/or Fc-containing fusion/conjugate molecules recognize a eukaryotic cell-specific surface antigen and are capable of stimulating receptor mediated endocytosis upon binding of the targeted minicell to the eukaryotic cell-specific surface antigen, (iv) further comprise an endosomal disrupting agent, and (v) further comprise a pharmaceutically acceptable carrier for intravenous administration. In some embodiments, therapeutic nucleic acids that exert their effects by way of gene silencing (siRNA and shRNA, or a eukaryotic DNA expression plasmid encoding for the same) include but are not limited to comprising one or more contiguous nucleotide sequences having homology to wild-type gene sequences and/or to one or more contiguous sequences containing germ-line and somatic mutations known to be involved in disease, such as cancer. The therapeutic nucleic acid sequences are preferred to have twenty-two (22) nucleotides of homology to the target gene of interest. The therapeutic nucleic acid molecules may be directed against mRNA transcripts of genes including but not limited to Androgen Receptor (AR), ABCB1/MDR1/PGY1 (P-glycoprotein; Pgp), CHK-1, HIF-1, Mcl-1, PDGFR, Tie-2, ABL1, ABL2, AKT2, ALK, BCL2, BCL3, BCL5, BCL6, BLC7A, BCL9, BCL10, BCL11A, BCL11B, Bcl-x, Bcr-Abl, BRAF, CCND1, CDK4, CHK-1, c-Met, c-myc, CTNNB1, DKC1, EGFR1, EGFR2, ERBB2, ERCC-1, EZH2, FES, FGFR1, FGFR2, FGFR3, FGFR-4, FLT1 (VEGFR1), FLT2, FLT3, FLT4, HER2, HER3, HRAS, IGFR, Interleukin 8 (IL-8), JAK, JAK2, KDR/Flk-1 (VEGFR-2), KIT, KRAS2, MET, MRP, mTOR, MYC, MYCL1, MYCN, NRAS, p53, PARP1, PDGFB, PDGFRA, PDGFRB, PI3KCA, PPAR, Rad51, Rad52, Rad53, RalA, REL, RET, RRM1, RRM2, STAT3, survivin, telomerase, TEP1, TERC, TERT, VEGF-A, VEGF-B, VEGF-C, VEGF-D, VEGF-E, Wnt-1, and XIAP. The antibody and/or Fc-containing fusion/conjugate molecules on the surface of minicells can preferentially recognize but are not limited to recognizing cell-specific surface antigens including α3β1 integrin, α4β1 integrin, α5β1 integrin, $\alpha_v\beta3$integrin, $\alpha_v\beta1$ integrin, β1 integrin, 5T4, CAIX, CD4, CD13, CD19, CD20, CD22, CD25, CD30, CD31, CD33, CD34, CD40, CD44v6, CD45, CD51, CD52, CD54, CD56, CD64, CD70, CD74, CD79, CD105, CD117, CD123, CD133, CD138, CD144, CD146, CD152, CD174, CD205, CD227, CD326, CD340, Cripto, ED-B, GD2, TMEFF2, VEGFR1, VEGFR2, FGFR, PDGFR, ANGPT1, TIE1, TIE2, NRP1, TEK (CD202B), TGFβR, Death Receptor 5 (Trail-R2), DLL4, EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6, FAP, GPNMB, ICAMs, VCAMs, PSMA, HER-2/neu, IL-13R alpha 2, MUC-1, MUC16, EGFR1 (HER-1), EGFR2 (HER-2/neu), EGFR3 (HER-3), IGF-1R, IGF-2R, c-Met (HGFR), Mesothelin, PDGFR, EDGR, TAG-72, transferrin receptor, EpCAM, CTLA-4, PSMA, tenascin C, alpha-fetoprotein, vimentin, C242 antigen, TRAIL-R1, TRAIL-R2, CA-125, GPNMB, CA-IX, GD3 ganglioside, RANKL, BAFF, IL-6R, TAG-72, HAMA, and CD166.

In some preferred embodiments, targeted therapeutic minicells are used as targeted therapeutic polypeptide delivery vehicles in vivo and are used to prevent, inhibit, and/or limit disease progression in an animal. In some embodiments, targeted minicells are (i) derived from Fc-binding minicells wherein the Fc-binding minicells display the Fc binding portion of Protein A on their surfaces, (ii) are loaded with one or more therapeutic polypeptides, (iii) further comprise surface localized antibodies and/or Fc-containing fusion/conjugate molecules that are bound to the Fc binding portion of the surface displayed Fc binding region of Protein A wherein the antibodies and/or Fc-containing fusion/conjugate molecules recognize a eukaryotic cell-specific surface antigen and are capable of stimulating receptor mediated endocytosis upon binding of the targeted minicell to the eukaryotic cell-specific surface antigen, (iv) further comprise an endosomal disrupting agent, and (v) further comprise a pharmaceutically acceptable carrier for intravenous administration. In some embodiments, therapeutic polypeptides that exert their effects by way of cellular toxicity (protein toxins) include but are not limited to cholesterol dependent cytolysins, ADP-ribosylating toxins, plant toxins, bacterial toxins, viral toxins, pore forming toxins, and cell penetrating peptides. The therapeutic polypeptides can be selected from the group including but not limited to gelonin, diphtheria toxin fragment A, diphtheria toxin fragment A/B, tetanus toxin, *E. coli* heat labile toxin (LTI and/or LTII), cholera toxin, *C. perfringes* iota toxin, *Pseudomonas* exotoxin A, shiga toxin, anthrax toxin, MTX (*B. sphaericus* mosquilicidal toxin), perfringolysin O, streptolysin, barley toxin, mellitin, anthrax toxins LF and EF, adenylate cyclase toxin, botulinolysin B, botulinolysin E3, botulinolysin C, botulinum toxin A, cholera toxin, *clostridium* toxins A, B, and alpha, ricin, shiga A toxin, shiga-like A toxin, cholera A toxin, pertussis S1 toxin, *E. coli* heat labile toxin (LTB), pH stable variants of listeriolysin O (pH-independent; amino acid substitution L461T), thermostable variants of listeriolysin O (amino acid substitutions E247M, D320K), pH and thermostable variants of listeriolysin O (amino acid substitutions E247M, D320K, and L461T), streptolysin O, streptolysin O c, streptolysin O e, sphaericolysin, anthrolysin O, cereolysin, thuringiensilysin O, weihenstephanensilysin, alveolysin, brevilysin, butyriculysin, tetanolysin O, novyilysin, lectinolysin, pneumolysin, mitilysin, pseudopneumolysin, suilysin, intermedilysin, ivanolysin, seeligeriolysin O, vaginolysin, and pyolysin The antibody and/or Fc-containing fusion/conjugate molecules on the surface of minicells can preferentially recognize but is not limited to recognizing cell-specific surface antigens including $\alpha 3\beta 1$ integrin, $\alpha 4\beta 1$ integrin, $\alpha 5\beta 1$ integrin, $\alpha_v\beta 3$ integrin, $\alpha_v\beta 1$integrin, $\beta 1$ integrin, 5T4, CAIX, CD4, CD13, CD19, CD20, CD22, CD25, CD30, CD31, CD33, CD34, CD40, CD44v6, CD45, CD51, CD52, CD54, CD56, CD64, CD70, CD74, CD79, CD105, CD117, CD123, CD133, CD138, CD144, CD146, CD152, CD174, CD205, CD227, CD326, CD340, Cripto, ED-B, GD2, TMEFF2, VEGFR1, VEGFR2, FGFR, PDGFR, ANGPT1, TIE1, TIE2, NRP1, TEK (CD202B), TGFβR, Death Receptor 5 (Trail-R2), DLL4, EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6, FAP, GPNMB, ICAMs, VCAMs, PSMA, HER-2/neu, IL-13R alpha 2, MUC-1, MUC16, EGFR1 (HER-1), EGFR2 (HER-2/neu), EGFR3 (HER-3), IGF-1R, IGF-2R, c-Met (HGFR), Mesothelin, PDGFR, EDGR, TAG-72, transferrin receptor, EpCAM, CTLA-4, PSMA, tenascin C, alpha-fetoprotein, vimentin, C242 antigen, TRAIL-R1, TRAIL-R2, CA-125, GPNMB, CA-IX, GD3 ganglioside, RANKL, BAFF, IL-6R, TAG-72, HAMA, and CD166.

In some preferred embodiments, targeted therapeutic minicells are used as targeted therapeutic polypeptide delivery vehicles in vivo and are used to prevent, inhibit, and/or limit disease progression in an animal. In some embodiments, targeted minicells are (i) derived from Fc-binding minicells wherein the Fc-binding minicells display the Fc binding portion of Protein G on their surfaces, (ii) are loaded with one or more therapeutic polypeptides, (iii) further comprise surface localized antibodies and/or Fc-containing fusion/conjugate molecules that are bound to the Fc binding portion of the surface displayed Fc binding region of Protein G wherein the antibodies and/or Fc-containing fusion/conjugate molecules recognize a eukaryotic cell-specific surface antigen and are capable of stimulating receptor mediated endocytosis upon binding of the targeted minicell to the eukaryotic cell-specific surface antigen, (iv) further comprise an endosomal disrupting agent, and (v) further comprise a pharmaceutically acceptable carrier for intravenous administration. In some embodiments, therapeutic polypeptides that exert their effects by way of cellular toxicity (protein toxins) include but are not limited to cholesterol dependent cytolysins, ADP-ribosylating toxins, plant toxins, bacterial toxins, viral toxins, pore forming toxins, and cell penetrating peptides. The therapeutic polypeptides may be selected from the group including but not limited to gelonin, diphtheria toxin fragment A, diphtheria toxin fragment A/B, tetanus toxin, *E. coli* heat labile toxin (LTI and/or LTII), cholera toxin, *C. perfringes* iota toxin, *Pseudomonas* exotoxin A, shiga toxin, anthrax toxin, MTX (*B. sphaericus* mosquilicidal toxin), perfringolysin O, streptolysin, barley toxin, mellitin, anthrax toxins LF and EF, adenylate cyclase toxin, botulinolysin B, botulinolysin E3, botulinolysin C, botulinum toxin A, cholera toxin, *clostridium* toxins A, B, and alpha, ricin, shiga A toxin, shiga-like A toxin, cholera A toxin, pertussis S1 toxin, *E. coli* heat labile toxin (LTB), pH stable variants of listeriolysin O (pH-independent; amino acid substitution L461T), thermostable variants of listeriolysin O (amino acid substitutions E247M, D320K), pH and thermostable variants of listeriolysin O (amino acid substitutions E247M, D320K, and L461T), streptolysin O, streptolysin O c, streptolysin O e, sphaericolysin, anthrolysin O, cereolysin, thuringiensilysin O, weihenstephanensilysin, alveolysin, brevilysin, butyriculysin, tetanolysin O, novyilysin, lectinolysin, pneumolysin, mitilysin, pseudopneumolysin, suilysin, intermedilysin, ivanolysin, seeligeriolysin O, vaginolysin, and pyolysin. The antibody and/or Fc-containing fusion/conjugate molecule on the surface of minicells can preferentially recognize but is not limited to recognizing cell-specific surface antigens including $\alpha 3\beta 1$ integrin, $\alpha4\beta1$ integrin, $\alpha5\beta1$ integrin, $\alpha_v\beta3$ integrin, $\alpha_v\beta1$ integrin, $\beta1$ integrin, 5T4, CALX, CD4, CD13, CD19, CD20, CD22, CD25, CD30, CD31, CD33, CD34, CD40, CD44v6, CD45, CD51, CD52, CD54, CD56, CD64, CD70, CD74, CD79, CD105, CD117, CD123, CD133, CD138, CD144, CD146, CD152, CD174, CD205, CD227, CD326, CD340, Cripto, ED-B, GD2, TMEFF2, VEGFR1, VEGFR2, FGFR, PDGFR, ANGPT1, TIE1, TIE2, NRP1, TEK (CD202B), TGF$\beta$R, Death Receptor 5 (Trail-R2), DLL4, EPHAL EPHA2, EPHA3, EPHA4, EPHA5, EPHA6, EPHA7, EPHA8, EPHA9, EPHA10, EPHB1, EPHB2, EPHB3, EPHB4, EPHB5, EPHB6, FAP, GPNMB, ICAMs, VCAMs, PSMA, HER-2/neu, IL-13R alpha 2, MUC-1, MUC16, EGFR1 (HER-1), EGFR2 (HER-2/neu), EGFR3 (HER-3), IGF-1R, IGF-2R, c-Met (HGFR), Mesothelin, PDGFR, EDGR, TAG-72, transferrin receptor, EpCAM, CTLA-4, PSMA, tenascin C, alpha-fetoprotein, vimentin, C242 antigen, TRAIL-R1, TRAIL-R2, CA-125, GPNMB, CA-IX, GD3 ganglioside, RANKL, BAFF, IL-6R, TAG-72, HAMA, and CD166.

In some preferred embodiments, targeted diagnostic minicells are used as targeted diagnostic imaging agents in vivo and are used to diagnose, detect, and/or monitor disease in an animal. In some embodiments, targeted minicells are (i) derived from Fc-binding minicells wherein the Fc-binding minicells display the Fc binding portion of Protein G on their surfaces, (ii) are loaded with one or more molecular imaging agents, (iii) further comprise surface localized antibodies and/or Fc-containing fusion/conjugate molecules that are bound to the Fc binding portion of the surface displayed Fc binding region of Protein G wherein the antibodies and/or Fc-containing fusion/conjugate molecules recognize a eukaryotic cell-specific surface antigen and are capable of stimulating receptor mediated endocytosis upon binding of the targeted minicell to the eukaryotic cell-specific surface antigen, and (iv) further comprise a pharmaceutically acceptable carrier for intravenous administration. The antibody and/or Fc-containing fusion/conjugate molecule(s) on the surface of minicells can preferentially recognize but is not limited to recognizing cell-specific surface antigens including $\alpha3\beta1$ integrin, $\alpha4\beta1$ integrin, $\alpha5\beta1$ integrin, $\alpha_v\beta3$integrin, $\alpha_v\beta1$integrin, $\beta1$ integrin, 5T4, CAIX, CD4, CD13, CD19, CD20, CD22, CD25, CD30, CD31, CD33, CD34, CD40, CD44v6, CD45, CD51, CD52, CD54, CD56, CD64, CD70, CD74, CD79, CD105, CD117, CD123, CD133, CD138, CD144, CD146, CD152, CD174, CD205, CD227, CD326, CD340, Cripto, ED-B, GD2, TMEFF2, VEGFR1, VEGFR2, FGFR, PDGFR, ANGPT1, TIE1, TIE2, NRP1, TEK (CD202B), TGFI$\beta$R, Death Receptor 5 (Trail-R2), DLL4, EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6, FAP, GPNMB, ICAMs, VCAMs, PSMA, HER-2/neu, IL-13R alpha 2, MUC-1, MUC16, EGFR1 (HER-1), EGFR2 (HER-2/neu), EGFR3 (HER-3), IGF-1R, IGF-2R, c-Met (HGFR), Mesothelin, PDGFR, EDGR, TAG-72, transferrin receptor, EpCAM, CTLA-4, PSMA, tenascin C, alpha-fetoprotein, vimentin, C242 antigen, TRAIL-R1, TRAIL-R2, CA-125, GPNMB, CA-IX, GD3 ganglioside, RANKL, BAFF, IL-6R, TAG-72, HAMA, and CD166.

In some preferred embodiments, targeted diagnostic minicells are used as targeted diagnostic imaging agents in vivo and are used to diagnose, detect, and/or monitor disease in an animal. In some embodiments, targeted minicells are (i) derived from Fc-binding minicells wherein the Fc-binding minicells display the Fc binding portion of Protein G on their surfaces, (ii) are loaded with one or more molecular imaging agents, (iii) further comprise surface localized antibodies and/or Fc-containing fusion/conjugate molecules that are bound to the Fc binding portion of the surface displayed Fc binding region of Protein G wherein the antibodies and/or Fc-containing fusion/conjugate molecules recognize a eukaryotic cell-specific surface antigen and do not stimulate receptor mediated endocytosis upon binding of the targeted minicell to the eukaryotic cell-specific surface antigen, and (iv) further comprise a pharmaceutically acceptable carrier for intravenous administration. The antibody and/or Fc-containing fusion/conjugate molecule(s) on the surface of minicells can preferentially recognize but is not limited to recognizing cell-specific surface antigens including $\alpha3\beta1$ integrin, $\alpha4\beta1$ integrin, $\alpha5\beta1$ integrin, $\alpha_v\beta3$integrin, $\alpha_v\beta1$integrin, $\beta1$ integrin, 5T4, CAIX, CD4, CD13, CD19, CD20, CD22, CD25, CD30, CD31, CD33, CD34, CD40, CD44v6, CD45, CD51, CD52, CD54, CD56, CD64, CD70, CD74, CD79, CD105, CD117, CD123, CD133, CD138, CD144, CD146, CD152, CD174, CD205, CD227, CD326, CD340, Cripto, ED-B, GD2, TMEFF2, VEGFR1, VEGFR2, FGFR, PDGFR, ANGPT1, TIE1, TIE2, NRP1, TEK (CD202B), TGF$\beta$R, Death Receptor 5 (Trail-R2), DLL4, EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6, FAP, GPNMB, ICAMs, VCAMs, PSMA, HER-2/neu, IL-13R alpha 2, MUC-1, MUC16, EGFR1 (HER-1), EGFR2 (HER-2/neu), EGFR3 (HER-3), IGF-1R, IGF-2R, c-Met (HGFR), Mesothelin, PDGFR, EDGR, TAG-72, transferrin receptor, EpCAM, CTLA-4, PSMA, tenascin C, alpha-fetoprotein, vimentin, C242 antigen, TRAIL-R1, TRAIL-R2, CA-125, GPNMB, CA-IX, GD3 ganglioside, RANKL, BAFF, IL-6R, TAG-72, HAMA, and CD166. Non-limiting examples of the molecular imaging agents include Gadolinium, $^{64}$Cu diacetyl-bis ($N^4$-methylthiosemicarbazone), $^{18}$F-flourodeoxyglucose, $^{18}$F-flouride, 3'-deoxy-3'-[$^{18}$F]fluorothymidine, $^{18}$F-fluoromisonidazole, gallium, technetium-99, thallium, barium, gastrografin, iodine contrasting agents, iron oxide, green fluorescent protein, luciferase, beta-galactosidase, and any combination of the preceding.

In some preferred embodiments, targeted diagnostic minicells are used as targeted diagnostic imaging agents in vivo and are used to diagnose, detect, and/or monitor disease in an animal. In some embodiments, targeted minicells are (i) derived from Fc-binding minicells wherein the Fc-binding minicells display the Fc binding portion of Protein A on their surfaces, (ii) are loaded with one or more molecular imaging agents, (iii) further comprise surface localized antibodies and/or Fc-containing fusion/conjugate molecules that are bound to the Fc binding portion of the surface displayed Fc binding region of Protein A wherein the antibodies and/or Fc-containing fusion/conjugate molecules recognize a eukaryotic cell-specific surface antigen and are capable of stimulating receptor mediated endocytosis upon binding of the targeted minicell to the eukaryotic cell-specific surface antigen, and (iv) further comprise a pharmaceutically acceptable carrier for intravenous administration. The antibody and/or Fc-containing fusion/conjugate molecule(s) on the surface of minicells can preferentially recognize but is not limited to recognizing cell-specific surface antigens including $\alpha3\beta1$ integrin, $\alpha4\beta1$ integrin, $\alpha5\beta1$ integrin, $\alpha_v\beta3$integrin, $\alpha_v\beta1$integrin, $\beta1$ integrin, 5T4, CAIX, CD4, CD13, CD19, CD20, CD22, CD25, CD30, CD31, CD33, CD34, CD40, CD44v6, CD45, CD51, CD52, CD54, CD56, CD64, CD70, CD74, CD79, CD105, CD117, CD123, CD133, CD138, CD144, CD146, CD152, CD174, CD205, CD227, CD326, CD340, Cripto, ED-B, GD2, TMEFF2, VEGFR1, VEGFR2, FGFR, PDGFR, ANGPT1, TIE1, TIE2, NRP1, TEK (CD202B), TGFβR, Death Receptor 5 (Trail-R2), DLL4, EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6, FAP, GPNMB, ICAMs, VCAMs, PSMA, HER-2/neu, IL-13R alpha 2, MUC-1, MUC16, EGFR1 (HER-1), EGFR2 (HER-2/neu), EGFR3 (HER-3), IGF-1R, IGF-2R, c-Met (HGFR), Mesothelin, PDGFR, EDGR, TAG-72, transferrin receptor, EpCAM, CTLA-4, PSMA, tenascin C, alpha-fetoprotein, vimentin, C242 antigen, TRAIL-R1, TRAIL-R2, CA-125, GPNMB, CA-IX, GD3 ganglioside, RANKL, BAFF, IL-6R, TAG-72, HAMA, and CD166.

Examples of the molecular imaging agent include, but are not limited to, Gadolinium, $^{64}$Cu diacetyl-bis($N^4$-methylthiosemicarbazone), $^{18}$F-flourodeoxyglucose, $^{18}$F-flouride, 3'-deoxy-3'-[$^{18}$F]fluorothymidine, $^{18}$F-fluoromisonidazole, gallium, technetium-99, thallium, barium, gastrografin, iodine contrasting agents, iron oxide, green fluorescent protein, luciferase, beta-galactosidase, and any combination of the preceding.

In some preferred embodiments, targeted therapeutic minicells are used as targeted minicell vaccines against infectious disease agents in vivo, ex vivo, and/or in vitro and are used to prevent, inhibit, and/or slow the progression of infectious disease agents in an animal by generating a recipient animal host immune response that negatively impacts the disease agent. In some embodiments, targeted minicells are (i) derived from Fc-binding minicells wherein the Fc-binding minicells display the Fc binding portion of Protein G on their surfaces, (ii) are loaded with one or more antigenic carbohydrates, protein antigens, and/or DNA vaccines any of which are derived from an infectious disease agent (iii) further comprise surface localized antibodies and/or Fc-containing fusion/conjugate molecules that are bound to the Fc binding portion of the surface displayed Fc binding region of Protein A wherein the antibodies and/or Fc-containing fusion/conjugate molecules recognize a eukaryotic antigen presenting cell-specific surface antigen and are capable of stimulating receptor mediated endocytosis upon binding of the targeted minicell to the eukaryotic antigen presenting cell-specific surface antigen, (iv) further comprise an endosomal disrupting agent, including but not limited to LLO, (v) further comprise a general and/or targeted molecular adjuvant, and (vi) further comprise a pharmaceutically acceptable carrier for an in vivo route of administration including but not limited to intravenous, intramuscular, subcutaneous, intraperitoneal, oral, and/or nasal administration. In some embodiments, targeted minicell vaccines elicit protective humoral (antibody-mediated) and/or cellular (cytotoxic T-cell mediated) immune responses in an animal. In one aspect, immune responses are protective against infectious disease agents including but not limited to agents of bacterial, viral, and parasitic origin. In some embodiments, the antibody and/or Fc-containing fusion/conjugate molecule(s) on the surface of the minicell vaccine recognizes but is not limited to recognizing one or more of CD11b, CD11c, DC-SIGN, CD8, DEC-205, CD105, Flt3, Flt3L, CD103, CD115, CD45, $CX_3CR1$, CCR7, SIRPa, CD205, DCIR2, CD40, M-CSFR, F4/80, CD123, and CD68. In some embodiments, the targeted molecular adjuvant stimulates TLR1, TLR2, TLR3, TLR4, TLR5, TLR6, TLR7, TLR8, TLR9, TLR10, M-CSFR, and any combination of the preceding.

In some preferred embodiments, targeted therapeutic minicells are used as targeted minicell vaccines against infectious disease agents in vivo, ex vivo, and/or in vitro and are used to prevent, inhibit, and/or slow the progression of infectious disease agents in an animal by generating a recipient animal host immune response that negatively impacts the disease agent. In this preferred embodiment targeted minicells are (i) derived from Fc-binding minicells wherein the Fc-binding minicells display the Fc binding portion of Protein A on their surfaces, (ii) are loaded with one or more antigenic carbohydrates, protein antigens, and/or DNA vaccines any of which are derived from an infectious disease agent (iii) further comprise surface localized antibodies and/or Fc-containing fusion/conjugate molecules that are bound to the Fc binding portion of the surface displayed Fc binding region of Protein A wherein the antibodies and/or Fc-containing fusion/conjugate molecules recognize a eukaryotic antigen presenting cell-specific surface antigen and are capable of stimulating receptor mediated endocytosis upon binding of the targeted minicell to the eukaryotic antigen presenting cell-specific surface antigen, (iv) further comprise an endosomal disrupting agent, including but not limited to LLO, (v) further comprise a general and/or targeted molecular adjuvant, and (vi) further comprise a pharmaceutically acceptable carrier for an in vivo route of administration including but not limited to intravenous, intramuscular, subcutaneous, intraperitoneal, oral, and/or nasal administration. In some embodiments, targeted minicell vaccines elicit protective humoral (antibody-mediated) and/or cellular (cytotoxic T-cell mediated) immune responses in an animal. In some embodiments, immune responses are protective against infectious disease agents including but not limited to agents of bacterial, viral, and parasitic origin. In some embodiments, the antibody and/or Fc-containing fusion/conjugate molecules on the surface of the minicell vaccine recognizes but is not limited to recognizing one or more of CD11b, CD11c, DC-SIGN, CD8, DEC-205, CD105, Flt3, Flt3L, CD103, CD115, CD45, $CX_3CR1$, CCR7, SIRPa, CD205, DCIR2, CD40, M-CSFR, F4/80, CD123, and CD68. In some embodiments, the targeted molecular adjuvant stimulates TLR1, TLR2, TLR3, TLR4, TLR5, TLR6, TLR7, TLR8, TLR9, TLR10, M-CSFR, and any combination of the preceding.

In some preferred embodiments, targeted therapeutic minicells are used as targeted minicell vaccines against tumors in vivo, ex vivo, and/or in vitro and are used to prevent, inhibit, and/or slow the progression of tumors in an animal by generating a recipient animal host immune response that negatively impacts the tumor(s). In this preferred embodiment targeted minicells are (i) derived from Fc-binding minicells wherein the Fc-binding minicells display the Fc binding portion of Protein G on their surfaces, (ii) are loaded with one or more antigenic carbohydrates, protein antigens, and/or DNA vaccines any of which are derived from a tumor cell (iii) further comprise surface localized antibodies and/or Fc-containing fusion/conjugate molecules that are bound to the Fc binding portion of the surface displayed Fc binding region of Protein A wherein the antibodies and/or Fc-containing fusion/conjugate molecules recognize a eukaryotic antigen presenting cell-specific surface antigen and are capable of stimulating receptor mediated endocytosis upon binding of the targeted minicell to the eukaryotic antigen presenting cell-specific surface antigen, (iv) further comprise an endosomal disrupting agent, including but not limited to cLLO, (v) further comprise a general and/or targeted molecular adjuvant, and (vi) further comprise a pharmaceutically acceptable carrier for an in vivo route of administration including but not limited to intravenous, intramuscular, subcutaneous, intraperitoneal, oral, and/or nasal administration. In some embodiments, targeted minicell vaccines elicit protective humoral (antibody-mediated) and/or cellular (cytotoxic T-cell mediated) immune responses in an animal. In one aspect, immune responses are protective against malignant and/or benign tumors of autologous origin. In some embodiments, the antibody and/or Fc-containing fusion/conjugate molecule(s) on the surface of the minicell vaccine recognizes but is not limited to recognizing one or more of CD11b, CD11c, DC-SIGN, CD8, DEC-205, CD105, Flt3, Flt3L, CD103, CD115, CD45, $CX_3CR1$, CCR7, SIRPa, CD205, DCIR2, CD40, M-CSFR, F4/80, CD123, and CD68. In some embodiments, the targeted molecular adjuvant stimulates TLR1, TLR2, TLR3, TLR4, TLR5, TLR6, TLR7, TLR8, TLR9, TLR10, M-CSFR, and any combination of the preceding.

In some preferred embodiments, targeted therapeutic minicells are used as targeted minicell vaccines against tumors in vivo, ex vivo, and/or in vitro and are used to prevent, inhibit, and/or slow the progression of tumors in an animal by generating a recipient animal host immune response that negatively impacts the tumor(s). In this preferred embodiment targeted minicells are (i) derived from Fc-binding minicells wherein the Fc-binding minicells display the Fc binding portion of Protein A on their surfaces, (ii) are loaded with one or more antigenic carbohydrates, protein antigens, and/or DNA vaccines any of which are derived from a tumor cell (iii) further comprise surface localized antibodies and/or Fc-containing fusion/conjugate molecules that are bound to the Fc binding portion of the surface displayed Fc binding region of Protein A, wherein the antibodies and/or Fc-containing fusion/conjugate molecules recognize a eukaryotic antigen presenting cell-specific surface antigen and are capable of stimulating receptor mediated endocytosis upon binding of the targeted minicell to the eukaryotic antigen presenting cell-specific surface antigen, (iv) further comprise an endosomal disrupting agent, including but not limited to LLO, (v) further comprise a general and/or targeted molecular adjuvant, and (vi) further comprise a pharmaceutically acceptable carrier for an in vivo route of administration including but not limited to intravenous, intramuscular, subcutaneous, intraperitoneal, oral, and/or nasal administration. In some embodiments, targeted minicell vaccines elicit protective humoral (antibody-mediated) and/or cellular (cytotoxic T-cell mediated) immune responses in an animal. In one aspect, immune responses are protective against malignant and/or benign tumors. In some embodiments, the antibody and/or Fc-containing fusion/conjugate molecule(s) on the surface of the minicell vaccine recognizes but is not limited to recognizing one or more of CD11b, CD11c, DC-SIGN, CD8, DEC-205, CD105, Flt3, Flt3L, CD103, CD115, CD45, $CX_3CR1$, CCR7, SIRPa, CD205, DCIR2, CD40, M-CSFR, F4/80, CD123, and CD68. In some embodiments, the targeted molecular adjuvant stimulates TLR1, TLR2, TLR3, TLR4, TLR5, TLR6, TLR7, TLR8, TLR9, TLR10, M-CSFR, and any combination of the preceding.

In some preferred embodiments, targeted therapeutic minicells are used as targeted minicell vaccines against tumors in vivo, ex vivo, and/or in vitro and are used to prevent, inhibit, and/or slow the progression of tumors in an animal by generating a recipient animal host immune response that negatively impacts the tumor(s). In some embodiments, targeted minicells are (i) derived from Fc-binding minicells wherein the Fc-binding minicells display the Fc binding portion of Protein G on their surfaces, (ii) are loaded with one or more antigenic carbohydrates, protein antigens, and/or DNA vaccines any of which are derived from a tumor cell (iii) further comprise surface localized antibodies and/or Fc-containing fusion/conjugate molecules that are bound to the Fc binding portion of the surface displayed Fc binding region of Protein G, wherein the antibodies and/or Fc-containing fusion/conjugate molecules recognize a eukaryotic antigen presenting cell-specific surface antigen and are capable of stimulating receptor mediated endocytosis upon binding of the targeted minicell to the eukaryotic antigen presenting cell-specific surface antigen, (iv) further comprise an endosomal disrupting agent, including but not limited to LLO, (v) further comprise a general and/or targeted molecular adjuvant, and (vi) further comprise a pharmaceutically acceptable carrier for an in vivo route of administration including but not limited to intravenous, intramuscular, subcutaneous, intraperitoneal, oral, and/or nasal administration. In some embodiments, targeted minicell vaccines elicit protective humoral (antibody-mediated) and/or cellular (cytotoxic T-cell mediated) immune responses in an animal. In one aspect, immune responses are protective against malignant and/or benign tumors. In some embodiments, the antibody and/or Fc-containing fusion/conjugate molecule(s) on the surface of the minicell vaccine recognizes but is not limited to recognizing one or more of CD11b, CD11c, DC-SIGN, CD8, DEC-205, CD105, Flt3, Flt3L, CD103, CD115, CD45, $CX_3CR1$, CCR7, SIRPa, CD205, DCIR2, CD40, M-CSFR, F4/80, CD123, and CD68. In some embodiments, the targeted molecular adjuvant stimulates TLR1, TLR2, TLR3, TLR4, TLR5, TLR6, TLR7, TLR8, TLR9, TLR10, M-CSFR, and any combination of the preceding.

In some preferred embodiments, the Fc-binding minicells described herein can be used as analyte detection reagents for diagnostic assays including but not limited to Lateral Flow Immunoassays (LFIAs). In some embodiments, the analyte-detecting Fc-binding minicells are comprised of (i) Fc-binding minicells that express and display the Fc-binding region of Protein A, (ii) an analyte-specific antibody or other analyte-specific Fc-containing fusion/conjugate molecule bound to the Fc-containing minicells, and (iii) a detection reagent including but not limited to a small molecule flourophore, a fluorescent protein, an enzyme, a magnetic particle, and colloidal gold wherein the detection reagent is encapsulated, displayed, or otherwise associated with the minicells. In a related permutation, Fc-binding minicells are used as a negative readout detection reagent for use in a competitive LFIA. In some embodiments, negative readout Fc-binding minicells are comprised of (i) Fc-binding minicells, (ii) an Fc/analyte fusion/conjugate bound to the Fc-containing minicells, and (iii) a detection reagent including but not limited to a small molecule flourophore, a fluorescent protein, an enzyme, a magnetic particle, and colloidal gold wherein the detection reagent is encapsulated, displayed, or otherwise associated with the minicells. Minicells are used as detection reagents in kits used to analyze clinical, veterinary, environmental, solid and liquid foodstuffs, pharmaceutical products, and drinking water for the presence or absence of a given relevant analyte in solution. Lateral Flow Immunoassays are constructed whereby they contain (i) product backing, (ii) a sample pad, (iii) a particle conjugate pad, (iv) a porous membrane (e.g. nitrocellulose), (v) a test line, (vi) a control line, and (vii) a wick material. LFIAs are used as rapid point-of-care diagnostics as well as for in-home use (e.g. pregnancy tests), and various field tests (e.g. determining toxin levels in drinking water or soil). The product backing is selected from the group including but not limited to polystyrene and/or another plastic polymer and may be coated with medium to high tack adhesive at the discretion of the artisan. The sample pad is selected from material types including but not limited to cellulose, glass fiber, rayon, polypropylene, and/or other commonly used filtration media known in the art and at the discretion of the artisan. The particle conjugate pad is selected from material types including but not limited to glass fiber, polyesters, polystyrene, polypropylene, rayons, and other filtration media known in the art at the discretion of the artisan. In addition, the conjugate pad component may be "blocked" by the addition by way of immersion into a solution containing proteins, polymers, surfactants, and any combination of the preceding. The porous analytical test membrane is selected from material types including nitrocellulose, nylon, polyvinylidene fluoride (PVDF), Fusion 5 matrix (Whatman), 4CastChip matrix (Amic, Uppsala, Sweden), and any combination of the preceding. In addition, the porous analytical test membrane component may be "blocked" by the addition by way of immersion into a solution containing proteins, polymers, surfactants, and any combination of the preceding. Blocking of the porous analytical membrane occurs after the test and control lines are incorporated into the porous analytical membrane. The test and control lines are incorporated into the porous analytical membrane by use of manufacturing equipment including but not limited to non-contact pump-driven solenoid dispensers, contact tip dispensers, quantitative airbrush dispensers, and any combination of the preceding. Test strips are comprised of an antibody or other test analyte-specific binding partner that is covalently or non-covalently linked to the porous analytical test membrane. Control strips are comprised of an antibody or other detection particle-specific binding partner (e.g. an anti-minicell antibody) such that the detection particle (i.e. minicell) can be bound by the control strip independent of binding of the detection particle to the test analyte. The wick component can be selected from material types including but not limited to high-density cellulose. Many wicking components are known to the artisan and can be utilized in the final product at the discretion of the artisan. An illustrative embodiment of a minicell-based Lateral Flow Immunoassay is depicted in FIG. 1. In some embodiments, test solutions are acquired in or are prepared in liquid solution, applied to the sample pad, mix with the analyte detection reagent (minicells), and then traverse the porous analytical membrane towards the wick. Analyte bound detection reagent accumulates at the positive test line and may be detected using any number of methods known in the art including photometric, charged coupled device camera, flourimetric analysis (e.g., LED excitation), radiometric analysis, and by Magnetic Assay Reader.

In some preferred embodiments, the Fc-binding minicells described herein are used as analyte detection reagents for diagnostic assays including but not limited to Lateral Flow Immunoassays (LFIAs). In some embodiments, the analyte-detecting Fc-binding minicells are comprised of (i) Fc-binding minicells that express and display the Fc-binding region of Protein G, (ii) an analyte-specific antibody or other analyte-specific Fc-containing fusion/conjugate molecule bound to the Fc-containing minicells, and (iii) a detection reagent including but not limited to a small molecule flourophore, a fluorescent protein, an enzyme, a magnetic particle, and colloidal gold wherein the detection reagent is encapsulated, displayed, or otherwise associated with the minicells. In a related permutation, Fc-binding minicells are used as a negative readout detection reagent for use in a competitive LFIA. In some embodiments, negative readout Fc-binding minicells are comprised of (i) Fc-binding minicells, (ii) an Fc/analyte fusion/conjugate bound to the Fc-containing minicells, and (iii) a detection reagent including but not limited to a small molecule flourophore, a fluorescent protein, an enzyme, a magnetic particle, and colloidal gold wherein the detection reagent is encapsulated, displayed, or otherwise associated with the minicells. Minicells are used as detection reagents in kits used to analyze clinical, veterinary, environmental, solid and liquid foodstuffs, pharmaceutical products, and drinking water for the presence or absence of a given relevant analyte in solution. Lateral Flow Immunoassays are constructed whereby they contain (i) product backing, (ii) a sample pad, (iii) a particle conjugate pad, (iv) a porous membrane (e.g. nitrocellulose), (v) a test line, (vi) a control line, and (vii) a wick material. LFIAs are used as rapid point-of-care diagnostics as well as for in-home use (e.g. pregnancy tests), and various field tests (e.g. determining toxin levels in drinking water or soil). The product backing is selected from the group including but not limited to polystyrene and/or another plastic polymer and may be coated with medium to high tack adhesive at the discretion of the artisan. The sample pad is selected from material types including but not limited to cellulose, glass fiber, rayon, polypropylene, and/or other commonly used filtration media known in the art and at the discretion of the artisan. The particle conjugate pad is selected from material types including but not limited to glass fiber, polyesters, polystyrene, polypropylene, rayons, and other filtration media known in the art at the discretion of the artisan. In addition, the conjugate pad component may be "blocked" by the addition by way of immersion into a solution containing proteins, polymers, surfactants, and any combination of the preceding. The porous analytical test membrane is selected from material types including nitrocellulose, nylon, polyvinylidene fluoride (PVDF), Fusion 5 matrix (Whatman), 4CastChip matrix (Amic, Uppsala, Sweden), and any combination of the preceding. In addition, the porous analytical test membrane component may be "blocked" by the addition by way of immersion into a solution containing proteins, polymers, surfactants, and any combination of the preceding. Blocking of the porous analytical membrane occurs after the test and control lines are incorporated into the porous analytical membrane. The test and control lines are incorporated into the porous analytical membrane by use of manufacturing equipment including but not limited to non-contact pump-driven solenoid dispensers, contact tip dispensers, quantitative airbrush dispensers, and any combination of the preceding. Test strips are comprised of an antibody or other test analyte-specific binding partner that is covalently or non-covalently linked to the porous analytical test membrane. Control strips are comprised of an antibody or other detection particle-specific binding partner (e.g. an anti-minicell antibody) such that the detection particle (i.e. minicell) can be bound by the control strip independent of binding of the detection particle to the test analyte. The wick component may be selected from material types including but not limited to high-density cellulose. Many wicking components are known to the artisan and can be utilized in the final product at the discretion of the artisan. A complete diagram of a minicell-based Lateral Flow Immunoassay is depicted in FIG. 1. In some embodiments, test solutions are acquired in or are prepared in liquid solution, applied to the sample pad, mix with the analyte detection reagent (minicells), and then traverse the porous analytical membrane towards the wick. Analyte bound detection reagent accumulates at the positive test line and may be detected using any number of methods known in the art including photometric, charged coupled device camera, flourimetric analysis (e.g. LED excitation), radiometric analysis, and by Magnetic Assay Reader.

Some embodiments provide an Fc-binding minicell-producing bacterium comprising: (i) an expressible gene encoding a minicell-producing gene product that modulates one or more of septum formation, binary fission, and chromosome segregation; (ii) an expressible "genetic suicide" gene encoding a heterologous endonuclease, where the chromosome of the minicell-producing bacteria comprises one or more recognition sites of the endonuclease; (iii) a defined auxotrophy; (iv) a deletion or mutation in the lpxM/msbB gene (or other functional equivalent); and (v) a recombinant expression cassette capable of the functional expression and surface display of the Fc binding region of Protein G. In some embodiments, the minicell-producing gene is a cell division gene. The cell division gene includes, but is not limited to ftsZ, sulA, ccdB, and sfiC. In some embodiments, the mincell-producing gene is expressed under the control of an inducible promoter. In some embodiments, the endonuclease suicide gene is located on the chromosome of the minicell-producing bacteria. In some embodiments, the endonuclease is a homing endonuclease. The homing endonuclease includes, but is not limited to, I-CeuI, PI-SceI, I-ChuI, I-CpaI, I-SceIII, I-CreI, I-MsoI, I-SceII, I-SceIV, I-CsmI, I-DmoI, I-PorI, PI-TliI, PI-TliII, and PI-ScpI. In some embodiments, the endonuclease is expressed under the control of an inducible promoter. In some embodiments, the auxotrophy is due to a deletion or inactivating mutation in an essential metabolic gene. In some embodiments the deletion or inactivating mutation is in the dapA gene or its functional homolog. In some embodiments, the minicell-producing bacteria further comprises a deletion or an inactivating mutation in a gene encoding a gene product that is involved in lipopolysaccharide synthesis, wherein the gene is genetically modified compared to a corresponding wild-type gene. In some embodiments, the inactivated gene is lpxM/msbB which encodes a gene product that causes the bacteria to produce an altered lipid A molecule compared to lipid A molecules in a corresponding wild-type bacterium. In some embodiments, the altered lipid A molecule is deficient with respect to the addition of myristolic acid to the lipid A portion of the lipopolysaccharide molecule compared to lipid A molecules in a corresponding wild-type bacterium. In some embodiments, the minicell-producing bacteria further comprise a deletion or inactivating mutation in a gene that is involved in homologous recombination, where the gene is genetically modified compared to a corresponding wild-type gene, where the minicell-producing bacteria are deficient in DNA damage repair. In some embodiments, the minicell-producing bacteria further comprise a mutation in or lack the gene coding for ribonuclease III (e.g., *E. coli's* rnc gene; degrades double-stranded RNAs in *E. coli*) such that the resulting minicells are deficient in this ribonuclease thereby increasing the half-life of double-stranded RNA molecules, including siRNA and shRNA in minicells. In some embodiments the minicell-producing bacterial strain further comprises a recombinant cLLO protein such that resulting minicells further comprise the cLLO protein. In some embodiments the Fc-binding minicell-producing bacterium is a Gram-negative bacterium including but not limited to *Campylobacter jejuni, Haemophilus influenzae, Bordetella pertussis, Brucella* spp., *Franciscella tularemia, Legionella pneumophilia, Neisseria meningitidis, Kliebsella, Yersinia* spp., *Helicobacter pylori, Neisseria gonorrhoeae, Legionella pneumophila, Salmonella* spp., *Shigella* spp., *Pseudomonas aeruginosa*, and *Escherichia coli*. In some embodiments the Fc-binding minicell-producing bacterium is a Gram-positive bacterium including but not limited to *Staphylococcus* spp., *Lactobacillus* spp., *Streptococcus* spp., *Bacillus subtilis, Clostridium difficile*, and *Bacillus cereus*.

Some embodiments provide an Fc-binding minicell-producing bacterium comprising: (i) an expressible gene encoding a minicell-producing gene product that modulates one or more of septum formation, binary fission, and chromosome segregation; (ii) an expressible "genetic suicide" gene encoding a heterologous endonuclease, where the chromosome of the minicell-producing bacteria comprises one or more recognition sites of the endonuclease; (iii) a defined auxotrophy; (iv) a deletion or mutation in the lpxM/msbB gene (or other functional equivalent); and (v) a recombinant expression cassette capable of the functional expression and surface display of the Fc binding region of Protein A. In some embodiments, the minicell-producing gene is a cell division gene. The cell division gene includes, but is not limited to ftsZ, sulA, ccdB, and sfiC. In some embodiments, the mincell-producing gene is expressed under the control of an inducible promoter. In some embodiments, the endonuclease suicide gene is located on the chromosome of the minicell-producing bacteria. In some embodiments, the endonuclease is a homing endonuclease. The homing endonuclease includes, but is not limited to, I-CeuI, PI-SceI, I-ChuI, I-CpaI, I-SceIII, I-CreI, I-MsoI, I-SceII, I-SceIV, I-CsmI, I-DmoI, I-PorI, PI-TliI, PI-TliII, and PI-ScpI. In some embodiments, the endonuclease is expressed under the control of an inducible promoter. In some embodiments, the auxotrophy is due to a deletion or inactivating mutation in an essential metabolic gene. In some embodiments the deletion or inactivating mutation is in the dapA gene or its functional homolog. In some embodiments, the minicell-producing bacteria further comprises a deletion or an inactivating mutation in a gene encoding a gene product that is involved in lipopolysaccharide synthesis, wherein the gene is genetically modified compared to a corresponding wild-type gene. In some embodiments, the inactivated gene is lpxM/msbB which encodes a gene product that causes the bacteria to produce an altered lipid A molecule compared to lipid A molecules in a corresponding wild-type bacterium. In some embodiments, the altered lipid A molecule is deficient with respect to the addition of myristolic acid to the lipid A portion of the lipopolysaccharide molecule compared to lipid A molecules in a corresponding wild-type bacterium. In some embodiments, the minicell-producing bacteria further comprise a deletion or inactivating mutation in a gene that is involved in homologous recombination, where the gene is genetically modified compared to a corresponding wild-type gene, where the minicell-producing bacteria are deficient in DNA damage repair. In some embodiments, the minicell-producing bacteria further comprise a mutation in or lack the gene coding for ribonuclease III (e.g., *E. coli's* mc gene; degrades double-stranded RNAs in *E. coli*) such that the resulting minicells are deficient in this ribonuclease thereby increasing the half-life of double-stranded RNA molecules, including siRNA and shRNA in minicells. In some embodiments the minicell-producing bacterial strain further comprises a recombinant cLLO protein such that resulting minicells further comprise the cLLO protein. In some embodiments the Fc-binding minicell-producing bacterium is a Gram-negative bacterium including but not limited to *Campylobacter jejuni, Haemophilus influenzae, Bordetella pertussis, Brucella* spp., *Franciscella tularemia, Legionella pneumophilia, Neisseria meningitidis, Kliebsella, Yersinia* spp., *Helicobacter pylori, Neisseria gonorrhoeae, Legionella pneumophila, Salmonella* spp., *Shigella* spp., *Pseudomonas aeruginosa*, and *Escherichia coli*. In some embodiments the Fc-binding minicell-producing bacterium is a Gram-positive bacterium including but not limited to *Staphylococcus* spp., *Lactobacillus* spp., *Streptococcus* spp., *Bacillus subtilis, Clostridium difficile*, and *Bacillus cereus.*

Some embodiments provide a method of making Fc-binding minicells, comprising culturing the Fc-binding minicell-producing bacteria disclosed herein and substantially separating minicells from the minicell-producing parent cells, thereby generating a composition comprising Fc-binding minicells. In some embodiments, the method further comprises inducing minicell formation from the minicell-producing parent cell. In some embodiments, the method further comprises inducing expression of the gene encoding the genetic suicide endonuclease. In some embodiments, minicell formation is induced by the presence of one or more chemical compounds selected from isopropyl β-D-1-thiogalactopyranoside (IPTG), rhamnose, arabinose, xylose, fructose, melibiose, and tetracycline. In some embodiments, the expression of the gene encoding the genetic suicide endonuclease is induced by a change in temperature. In some embodiments, the method further comprises purifying the Fc-binding minicells from the composition. In some embodiments, the minicells are substantially separated from the parent cells by a process selected from the group including but not limited to centrifugation, filtration, ultrafiltration, ultracentrifugation, density gradation, immunoaffinity, immunoprecipitation, and any combination of the preceding purification methods.

Some embodiments provide a eubacterial minicell comprising an outer membrane, where the lipopolysaccharide constituents of the outer membrane comprises Lipid A molecules having no myristolic acid moiety ("detoxified lipopolysaccharide" or "detoxified LPS"). Detoxified LPS results in the reduction of pro-inflammatory immune responses in a mammalian host compared to the inflammatory response induced by the outer membrane of eubacterial minicells that are derived from a corresponding wild-type bacterium.

In some embodiments, the targeted therapeutic minicell further comprises one or more biologically active compounds. In some embodiments, at least one of the biologically active compounds is selected from the group consisting of a radioisotope, a polypeptide, a nucleic acid, and a small molecule drug. The biologically active compound(s) are selected from the group including but not limited to therapeutic nucleic acid(s), small molecule drug(s), pro-drug(s), therapeutic polypeptide(s), small molecule imaging agent (s), protein-based imaging agent(s), a eukaryotic expression plasmid encoding for protein-based imaging agent(s), pro-drug converting enzyme(s) and any combination of the preceding. The biologically active compound can also be a combination of a nucleic acid and a small molecule; a combination of a small molecule imaging agent and a small molecule drug; a combination of a small molecule drug, a small molecule imaging agent, and a nucleic acid; or a combination of a nucleic acid and a polypeptide.

The present application describes a composition comprising Fc-binding eubacterial minicells capable of binding and displaying antibodies and/or Fc-containing fusion/conjugate molecules to facilitate the minicell-based targeted delivery of several classes of bioactive payload in concert or singular wherein the final preparation of targeted minicells is sufficiently devoid of remaining viable contaminating parent cells. The minicells may or may not further comprise a detoxified form of lipopolysaccharide at the option and discretion of the artisan.

1. Minicell Production

Minicells are achromosomal, membrane-encapsulated biological nano-particles (approximately 250-500 nm in diameter depending on the strain type and growth conditions used) that are formed by bacteria following a disruption in the normal cell division apparatus. In essence, minicells are small, metabolically active replicas of normal bacterial cells with the exception that they contain no chromosomal DNA and as such, are non-dividing and non-viable. Although minicells do not contain chromosomal DNA, plasmid DNA, RNA, native and/or recombinantly expressed proteins, and other metabolites have all been shown to segregate into minicells.

Disruptions in the coordination between chromosome replication and cell division lead to minicell formation from the polar region of most rod-shaped prokaryotes. Disruption of the coordination between chromosome replication and cell division can be facilitated through the over-expression of some of the genes involved in septum formation and binary fission. Alternatively, minicells can be produced in strains that harbor mutations in genes involved in septum formation and binary fission. Impaired chromosome segregation mechanisms can also lead to minicell formation as has been shown in many different prokaryotes.

Similarly, minicell production can be achieved by the over-expression or mutation of genes involved in the segregation of nascent chromosomes into daughter cells. For example, mutations in the parC or mukB loci of *E. coli* have been demonstrated to produce minicells. Both affect separate requisite steps in the chromosome segregation process in Enterobacteriacea. It can be assumed that like the cell division genes described above, manipulation of wild type levels of any given gene involved in the chromosome segregation process that result in minicell production will have similar effects in other family members.

Because the cell division and chromosome replication processes are so critical to survival, there exists a high level of genetic and functional conservation amongst prokaryotic family members with respect to genes responsible for these processes. As a result, the over-expression or mutation of a cell division gene capable of driving minicell production in one family member, can be used to produce minicells in another. For example, it has been shown that the over-expression of the *E. coli* ftsZ gene in other Enterobacteriacea family members such as *Salmonella* spp. and *Shigella* spp as well as other class members such as *Pseudomonas* spp. will result in similar levels of minicell production.

The same can be demonstrated in the mutation-based minicell producing strains of the family Enterobacteriacea. For example, deletion of the min locus in any of Enterobacteriacea family members results in minicell production. Cell division genes from the Enterobacteriacea in which mutation can lead to minicell formation include but are not limited to the min genes (MinCDE). While minicell production from the min mutant strains is possible, these strains have limited commercial value in terms of being production strains. The reason for this is that strains with deletions or mutations within the min genes make minicells at constitutively low levels. This presents two problems in terms of commercialization and economies of scale. The first is that minicell yields from these strains are low, which increases production cost. The second is that minicell yields are highly variable with the mutant strains and lot-to-lot variability has an enormous impact on production cost, manufacturing quality control and regulatory compliance. Using cell division mutant strains to produce minicells that encapsulate biologically active molecules such as proteins, RNA, DNA, and other catabolites for diagnostic or therapeutic delivery is problematic. The onset of minicell production in the mutant strains cannot be controlled and occurs at a low level so that the end result is that some minicells will contain no biologically active molecules while others will contain widely variable amounts of biologically active molecules. These shortcomings when taken together or separately greatly restrict the utility of these mutant strains for commercial purposes.

Minicell-producing strains that overexpress cell division genes ("overexpressers") are preferred over mutation-based strains because the minicell-production phenotype is controllable as long as the cell division genes to be overexpressed are placed under the control of an inducible or other conditionally active eubacterial promoter system. Minicell production from strains overexpres sing the cell division gene ftsZ were discovered by researchers who were identifying essential cell division genes in *E. coli* using plasmid-based complementation studies. In these studies, the ftsZ gene was present in over 10 copies per cell. The presence of multiple gene copies of ftsZ was demonstrated to produce minicells and extremely long filamented cells. Ultimately, this transition into the irreversible filamentous phenotype negatively impacts minicell yields from strains overexpressing ftsZ from multi-copy plasmids, although the number of minicells produced is still higher than that of any mutant strain. It has since been demonstrated that by reducing the number of ftsZ gene copies to a single, chromosomal duplication, the number of minicells produced increases over those strains where ftsZ is located on multi-copy plasmids and that the filamentous phenotype is less profound. Thus, the preferred composition(s) are minicell-producing strains that inducibly overexpress the ftsZ gene from a duplicate, chromosomally integrated copy of ftsZ. The duplicate ftsZ gene used can be derived directly from the species of bacteria in which the minicell-production phenotype is being engineered and can also be derived from the ftsZ gene sequence from other species of bacteria. By way of non-limiting example, overexpression of the ftsZ gene of *Escherichia coli* can be used to generate minicells from *Escherichia coli* and *Salmonella typhimurium*. Resulting strains are comprised of the wild type ftsZ gene and a separate, duplicative, and inducible copy of the ftsZ gene on the chromosome and the inducible genetic suicide mechanism(s) described in U.S. patent publication No. 2010/0112670, which is incorporated herein by its entirety. By way of non-limiting example, division genes that can be over-expressed to produce minicells in the family Enterobacteriaceae include but are not limited to ftsZ, minE, sulA, ccdB, and sfiC. The preferred composition is to have a duplicate copy(s) of a cell division gene(s) under the control of an inducible promoter that is stably integrated into the chromosome of a given eubacterial strain. It is easily recognized by one skilled in the art that this same strategy could be imparted if the inducible cell division gene cassette were present on a plasmid, cosmid, bacterial artificial chromosome (BAC), recombinant bacteriophage or other episomal DNA molecule present in the cell.

This inducible phenotype approach to minicell production has several distinct advantages over the mutant systems. The first is that because there are no constitutive genetic mutations in these strains, there exists no selective pressure during normal growth and the cells of the culture maintain a very stable and normal physiology until the minicell phenotype is induced. The end result is that inducible minicell producing strains are healthier and more stable, which ultimately results in higher yields of minicells. Another distinct advantage of using the inducible phenotype approach to minicell production is in cases where minicells are to be used to deliver biologically active molecules such as proteins, therapeutic RNAs, plasmid DNAs, and other bioactive catabolites that can be made by the minicell-producing parent cells such that the minicells that are produced encapsulate those biologically active molecules. In these cases, the preferred method is to induce the formation of the biologically active molecule(s) within the parental cells prior to inducing the minicell phenotype, so that all of the minicells produced will contain the desired amount of the biologically active molecule(s). Alternatively, the minicells themselves are capable of producing the bioactive molecule after being separated from the parental cells. This includes but is not limited to forming the bioactive molecule from an episomal nucleic acid or RNA encoding for the bioactive molecule located within the minicell or by preexisting protein constituents of minicells after being separated from the parental cells. Any of these expression strategies can be employed to express and display binding moieties on the surfaces of minicells. These advantages, when used in combination, result in a higher quality and quantity of minicells. In addition, these minicells can further comprise small molecule drugs that can be loaded into minicells as described in more detail below.

2. Minicell Purification

Because minicells are derived from some bacteria that are pathogenic or opportunistically pathogenic, it is of the utmost importance that any contaminating parental cells be functionally eliminated from a given population before administration. Conventionally, live parental cells have been eliminated through either physical means or biological means or both.

Physical means include the use of centrifugation-based separation procedures, filtration methodologies, chromatography methodologies, or any combination thereof.

Biological elimination is achieved by but not limited to the preferential lysis of parental cells, the use of auxotrophic parental strains, treatment with antibiotics, treatment with UV radiation, diaminopimelic acid (DAP) deprivation, selective adsorption of parental cells, treatment with other DNA damaging agents, and induction of a suicide gene.

Preferential lysis of parental cells is typically mediated by inducing the lytic cycle of a lysogenic prophage. In the case of minicell producing strains, it is most useful to use a prophage that is lysis competent but defective at re-infection, such that minicells are not subsequently infected and lysed during activation of the lytic phenotype. Alternatively and by way of non-limiting example, individual genes such as those classified as members of the holin gene family, can be expressed to achieve similar levels of lysis without the concerns over re-infection inherent to the use of lysogenic prophages. Both approaches are limited by the fact that the lysis event, regardless of the method used to achieve it, expels unacceptable amounts of free endotoxin into the media. Removal of such large amounts of free endotoxin is time consuming, suffers from lot to lot variability, and is ultimately cost prohibitive.

The use of auxotrophic strains raises concerns over reversion and as such can only be used in cases where minicells are to be produced from commensal or non-pathogenic strains of bacteria. Thus, their application is limited with respect to being used as a method for elimination of live non-pathogenic parental cells used in minicell production.

The use of antibiotics can be of benefit in the production of minicells when used on samples that have been enriched for minicells (by differential centrifugation or preliminary filtration for example). With many fewer parental cells present, the potential for the development of antibiotic resistance is reduced to nearly zero. The use of antibiotics on primary minicell production cultures that still contain high numbers of viable parental cells is undesirable as the chances for the development of antibiotic resistance increases proportionally to the number of viable parental cells.

Treatment with UV irradiation can be useful in the elimination of live parental cells on a minicell production run with the exception of the fact that UV irradiation is random with respect to its effects on nucleic acids and results are highly variable from lot to lot. In addition, this method is not preferred when using minicells to deliver therapeutic or prophylactic nucleic acids as UV irradiation randomly damages all nucleic acids. For instance, plasmid DNA would also be highly susceptible to DNA damage by UV irradiation and may be rendered ineffective although still effectively delivered by minicells.

Diaminopimelic acid (DAP) deprivation can be useful in the elimination of live parental cells with the exception that this approach is limited by the number of species it can be used for. In other words, not all parent cell species capable of producing minicells require DAP for survival. DAP mutants in *E. coli* minicell-producing strains are of great advantage and in some cases preferred over the wild type. The advantage of using DAP is that this compound (diaminopimelic acid, an *E. coli* cell wall constituent) is critical for the growth of *E. coli* and is not present in or produced by animals. Thus, should a "viable" *E. coli* minicell-producing parental cell be administered along with targeted minicells, the parental cell will be unable to grow and will thereby be inert to the animal and with respect to minicell activity. A similar approach can be used with *Salmonella* spp. based minicell-producing parental strains except in that case the aro genes, preferably aroB are removed.

Selective adsorption methodologies have yet to be explored with respect to purifying minicells from viable parental cells. Selective adsorption is defined as any process by which parental cells or minicells are preferentially adsorbed to a substrate by virtue of their affinity for the substrate. By way of non-limiting example, high affinity protein-protein interactions could be exploited for this use. By way of non-limiting example, the outer membrane protein Invasin from the gram-negative species *Yersinia pseudotuberculosis* has a high affinity for mammalian integrins. The gene encoding for invasin under the control an inducible promoter could easily be introduced on to the chromosome of a minicell producing strain. Minicells could be produced from this strain prior to the activation of expression of the invasin gene such that the minicells produced do not express or display invasin on their cell surface. Once the desired quantity of minicells is produced from the strain, the viable cells within the culture could be given the signal to produce the invasin protein such that invasin is only expressed and displayed upon viable cells. Once invasin is preferentially expressed on the surface of viable parental cells, they can be easily adsorbed to a substrate coated with integrins or other invasin-specific protein binding motifs embedded into a synthetic polypeptide or other recombinant protein. Once absorbed, minicells can be selectively purified away from viable parental cells by a number of different means dependent upon the substrate type used. Substrates include but are not limited to solid-phase chromatographic columns used in gravity filtration applications, magnetic beads, ion exchange columns, or HPLC columns. This approach is limited by the disadvantage that no single protein-protein interaction will work for all species of minicell producing parent cells. For instance, the invasin-integrin approach described above would be useful for most Gram-negative Enterobacteriacea family members but not for use with minicell producing Gram-positive Bacillaceae family members.

In some embodiments, minicells are substantially separated from the minicell-producing parent cells in a composition comprising minicells. For example, after separation, the composition comprising the minicells is less than about 99.9%, 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 65%, 60%, 55%, 50%, 45%, 40%, 35% or 30% free of minicell-producing parent cells. In some embodiments, the composition contains less than about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% minicell-producing parent cells.

Preferably, the final composition contains few enough contaminating parental cells, viable or otherwise, so as not to be too toxic or interfere with the activity of targeted minicells when administered in vivo for therapeutic purposes.

Some preferred method of sufficiently eliminating contaminating viable parental bacterial cells is through the incorporation and activation of an inducible genetic suicide mechanism, including but not limited to the activation and expression of a homing endonuclease or functional equivalent thereof as described in U.S. Patent Publication No. 20100112670 prior to further physical separation methodologies such as standard filtration techniques known in the art.

3. Targeting Minicells to Specific Cells, Tissues, and Organs

Following production, activation of the genetic suicide mechanism, and subsequent purification, minicells are used as targeted delivery vehicles. Minicells expressing the Fc binding region of Protein G or Protein A and further displaying antibodies, Fc-containing antibody derivatives, and/or Fc-containing fusion/conjugate targeting molecules on their surfaces are used to target specific cell types involved in disease in vivo to preferentially deliver their bioactive payloads to the targeted tissue, organ, and cell type.

Antibodies, or any portion thereof, intended to aid in the targeting of minicells to a specific tissue, organ, and cell type involved in disease can be derived from or be part of any immunoglobulin subclass, including but not limited to IgA, IgM, IgD, IgG, or IgE. Antibodies of any subclass intended for facilitating the targeting function of minicells can be "humanized", although any antibody of any subclass against a cell specific antigen can be raised in any animal known to generate antibody responses through adaptive immunity to achieve the same goal. In nature, antibodies are generated such that they contain two separate arms (Fab' s), each of which recognizes the same epitope of a particular antigen.

In the laboratory, antibodies can be engineered to be independently specific for different antigens, such that a single antibody targets two separate antigens simultaneously. By way of non-limiting example, antibodies can be engineered to recognize putative surface components of a given eubacterial minicell (e.g., LPS O-antigens) on one arm and the other arm be engineered to recognize a eukaryotic cell-specific surface antigen such as those listed above. Additionally, those skilled in the art readily recognize that other bi-specific antibody approaches may be implemented to achieve the same effect. By way of non-limiting example, one skilled in the art would readily recognize that two separate antibodies, with separate specificities, can be non-covalently attached by coupling them to Protein A/G to form a crude "bi-specific" antibody derivative capable of adhering to the surface of minicells wherein one antibody within the complex specifically adheres to the surface of the minicell and the other antibody is displayed to specifically recognize and thereby "target" a specific cell, tissue, or organ type involved in disease in vivo. Similarly, one skilled in the art will recognize that two separate antibodies, with separate specificities, could be covalently linked using various cross-linking techniques to achieve the same effect. All of these potential approaches to targeting are readily recognized by those skilled in the art.

In some embodiments, other non-antibody based targeting approaches that are collectively based on Fc-containing fusions/conjugates can be used. Examples of molecular targeting moiety that can be used, including but not limited to receptor ligands, polypeptides, hormones, carbohydrates, aptamers, antibody-like molecules, and DARPins. Fc-conjugation may be achieved using a variety of approaches known in the art. In the case of Fc-containing polypeptide fusions, including but not limited to receptor ligand/Fc fusions, Fc-containing peptide fusions, and Fc-containing DARPins, recombinant expression of the fusion is the preferred method of construction. In the recombinant expression context, Fc regions may be fused to either the amino or carboxy terminus of a given recombinant fusion at the discretion of the artisan such that fusion to the Fc region does not affect ligand activity with respect to receptor binding and stimulation of receptor-mediated endocytosis. Another approach to making Fc-containing polypeptides, peptides, and DARPins is by chemical conjugation (a.k.a. cross-linking) of purified recombinant Fc region molecules to recombinant polypeptide, peptide, and/or DARPin molecules using any of the well known cross-linking techniques known in the art. In the context of chemical cross-linking, it is advantageous to include "reactive" amino acid groups on either or both of the purified recombinant Fc-region or the polypeptide, peptide, and/or DARPin molecule to be conjugated. Reactive amino acids typically include but are not limited to those that contain sulfhydryl groups, preferably a cysteine residue. For use with popular heterobifunctional cross-linking reagents, it is preferable to include a lysine residue at the linkage site of the opposing conjugate (e.g. Fc-region contains a cysteine residue while polypeptide contains a lysine or vice versa). In instances where purified recombinant Fc regions are cross-linked to hormones, carbohydrates, aptamers, and other non amino acid and/or peptide based molecules, the skilled artisan will recognize that many other cross-linking reagents can be employed to achieve the same. Cross-linking reagents can be "homobifunctional" or "heterobifunctional" (having the same or different reactive groups, respectively) Examples of cross-linking reagents include, but are not limited to, those listed in Table 1. Table 1 also illustrates which cross-linking reagents are appropriate and preferable for each conjugate molecule type/approach. In utilizing this approach, construction and administration of the targeted therapeutic minicells can be achieved by (i) producing or purchasing recombinant Fc region, (ii) producing or purchasing the targeting molecule to be conjugated to the Fc region, (iii) mixing the recombinant Fc region with the targeting molecule in the presence of the appropriate cross-linking reagent (see Table 1) and incubating the mixture under conditions that will allow cross-linking to occur, (iv) purifying resulting Fc-containing conjugates away from the reaction mixture followed by quantification of the Fc-containing conjugates, (v) incubating payload-containing minicells with an amount of Fc-containing conjugate sufficient enough to occupy all Fc-binding sites on the surface of the minicells in the appropriate binding buffer, (vi) removing any unbound conjugates by any one or more conventional means (e.g., tangential flow filtration), (vii) concentrating and/or lyophilizing targeted therapeutic minicells, (v) formulating for product administration the targeted therapeutic minicells by reconstituting in an appropriate volume of a pharmaceutically acceptable carrier.

The minicells described herein are genetically engineered to express and display the Fc binding region of Protein G or Protein A on their surfaces. A preferred method to achieve expression and surface display of the Fc region of Protein G or Protein A is by fusion of the Fc binding region with an outer membrane of the "autotransporter" family. The monomeric autotransporters belonging to the sub-class type 5 secretion system of autotransporters (commonly classified as type 5a) are most preferred. Included in that family of autotransporters classified as type 5a, is the IgA protease (IgAP) of *Neisseria gonorrhoeae*. The IgAP autotransporter passenger domain is easily replaced by the Fc binding region of Protein G or Protein A. Several different antibody fragments and antibody fragment types have been displayed and characterized using the IgAP system in *E. coli* although this approach is entirely novel with respect to its use to express and display the Fc binding region of Protein G or Protein A to produce Fc-binding minicells. The adhesin-involved-in-diffuse-adherance (AIDA-I) autotransporter from *E. coli* can also be used for display of Fc binding regions of Protein G or Protein A. Once the Fc-binding minicells are bound to the antibody and/or Fc containing fusion/conjugate targeting molecule, they become targeting-competent and are capable of preferentially localizing and accumulating in target tissues, organs, or cell types.

Some preferred embodiments for displaying the Fc region of Protein G or Protein A on the surface of minicells include the use of fusion with Lpp-OmpA (SEQ ID NO 22 and SEQ ID NO:23, respectively). OmpA is an outer membrane protein of *Escherichia coli* that when fused to a lipoprotein leader sequence and a display protein of interest, can be exported to the surface of *E. coli*. Because *E. coli* minicells are derived from parental *E. coli*, Lpp-OmpA fusion proteins will be localized on the surface of minicells as well. Several different antibody fragments and antibody fragment types have been displayed and characterized using the Lpp-OmpA system in *E. coli* although this approach is entirely novel with respect to its use to express and display the Fc binding region of Protein G or Protein A to produce Fc-binding minicells. Once the Fc-binding minicells are bound to the antibody and/or Fc-containing fusion/conjugate targeting molecule, they become targeting-competent and are capable of preferentially localizing and accumulating in target tissues, organs, or cell types.

Other native outer membrane proteins that can be used as fusion partners to express and display one or more of the Fc binding regions of Protein G or Protein A on the surface of minicells include but are not limited to LamB, OmpF, OmpC, OmpD, PhoE, PAL, Type III secretion systems, pilus proteins, bacterial autotransporter protein family members, and various flagellin proteins. Generally, the same approach could be used to express and display one or more of the Fc binding regions of Protein G or Protein A on the surface of minicells derived from any Enterobacteriacea or Bacillaceae family member such that the minicells become Fc-binding minicells capable of further binding antibodies and/or Fc-containing fusion/conjugate targeting molecules specific for eukaryotic cell-specific surface antigens, thereby becoming targeting-competent minicells capable of preferentially localizing and accumulating in target tissues, organs, or cell types involved in disease. One skilled in the art will recognize that achieving this goal is a matter of creating a nucleic acid sequence encoding a fusion protein between a putative or predicted outer membrane protein or outer membrane localization sequence and one or more of the Fc binding regions of Protein G or Protein A.

Fc-binding minicells bind antibodies and/or Fc-containing fusion/conjugate targeting molecules that are specific for cell-specific surface antigens to become targeting-competent minicells. Targeting-competent minicells are further loaded with and/or recombinantly express and encapsulate a bioactive payload including but not limited to small molecule drugs, bioactive nucleic acids, bioactive proteins, bioactive radionuclides, imaging agents, and bioactive lipopolysaccharides, and any combination of the proceeding to produce a "biological effect" (synonymous with biological response) that negatively impacts diseased cells, tissues, or organs or positively effects the production of signals that indirectly mitigate diseased, cells, tissues, or organs in an animal. Targeting-competent minicells are made to target eukaryotic cell-specific surface antigens of choice including, but not limited to including α3β1 integrin, α4β1 integrin, α5β1 integrin, $\alpha_v\beta3$ integrin, $\alpha_v\beta1$ integrin, β1 integrin, 5T4, CAIX, CD4, CD13, CD19, CD20, CD22, CD25, CD30, CD31, CD33, CD34, CD40, CD44v6, CD45, CD51, CD52, CD54, CD56, CD64, CD70, CD74, CD79, CD105, CD117, CD123, CD133, CD138, CD144, CD146, CD152, CD174, CD205, CD227, CD326, CD340, Cripto, ED-B, GD2, TMEFF2, VEGFR1, VEGFR2, FGFR, PDGFR, ANGPT1, TIE1, TIE2, NRP1, TEK (CD202B), TGFβR, Death Receptor 5 (Trail-R2), DLL4, EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6, FAP, GPNMB, ICAMs, VCAMs, PSMA, HER-2/neu, IL-13R alpha 2, MUC-1, MUC16, EGFR1 (HER-1), EGFR2 (HER-2/neu), EGFR3 (HER-3), IGF-1R, IGF-2R, c-Met (HGFR), Mesothelin, PDGFR, EDGR, TAG-72, transferrin receptor, EpCAM, CTLA-4, PSMA, tenascin C, alpha-fetoprotein, vimentin, C242 antigen, TRAIL-R1, TRAIL-R2, CA-125, GPNMB, CA-IX, GD3 ganglioside, RANKL, BAFF, IL-6R, TAG-72, HAMA, and CD166. Previously described target-specific antibodies that are used as the targeting component, in some embodiments, include but are not limited to mAb 3F8, mAb CSL362, mAb 360, mAb J591, Abagovomab, Abciximab, Adalimumab, Afelimomab, Afutuzumab, Alacizumab, ALD518, Alemtuzumab, Altumomab, Anatumomab, Anrukinzumab, Apolizumab, Arcitumomab, Aselizumab, Atlizumab, Atorolimumab, Bapineuzmab, Basiliximab, Bavituximab, Bectumomab, Belimumab, Benralizumab, Bertilimumab, Besilesomab, Bevacizumab, Biciromab, Bivatuzumab, Blinatumomab, Brentuximab, Briakinumab, Canakinumab, Cantuzumab, Capromab, Catumaxomab, CC49, Cedelizumab, Certolizumab, Cetuximab, mAb528, Citatuzumab, Cixutumumab, Clenoliximab, Clivatuzumab, Conatumumab, CR6261, Dacetuzumab, Daclizumab, Daratumumab, Denosumab, Detumomab, Dorlimomab, Dorlixizumab, Ecromeximab, Eculizumab, Edobacomab, Edrecolomab, Efalizumab, Efungumab, Elotuzumab, Elsilimomab, Enlimomab, Epitumomab, Epratuzumab, Erlizumab, Ertumaxomab, Etaracizumab, Exbivirumab, Fanolesomab, Faralimomab, Farletuzumab, Felvizumab, Fezakinumab, Figitumumab, Fontolizumab, Foravirumab, Fresolimumab, Galiximab, Gantenerumab, Gavilimomab, Gemtuzumab, Girentuximab, Glembatumumab, Golimumab, Gomiliximab, Ibalizumab, Irbitumomab, Igovomab, Imciromab, Infliximab, Intetumumab, Inolimomab, Inotuzumab, Ipilimumab, Iratumumab, J591, Keliximab, Labetuzumab, Lebrikizumab, Lemalesomab, Lerdelimumab, Lexatumumab, Libivirumab, Lintuzumab, Lorvotuzumab, Lucatumumab, Lumiliximab, Mapatumumab, Maslimomab, Matuzumab, Mepolizomab, Metelimumab, Milatuzumab, Minretumomab, Mitumomab, Morolimumab, Motavizumab, Muromonab, Nacolomab, Naptumomab, Natalizumab, Nebacumab, Necitutumab, Nerelimomab, Nimotuzumab, Nofetumomab, Ocrelizumab, Odulimomab, Ofatumumab, Olaratumab, Omalizumab, Oportuzumab, Oregovomab, Otelixizumab, Pagibaximab, Palivizumab, Panitumumab, Panobacumab, Pascolizumab, Pemtumomab, Pertuzumab, Pexelizumab, Pintumomab, Priliximab, Pritumumab, PRO140, Rafivirumab, Ramucirumab, Ranibizumab, Raxibacumab, Regavirumab, Resilizumab, Rilotumumab, Rituximab, Robatumumab, Rontalizumab, Rovelizumab, Ruplizumab, Satumomab, Sevirumab, Sibrotuzumab, Sifalimumab, Siltuximab, Siplizumab, Solanezumab, Sonepcizumab, Sontuzumab, Stamulumab, Sulesomab, Tacatuzumab, Tadocizumab, Talizumab, Tanezumab, Taplitumomab, Tefibazumab, Telimomab, Tenatumomab, Teplizumab, TGN1412, Ticilimumab, Tigatuzumab, TNX-650, Tocilizumab, Toralizumab, Tositumomab, Trastuzumab, Tremelimumab, Tucotuzumab, Tuvirumab, Urtoxazumab, Ustekinumab, Vapaliximab, Vedolizumab, Veltuzumab, Vepalimomab, Visilizumab, Volociximab, Votumumab, Zalutumumab, Zanolimumab, Ziralimumab, Zolimomab, and any combination of the preceding.

4. Loading Payloads into Minicells

Eubacterial minicells are capable of encapsulating and delivering several classes of biologically active compounds that have therapeutic, prophylactic, or diagnostic benefit to an animal. Types of the biologically active compounds (payloads) that can be delivered by minicells include but are not limited to small molecules (including small molecule drugs), nucleic acids, polypeptides, radioisotope, lipids, lipopolysaccharides, and any combination thereof.

Small molecules can include any number of therapeutic agents presently known and used, or can be small molecules synthesized in a library of such molecules for the purpose of screening for biological function(s).

Some embodiments relate to inducing the minicell production phenotype from an optimized eubacterial minicell-producing strain from, but not limited to, the family Enterobacteriaceae such that it may be "loaded" with small molecule(s) including but not limited to a drug, a pro-drug, or a hormone incorporated following purification of the Fc-binding minicells from the parental cells. Following production of the desired quantity of "empty" Fc-binding minicells from a given culture and condition, activation of the genetic suicide mechanism would be accomplished by exposure of the culture or cells to a known signal. Following purification, Fc-binding minicells are "loaded" with the small molecule(s) by a simple incubation with a high concentration of the small molecule at a temperature ranging from 4° C. to 65° C. Further details regarding the loading of small molecules, including many of those listed herein, are known in the art.

Small molecules include without limitation organic compounds, peptidomimetics and fusion/conjugates thereof. As used herein, the term "organic compound" refers to any carbon-based compound other than the macromolecules nucleic acids and polypeptides. In addition to carbon, organic compounds can contain calcium, chlorine, fluorine, copper, hydrogen, iron, potassium, nitrogen, oxygen, sulfur and other elements. An organic compound may be in an aromatic or aliphatic form. Non-limiting examples of organic compounds include acetones, alcohols, anilines, carbohydrates, monosaccharides, oligosaccharides, polysaccharides, amino acids, nucleosides, nucleotides, lipids, retinoids, steroids, proteoglycans, ketones, aldehydes, saturated, unsaturated and polyunsaturated fats, oils and waxes, alkenes, esters, ethers, thiols, sulfides, cyclic compounds, heterocylcic compounds, imidizoles, and phenols. An organic compound as used herein also includes nitrated organic compounds and halogenated (e.g., chlorinated) organic compounds.

Small molecules can be synthetic, naturally occurring, and purified from a natural source. Examples of small molecules include, but are not limited to, small molecule drugs, toxins, radionuclides, and small molecule imaging agents. Types of small molecule drugs include those that prevent, inhibit, stimulate, mimic, or modify a biological or biochemical process within a cell, tissue type, or organ to the benefit of an animal suffering from a disease, whether somatic, germinal, infectious, or otherwise. Examples of drugs include chemotherapeutic agents (cancer drugs), antibiotics, antivirals, antidepressants, antihistamines, anticoagulants, and any other class or subclass thereof as listed in the Physicians' Desk Reference. Small molecules also include the class of molecules collectively known as fluorophores. Minicells encapsulating fluorophores and displaying cell-specific targeting moieties can be used for in vivo imaging of cell types, tissues, organs, or tumors in an animal. Small molecule fluorophores include but are not limited to DAPI, Cybr Gold, Cybr Green, Ethidium Bromide, Alexa Flour, Texas Red, CFSE, and the like. Other types of molecular imaging agents are selected from the group including but not limited to Gadolinium, $^{64}$Cu diacetyl-bis(N$^{4}$-methylthiosemicarbazone), $^{18}$F-flourodeoxyglucose, $^{18}$F-flouride, 3'-deoxy-3'-[$^{18}$F]fluorothymidine, $^{18}$F-fluoromisonidazole, gallium, technetium-99, thallium, barium, gastrografin, iodine contrasting agents, iron oxide, green fluorescent protein, luciferase, beta-galactosidase, and any combination of the preceding.

Small molecule chemotherapeutic agents can be targeted and delivered to tissues, cells, and organs using minicells displaying targeting molecules. The term "chemotherapeutic agent" used herein refers to anti-cancer, anti-metastatic, anti-angiogenic, and other anti-proliferative agents. In some embodiments, a chemotherapeutic agent is a chemical agent intended to inhibit the proliferation of or kill cells. Examples of chemotherapeutic agent include, but are not limited to: (1) DNA damaging agents and agents that inhibit DNA synthesis such as anthracyclines (doxorubicin, daunorubicin, epirubicin), alkylating agents (bendamustine, busulfan, carboplatin, carmustine, cisplatin, chlorambucil, cyclophosphamide, dacarbazine, hexamethylmelamine, ifosphamide, lomustine, mechlorethamine, melphalan, mitotane, mytomycin, pipobroman, procarbazine, streptozocin, thiotepa, and triethylenemelamine), platinum derivatives (cisplatin, carboplatin, cis diamminedichloroplatinum), telomerase and topoisomerase inhibitors (Camptosar), (2) microtubule and tubulin binding agents including but not limited to taxanes and taxane derivatives (paclitaxel, docetaxel, BAY 59-8862), (3) anti-metabolites such as capecitabine, chlorodeoxyadenosine, cytarabine (and its activated form, ara-CMP), cytosine arabinoside, dacarbazine, floxuridine, fludarabine, 5-fluorouracil, 5-DFUR, gemcitabine, hydroxyurea, 6-mercaptopurine, methotrexate, pentostatin, trimetrexate, and 6-thioguanine (4) anti-angiogenics (thalidomide, sunitinib, lenalidomide), vascular disrupting agents (flavonoids/flavones, DMXAA, combretastatin derivatives such as CA4DP, ZD6126, AVE8062A, etc.), (5) endocrine therapy such as aromatase inhibitors (4-hydroandrostendione, exemestane, aminoglutethimide, anastrozole, letrozole), (6) anti-estrogens (Tamoxifen, Toremifene, Raloxifene, Faslodex), steroids such as dexamethasone, (7) immuno-modulators such as Toll-like receptor agonists or antagonists, (8) inhibitors to integrins, other adhesion proteins and matrix metalloproteinases), (9) histone deacetylase inhibitors, (10) inhibitors of signal transduction such as inhibitors of tyrosine kinases like imatinib (Gleevec), (11) inhibitors of heat shock proteins, (12) retinoids such as all trans retinoic acid, (13) inhibitors of growth factor receptors or the growth factors themselves, (14) anti-mitotic compounds such as navelbine, vinblastine, vincristine, vindesine, and vinorelbine, (15) anti-inflammatories such as COX inhibitors and (16) cell cycle regulators such as check point regulators and telomerase inhibitors, (17) transcription factor inhibitors, and apoptosis inducers, such as inhibitors of Bcl-2, Bcl-x and XIAP.

Nucleic acids include DNA and RNA and their structural equivalents such as RNA molecules or DNA molecules that utilize phosphorothioate backbones as opposed to the naturally occurring phosphodiester backbones. DNA molecules include episomal DNA (not located on or part of the host cell chromosome) which further include plasmid DNA, cosmid DNA, bacteriophage DNA, and bacterial artificial chromosomes (BACs), and the like. DNA molecules encode for proteins as described by the central dogma of molecular biology. Thus DNA may encode for proteins of any origin, naturally occurring or synthetic. Likewise, DNA can be engineered to contain "promoter sequences" that are recognized by host cell machinery to activate expression of the encoded proteins. Promoter sequences can be cell specific, tissue specific, or inducer specific. Inducers are exogenously applied signals that help to activate the promoters to produce the proteins. Inducers can be chemical or physical in nature. Many promoter systems are known to those skilled in the art as are the sequences that render them functional. Preferred prokaryotic expression sequences include but are not limited to the pRHA system, the pBAD system, the T7 polymerase system, the pLac system and its myriad derivatives, the pTet system, and the CI857ts system. Preferred eukaryotic promoter systems include but are not limited to the CMV promoter, the SV40 promoter system, and the BGH promoter system. Examples of RNAs include, but are not limited to, messenger RNA (mRNA), transfer RNA (tRNA), and small nuclear RNAs. Many RNAs, classified as antisense RNAs, include but are not limited to small-interfering RNAs (siRNA), short hairpin RNAs (shRNAs), and full length antisense RNAs. Micro RNAs are also included. Preferred targets of siRNA or shRNA include but are not limited to Androgen Receptor (AR), ABCB1/MDR1/PGY1 (P-glycoprotein; Pgp), CHK-1, HIF-1, Mcl-1, PDGFR, Tie-2, ABL1, ABL2, AKT2, ALK, BCL2, BCL3, BCL5, BCL6, BLC7A, BCL9, BCL10, BCL11A, BCL11B, Bcl-x, Bcr-Abl, BRAF, CCND1, CDK4, CHK-1, c-Met, c-myc, CTNNB1, DKC1, EGFR1, EGFR2, ERBB2, ERCC-1, EZH2, FES, FGFR1, FGFR2, FGFR3, FGFR-4, FLT1 (VEGFR1), FLT2, FLT3, FLT4, HER2, HER3, HRAS, IGFR, Interleukin 8 (IL-8), JAK, JAK2, KDR/Flk-1 (VEGFR-2), KIT, KRAS2, MET, MRP, mTOR, MYC, MYCL1, MYCN, NRAS, p53, PARP1, PDGFB, PDGFRA, PDGFRB, PI3KCA, PPAR, Rad51, Rad52, Rad53, RalA, REL, RET, RRM1, RRM2, STATS, survivin, telomerase, TEP1, TERC, TERT, VEGF-A, VEGF-B, VEGF-C, VEGF-D, VEGF-E, Wnt-1, XIAP, and any against any nucleotide sequence from the list of genes above that contains somatic or germline mutations compared to the wild type gene sequence.

Proteins are comprised of polypeptides and are encoded by DNA. Proteins can be biologically functional, such as enzymes, toxins, or signaling proteins. Proteins can be structural, such as is the case for actin and the like. Proteins can provide localization signals by being fluorescent or bioluminescent. Proteins can serve as immunogens or serve other therapeutic purposes (such as supplying or restoring enzyme in a target cell, tissue, organ, or animal). Proteins can aid in the post-endocytosis intracellular transfer of other payload types. For example, proteins such as listeriolysin O from *Listeria monocytogenes* can be employed to facilitate the transfer of the minicell payload(s) from the endocytotic compartment(s) of a target cell to the cytosol of a target cell. Proteins can also be pro-drug converting enzymes. Preferred proteins include listeriolysin O, green fluorescent protein, red fluorescent protein and any member of the luciferase family of proteins. Recombinantly expressed/produced therapeutic polypeptides to be delivered by targeted minicells include but are not limited to protein toxins, cholesterol-dependent cytolysins, functional enzymes, activated caspases, pro-caspases, cytokines, chemokines, cell-penetrating peptides, and any combination of the proceeding. Recombinant expression of a therapeutic polypeptide(s) can be the result of expression from any of the various episomal recombinant prokaryotic expression vectors known in the art including but not limited to plasmids, cosmids, phagemids, and bacterial artificial chromosomes (BACs), and any combination of the preceding. In similar fashion, recombinant expression can be achieved by a chromosomally located prokaryotic expression cassette present in one or more copies of the minicell-producing parent cell chromosome. The delivery of protein toxins using the targeted minicells disclosed herein is a particularly attractive approach in applications where selective elimination of cells in vivo is desirable. Protein toxins include but are not limited to gelonin, diphtheria toxin fragment A, diphtheria toxin fragment A/B, tetanus toxin, *E. coli* heat labile toxin (LTI and/or LTII), cholera toxin, *C. perfringes* iota toxin, *Pseudomonas* exotoxin A, shiga toxin, anthrax toxin, MTX (*B. sphaericus* mosquilicidal toxin), perfringolysin O, streptolysin, barley toxin, mellitin, anthrax toxins LF and EF, adenylate cyclase toxin, botulinolysin B, botulinolysin E3, botulinolysin C, botulinum toxin A, cholera toxin, clostridium toxins A, B, and alpha, ricin, shiga A toxin, shiga-like A toxin, cholera A toxin, pertussis S1 toxin, *E. coli* heat labile toxin (LTB), pH stable variants of listeriolysin O (pH-independent; amino acid substitution L461T), thermostable variants of listeriolysin O (amino acid substitutions E247M, D320K), pH and thermostable variants of listeriolysin O (amino acid substitutions E247M, D320K, and L461T), streptolysin O, streptolysin O c, streptolysin O e, sphaericolysin, anthrolysin O, cereolysin, thuringiensilysin O, weihenstephanensilysin, alveolysin, brevilysin, butyriculysin, tetanolysin O, novyilysin, lectinolysin, pneumolysin, mitilysin, pseudopneumolysin, suilysin, intermedilysin, ivanolysin, seeligeriolysin O, vaginolysin, and pyolysin. Therapeutic polypeptides may be localized to different sub-cellular compartments of the minicell at the discretion of the artisan. When targeted minicells disclosed herein are derived from a Gram-negative parental minicell-producing strain, recombinantly expressed therapeutic polypeptides produced therefrom can be localized to the cytosol, the inner leaflet of the inner membrane, the outer leaflet of the inner membrane, the periplasm, the inner leaflet of the outer membrane, the outer membrane of minicells, and any combination of the proceeding. When targeted minicells disclosed herein are derived from a Gram-positive parental minicell-producing strain, recombinantly expressed therapeutic polypeptides produced therefrom can be localized to the cytosol, the cell wall, the inner leaflet of the membrane, the membrane of minicells, and any combination of the proceeding.

Any and all of the payload types described herein can be used in combination or singular at the discretion of the user. One skilled in the art will appreciate and recognize which combinations are to be used for which therapeutic purpose(s) (e.g., the combination of a small molecule cytotoxic cancer drug and an si/shRNA against a gene product conferring resistance to the drug).

5. Pharmaceutical Compositions

The present application also relates to compositions, including but not limited to pharmaceutical compositions. The term "composition" used herein refers to a mixture comprising at least one carrier, preferably a physiologically acceptable carrier, and one or more minicell compositions. The term "carrier" used herein refers to a chemical compound that does not inhibit or prevent the incorporation of the biologically active peptide(s) into cells or tissues. A carrier typically is an inert substance that allows an active ingredient to be formulated or compounded into a suitable dosage form (e.g., a pill, a capsule, a gel, a film, a tablet, a microparticle (e.g., a microsphere), a solution; an ointment; a paste, an aerosol, a droplet, a colloid or an emulsion etc.). A "physiologically acceptable carrier" is a carrier suitable for use under physiological conditions that does not abrogate (reduce, inhibit, or prevent) the biological activity and properties of the compound. For example, dimethyl sulfoxide (DMSO) is a carrier as it facilitates the uptake of many organic compounds into the cells or tissues of an organism. Preferably, the carrier is a physiologically acceptable carrier, preferably a pharmaceutically or veterinarily acceptable carrier, in which the minicell composition is disposed.

A "pharmaceutical composition" refers to a composition wherein the carrier is a pharmaceutically acceptable carrier, while a "veterinary composition" is one wherein the carrier is a veterinarily acceptable carrier. The term "pharmaceutically acceptable carrier" or "veterinarily acceptable carrier" used herein includes any medium or material that is not biologically or otherwise undesirable, i.e., the carrier may be administered to an organism along with a minicell composition without causing any undesirable biological effects or interacting in a deleterious manner with the complex or any of its components or the organism. Examples of pharmaceutically acceptable reagents are provided in The United States Pharmacopeia, The National Formulary, United States Pharmacopeial Convention, Inc., Rockville, Md. 1990, hereby incorporated by reference herein into the present application. The terms "therapeutically effective amount" and "pharmaceutically effective amount" refer to an amount sufficient to induce or effectuate a measurable response in the target cell, tissue, or body of an organism. What constitutes a therapeutically effective amount will depend on a variety of factors, which the knowledgeable practitioner will take into account in arriving at the desired dosage regimen.

The compositions can also comprise other chemical components, such as diluents and excipients. A "diluent" is a chemical compound diluted in a solvent, preferably an aqueous solvent, that facilitates dissolution of the composition in the solvent, and it may also serve to stabilize the biologically active form of the composition or one or more of its components. Salts dissolved in buffered solutions are utilized as diluents in the art. For example, preferred diluents are buffered solutions containing one or more different salts. An unlimiting example of preferred buffered solution is phosphate buffered saline (particularly in conjunction with compositions intended for pharmaceutical administration), as it mimics the salt conditions of human blood. Since buffer salts can control the pH of a solution at low concentrations, a buffered diluent rarely modifies the biological activity of a given compound or pharmaceutical composition.

An “excipient” is any more or less inert substance that can be added to a composition in order to confer a suitable property, for example, a suitable consistency or to produce a drug formulation. Suitable excipients and carriers include, in particular, fillers such as sugars, including lactose, sucrose, mannitol, or sorbitol cellulose preparations such as, for example, maize starch, wheat starch, rice starch, agar, pectin, xanthan gum, guar gum, locust bean gum, hyaluronic acid, casein potato starch, gelatin, gum tragacanth, methyl cellulose, hydroxypropylmethyl-cellulose, polyacrylate, sodium carboxymethylcellulose, and/or polyvinylpyrrolidone (PVP). If desired, disintegrating agents can also be included, such as cross-linked polyvinyl pyrrolidone, agar, or alginic acid or a salt thereof such as sodium alginate. Other suitable excipients and carriers include hydrogels, gellable hydrocolloids, and chitosan. Chitosan microspheres and microcapsules can be used as carriers. See e.g., WO 98/52547 (which describes microsphere formulations for targeting compounds to the stomach, the formulations comprising an inner core (optionally including a gelled hydrocolloid) containing one or more active ingredients, a membrane comprised of a water insoluble polymer (e.g., ethylcellulose) to control the release rate of the active ingredient(s), and an outer layer comprised of a bioadhesive cationic polymer, for example, a cationic polysaccharide, a cationic protein, and/or a synthetic cationic polymer; U.S. Pat. No. 4,895,724. Typically, chitosan is cross-linked using a suitable agent, for example, glutaraldehyde, glyoxal, epichlorohydrin, and succinaldehyde. Compositions employing chitosan as a carrier can be formulated into a variety of dosage forms, including pills, tablets, microparticles, and microspheres, including those providing for controlled release of the active ingredient(s). Other suitable bioadhesive cationic polymers include acidic gelatin, polygalactosamine, polyamino acids such as polylysine, polyhistidine, polyornithine, polyquaternary compounds, prolamine, polyimine, diethylaminoethyldextran (DEAE), DEAE-imine, DEAE-methacrylate, DEAE-acrylamide, DEAE-dextran, DEAE-cellulose, poly-p-aminostyrene, polyoxethane, copolymethacrylates, polyamidoamines, cationic starches, polyvinylpyridine, and polythiodiethylaminomethylethylene.

The compositions can be formulated in any suitable manner. Minicell compositions may be uniformly (homogeneously) or non-uniformly (heterogeneously) dispersed in the carrier. Suitable formulations include dry and liquid formulations. Dry formulations include freeze dried and lyophilized powders, which are particularly well suited for aerosol delivery to the sinuses or lung, or for long term storage followed by reconstitution in a suitable diluent prior to administration. Other preferred dry formulations include those wherein a composition disclosed herein is compressed into tablet or pill form suitable for oral administration or compounded into a sustained release formulation. When the composition is intended for oral administration to be delivered to epithelium in the intestines, it is preferred that the formulation be encapsulated with an enteric coating to protect the formulation and prevent premature release of the minicell compositions included therein. As those in the art will appreciate, the compositions disclosed herein can be placed into any suitable dosage form. Pills and tablets represent some of such dosage forms. The compositions can also be encapsulated into any suitable capsule or other coating material, for example, by compression, dipping, pan coating, spray drying, etc. Suitable capsules include those made from gelatin and starch. In turn, such capsules can be coated with one or more additional materials, for example, and enteric coating, if desired. Liquid formulations include aqueous formulations, gels, and emulsions.

Some preferred embodiments provide compositions that comprise a bioadhesive, preferably a mucoadhesive, coating. A “bioadhesive coating” is a coating that allows a substance (e.g., a minicell composition) to adhere to a biological surface or substance better than occurs absent the coating. A “mucoadhesive coating” is a preferred bioadhesive coating that allows a substance, for example, a composition to adhere better to mucosa occurs absent the coating. For example, minicells can be coated with a mucoadhesive. The coated particles can then be assembled into a dosage form suitable for delivery to an organism. Preferably, and depending upon the location where the cell surface transport moiety to be targeted is expressed, the dosage form is then coated with another coating to protect the formulation until it reaches the desired location, where the mucoadhesive enables the formulation to be retained while the composition interacts with the target cell surface transport moiety.

Compositions disclosed herein can be administered to any organism, preferably an animal, preferably a mammal, bird, fish, insect, or arachnid. Preferred mammals include bovine, canine, equine, feline, ovine, and porcine animals, and non-human primates. Humans are particularly preferred. Multiple techniques of administering or delivering a compound exist in the art including, but not limited to, oral, rectal (e.g. an enema or suppository) aerosol (e.g., for nasal or pulmonary delivery), parenteral, and topical administration. Preferably, sufficient quantities of the biologically active peptide are delivered to achieve the intended effect. The particular amount of composition to be delivered will depend on many factors, including the effect to be achieved, the type of organism to which the composition is delivered, delivery route, dosage regimen, and the age, health, and sex of the organism. As such, the particular dosage of a composition incorporated into a given formulation is left to the ordinarily skilled artisan's discretion.

Those skilled in the art will appreciate that when the compositions disclosed herein are administered as agents to achieve a particular desired biological result, which may include a therapeutic, diagnostic, or protective effect(s) (including vaccination), it may be possible to combine the minicell composition with a suitable pharmaceutical carrier. The choice of pharmaceutical carrier and the preparation of the minicells as a therapeutic or protective agent will depend on the intended use and mode of administration. Suitable formulations and methods of administration of therapeutic agents include those for oral, pulmonary, nasal, buccal, ocular, dermal, rectal, intravenous, or vaginal delivery.

Depending on the mode of delivery employed, the context-dependent functional entity can be delivered in a variety of pharmaceutically acceptable forms. For example, the context-dependent functional entity can be delivered in the form of a solid, solution, emulsion, dispersion, and the like, incorporated into a pill, capsule, tablet, suppository, aerosol, droplet, or spray. Pills, tablets, suppositories, aerosols, powders, droplets, and sprays may have complex, multilayer structures and have a large range of sizes. Aerosols, powders, droplets, and sprays may range from small (1 micron) to large (200 micron) in size.

Pharmaceutical compositions disclosed herein can be used in the form of a solid, a lyophilized powder, a solution, an emulsion, a dispersion, and the like, wherein the resulting composition contains one or more of the compounds disclosed herein, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Examples of a stabilizing dry agent include triulose, preferably at concentrations of 0.1% or greater (See, e.g., U.S. Pat. No. 5,314,695). The active compound is included in the pharmaceutical composition in an amount sufficient to produce the desired effect upon the process or condition of diseases.

6. Therapeutic Indications

The present application relates to diagnostic imaging and therapy of cancer(s) including but not limited to solid tumors, metastatic tumors, and liquid tumors. Solid and metastatic tumors include those of epithelial origin and include but are not limited to breast, lung, pancreatic, prostatic, testicular, ovarian, gastric, intestinal, mouth, tongue, pharynx, hepatic, anal, rectal, colonic, esophageal, urinary bladder, gall bladder, skin, uterine, vaginal, penal, and renal cancers. Other solid cancer types that may be treated with the targeted minicells disclosed herein include but are not limited to adenocarcinomas, sarcomas, fibrosarcomas, and cancers of the eye, brain, and bone. Liquid tumors that can be treated by the targeted minicells disclosed herein include but are not limited to non-Hodgkin's lymphoma, myeloma, Hodgkin's lymphoma, acute lymphocytic leukemia, chronic lymphocytic leukemia, acute myeloid leukemia, chronic myeloid leukemia, and other leukemias. The targeted minicells disclosed herein are targeted to eukaryotic cancer cell-specific surface antigens that include but are not limited to α3β1 integrin, α4β1 integrin, α5β1 integrin, $\alpha_v\beta3$integrin, $\alpha_v\beta1$integrin, β1 integrin, 5T4, CAIX, CD4, CD13, CD19, CD20, CD22, CD25, CD30, CD31, CD33, CD34, CD40, CD44v6, CD45, CD51, CD52, CD54, CD56, CD64, CD70, CD74, CD79, CD105, CD117, CD123, CD133, CD138, CD144, CD146, CD152, CD174, CD205, CD227, CD326, CD340, Cripto, ED-B, GD2, TMEFF2, VEGFR1, VEGFR2, FGFR, PDGFR, ANGPT1, TIE1, TIE2, NRP1, TEK (CD202B), TGFβR, Death Receptor 5 (Trail-R2), DLL4, EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6, FAP, GPNMB, ICAMs, VCAMs, PSMA, HER-2/neu, IL-13R alpha 2, MUC-1, MUC16, EGFR1 (HER-1), EGFR2 (HER-2/neu), EGFR3 (HER-3), IGF-1R, IGF-2R, c-Met (HGFR), Mesothelin, PDGFR, EDGR, TAG-72, transferrin receptor, EpCAM, CTLA-4, PSMA, tenascin C, alpha-fetoprotein, vimentin, C242 antigen, TRAIL-R1, TRAIL-R2, CA-125, GPNMB, CA-IX, GD3 ganglioside, RANKL, BAFF, IL-6R, TAG-72, HAMA, and CD166.

The present application also relates to diagnostic imaging and therapy of conditions and diseases in an animal caused, at least in part, by aberrant vasculogenesis or angiogenesis. Such conditions and diseases include but are not limited to cancer, inflammatory conditions, including, but not limited to, rheumatoid arthritis, psoriasis and inflammatory bowel disease, metabolic disorders, including diabetic retinopathy and diabetic nephropathy and ocular conditions, including, but not limited to, neovascular (wet) AMD and macular edema. A role for vasculogenesis or angiogenesis has been established in each of these diseases or conditions as a result of genetic, mechanistic, histopathological, preclinical and/or clinical studies. For example, tumors cannot grow beyond 1 to 2 mm in diameter in the absence of neovascularization. The important role of neovascularization in cancer and certain ocular diseases has been validated clinically via the approval of several anti-angiogenic therapeutics, including bevacizumab for cancer and ranibizumab for AMD. In addition, aberrant vascular remodeling and angiogenesis play an important role in several stages of inflammation. The first acute phase of inflammation involves functional changes in vasculature, such as dilation, increased permeability and endothelial cell activation. The second subacute phase of inflammation involves capillary and venule remodeling, with extensive endothelial mitotic activity. In the chronic setting, neovascularization and/or expansion of microvasculature is observed, including in rheumatoid arthritis, psoriasis, diabetic retinopathy and diabetic nephropathy. All of these vascular changes promote and sustain inflammatory responses by enhancing infiltration and/or release of nutrients, cytokines, chemokines, proteases and inflammatory leukocytes. Thus, targeted minicells described herein can be used as anti-angiogenic therapeutics by incorporating antibodies that recognize cell surface antigens of cell types contributing to the misregulation of angiogenesis in a given disease setting. By way of non-limiting example, endothelial cells, circulating endothelial cells, angioblasts, hemangioblasts, pericytes, myofibroblasts, and endothelial progenitor cells are all targets for the prevention of vasculogenesis or angiogenesis. Endothelial cells and their progenitors, in particular, are critical vasculogenic and angiogenic cell types that can be targeted using anti-angiogenic minicells. Many endothelial cells overexpress, preferentially express, and/or differentially express distinct cell surface proteins at sites of vasculogenesis and angiogenesis. Additionally, circulating endothelial cells and circulating endothelial progenitor cells (present in the blood and lymph) are targets for anti-angiogenic minicells. Circulating endothelial cells and endothelial progenitors also express cell surface antigens that distinguish them from other cell types, serving as a basis for the preferential targeting of anti-angiogenic minicells. Collectively, these cell surface molecules are termed angiogenesis-specific antigens. Many antibodies that specifically recognize angiogenesis-specific antigens, and nucleic acid sequences of the variable regions thereof, are already known in the art. Any of these antibodies can be used in exogenous fashion with the present application. Many angiogenesis-specific antigens have been identified to which no reported antibodies exist. However, methods to produce antibodies to these antigens are well known in the art and any and all antibodies to angiogenesis-specific antigens, or any other angiogenesis-related surface antigen, can be incorporated into the composition as described. Angiogenesis-specific antigens of choice include, but are not limited to α4β1 integrin, α5β1 integrin, $\alpha_v\beta3$integrin, $\alpha_v\beta1$integrin, β1 integrin, CD13, CD31, CD34, CD45, CD54, CD105, CD117, CD133, CD144, CD146, VEGFR1, VEGFR2, FGFR, PDGFR, ANGPT1, TIE1, TIE2, NRP1, TEK (CD202B), TGFβR, DLL4, EPHA1, EPHA2, EPHA3, EPHA4, EPHA5, EPHA6, EPHA7, EPHA8, EPHA9, EPHA10 EPHB1, EPHB2, EPHB3, EPHB4, EPHB5, EPHB6, ICAMs, VCAMs, and PSMA.

7. Minicell Preparations

Some embodiments relate to creating an optimized strain and preparing Fc-binding minicells from, but not limited to, the family Enterobacteriaceae that contains or produces any subclass of therapeutic RNA, including but not limited to antisense RNA (siRNA and shRNA as an example), ribozymes, and miRNA such that the resulting minicells comprise an enriched amount of the therapeutic RNA molecules by way of encapsulation after expression of the therapeutic RNA molecule by the parental cell or the minicells themselves. Following production of the desired quantity of minicells from the culture and condition, activation of the genetic suicide mechanism would be accomplished by exposure of the culture or cells to a known signal. Alternatively, loading of any of the above RNA molecules into Fc-binding minicells can also be accomplished by incubating minicells with high concentrations of exogenous RNA molecules (as opposed to, or in combination with, expression of the same or different therapeutic RNA by the minicell-producing parental strain such that the resulting minicells comprise the therapeutic RNA).

Some embodiments relate to creating an optimized strain and preparing Fc-binding minicells from, but not limited to, the family Enterobacteriaceae that contain or produce a protein molecule, such that the resulting minicells contain the protein molecule by way of encapsulation after expression of the protein molecule by the parental cell or by the minicells themselves. Following production of the desired quantity of minicells from a given culture and condition, activation of the genetic suicide mechanism would be accomplished by exposure of the culture or cells to a known signal.

Some embodiments relate to creating an optimized strain and preparing Fc-binding minicells from, but not limited to, the family Enterobacteriaceae that contains or produces DNA molecules (e.g. a eukaryotic expression plasmid) encoding for a therapeutic or deleterious gene or gene product, any subclass of RNA, and/or proteins, such that the resulting minicells contain the combination of molecules by way of encapsulation. Following production of the desired quantity of minicells from a given culture and condition, activation of the genetic suicide mechanism would be accomplished by exposure of the culture or cells to a known signal.

Some embodiments relate to creating an optimized strain and preparing Fc-binding minicells from, but not limited to, the family Enterobacteriaceae such that the minicells may be "loaded" with small molecules that comprise but are not limited to a drug, a pro-drug, or a hormone following purification. Following production of the desired quantity of minicells from a given culture and condition, activation of the genetic suicide mechanism would be accomplished by exposure of the culture or cells to a known signal. Following purification, minicells would be "loaded" with the small molecule(s) by incubation with a high concentration of the small molecule at a temperature ranging from 0° C. to 65° C. This procedure is performed with minicells with "empty" Fc-binding minicells such that the small molecule is the only exogenous therapeutic molecule in the resulting targeted minicells. This procedure may also be performed with minicells that further comprise any combination of therapeutic DNA, therapeutic RNA, or therapeutic protein, such that the end composition contains the small molecule and any combination of the therapeutic DNA, therapeutic RNA, and/or therapeutic protein. The Fc-binding minicells are the made targeting competent by the addition of antibodies and/or Fc-fusion/conjugated targeting molecules on their surfaces.

Some embodiments relate to creating an optimized strain and preparing Fc-binding minicells from, but not limited to, the family Bacillaceae that contains or produces a DNA molecule encoding for a therapeutic or deleterious gene or gene product, such that the resulting minicell contains the DNA molecule by way of encapsulation. Following production of the desired quantity of minicells from a given culture and condition, activation of the genetic suicide mechanism would be accomplished by exposure of the culture or cells to a known signal.

Some embodiments relate to creating an optimized strain and preparing Fc-binding minicells from, but not limited to, the family Bacillaceae that contains or produces any subclass of therapeutic RNA, including but not limited to antisense RNA (siRNA and shRNA as an example), ribozymes, and miRNA such that the resulting minicells comprise an enriched amount of the therapeutic RNA molecules by way of encapsulation after expression of the therapeutic RNA molecule by the parental cell or the minicells themselves. Following production of the desired quantity of minicells from the culture and condition, activation of the genetic suicide mechanism would be accomplished by exposure of the culture or cells to a known signal. Alternatively, loading of any of the above RNA molecules into Fc-binding minicells can also be accomplished by incubating minicells with high concentrations of exogenous RNA molecules (as opposed to, or in combination with, expression of the same or different therapeutic RNA by the minicell-producing parental strain such that the resulting minicells comprise the therapeutic RNA).

Some embodiments relate to creating an optimized strain and preparing Fc-binding minicells from, but not limited to, the family Bacillaceae that contains or produces a protein molecule, such that the resulting minicell contains the protein molecule by way of encapsulation after expression of the protein molecule by the parental cell or by the minicell itself. Following production of the desired quantity of minicells from a given culture and condition, activation of the genetic suicide mechanism would be accomplished by exposure of the culture or cells to a known signal.

Some embodiments relate to creating an optimized strain and preparing Fc-binding minicells from, but not limited to, the family Bacillaceae that contains or produces a predetermined and deliberate combination of DNA molecules encoding for a therapeutic or deleterious gene or gene product, any subclass of RNA, and/or proteins, such that the resulting minicell contains the combination of molecules by way of encapsulation. Following production of the desired quantity of minicells from a given culture and condition, activation of the genetic suicide mechanism would be accomplished by exposure of the culture or cells to a known signal. The signal would be applied in each step of the purification process to ensure maximal killing of viable cells in the final preparation.

Some embodiments relate to creating an optimized strain and preparing Fc-binding minicells from, but not limited to, the family Bacillaceae such that the minicells may be "loaded" with small molecules that comprise but are not limited to a drug, a pro-drug, or a hormone following purification. Following production of the desired quantity of minicells from a given culture and condition, activation of the genetic suicide mechanism would be accomplished by exposure of the culture or cells to a known signal. Following purification, minicells would be "loaded" with the small molecule(s) by incubation with a high concentration of the small molecule at a temperature ranging from 0 to 65° C. This procedure is performed with minicells with "empty" Fc-binding minicells such that the small molecule is the only exogenous therapeutic molecule species in the resulting targeted minicells. This procedure may also be performed with minicells that further comprise any combination of therapeutic DNA, therapeutic RNA, or therapeutic protein, such that the end composition contains the small molecule and any combination of the therapeutic DNA, therapeutic RNA, and/or therapeutic protein. The Fc-binding minicells are the made targeting competent by the addition of antibodies and/or Fc-fusion/conjugated targeting molecules on their surfaces.

In some embodiments, the level of minicell producing parental cell contamination is less than 1 in $10^7$ targeted therapeutic minicells.

In some embodiments, the level of minicell producing parental cell contamination is less than 1 in $10^8$ targeted therapeutic minicells.

In some embodiments, the level of minicell producing parental cell contamination is less than 1 in $10^9$ targeted therapeutic minicells.

In some embodiments, the level of minicell producing parental cell contamination is less than 1 in $10^{10}$ targeted therapeutic minicells.

In some embodiments, the level of minicell producing parental cell contamination is less than 1 in $10^{11}$ targeted therapeutic minicells.

In some embodiments, the level of minicell producing parental cell contamination is less than 1 in $10^{12}$ targeted therapeutic minicells.

In some embodiments, the level of minicell producing parental cell contamination is less than 1 in $10^{13}$ targeted therapeutic minicells.

In some embodiments, the level of minicell producing parental cell contamination is less than 1 in $10^{14}$ targeted therapeutic minicells.

In some embodiments, the level of minicell producing parental cell contamination is less than 1 in $10^{15}$ targeted therapeutic minicells.

In some embodiments, the level of minicell producing parental cell contamination is less than 1 in $10^{16}$ targeted therapeutic minicells.

Unless defined otherwise, all technical and scientific terms used herein have the same meaning as commonly understood by one of ordinary skill in the art. Although the present application has been described with reference to embodiments and examples, it should be understood that various modifications can be made without departing from the spirit of the invention. All references cited herein are expressly incorporated herein by reference in their entirety.

Embodiments of the present application are disclosed in further detail in the following examples, which are not in any way intended to limit the scope of the present application.

EXAMPLES

Example 1

Expression and display of the Fc binding region of Protein A or Protein G on the surface of minicells demonstrated by enzyme linked immunoabsorbent assay (ELISA). Minicell-producing *E. coli* strain VAX12B4 was transformed with either (i) the L-rhamnose inducible expression plasmid pVX-119 (codes for Lpp-OmpAΩProtein A; SEQ ID NO:1), (ii) the L-rhamnose inducible expression plasmid pVX-120 (codes for Lpp-OmpAΩProtein G; SEQ ID NO:2) or (iii) with an empty vector control plasmid, to create minicell-producing strains VAX13B7 (Protein A), VAX13C4 (Protein G), and VAX12C4 (vector control), respectively. Each of VAX13B7, VAX13C4, and VAX12C4 were grown overnight in 20 mL of Luria-Bertani (LB) broth containing 0.2% glucose, 10 mg/mL diaminopimelic acid (DAP), 11 mg/mL lysine and 50 mg/mL Kanamycin. The following day, each strain was independently subcultured by a 1/100 dilution of the overnight culture into 700 mL of fresh LB broth containing DAP, lysine and kanamycin, as above. Cultures were grown to an optical density (O.D.$_{600}$) of 0.1 at which time L-rhamnose was added to a final concentration of 10 micromolar to induce fusion protein expression. When the cultures reached an O.D.$_{600}$ of 1.0, 20 micromolar Isopropyl β-D-1-thiogalactopyranoside (IPTG) was added to induce minicell formation. Eight hours post L-rhamnose induction, the cultures were transferred to 42° C. and incubated overnight to induce parental cell suicide. Minicells were then purified from the culture by sucrose density fractionation, and analyzed for surface display of either Protein A or Protein G by ELISA. ELISAs were performed by incubating 1e07 minicells derived from VAX13B7, VAX13C4, or VAX12C4 in sodium bicarbonate buffer (pH 9.5) in a 96-well polystyrene plate overnight to allow minicells to bind to the plate. The following day, plate wells were washed three times each with phosphate buffered saline, pH 7.4 (PBS) containing 0.05% Tween-20, and then blocked using PBS containing 1% gelatin for 1 hour at room temperature. Wells were then washed three times each with PBS containing 0.05% Tween-20 and then incubated with an HRP-conjugated chicken IgY antibody against either Protein A or Protein G for 1 hour at room temperature. Following incubation, the plates were washed five times each with PBS containing 0.5% Tween-20, and then TMB was added to each well. Reactions were stopped before the standard (recombinant Protein A/G) signal was saturated, by the addition of 1M sulfuric acid and the plates were then analyzed on a SpectraMax M3 plate reader (Molecular Devices, Inc.). The level of surface fusion protein display was determined by comparing the experimental ELISA signal to a standard curve created by titration of recombinant Protein A/G (Pierce, Inc.) and shown in FIG. 2.

Figure 2:
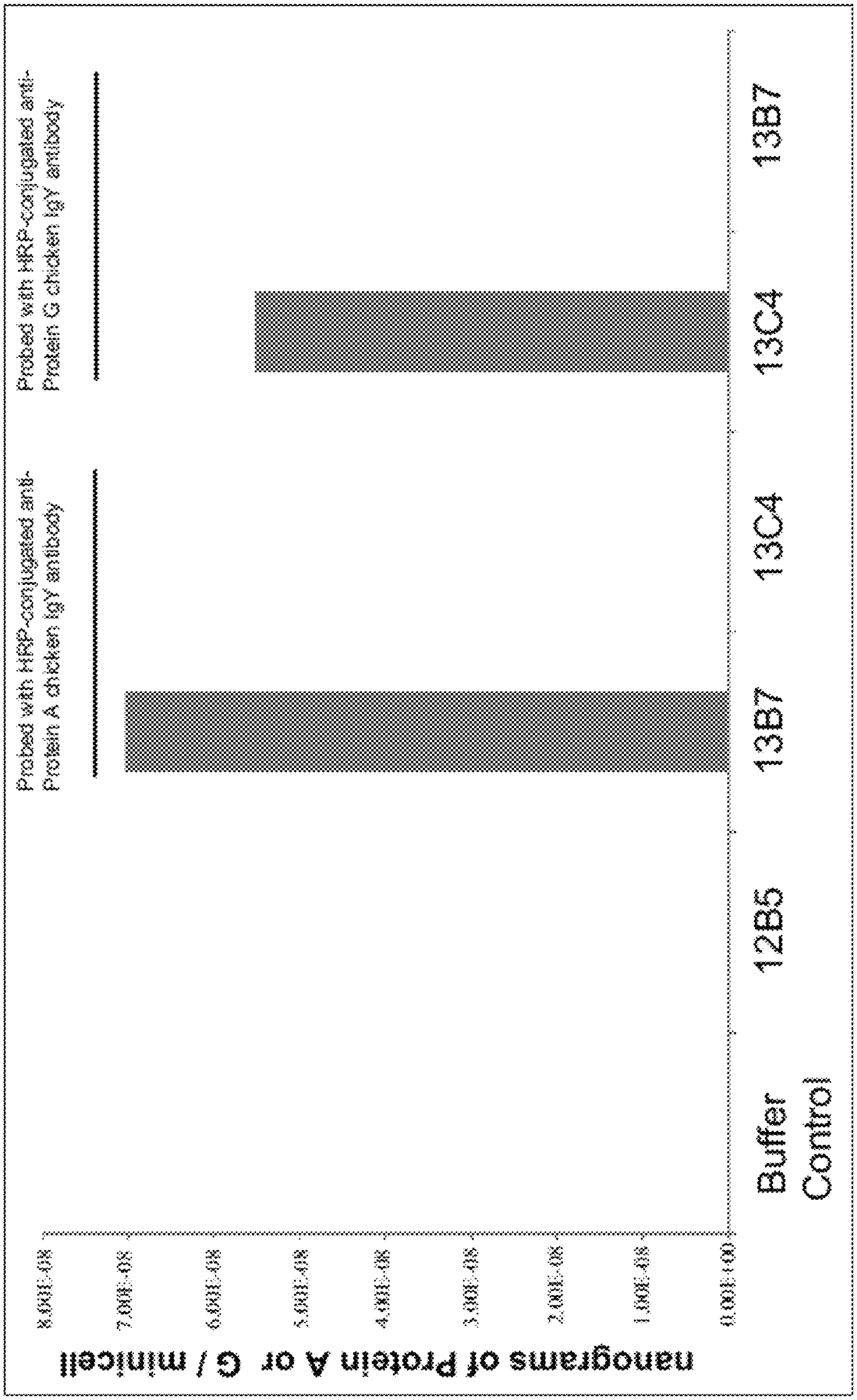
FIG. 2 is a graph showing the level of minicell surface expression and display of the Fc-binding region of either Protein A or Protein G measured by ELISA.

As shown in FIG. 2, protein A-displaying minicells were only detected when an HRP-conjugated anti-Protein A chicken IgY secondary antibody was used. Protein G-displaying minicells were only detected when an HRP-conjugated anti-Protein G chicken IgY secondary antibody was used. These results confirmed the expression, identity and minicell surface display of the fusion proteins.

Example 2

Figure 3:
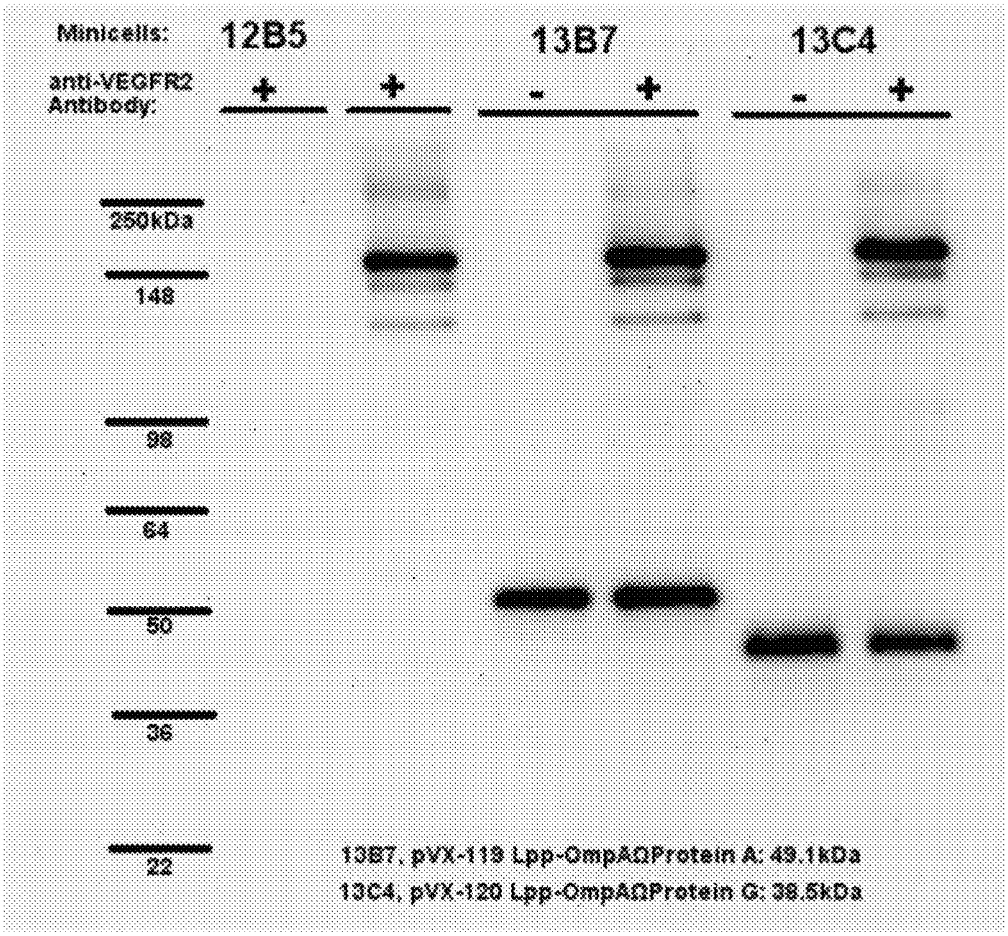
FIG. 3 is a Western Blot showing binding and display of VEGFR2 antibody to the surface of minciells expressing and displaying the Fc binding portion of Protein A or Protein G.

Binding and display of VEGFR2 antibody by miniciells expressing the Fc binding portion of Protein A or Protein G. Minicells (1e09) purified from strain VAX13B7 (Protein A-displaying), VAX13C4 (Protein G-displaying), and VAX12B5 (negative control) were incubated with 1 microgram each without (−) or with (+) a mouse monoclonal IgG antibody against human VEGFR2 for 1 hour at room temperature to allow antibodies to bind to the minicells. After incubation, minicells were washed three times each with 1 mL of PBS (pH 7.4) to remove any unbound antibody. Minicells (1e08) were then analyzed by Western blot using an HRP-conjugated rabbit anti-mouse polyclonal antibody as the secondary antibody. The Western Blot is shown in FIG. 3. Specific binding of the secondary antibody was visualized using an Amersham ECL Detection Kit (GE Healthcare). Mouse anti-VEGFR2 antibody (100 ng) was loaded as a positive control (lane after 12B5).

FIG. 3 shows that the Fc region of the HRP-conjugated rabbit anti-mouse secondary antibody was bound by the Protein A and Protein G fusion proteins in the 13B7 and 13C4 minicells (49.1 kDa and 38.5 kDa, respectively), independent of the VEGFR2 antibody. In addition, the Fab region of the secondary antibody binds to and detects the intact VEGFR2 antibody (~150 kDa) bound to the 13B7 and 13C4 minicells.

Example 3

Figure 4:
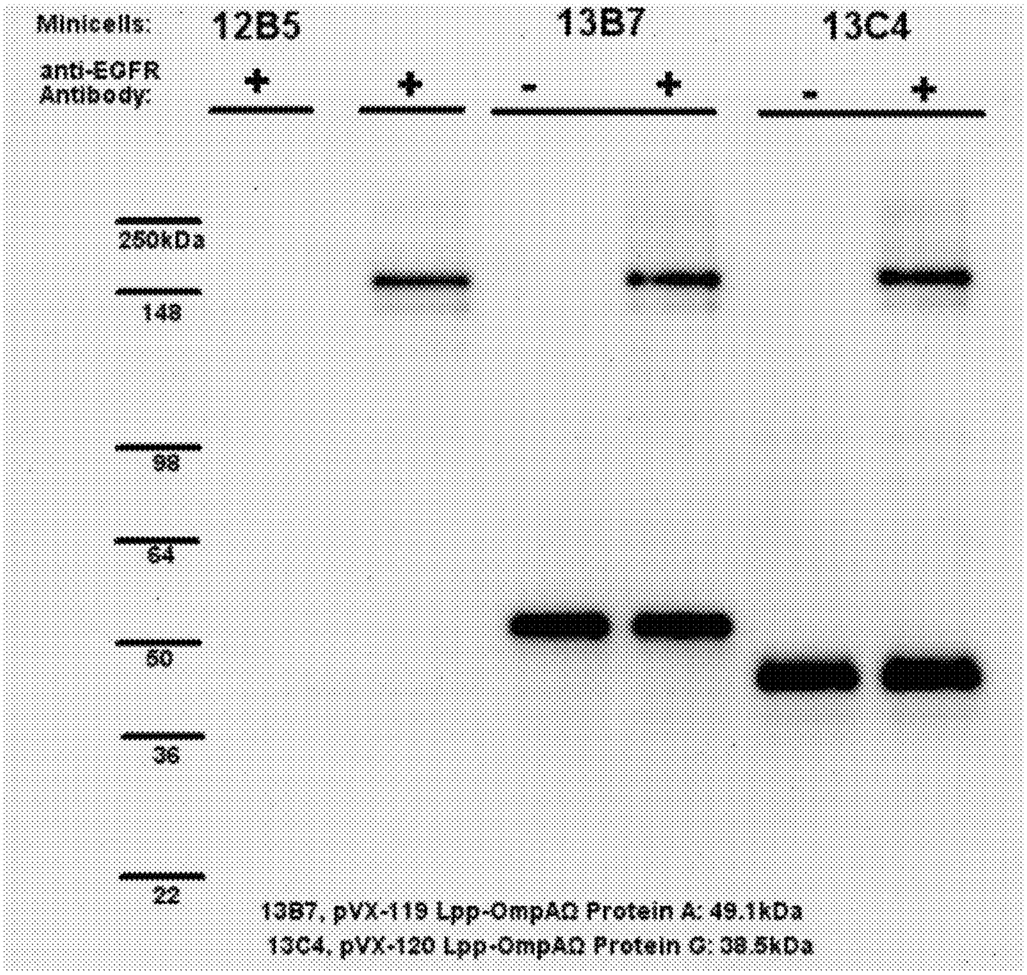
FIG. 4 is a Western Blot showing binding and display of EGFR1 antibody to the surface of minciells expressing and displaying the Fc binding portion of Protein A or Protein G.

Binding and display of EGFR1 antibody by miniciells expressing the Fc binding portion of Protein A or Protein G. Minicells (1e09) purified from strain VAX13B7 (Protein A-displaying), VAX13C4 (Protein G-displaying), and VAX12B5 (negative control) were incubated with 1 microgram each without (−) or with (+) a mouse monoclonal IgG antibody against human EGFR1 (mAb528) for 1 hour at room temperature to allow antibodies to bind to the minicells. After incubation, minicells were washed three times each with 1 mL of PBS (pH 7.4) to remove any unbound antibody. Minicells (1e08) were then analyzed by Western blot using an HRP-conjugated rabbit anti-mouse polyclonal antibody as the secondary antibody. The Western Blot is shown in FIG. 4. Specific binding of the secondary antibody was visualized using an Amersham ECL Detection Kit (GE Healthcare). Mouse anti-EGFR antibody (100 ng) was loaded as a positive control (lane after 12B5).

As shown in FIG. 4, the Fc region of the HRP-conjugated rabbit anti-mouse secondary antibody was bound by the Protein A and Protein G fusion proteins in the 13B7 and 13C4 minicells (49.1 kDa and 38.5 kDa, respectively), independent of the EGFR1 antibody. In addition, the Fab region of the secondary antibody binds to and detects the intact EGFR1 antibody (~150 kDa) bound to the 13B7 and 13C4 minicells.

Example 4

Minicells binding and displaying the anti-human EGFR1 antibody mAb528 are selectively targeted to EGFR1-expressing human non-small cell lung carcinoma cell line H460 in vitro. Minicells expressing and displaying Lpp-OmpA-Protein G (13C4) and the appropriate Lpp-OmpA-Protein G deficient minicell control (12B4) were stained with the membrane-specific fluorescent imaging agent FM-143 for 1 hour and then washed 3 times each in an equal volume of 1× PBS. Following staining, 13C4 minicells (expressing the Lpp-OmpA-Protein G fusion) were co-incubated with an excess of mAb528 or species/isotype matched control antibody against Keyhole Limpet Hemocyanin (KLH; not present in mammalian cells) to allow binding of antibodies to the surface of 13C4 minicells. As an additional control, 12B4 minicells, which do not express Lpp-OmpA-Protein G fusion, were also co-incubated with an equal concentration of mAb528. Following antibody binding, samples were washed three times each and then allowed to incubate with cultured H460 cells at a minicell to H460 cell ratio of 5000:1 for 2 hours. Following the 2 hour incubation, cells were washed three times each in cell culture medium and then visualized for the uptake of fluorescent minicells using fluorescence microscopy. The fluorescence microscopy results are shown in FIG. 5.

Figure 5:
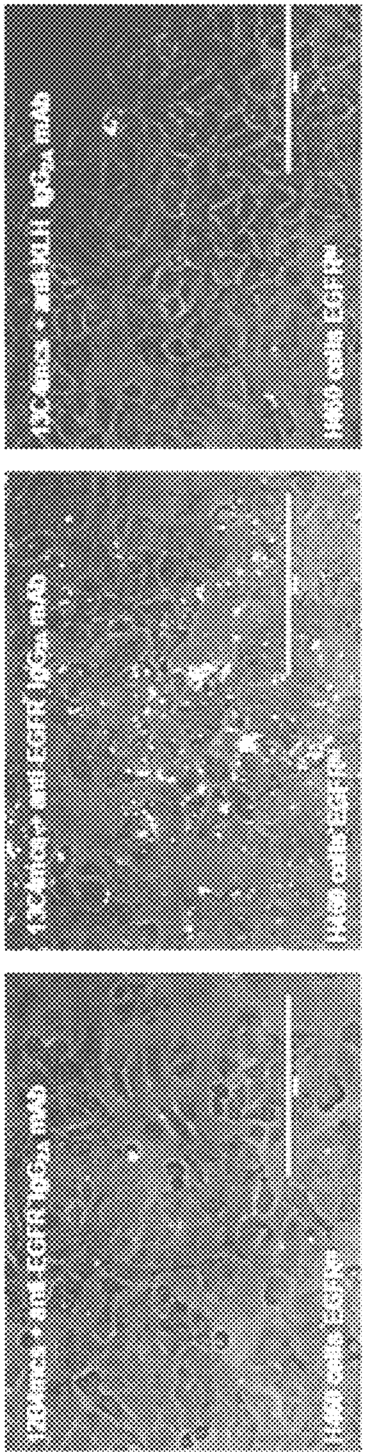
FIG. 5 are images showing fluorescently stained, EGFR1 targeted minicells are internalized by EGFR1-expressing H460 human NSCLC cells in antibody-dependent fashion using Fc-binding minicells expressing and displaying Protein G.

As shown in the left panel of FIG. 5, minicells that did not express Lpp-OmpA-Protein G (12B4) did not bind the EGFR1-targeting antibody and were not efficiently internalized by EGFR1-expressing H460 cells. Middle panel of FIG. 5 shows that minicells expressing Lpp-OmpA-Protein G (13C4) bound the EGFR1-targeting antibody and were readily internalized by EGFR1-expressing H460 cells, demonstrating targeting-dependent uptake. Right panel of FIG. 5 shows that minicells expressing Lpp-OmpA-Protein G (13C4) and displaying a non-specific isotype matched control antibody (antibody targets KLH; not expressed in H460 cells) were not efficiently internalized by EGFR1-expressing H460 cells, demonstrating a need for specific targeting.

Example 5

Figure 6:
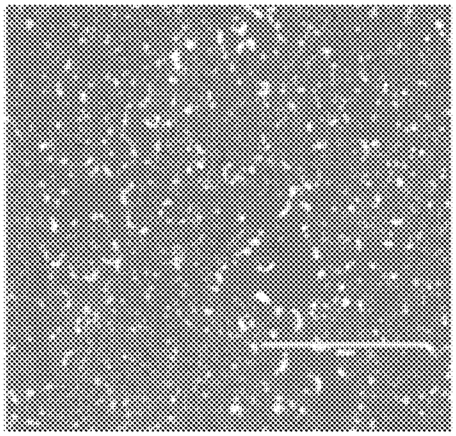
FIG. 6A-D are images showing fluorescently stained, EGFR1 targeted minicells are internalized by EGFR1-expressing H460 human NSCLC cells in antibody-dependent fashion using Fc-binding minicells expressing and displaying Protein A.
Figure 6:
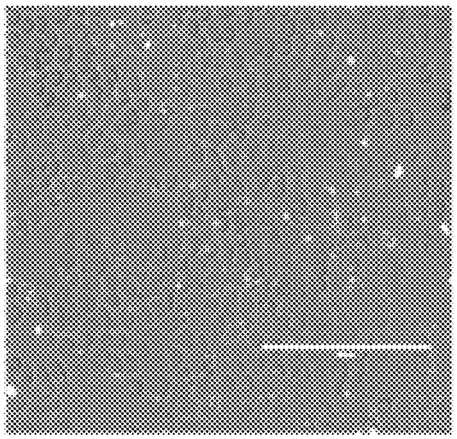
Figure 6:
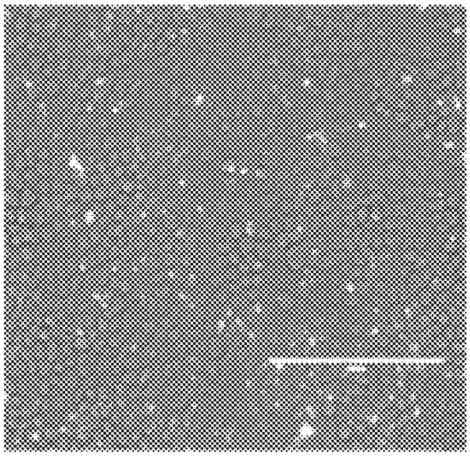
Figure 6:
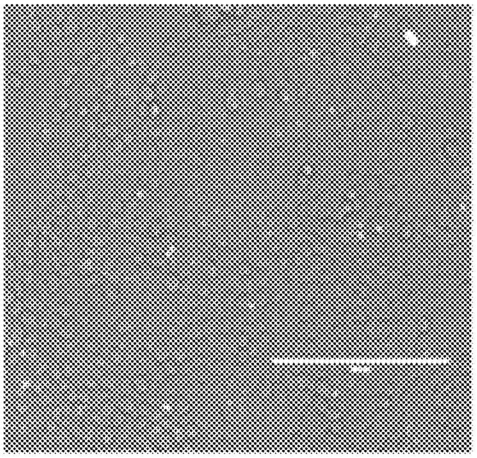
Figure 7:
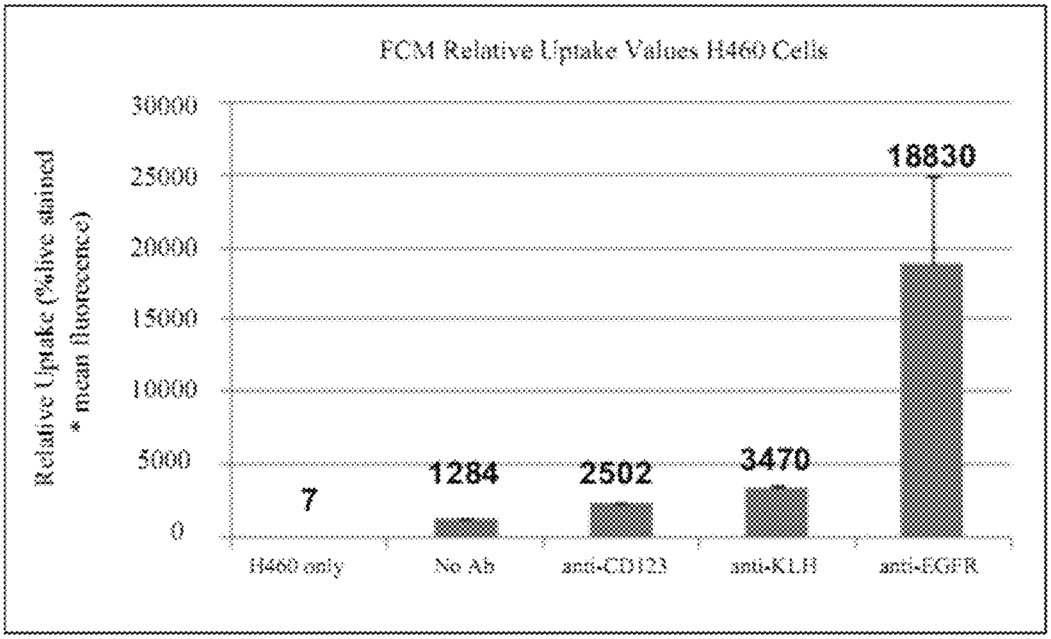
FIG. 7 is a histogram showing relative levels of EGFR1 targeted H460 human NSCLC tumor cell internalization of fluorescent minicells expressing and displaying Protein A measured by FACS analysis of trypsinized cells.

Lpp-OmpA-Protein A 2 Fc (Protein A) minicells with a fusion protein were purified after growth of bacteria at 30° C. using a 1.0 micron cut-off filter instead of low speed centrifugation to enrich for minicells, and then by using a Ficoll density gradient instead of sucrose. The Protein A portion of the fusion protein is capable of binding antibodies through their Fc-regions but is defective in $F(ab')_2$ binding and resistant to OmpT protease. Following purification, Protein A minicells (expressing Lpp-OmpA-Protein A 2 Fc) were stained with the fluorescent imaging agent CFSE (carboxyfluorescein diacetate, succinimidyl ester) and then decorated with anti-human EGF receptor, anti-KLH or anti-human CD123 (IL-3 receptor; not expressed by H460) antibodies as described in Example 4. Following removal of excess unbound antibody, the minicells were incubated with H460 cells (human non-small cell lung carcinoma cell line expressing EGFR1) for 40 minutes and washed. Tumor cell internalization of fluorescent minicells was determined by fluorescence microscopy. FIG. 6 shows fluorescence microscope images of H460 cell monolayers incubated with minicells decorated with various antibodies with prominent EGFR1 targeted minicell uptake demonstrated in FIG. 6A versus anti-KLH (FIG. 6B) or anti-CD123 (FIG. 6C) targeted minicells. The no antibody control also demonstrated no uptake as expected (FIG. 6D). In the same experiment outlined for FIG. 6, the results of relative minicell uptake measured quantitatively by FACS analysis of trypsinized cells are shown in FIG. 7.

TABLES

TABLE 1

| Cross-linking target(s) | Cross-linking reagent(s) | Purpose(s) |
|---|---|---|
| Amine to amine (homobifunctional) | disuccinimidyl glutarate (DSG), disuccinimidyl suberate (DSS), bis(sulfosuccinimidyl)suberate (BS3), tris(succinimidyl)aminotriacetate (TSAT), BS(PEG)5, BS(PEG)9, Lomant's reagent (DSP), 3,3'- | Used to cross-link Fc-regions to polypeptides, peptides, DARPins, |

TABLE 1-continued

| Cross-linking target(s) | Cross-linking reagent(s) | Purpose(s) |
|---|---|---|
| | dithiobis(sulfosuccinimidylpropionate) (DTSSP), disuccinimidyl tartrate (DST), Bis[2-(succinimidooxycarbonyloxy)ethyl]sulfone (BSOCOES), ethylene glycol bis[succinimidylsuccinate] (EGS), ethylene glycol bis[sulfosuccinimidylsuccinate] (Sulfo-EGS), dimethyl adipimidate (DMA), dimethyl pimelimidate (DMP), dimethyl suberimidate (DMS), dimethyl 3,3'-dithiobispropionimidate (DTBP), 1,5-difluoro-2,4-dinitrobenzene (DFDNB) | and other amine-containing conjugates in non-selective amino acid positions. Also used to attach Fc regions to DNA aptamers when the aptamers contain a primary amine. |
| Sulfhydryl to sulfhydryl (homobifunctional) | Maleimides (BMOE, BMB, BMH, TMEA, BM[PEG]2, BM[PEG]3, BMBD, and DTME), Pyridyldthiols (DPDPB), vinylsulfone | Used to cross-link Fc-regions to polypeptides, peptides, DARPins, and other amine-containing conjugates in selective fashion through naturally occurring or recombinantly engineered cysteine residues within both the Fc region as well as the molecule to be conjugated. Also used to attach cysteine containing Fc regions to DNA aptamers when the aptamers and Fc region both contain a sulfhydryl group. |
| Non-selective (homobifunctional) | Bis-[b-(4-Azidosalicylamido)ethyl]disulfide (BASED) | Used to cross-link Fc-regions to polypeptides, peptides, DARPins, amine-containing conjugates, carbohydrates, aptamers, nucleic acids, and hormones in non-selective fashion. |
| Amine to sufhydryl (heterobifunctional) | N-(a-Maleimidoacetoxy) succinimide ester (AMAS), BMPS, GMBS, Sulfo-GMBS, MBS, Sulfo-MBS, Succinimidyl-4-(N-maleimidomethyl)cyclohexane-1-carboxylate (SMCC), Sulfosuccinimidyl-4-(N-maleimidomethyl)cyclohexane-1-carboxylate (Sulfo-SMCC), EMCS, Sulfo-EMCS, SMPB, Sulfo-SMPB, SMPH, LC-SMCC, Sulfo-KMUS, SM(PEG)2, SM(PEG)4, SM(PEG)6, SM(PEG)8, SM(PEG)12, SM(PEG)24, SPDP, LC-SPDP, Sulfo-LC-SPDP, SMPT, Sulfo-SMPT, SIA, SBAP, SIAB, Sulfo-SIAB, | Used to cross-link Fc-regions to polypeptides, peptides, DARPins, and other amine-containing conjugates in selective fashion through naturally occurring or recombinantly engineered cysteine residues wherein the cysteine is present in the Fc region or the conjugate molecule. Also used to attach amine containing Fc regions to DNA aptamers and other nucleic acids (e.g. siRNA) when the nucleic acids contain a sulfhydryl group. Conversely, listed reagents can be used to attach cysteine containing Fc regions to aptamers or other nucleic acid molecules (e.g. siRNA) that contain primary amines. |

TABLE 1-continued

| Cross-linking target(s) | Cross-linking reagent(s) | Purpose(s) |
|---|---|---|
| Amine to non-selective | N-Hydroxysuccinimidyl-4-azidosalicylic acid (NHS-ASA), ANB-NOS, Sulfo-HSAB, Sulfo-NHS-LC-ASA, SANPAH, Sulfo-SANPAH, Sulfo-SFAD, Sulfo-SAND, Sulfo-SAED, succinimidyl-diazirine (SDA), Sulfo-SDA, LC-SDA, Sulfo-LC-SDA | Used to cross-link Fc-regions to polypeptides, peptides, DARPins, and other amine-containing conjugates in semi-selective fashion through naturally occurring or engineered amine groups. Also used to attach amine containing Fc regions to DNA aptamers and other nucleic acids (e.g., siRNA). |
| Amine to carboxyl | Carbodiimides (dicyclohexylcarbodiimide [DCC], 1-Ethyl-3-[3-dimethylaminopropyl]carbodiimide hydrochloride [EDC or EDAC]) | Used to cross-link Fc-regions to polypeptides, peptides, DARPins, and other amine-containing conjugates in selective fashion through the carboxy terminus of either the Fc region or the conjugate. |
| Sulfhydryl to non-selective | Pyridyldithiol/Aryl Azide (ADPD) | Used to cross-link Fc-regions to polypeptides, peptides, DARPins, and other sulfhydryl-containing conjugates in semi-selective fashion through naturally occurring or engineered sulfhydryl groups. Also used to attach sulfhydryl containing Fc regions to DNA aptamers and other nucleic acids (e.g., siRNA). |
| Sulfhydryl to carbohydrate | Maleimide/Hydrazide, BMPH, 3,3'-N-[e-Maleimidocaproic acid] hydrazide, trifluoroacetic acid salt (EMCH), MPBH, KMUH | Used to cross-link sulfhydryl containing Fc-regions to carbohydrates. |
| Hydroxyl to sulfydryl | Isocyanate/Malemide (PMPI) | Used to cross-link sulfhydryl containing Fc-regions to nucleic acids and other conjugate molecules containing free hydroxyls. |
| Amine to DNA | NHS ester/Psoralen (SPB) | Used to cross-link Fc-regions to nucleic acids. |

TABLE 2

Description of sequences provided in the sequence listing

| SEQ ID NO. | ORF 1 | ORF 2 | ORF 3 | Plasmid Name |
|---|---|---|---|---|
| 1 | Lpp-OmpA-Protein A | — | — | pVX-119 |
| 2 | Lpp-OmpA-Protein G | — | — | pVX-120 |
| 3 | Lpp-OmpA-Protein G | cLLO | — | pVX-127 |
| 4 | Lpp-OmpA-Protein G | sLLO | — | pVX-175 |
| 5 | Lpp-OmpA-Protein G | sLLOpH | — | pVX-176 |

TABLE 2-continued

| Description of sequences provided in the sequence listing | | | | |
|---|---|---|---|---|
| 6 | Lpp-OmpA-Protein G | PFO | — | pVX-177 |
| 7 | Lpp-OmpA-ProteinG | Diphtheria Toxin Fragment A with native signal secretion signal sequence | — | pVX-199 |
| 8 | Lpp-OmpA-ProteinG | Diphtheria Toxin Fragment A with no secretion signal sequence | — | pVX-198 |
| 9 | Lpp-OmpA-ProteinG | Gelonin | — | pVX-200 |
| 10 | Lpp-OmpA-Protein G | cLLO | Diphtheria Toxin Fragment A with native signal secretion sequence | pVX-195 |
| 11 | Lpp-OmpA-Protein G | sLLO | Diphtheria Toxin Fragment A with native signal secretion sequence | pVX-180 |
| 12 | Lpp-OmpA-Protein G | sLLOpH | Diphtheria Toxin Fragment A with native signal secretion sequence | pVX-192 |
| 13 | Lpp-OmpA-Protein G | PFO | Diphtheria Toxin Fragment A with native signal secretion sequence | pVX-184 |
| 14 | Lpp-OmpA-Protein G | cLLO | Diphtheria Toxin Fragment A with no signal sequence | pVX-158 |
| 15 | Lpp-OmpA-Protein G | sLLO | Diphtheria Toxin Fragment A with no signal sequence | pVX-179 |
| 16 | Lpp-OmpA-Protein G | sLLOpH | Diphtheria Toxin Fragment A with no signal sequence | pVX-191 |
| 17 | Lpp-OmpA-Protein G | PFO | Diphtheria Toxin Fragment A with no signal sequence | pVX-183 |
| 18 | Lpp-OmpA-Protein G | cLLO | Gelonin | pVX-196 |
| 19 | Lpp-OmpA-Protein G | sLLO | Gelonin | pVX-181 |
| 20 | Lpp-OmpA-Protein G | sLLOpH | Gelonin | pVX-193 |
| 21 | Lpp-OmpA-Protein G | PFO | Gelonin | pVX-185 |
| 33 | PFOsL462F (PFOf) | NA | NA | NA |
| 35 | PFOsG137Q (PFOq) | NA | NA | NA |
| 37 | PFOsH438Y (PFOy) | NA | NA | NA |
| 39 | Lpp-OmpA-Protein A-2Fc | NA | NA | NA |
| 41 | Lpp-OmpA-Protein A 2Fc-OTR (OmpT resistant) | NA | NA | NA |

| SEQ ID NO. | Protein Name |
|---|---|
| 22 | Lpp-OmpA-ProteinG |
| 23 | Lpp-OmpA-ProteinA |
| 24 | Gelonin |
| 25 | Diphtheria toxin Fragment A with native signal sequence |
| 26 | Diphtheria toxin Fragment A lacking signal sequence |
| 27 | Perfringolysin O (PFO; from S et al.) |
| 28 | Perfringolysin O (PFO; from Tweeten et al.) |
| 28 | Listeriolysin O (LLO) |
| 29 | Listeriolysin O lacking signal sequence (cLLO) |
| 30 | Listeriolysin O (stabilized; sLLO) |
| 31 | Listeriolysin O (pH stabilized; sLLOpH) |
| 34 | Perfringolysin O (from S et al., point mutant)—PFOsL462F (PFOf) |
| 36 | Perfringolysin O (from S et al., point mutant)—PFOsG137Q (PFOq) |
| 38 | Perfringolysin O (from S et al., point mutant)—PFOsH438Y (PFOy) |
| 40 | Lpp-OmpA-Protein A-2Fc—No F(ab) binding |
| 42 | Lpp-OmpA-Protein A 2Fc-OTR (OmpT resistant)—No F(ab) binding |

What is claimed is:

1. A bacterial minicell, comprising:

(i) an Fc-binding fusion protein displayed on the surface of the minicell, wherein the Fc-binding fusion protein comprises a) an outer membrane anchoring domain and b) an Fc binding portion of Protein A, wherein the Fc-binding portion of Protein A has no $F(ab')_2$ binding capability and comprises no cleavage sites by OmpT protease;

(ii) one or more bioactive molecules; and (iii) one or more Fc-containing targeting molecules bound to said Fc binding portion, wherein said one or more Fc-containing targeting molecules recognize a eukaryotic antigen.

2. The minicell of claim 1, wherein at least one of the one or more bioactive molecules is a protein toxin.

3. The minicell of claim 2, wherein said protein toxin is selected from the group consisting of gelonin, diphtheria toxin fragment A, diphtheria toxin fragment A/B, tetanus toxin, *E. coli* heat labile toxin LTI, *E. coli* heat labile toxin LTII, cholera toxin, *C. perfringes* iota toxin, *Pseudomonas* exotoxin A, shiga toxin, anthrax toxin, MTX (*B. sphaericus* mosquilicidal toxin), perfringolysin O, streptolysin, barley toxin, mellitin, anthrax toxins LF and EF, adenylate cyclase toxin, botulinolysin B, botulinolysin E3, botulinolysin C, botulinum toxin A, cholera toxin, *clostridium* toxins A, B, and alpha, ricin, shiga A toxin, shiga-like A toxin, cholera A toxin, pertussis S1 toxin, *E. coli* heat labile toxin (LTB), pH stable variants of listeriolysin O, thermostable variants of listeriolysin O, pH and thermostable variants of listeriolysin O, streptolysin O, streptolysin O c, streptolysin O e, sphaericolysin, anthrolysin O, cereolysin, thuringiensilysin O, weihenstephanensilysin, alveolysin, brevilysin, butyriculysin, tetanolysin O, novyilysin, lectinolysin, pneumolysin, mitilysin, pseudopneumolysin, suilysin, intermedilysin, ivanolysin, seeligeriolysin O, vaginolysin, pyolysin, and any combination thereof.

4. The minicell of claim 1, wherein at least one of the one or more bioactive molecules is a therapeutic small molecule drug.

5. The minicell of claim 4, wherein said therapeutic small molecule drug is selected from the group consisting of DNA damaging agents, agents that inhibit DNA synthesis, microtubule and tubulin binding agents, anti-metabolites, inducers of oxidative damage, anti-angiogenics, endocrine therapies, anti-estrogens, immuno-modulators, histone deacetylase inhibitors, inhibitors of signal transduction, inhibitors of heat shock proteins, retinoids, inhibitors of growth factor receptors, anti-mitotic compounds, anti-inflammatories, cell cycle regulators, transcription factor inhibitors, and apoptosis inducers, and any combination thereof.

6. The minicell of claim 1, wherein at least one of the one or more bioactive molecules is a therapeutic nucleic acid.

7. The minicell of claim 1, wherein at least one of the one or more bioactive molecules is a therapeutic polypeptide.

8. The minicell of claim 1, wherein at least one of the one or more bioactive molecules is a combination of a small molecule drug and a therapeutic nucleic acid.

9. The minicell of claim 1, wherein at least one of the one or more Fc-containing targeting molecules is specific for a tumor cell surface molecule.

10. The minicell of claim 1, wherein at least one of the one or more Fc-containing targeting molecules is specific for an endothelial cell surface molecule.

11. The minicell of claim 1, wherein at least one of the one or more Fc-containing targeting molecules is specific for a target common to both a tumor cell and an endothelial cell.

12. The minicell of claim 1, wherein said minicell further comprises an endosomal escape agent.

13. A composition, comprising the minicell of claim 1 and a pharmaceutically acceptable carrier.

14. The minicell of claim 1, wherein at least one of the one or more bioactive molecules is a protein from an infectious agent.

15. The minicell of claim 14, wherein at least one of the one or more Fc-containing targeting molecules is specific for a professional antigen presenting cell.

16. The minicell of claim 15, wherein said professional antigen presenting cell is a eukaryotic dendritic cell or macrophage.

17. The minicell of claim 1, wherein at least one of the one or more bioactive molecules is a protein antigen from a tumor.

18. The minicell of claim 17, wherein at least one of the one or more Fc-containing targeting molecules is specific for a eukaryotic dendritic cell, eosinophil, neutrophil, basophil, T-cell, B-cell, mast cell, or macrophage.

19. The minicell of claim 14, wherein said minicell further comprises an endosomal escape agent, or an immunomodulatory adjuvant.

20. A composition, comprising the minicell of claim 14 and a pharmaceutically acceptable carrier.

21. The minicell of claim 1, wherein the Fc-binding fusion protein further comprises an autotransporter of type 5a secretion system.

22. The minicell of claim 1, wherein the minicell is fully intact.

23. The minicell of claim 1, wherein the Fc-binding portion of Protein A comprises an amino acid substitution of glycine to alanine at glycine 29.

24. The minicell of claim 5, wherein the immune-modulators are Toll-like receptor agonists or antagonists.

* * * * *

UNITED STATES PATENT AND TRADEMARK OFFICE

CERTIFICATE OF CORRECTION

PATENT NO. : 10,005,820 B2
APPLICATION NO. : 13/397313
DATED : June 26, 2018
INVENTOR(S) : Matthew J. Giacalone et al.

It is certified that error appears in the above-identified patent and that said Letters Patent is hereby corrected as shown below:

On the Title Page

Column 1, Item (*) Notice, Line 3, change "0 days. days." to --0 days--

In the Specification

In Column 4, Line 21, change "embodimens" to --embodiments--

In Column 4, Line 35, change "minciells" to --minicells--

In Column 4, Line 38, change "minciells" to --minicells--

In Column 4, Line 45, change "FIG." to --FIGS.--

In Column 14, Line 12, change "if" to --of--

In Column 20, Line 3, change "N0:29)" to --NO:29)--

In Column 43, Line 16 (Approx.), change "mincell-producing" to --minicell-producing--

In Column 44, Line 18, change "mincell-producing" to --minicell-producing--

In Column 44, Line 41, change "myristolic" to --myristoleic--

In Column 45, Line 32 (Approx.), change "myristolic" to --myristoleic--

In Column 66, Line 56, change "miniciells" to --minicells--

In Column 67, Line 17 (Approx.), change "miniciells" to --minicells--

Signed and Sealed this
Fourth Day of June, 2019

Andrei Iancu
*Director of the United States Patent and Trademark Office*

In the Claims

In Column 254, Line 51, in Claim 3, change "perfringes" to --perfringens--

In Column 254, Line 53, in Claim 3, change "mosquilicidal" to --mosquitocidal--

In Column 254, Line 54, in Claim 3, change "mellitin," to --melittin,--

In Column 254, Line 65, in Claim 3, change "mitilysin," to --mitilysine,--